(12) United States Patent
Verbsky et al.

(10) Patent No.: US 7,368,629 B2
(45) Date of Patent: May 6, 2008

(54) NUCLEIC ACIDS ENCODING ANTHELMINTIC AGENTS AND PLANTS MADE THEREFROM

(75) Inventors: Michelle L. Verbsky, St. Louis, MO (US); Catherine Baublite, St. Louis, MO (US); Andrew P. Kloek, San Francisco, CA (US); Jennifer A. Davila-Aponte, St. Louis, MO (US); Michelle Coutu Hresko, Chesterfield, MO (US); Merry B. McLaird, Kirkwood, MO (US); Rodolfo Zentella, St. Louis, MO (US); Deryck J. Williams, University City, MO (US)

(73) Assignee: Divergence, Inc., Saint Louis, MO (US)

( * ) Notice: Subject to any disclaimer, the term of this patent is extended or adjusted under 35 U.S.C. 154(b) by 288 days.

(21) Appl. No.: 10/912,534

(22) Filed: Aug. 4, 2004

(65) Prior Publication Data

US 2005/0172358 A1 Aug. 4, 2005

Related U.S. Application Data

(63) Continuation-in-part of application No. 10/772,227, filed on Feb. 4, 2004.

(51) Int. Cl.
*C12N 15/09* (2006.01)
*C12N 15/29* (2006.01)
*C12N 15/82* (2006.01)
*A01H 5/00* (2006.01)

(52) U.S. Cl. .................. 800/279; 800/278; 800/298; 800/287; 800/317.2; 800/317.3; 435/468; 435/320.1; 536/23.2; 536/23.6

(58) Field of Classification Search ............... 800/279, 800/287
See application file for complete search history.

(56) References Cited

U.S. PATENT DOCUMENTS

| | | | |
|---|---|---|---|
| 4,761,373 A | 8/1988 | Anderson et al. | |
| 4,769,061 A | 9/1988 | Comai | |
| 4,771,571 A | 9/1988 | Obrero et al. | |
| 4,810,648 A | 3/1989 | Stalker | |
| 4,851,341 A | 7/1989 | Hopp et al. | |
| 4,940,835 A | 7/1990 | Shah et al. | |
| 4,975,374 A | 12/1990 | Goodman et al. | |
| 5,001,912 A | 3/1991 | DeWalch | |
| 5,013,659 A | 5/1991 | Bedbrook et al. | |
| 5,093,124 A | 3/1992 | Kulenkampff | |
| 5,162,602 A | 11/1992 | Somers et al. | |
| 5,192,546 A | 3/1993 | Abercrombie | |
| 5,204,253 A | 4/1993 | Sanford et al. | |
| 5,246,716 A | 9/1993 | Sedun et al. | |
| 5,346,698 A | 9/1994 | Abercrombie | |
| 5,491,084 A | 2/1996 | Chalfie et al. | |
| 5,554,798 A | 9/1996 | Lundquist et al. | |
| 5,668,292 A | 9/1997 | Somerville et al. | |
| 5,674,897 A | 10/1997 | Kim et al. | |
| 5,698,592 A | 12/1997 | Kim et al. | |
| 5,750,386 A | 5/1998 | Conkling et al. | |
| 5,767,366 A | 6/1998 | Sathasivan et al. | |
| 5,801,026 A | 9/1998 | Somerville et al. | |
| 5,846,784 A | 12/1998 | Hitz | |
| 5,928,937 A | 7/1999 | Kakefuda et al. | |
| 5,965,793 A | 10/1999 | Broun et al. | |
| 6,013,863 A | 1/2000 | Lundquist et al. | |
| 6,028,248 A | 2/2000 | Somerville et al. | |
| 6,048,714 A | 4/2000 | Hiromoto | |
| 6,084,155 A | 7/2000 | Volrath et al. | |
| 6,124,359 A | 9/2000 | Feitelson et al. | |
| 6,194,167 B1 | 2/2001 | Browse et al. | |
| 6,225,528 B1 | 5/2001 | Chin et al. | |
| 6,291,742 B1 | 9/2001 | Somerville et al. | |
| 6,310,194 B1 | 10/2001 | Somerville et al. | |
| 6,329,518 B1 | 12/2001 | Green et al. | |
| 6,333,448 B1 | 12/2001 | Bafor et al. | |
| 2001/0016956 A1 | 8/2001 | Ward et al. | |

FOREIGN PATENT DOCUMENTS

| | | |
|---|---|---|
| EP | 0 242 246 | 10/1987 |
| WO | WO 98/46762 | 10/1998 |

OTHER PUBLICATIONS

Broun et al (1997). Plant Physiology 113:933-942.*
Rezzonico et al. Theor. Appl. Genet (2004) 109:1077-1082.*
Iwabuchit et al. Journal of Biol. Chemistry (2003), 278 (7):4603-4610.*
Broun et al. The PLant Journal (1998) 13(2):201-210.*
GenBank Accession No. CAA76156 dated May 13, 1998, 2 pages.
Altschul et al., "Gapped BLAST and PSI-BLAST: a new generation of protein database search programs," *Nucl. Acids Res.*, 1997, 25(17):3389-3402.
Atkinson et al., "Engineering Resistance to Plant-parasitic Nematodes," *The Physiology and Biochemistry of Free-Living and Plant-Parasitic Nematodes*, 1998, Perry & Wright (eds.), CAB International, Chapter 15, pp. 381-413.
Atkinson et al., "Image Analysis of the Growth of *Globodera pallida* and *Meloidogyne incognita* on Transgenic Tomato Roots Expressing Cystatins," *J. Nematol.*, 1996, 28(2):209-215.
Banaś et al., "The involvement of phospholipids: diacylglycerol acyltransferases in triacylglycerol production," *Biochem. Soc. Trans.*, 2000, 28(6):703-705.
Barker et al., "Plant and Soil Nematodes: Societal Impact and Focus for the Future," *J. Nematol.*, 1994, 26(2):127-137.

(Continued)

*Primary Examiner*—Medina A. Ibrahim
(74) *Attorney, Agent, or Firm*—Fish & Richardson P.C.

(57) ABSTRACT

The present invention provides DNA constructs, transgenic plants containing such constructs, and methods of making the plants. The DNA constructs encode a polypeptide that when expressed results in the production of fatty acid compounds having anthelmintic activity. Transgenic plants expressing such a polypeptide can exhibit enhanced resistance to plant parasitic nematodes, particularly when expressed in vegetative tissues. Transgenic plants expressing such a polypeptide can also be useful for non-pesticidal industrial uses.

37 Claims, 7 Drawing Sheets

OTHER PUBLICATIONS

Bateman et al., "Pfam 3.1: 1313 multiple alignments and profile HMMs match the majority of proteins," *Nucl. Acids Res.*, 1999, 27:260-262.

Bouvier-Navé et al., "Expression in yeast of an acyl-CoA:diacylglycerol acyltransferase cDNA from *Caenorhabditis elegans*," *Biochem. Soc. Trans.*, 2000, 28(6):692-695.

Bouvier-Navé et al., "Expression in yeast and tobacco of plant cDNAs encoding acyl CoA:diacylglycerol acyltransferase," *Eur. J. Biochem.*, 2000, 267(1):85-96.

Broadwater et al., "Desaturation and Hydroxylation. Residues 148 and 324 of *Arabidopsis* FAD2, in Addition to Substrate Chain Length, Exert A Major Influence in Partitioning of Catalytic Specificity," *J. Biol. Chem.*, 2002, 277(18):15613-15620.

Broun & Sommerville, "Accumulation of Ricinoleic, Lesquerolic, and Densipolic Acids in Seeds of Transgenic Arabidopsis Plants That Express a Fatty Acyl Hydroxylase cDNA from Castor Bean," *Plant Physiol.*, 1997, 113(3):933-942.

Broun et al., "A bifunctional oleate 12-hydroxylase: desaturase from *Lesquerella fendleri*," *Plant J.*, 1998, 13(2):201-210.

Broun et al., "Catalytic Plasticity of Fatty Acid Modification Enzymes Underlying Chemical Diversity of Plant Lipids," *Science*, 1998, 282(5392):1315-1317.

Bustos et al., "Regulation of β-Glucuronidase Expression in Transgenic Tobacco Plants by an A/T-Rich, *cis*-Acting Sequence Found Upstream of a French Bean β=Phaseolin Gene," *Plant Cell*, 1989, 1:839-853.

Cahoon et al., "Transgenic Production of Epoxy Fatty Acids by Expression of a Cytochrome P450 Enzyme from *Euphorbia lagascae* Seed," *Plant Physiol.*, 2002, 128:615-624.

Carpenter et al., "Township limits on 1,3-D will impact adjustment to methyl bromide phase-out," *California Agriculture*, 2001, 55(3):12-18.

Carter, "Costs uncertain: Methyl bromide phase-out becomes reality," *California Agriculture*, 2001, 55(3):2.

Clough & Bent, "Floral dip: a simplified method for *Agrobacterium*-mediated transformation of *Arabidopsis thaliana*," *Plant J.*, 1998, 16(6):735-743.

Dahlqvist et al., "Phospholipid:diacylglycerol acyltransferase: An enzyme that catalyzes the acyl-CoA-independent formation of triacylglycerol in yeast and plants," *Proc. Natl. Acad. Sci USA*, 2000, 97(12):6487-6492.

Davis et al., "Nematicidal Activity of Fatty Acid Esters on Soybean Cyst and Root-knot Nematodes," *J. Nematol.*, 1997, 29(4S):677-684.

Djian et al., "Nematocidal Properties of Carboxylic Acids and Derivatives," *Pestic. Biochem. Physiol.*, 1994, 50(3):229-239.

Eisenback, "Techniques for Measuring Nematode Development and Egg Production," *Laboratory Techniques in Nematode Ecology*, Wheeler et al. (eds.), Society of Nematologists, Hyattsville, MD, pp. 1-4.

Fire et al., "Potent and specific genetic interference by double-stranded RNA in *Caenorhabditis elegans*," *Nature*, 1998, 391:806-811.

Gaginella et al., "Actions on Ricinoleic Acid and Structurally Related Fatty Acids on the Gastrointestinal Tract. II. Effects on Water and Electrolyte Absorption In Vitro," *J. Pharmacol. Exp. Ther.*, 1975, 195(2):355-361.

Gaginella et al., "Cytotoxicity of Ricinoleic Acid (Castor Oil) And Other Intestinal Secretagogues on Isolated Intestinal Epithelial Cells," *J. Pharmacol. Exp. Ther.*, 1977, 201(1):259-266.

Gamborg et al., "Nutrient Requirements of Suspension Cultures of Soybean Root Cells," *Exp. Cell Res.*, 1968, 50:151-158.

Gönczy et al., "Functional genomic analysis of cell division in *C. elegans* using RNAi of genes on chromosome III," *Nature*, 2000, 408:331-336.

Green et al., "Binding site requirements for pea nuclear protein factor GT-1 correlate with sequences required for light-dependent transcriptional activation of the *rbcS-3A* gene," *EMBO J.*, 1988, 7(13):4035-4044.

Hackney & Dickerson, "Marigold, Castor Bean, and Chrysanthemum as Controls of *Meloidogyne incognita* and *Pratylenchus alleni*," *J. Nematol.*, 1975, 7(1):84-90.

Heinrich et al., "PotRb7—A Gene Equivalent to tobRB7 from Potato (Accession No. U65700)," *Plant Physiol.*, 1996, 112(2):862.

Hussey & Barker, "A Comparison of Methods of Collecting Inocula of *Meloidogyne* Spp., Including a New Technique," *Plant Disease Reporter*, 1973, 57(12):1025-1028.

Jako et al., "Seed-Specific Over-Expression of an *Arabidopsis* cDNA Encoding a Diacylglycerol Acyltransferase Enhances Seed Oil Content and Seed Weight," *Plant Physiol.*, 2001, 126(2):861-874.

Jordano et al., "A Sunflower Helianthinin Gene Upstream Sequence Ensemble Contains an Enhancer and Sites of Nuclear Protein Interaction," *Plant Cell*, 1989, 1:855-866.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Lasota & Dybas, "Abamectin As A Pesticide for Agricultural Use," *Acta Leidensia*, 1990, 59(1-2):217-225.

Lee et al., "Identification of Non-Heme Diiron Proteins That Catalyze Triple Bond and Epoxy Group Formation," *Science*, 1998, 280:915-918.

Marroquin et al., "*Bacillus thuringiensis* (*Bt*) Toxin Susceptibility and Isolation of Resistance Mutants in the Nematode *Caenorhabditis elegans*," *Genetics*, 2000, 155(4):1693-1699.

McCormick, "Transformation of tomato with *Agrobacterium tumefaciens*," *Plant Tissue Culture Manual*, 1991, B6:1-9.

McElroy et al., "Development of *gusA* reporter gene constructs for cereal transformation: Availability of plant transformation vectors from the CAMBIA Molecular Genetic Resource Service," *Mol. Breed.*, 1995, 1:27-37.

Meier et al., "Elicitor-Inducible and Constitutive in Vivo DNA Footprints Indicate Novel *cis*-Acting Elements in the Promoter of a Parsley Gene Encoding Pathogenesis-Related Protein 1," *Plant Cell*, 1991, 3:309-315.

Mello et al., "Efficient gene transfer in *C.elegans*: extrachromosomal maintenance and integration of transforming sequences," *EMBO J.*, 1991, 10(12):3959-3970.

Millar et al., "All fatty acids are not equal: discrimination in plant membrane lipids," *Trends Plant Sci.*, 2000, 5(3):95-101.

Miquel & Browse, "*Arabidopsis* Mutants Deficient in Polyunsaturated Fatty Acid Synthesis. Biochemical and Genetic Characterization of a Plant Oleoyl-Phosphatidylcholine Desaturase," *J. Biol. Chem.*, 1992, 267(3):1502-1509.

Momin & Nair, "Pest-Managing Efficacy of *trans*-Asarone Isolated from *Daucus carota* L. Seeds," *J. Agric. Food Chem.*, 2002, 50(16):4475-4478.

Moon et al., "A Condensing Enzyme from the Seeds of *Lesquerella fendleri* That Specifically Elongates Hydroxy Fatty Acids," *Plant Physiol.*, 2001, 127(4):1635-1643.

Peyou-Ndi et al., "Identification and Characterization of an Animal $\Delta^{12}$ Fatty Acid Desaturase Gene by Heterologous Expression in *Saccharomyces cerevisiae*," *Arch. Biochem. Biophys.*, 2000, 376(2):399-408.

Sarda et al., "Characterization of closely related δ-TIP genes encoding aquaporins which are differentially expressed in sunflower roots upon water deprivation through exposure to air," *Plant Mol. Biol.*, 1999, 40(1):179-191.

Singh et al., "Inhibition of polyunsaturated fatty acid accumulation in plants expressing a fatty acid epoxygenase," *Biochem. Society Trans.*, 2000, 28(6):940-942.

Singh et al., "Transgenic expression of a Δ12-epoxygenase gene in *Arabidopsis* seeds inhibits accumulation of linoleic acid," *Planta*, 2001, 212:872-879.

Sonnhammer et al., "Pfam: A Comprehensive Database of Protein Domain Families Based on Seed Alignments," *Proteins: Structure, Function, and Genetics*, 1997, 28:405-420.

Sonnhammer et al., "Pfam: multiple sequence alignments and HMM-profiles of protein domains," *Nucl. Acids Res.*, 1998, 26(1):320-322.

Spychalla et al., "Identification of an animal ω-3 fatty acid desaturase by heterologous expression in *Arabidopsis*," *Proc. Natl. Acad. Sci. USA*, 1997, 94(4):1142-1147.

Stadler et al., "Fatty Acids and Other Compounds with Nematicidal Activity from Cultures of Basidiomycetes," *Planta Medica*, 1994, 60(2):128-132.

van de Loo et al., "Unusual Fatty Acids," *Lipid Metabolism in Plants*, 1993, CRC Press, Boca Raton, Chapter 3, pp. 91-126.

van de Loo et al., "An oleate 12-hydroxylase from *Ricinus communis* L. is a fatty acyl desaturase homolog," *Proc. Natl. Acad. Sci. USA*, 1995, 92(15):6743-6747.

van Engelen et al., "pBINPLUS: an improved plant transformation vector based in bPIN19," *Transgenic Res.*, 1995, 4:288-290.

Vos et al., "The tomato *Mi-1* gene confers resistance to both roo-knot nematodes and potato aphids," *Nat. Biotechnol.*, 1998, 16:1365-1369.

Wright & Perry, "Musculature and Neurobiology," *The Physiology and Biochemistry of Free-Living and Plant-parasitic Nematodes*, 1998, CAB International, Chapter 3, pp. 49-73.

Yamamoto et al., "Characterization of *cis*-Acting Sequences Regulating Root-Specific Gene Expression in Tobacco," *Plant Cell*, 1991, 3:371-382.

Ye et al., "*Arabidopsis* ovule is the target for *Agrobacterium in planta* vacuum infiltration transformation," *Plant J.*, 1999, 19(3):249-257.

Zhang et al., "DNA Sequences That Activate Isocitrate Lyase Gene Expression during Late Embryogenesis and during Postgerminative Growth," *Plant Physiol.*, 1996, 110:1069-1079.

* cited by examiner

FIG. 1
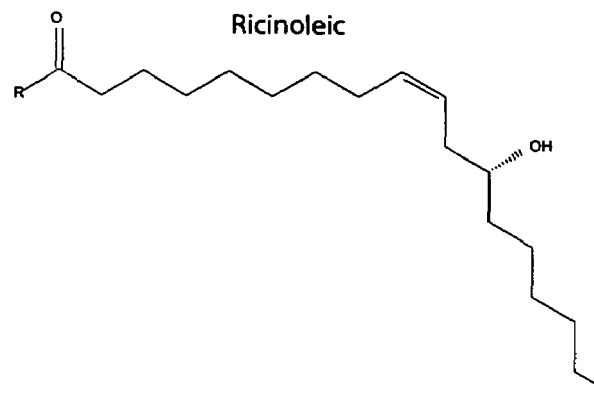
Ricinoleic
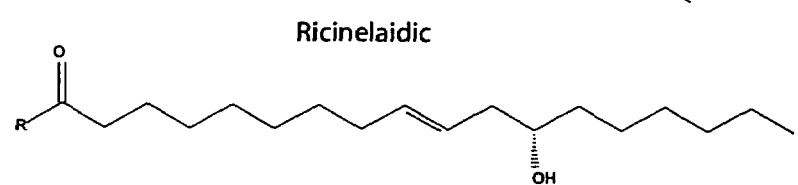
Ricinelaidic
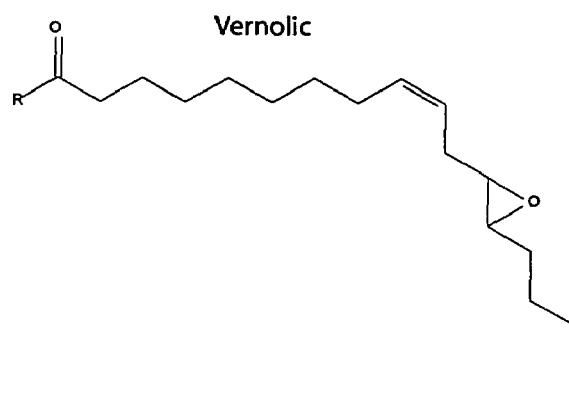
Vernolic
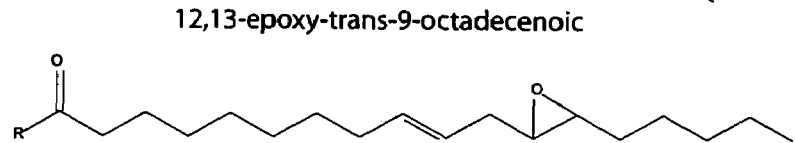
12,13-epoxy-trans-9-octadecenoic
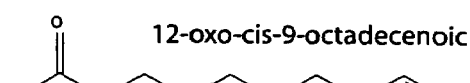
12-oxo-cis-9-octadecenoic
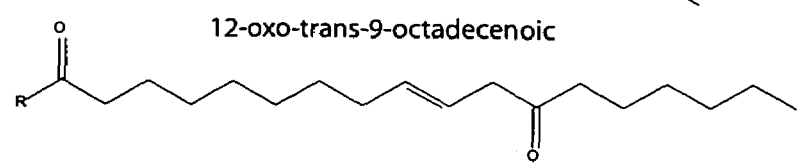
12-oxo-trans-9-octadecenoic

```
                    *..*                      .*.         *::  ::::***  ***:**.  **  *:  *.  :        ::  :*   ::  :.  *  .  :      :**
SEQ_ID_NO_37     MASSGRMSTVITSNMSEKKGG--SSHLKRAPHTKPPFTLGDLKRAIPPHCFERSFVRSFSXVAYDVCLSPLFYSIATNFFPYISSPLS-YVAWLVYWLF    96
SEQ_ID_NO_39     MASSGRMSTVITSNMSEKKGG--SSHLKRAPHTKPPFTLGDLKRAIPPHCFERSPVRSFSXVAYDVCLSPLFYSIATNFFPYISSPLS-YVAWLVYWLF    96
SEQ_ID_NO_13     MGGGGRMSTVITSNMSEKKGG--SSHLKRAPHTKPPFTLGDLKRAIPPHCFERSFVRSFSXVAYDVCLSPLFYSIATNFFPYISSPLS-YVAWLVYWLF    96
SEQ_ID_NO_34     MGGGGRMSTVITSNMSE-----SSHLKRAPHTKPPFTLGDLKRAIPPHCFERSPVRSFSVVAYDVCLSPLFYSIATNFFPYISSPLS-YVAWLVYWLF    92
SEQ_ID_NO_19     MGAGGRMPVPTSSKKSE-----TDTTKRVPCEKPPFSVGDLKKAIPPHCFERSPVRSFSXVAYDVCLSPLFYSIATNFFPYISSPLS-YVAWLVYWLF    92
SEQ_ID_NO_127    MGAGGRTDVPPANRKSE-----VDPLKRVPPEKPQPSLSQIKKAIPPHCFQRSVLRSFSYVVDLTIAFCLYYVATHYFHLLPGPLS-FRGMAIYWAV    92
SEQ_ID_NO_128    MGAGGRMSDPTTKDEQK-----KNPLQRVPYAKPPPTLGDIKKAIPPHCFERSVGRSFSYVVVDLVIVPLLYYIATSYPHLLPSPYC-YLAWPIYWAV    92
SEQ_ID_NO_17     MGAGGRIMVTPSSKKSE-----TEALKRGPCEKPPFTVKDLKKAIPQHCFQRSIPRSFSYLLTDITLVSCFYYVATNYFSLLPQPLS-YLAWPLYWVC    93
SEQ_ID_NO_35     MGAGGRIMVTPSSKKSE-----TEALKRGPCEKPPFTVKDLKKAIPQHCFQRSIPRSFSYLLTDITLVSCFYYVATNYFSLLPQPLS-YLAWPLYWVC    92
SEQ_ID_NO_40     MASSGRIMVTPSSKKSE-----TEALKRGPCEKPPFTVKDLKKAIPQHCFQRSIPRSFSYLLTDITLVSCFYYVATNYFSLLPQPLSTYLAWPLYWVC    93
SEQ_ID_NO_14     MGAGGRIMVTPSSKKSE-----TEALKRGPCEKPPFTVKDLKKAIPQHCFQRSIPRSFSYLLTDITLVSCFYYVATNYFSLLPQPLSTYLAWPLYWVC    93
SEQ_ID_NO_20     MGAGGRMPVPTSSKKSE-----TDTTKRVPCEKPPFSVGDLKKAIPQHCFQRSIPRSFSYLLTDITLVSCFYYVATNYFSLLPQPLSTYLAWPLYWVC    93
SEQ_ID_NO_23     MGAGGRMPVPTSSKKSE-----TDTTKRVPCEKPPFSVGDLKKAIPQHCFQRSIPRSFSYLLTDITLVSCFYYVATNYFSLLPQPLSTYLAWPLYWVC    93
SEQ_ID_NO_15     MGAGGRIMVTPSSKKSK-----PEALRRGPGEKPPFTVQDLKKAIPRECFKRSIPRSFSYLLTDIILASCFYYVATNYFSLLPQPLSTYFAWPLYWVC    93
SEQ_ID_NO_21     MGAGGRMPVPTSSKKSE-----TDTTKRVPCEKPPFSVGDLKKAIPRECFKRSIPRSFSYLLTDIILASCFYYVATNYFSLLPQPLSTYPAWPLYWVC    93
SEQ_ID_NO_16     MGAGGRIMVTPSSKKSE-----PQALRRGPCEKPPFTVKDLKKAIPPHCFKRSIPRSFSYLLTDFILASCFYYVATNYFSLLPQPVSNYLAWPLYWIC    93
SEQ_ID_NO_22     MGAGGRMPVPTSSKKSE-----TDTTKRVPCEKPPPSVGDLKKAIPPHCFKRSIPRSFSYLLTDFILASCFYYVATNYFSLLPQPVSNYLAWPLYWIC    93
SEQ_ID_NO_125    MGAGGRMPVPTSSKKSE-----TDTTKRVPCEKPPFSVGDLKKAIPPHCFKRSIPRSFSYLISDIIIASCFYYVATNYFSLLPQPLS-YLAWPLYWAC    92
SEQ_ID_NO_126    MGAGGRMQVSPPSKKSE-----TDTIKRVPCEFPPFTVGELKKAIPPHECFKRSIPRSFSYLIWDIIIASCFYYVATTYFPLLPHPLS-YFAWPLYWAC    92
SEQ_ID_NO_18     MGAHG------HGRTSK-----KSVMERVSVDPVPPSLSDLKQAIPPHCFQRSVIRSSYYVVHDLIIAYIFYPLADKYIPILPAPLA-YLAWPLYWFC    86
SEQ_ID_NO_41     MASSG------HSRTSK-----KSVMERVSVDPVPPSLSDLKQAIPPHCFQRSVIRSSYYVVHDLIIAYIFYFLADKYIPILPAPLA-YLAWPLYWFC    86
SEQ_ID_NO_24     MGAGGRMPVPTSSKKSE-----TDTTKRVPCEKPPFSVGDLKKAIPPHCFQRSVIRSSYYVVHDLIIAYIFYFLADKYIPILPAPLA-YLAWPLYWFC    92
SEQ_ID_NO_38     MASSGR-----MSDLSDG----KNLLKRVPVDP-PFTLSDIKKAIPPHCFKRSVIRSSYIVVHDLIVSYVPPFLATTYITVLPAPLA-YIANPVYWFC    87
SEQ_ID_NO_42     MASSGR-----MSDLSDG----KNLLKRVPVDP-PFTLSDIKKAIPPHCFKRSVIRSSYIVVHDLIVSYVPPFLATTYITVLPAPLA-YIANPVYWFC    87
SEQ_ID_NO_36     MGAGGR-----MSDLSDG----KNLLKRVPVDP-PFTLSDIKKAIPPHECFKRSVIRSSYYVVHDLIVSYVPPFLATTYITVLPAPLA-YIANPVYWFC    87
      ruler      1.......10........20........30........40........50........60........70........80........90.......1

*...:   **:*:::.*****:****:*      **  **::.*:  **  ***********.**:*  .*::.***:;*   *:   :   *  ****  **   .  :    :  **:
SEQ_ID_NO_37     QGCILTGLWVIGHECGHHAFSEYQLADDIVGLIVHSALLVPYFSWKYSHRRHHSNIGSLERDEVFVPKSKSKISWYSKYLNNPPGRVLTLAATLLLGW   194
SEQ_ID_NO_39     QGCILTGLWVIGHECGHHAFSEYQLADDIVGLIVHSALLVPYFSWKYSHRRHHSNIGSLERDEVFVPKSKSKISWYSKYLNNPPGRVLTLAATLLLGW   194
SEQ_ID_NO_13     QGCILTGLWVIGHECGHHAFSEYQLADDIVGLIVHSALLVPYFSWKYSHRRHHSNIGSLERDEVFVPKSKSKISWYSKYLNNPPGRVLTLAATLLLGW   194
SEQ_ID_NO_34     QGCILTGLWVIGHECGHHAFSEYQLADDIVGLIVHSALLVPYFSWKYSHRRHHSNIGSLERDEVFVPKSKSKISWYSKYLNNPPGRVLTLAATLLLGW   190
SEQ_ID_NO_19     QGCILTGLWVIGHECGHHAFSSYQLADDIVGLIVHSALLVPYFSWKYSHRRHHSNIGSLERDEVFVPKSKSKISWYSKYLNNPPGRVLTLAATLLLGW   190
SEQ_ID_NO_127    QGCILTGVWVIGHECGHHAFSDYQLLDDIVGLILHSALLVPYFSWKYSHRRHHSNTGSLERDEVFVPKQKSCIKWYSKYLNNPLGRVLTLAVTLTLGW   190
SEQ_ID_NO_128    QGCVCTGIWVIAHECGHHAFSDYQWLDDTVGLILHSALLVPYFSWKYSHRRHHSNTGSLERDSVFVPKPKSRVSWYSKYLNMPLGRVITLVVTLTLGW   190
SEQ_ID_NO_17     QGCVLTGIWVLGHECGHHAFSDYQWLDDTVGFIFHSLLLVPYFSWKYSHRRHHSNNGSLEKDEVFVPPKKAAVKWYVKYLNNPLGRILVLTVRPILGW   191
SEQ_ID_NO_35     QGCVLTGIWVLGHECGHHAFSDYQWLDDTVGFIPHSLLLVPYFSWKYSHRRHHSNNGSLEKDEVFVPPKKAAVKWYVKYLNNPLGRILVLTVRPILGW   190
SEQ_ID_NO_40     QGCVLTGIWVLGHECGHHAFSDYQWLDDTVGFIFHSLLLVPYFSWKYSHRRHHSNNGSLEKDEVFVPPKKAAVKWYVKYLNNPLGRILVLTVRPILGW   191
SEQ_ID_NO_14     QGCVLTGIWVIGHECGHHAFSDYQWVDDTVGFIFHSFLLVPYFSWKYSHRRHHSNNGSLEKDEVFVPPKKAAVKWYVKYLNNPLGRILVLTVQPILGW   191
SEQ_ID_NO_20     QGCVLTGIWVLGHECGHHAFSDYQWVDDTVGFIFHSFLLVPYFSWKYSHRRHHSNNGSLEKDEVFVPPKKAAVKWYVKYLNNPLGRILVLTVQPILGW   191
SEQ_ID_NO_23     QGCVLTGIWVLGHECGHHAFSDYQWLDDTVGFIFHSLLLVPYFSWKYSHRRHHSNNGSLEKDEVFVPPKKAAVKWYVKYLNNPLGRILVLTVRPILGW   191
SEQ_ID_NO_15     QGCVLTGVWVLGHECGHQAPSDYQWVDDTVGFIIHTFLLIPYFSWKYSHRRHHANNGSLERDEVFVPPKKAAVKWYVKYLNNPLGRTVVLIVQFVLGW   191
SEQ_ID_NO_21     QGCVLTGVWVLGHECGHQAPSDYQWVDDTVGFIIHTFLLIPYFSWKYSHRRHHANNGSLERDEVFVPPKKAAVKWYVKYLNNPLGRTVVLIVQFVLGW   191
SEQ_ID_NO_16     QGCVLTGVWVLGHECGHHAFSDYQWVDDTVGFIIHESFLLVPYFSWKYSHRRHHSNNGSLEKDEVFVPPKKAAVKWYVKYLNNPLGRTVVLIVQFVLGW   191
SEQ_ID_NO_22     QGCVLTGVWVLGHECGHHAFSDYQWVDDTVGFIIHESFLLVPYFSWKYSHRRHHSNNGSLEKDEVFVPPKKAAVKWYVKYLNNPLGRTVVLIVQFVLGW   191
SEQ_ID_NO_125    QGCVLTGIWVIAHECGHHAFSDYQWLDDTVGLIPHSPLLVPYFSWKYSHRRHHSNTGSLERDEVFVPKQRSAIEKWYGKYLNNPLGRIMMLTVQFVLGW   190
SEQ_ID_NO_126    QGCVLTGIWVIAHECGHHAFSDYQWLDDTVGLIFHSFLLVPYFSWKYSHRRHHSNTGSLERDEVFVPKKKSDIKWYGKYLNNPLGRTVMLTVQFFLGW   190
SEQ_ID_NO_18     QASILTGLWILGHECGHHAFSEYQWVDDTVGFMVHSPLLTPYFSWKYSHRNHHANTSSIDNDEVYIPKSKSKLALTYKLLNNPPGRLLVMVIMFTLGF   184
SEQ_ID_NO_41     QASILTGLWILGHECGHHAFSEHQWVDDTVGFMVHSPLLTPYFSWKYSHRNHHANTSSIDNDEVYIPKSKSKLALTYKLLNNPPGRLLVMVIMFTLGF   184
SEQ_ID_NO_24     QASILTGLWILGHECGHHAFSEYQWVDDTVGFMVHSPLLTPYFSWKYSHRNHHANTSSIDNDEVYIPKSKSKLALTYKLLNNPPGRLLVMVIMFTLGF   190
SEQ_ID_NO_38     QASILTGLWVIGHECGHHAFSEYQWIDDTVGFILHESALLTPYFSWKYSERNHHANTNSLDNDEVYIPKRKSKVKIYSKILNNPPGRVFTLVFRLTLGF   185
SEQ_ID_NO_42     QASILTGLWVIGHECGHHAFSETQWIDDTVGFILHESALLTPYFSWKYSERNHHANTNSLDNDEVYIPKRKSKVKIYSKILNNPPGRVFTLVFRLTLGF   185
SEQ_ID_NO_36     QASILTGLWVIGHECGHHAFSBYQWIDDTVGFILHESALLTPYFSWKYSERNHHANTNSLDNDEVYIPKRKSKVKIYSKILNNPPGRVFTLVFRLTLGF   185
      ruler      00.......110.......120........130........140........150.......160........170........180........190....

****   *:**:   *:   **   *:  *  .**:  :***:::    ::*   *::*.      :        .*     .   .****  *  *    ::  ::*:*:***    :   *:*    *:**
SEQ_ID_NO_37     PLYLAFNVSGRPYDR-FACHYDPYGPIFSERERLQIYIADLGIFATTFVLYQATMAKGLAWVMRIYGVPLLIVNCPLVMITYLQHTHPAIPRYGSSEW   291
SEQ_ID_NO_39     PLYLAFNVSGRPYDR-FACHYDPYGPIFSERERLQIYIADLGIFATTFVLYQATMAKGLAWVMRIYGVPLLIVNCPLVMITYLQHTHPAIPRYGSSEW   291
SEQ_ID_NO_13     PLYLAFNVSGRPYDR-FACHYDPYGPIFSERERLQIYIADLGIFATTFVLYQATMAKGLAWVMRIYGVPLLIVNCPLVMITYLQHTHPAIPRYGSSEW   291
SEQ_ID_NO_34     PLYLAFNVSGRPYDR-FACHYDPYGPIFSERERLQIYIADLGIFATTFVLYQATMAKGLAWVMRIYGVPLLIVNCPLVMITYLQHTHPAIPRYGSSEW   287
SEQ_ID_NO_19     PLYLAFNVSGRPYDR-FACHYDPYGPIFSERERLQIYIADLGIFATTFVLYQATMAKGLAWVMRIYGVPLLIVNCPLVMITYLQHTHPAIPRYGSSEW   287
SEQ_ID_NO_127    PLYIALNVSGRPYDR-FACHYDPYGPYISDRERLQIYISDAGVLAVVYGLYRLAMAEKGLAWVMRIYGVPLLUVNGPLVLTIFLQHTPALPHYTSSEW   287
SEQ_ID_NO_128    PLYLLFNVSGRPYNR-FACHFDPYGPIYNDRERLQIPISDAGIIAAVCVLYRVALVKGLAWLVCVVGVPLLIVNGPLVLITFLQHTPSLPHYDSSEW   287
SEQ_ID_NO_17     PLYLAFNVSGRPYDG-FASHFPPHAPIFKDRERLQIYISDAGILAVCTGLYRYVAASQGLUTAMICVYGVPLVVNFPLVLVTPLQHTHPSLPHYDSTEW   288
SEQ_ID_NO_35     PLYLAFNVSGRPYDG-FASHFPPHAPIFKDRERLQIYISDAGILAVCTGLYRYVAASQGLUTAMICVYGVPLVVNFPLVLVTPLQHTHPSLPHYDSTEW   287
SEQ_ID_NO_40     PLYLAFNVSGRPYDG-FASHFPPHAPIFKDRERLQIYISDAGILAVCTGLYRYAASQGLUTAMICVYGVPLLIVNFFLVLVTPLQHTHPSLPHYDSTEW   288
SEQ_ID_NO_14     PLYLPFNVSGRPYDG-FASHFFPHAPIFKDRERLQIYISDAGILAVCTYGLYRYAASQGLUTAMICVYGVPLLIVNFPLVLVTPLQHTHPSLPHYDSTEW   288
SEQ_ID_NO_20     PLYLPFNVSGRPYDG-FASHFFPHAPIFKDRERLQIYISDAGILAVCTYGLYRYAASQGLUTAMICVYGVPLLIVNFPLVLVTPLQHTHPSLPHYDSTEW   288
SEQ_ID_NO_23     PLYLAFNVSGRPYDG-FASHFFPHAPIFKDRERLQIYISDAGILAVCTGLYRYAASQGLUTAMICVYGVPLLIVNFPLVLVTPLQHTHPSLPHYDSTEW   288
SEQ_ID_NO_15     PLYLAFNVSGRSYDG-FASHFFPHAPIFKDRERLHIYITDAGILAVCTGLYRYAATKGLTAMICVYGVPLVVNFFLVLVTPLQHTHPSLPHYDSTEW   288
SEQ_ID_NO_21     PLYLAFNVSGRSYDG-FASHFFPHAPIFKDRERLHIYITDAGILAVCTGLYRYAATKGLTAMICVYGVPPLVVNFFLVLVTPLQHTHPSLPHYDSTEW   288
SEQ_ID_NO_16     PLYLAFNVSGRPYDG-FASHFPPHAPIFRDRERLHIYITDAGILAVCTGLYRYAASKGLTAMICVYGVPLLIVNFPLVLVTPLQHTHPSLPHYDSTEW   288
SEQ_ID_NO_22     PLYLAFNVSGRPYDG-FASHFPPHAPIFRDRERLHIYITDAGILAVCTGLYRYAASKGLTAMICVYGVPLLIVNFPLVLVTPLQHTHPSLPHYDSTEW   288
SEQ_ID_NO_125    PLYLAFNVSGRPYDG-FACHFFPNAPIYNDRERLQIYLSDAGILAVCPGLYRYAAAQGMASHICLYGVPLLIVNAPLVLITYLQHTHPSLPHYDSSEW   287
SEQ_ID_NO_126    PLYLAFNVSGRPYDGPACHFHPNAPIYNDRERLQIYISDAGILAVCYGLPRYAAAQGVASHVCPYGVPLLIVNGLLVLITYLQHTHPSLPHYDSSEW   288
SEQ_ID_NO_18     PLYLLTNISGKKYDR-FANHFDPMSPIFKRERBRFQVLLSDLGLLAVFYGIKVAVARKGAAWVACMYGVPMLGVPTLFDIITYLHHTHQSSPHYDSTEW   281
SEQ_ID_NO_41     PLYLLTNISGKKYDR-FANHFDPMSPIFKRERBRFQVLLSDLGLLAVFYGIKVAVARKGAAWVACMYGVPMLGVPTLFDIITYLHHTHQSSPHYDSTEW   281
SEQ_ID_NO_24     PLYLLTNISGKKYDR-FANHFDPMSPIFKRERBRFQVLLSDLGLLAVFYGIKVAVARKGAAWVACMYGVPMLGVPTLFDIITYLHHTHQSSPHYDSTEW   287
SEQ_ID_NO_38     PLYLLTNISGKKYQR-FANHFDPLSPIFTERERIQVLSDLGLLAVIYAIKLLVAAKGAVWVTCIYGVPVLGVSVPPVLITYLHHTHLSLPHYDSTEW   282
SEQ_ID_NO_42     PLYLLTNISGKKYQR-FANHFDPLSPIFTERERIQVLVSDLGLLAVIYAIKLLVAAKGAVWVTCIYGVPVLGVSVPFVLITYLHHTHLSLPHYDSTEW   282
SEQ_ID_NO_36     PLYLLTNISGKKYQR-FANHFDPLSPIFTERERIQVLVSDLGLLAVIYAIKLLVAAKGAVWVTCIYGVPVLGVSVPFVLITYLHHTHLSLPHYDSTEW   282
      ruler      .200.......210.......220........230........240........250........260........270........280........290....
```

FIG. 2-1

```
                  :*:***: ::***:*.:* ***:::.*** **::: :***:* ** .**:.::*:** * **  *::***::*:::* *    :**::*.:
SEQ_ID_NO_37   DWLRGAMVTVDRDYGVLNKVFHNIADTHVAHHLPATVPHYHAMEATKAIKPIMGEYYRYDGTPPYKALWREAKECLFVEPDEGAPTQGVPWYRNKY  387
SEQ_ID_NO_39   DWLRGAMVTVDRDYGVLNKVFHNIADTHVAHHLPATVPHYHAMEATKAIKPIMGEYYRYDGTPPYKALWREAKECLFVEPDEGAPTQGVPWYRNKY  387
SEQ_ID_NO_13   DWLRGAMVTVDRDYGVLNKVFHNIADTHVAHHLPATVPHYHAMEATKAIKPIMGEYYRYDGTPPYKALWREAKECLFVEPDEGAPTQGVPWYRNKY  387
SEQ_ID_NO_34   DWLRGAMVTVDRDYGVLNKVFHNIADTHVAHHLPATVPHYHAMEATKAIKPIMGEYYRYDGTPPYKALWREAKECLFVEPDEGAPTQGVPWYRNKY  383
SEQ_ID_NO_19   DWLRGAMVTVDRDYGVLNKVFHNIADTHVAHHLPATVPHYHAMEATKAIKPIMGEYYRYDGTPPYKALWREAKECLFVEPDEGAPTQGVPWYRNKY  383
SEQ_ID_NO_127  DWLRGALATVDRDYGILNKVFHNITDTHVAHHLPSTMPHYHAMEATKAIKPILGEYYRFDETPPVKAMWREARECIYVEPDQSTESKGVPWYNNKL  383
SEQ_ID_NO_128  DWLRGALATVDRDYGVLNKVFHNITDTHVTHHLPSTMPHYHAMEATKAIKPILGQYYQFDGTPPYKAMWREAKECLYVEPDESTPDKGVPWYKNKP  383
SEQ_ID_NO_17   EWIRGALVTVDRDYGILNKVFHNITDTHVAHHLPATIPHYNAMEATEAIKPILGDYYHFDGTPWYVAMYREAKECLYVEPDTERGKKGVYYYNNKL  384
SEQ_ID_NO_35   EWIRGALVTVDRDYGILNKVFHNITDTHVAHHLPATIPHYNAMEATEAIKPILGDYYHFDGTPWYVAMYREAKECLYVEPDTERGKKGVYYYNNKL  383
SEQ_ID_NO_40   EWIRGALVTVDRDYGILNKVFHNITDTHVAHHLPATIPHYNAMEATEAIKPILGDYYHFDGTPWYVAMYREAKECLYVEPDTERGKKGVYYYNNKL  384
SEQ_ID_NO_14   EWIRGALVTVDRDYGILNKVFHNITDTHVAHHLPATIPHYNAMEATEAIKPILGDYYHFDGTPWYVAMYREAKECLYVEPDTERGKKGVYYYNNKL  384
SEQ_ID_NO_20   EWIRGALVTVDRDYGILNKVFHNITDTHVAHHLPATIPHYNAMEATEAIKPILGDYYHFDGTPWYVAMYREAKECLYVEPDTERGKKGVYYYNNKL  384
SEQ_ID_NO_23   EWIRGALVTVDRDYGILNKVFHNITDTHVAHHLPATIPHYNAMEATEAIKPILGDYYHFDGTPWYVAMYREAKECLYVEPDTERGKKGVYYYNNKL  384
SEQ_ID_NO_15   DWIRGAMVTVDRDYGILNKVFHNITDTHVAHHLPATIPHYNAMEATEAIKPILGDYYHFDGTPWYVAMYREAKQCLYVEQDTEK-KKGVYYYNNKL  383
SEQ_ID_NO_21   DWIRGAMVTVDRDYGILNKVFHNITDTHVAHHLPATIPHYNAMEATEAIKPILGDYYHFDGTPWYVAMYREAKQCLYVEQDTEK-KKGVYYYNNKL  383
SEQ_ID_NO_16   EWIRGALVTVDRDYGILNKVFHNITDTHVAHHLPATIPHYNAMEATEAIKPILGDYYHFDGTPWYVAMYREAKECLYVEQDTERGKKGVYYYNNKL  384
SEQ_ID_NO_22   EWIRGALVTVDRDYGILNKVFHNITDTHVAHHIPATIPHYNAMEATEAIKPILGDYYHFDGTPWYVAMYREAKECLYVEQDTERGKKGVYYYNNKL  384
SEQ_ID_NO_125  DWLRGALATVDRDYGILNKVFHNITDTHVAHHLPSTMPHYNAMEATKAIKPILGDYYQFDGTPWYVAMYREAKECIYVEPDREGDKKGVYWYNNKL  383
SEQ_ID_NO_126  DWLRGALATVDRDYGILNKVFHNITDTHVAHHLPSTMPHYHAMEATKAIKPILGEYYQFDGTPVVKAMWREAKECIYVEPDRQGEKKGVPWYNNKL  384
SEQ_ID_NO_18   NWIRGALSAIDRDFGFMNSVFHDVTHTHVMHHMFSYIPHYHAKEARDAINTIIGDYYMIDRTPILKALWREAKECMYIEPD--SKRKGVYWYHKL-  374
SEQ_ID_NO_41   NWIRGALSAIDRDFGFMNSVFHDVTHTHVMHHMFSYIPHYHAKEARDAINTIIGDYYMIDRTPILKALWREAKECMYIEPD--SKRKGVYWYHKL-  374
SEQ_ID_NO_24   NWIRGALSAIDRDFGFMNSVFHDVTHTHVMHHMFSYIPHYHAKEARDAINTIIGDYYMIDRTPILKALWREAKECMYIEPD--SKRKGVYWYHKL-  380
SEQ_ID_NO_38   NWIRGALSTIDRDFGFLNRVFHDVTHTHVLHHLISYIPHYHAKEARDAIKPVLGDYYKIDRTPIFKAMWREAKECIYIEPDEDTEHKGVYWYHKM-  377
SEQ_ID_NO_42   NWIRGALSTIDRDFGFLNRVFHDVTHTHVLHHLISYIPHYHAKEARDAIKPVLGDYYKIDRTPIFKAMWREAKECIYIEPDEDTEHKGVYWYHKM-  377
SEQ_ID_NO_36   NWIRGALSTIDRDFGFLNRVFHDVTHTHVLHHLISYIPHYHAKEARDAIKPVLGDYYKIDRTPIFKAMWREAKECIYIEPDEDTEHKGVYWYHKM-  377
     ruler     ...300.......310.......320.......330.......340.......350.......360.......370.......380.......390
```

FIG. 2-2

NUCLEIC ACIDS ENCODING ANTHELMINTIC AGENTS AND PLANTS MADE THEREFROM

This application is a continuation-in-part (and claims the benefit of priority under 35 USC 120) of U.S. application Ser. No. 10/772,227, filed Feb. 4, 2004, which is incorporated by reference in its entirety.

FIELD OF THE INVENTION

This invention relates to the field of plant pathology and plant genetic transformation. More particularly, the invention relates to methods and compositions for the increased production of novel fatty acids in transgenic plants for industrial purposes including controlling plant pathogens such as plant-parasitic nematodes.

BACKGROUND OF THE INVENTION

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved to be very successful parasites of both plants and animals and are responsible for significant economic losses in agriculture and livestock and for morbidity and mortality in humans (Whitehead (1998) *Plant Nematode Control*. CAB International, New York).

Nematode parasites of plants can inhabit all parts of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The application of chemical nematicides remains the major means of nematode control. However, in general, chemical nematicides are highly toxic compounds known to cause substantial environmental impact and are increasingly restricted in the amounts and locations in which they can be used. For example, the soil fumigant methyl bromide which has been used effectively to reduce nematode infestations in a variety of specialty crops, is regulated under the U.N. Montreal Protocol as an ozone-depleting substance and is scheduled for elimination in 2005 in the US (Carter (2001) *California Agriculture*, 55(3): 2). It is expected that strawberry and other commodity crop industries will be significantly impacted if a suitable replacement for methyl bromide is not found. Similarly, broad-spectrum nematicides such as Telone (various formulations of 1,3-dichloropropene) have significant restrictions on their use because of toxicological concerns (Carter (2001) *California Agriculture, Vol.* 55(3): 12-18).

The macrocyclic lactones (e.g., avermectins and milbemycins), as well as delta-endotoxins from *Bacillus thuringiensis* (Bt), are chemicals that in principle provide excellent specificity and efficacy which should allow environmentally safe control of plant parasitic nematodes. Unfortunately, in practice, these two nematicidal agents have proven less effective in agricultural applications against root pathogens. Although certain avermectins show exquisite activity against plant parasitic nematodes these chemicals are hampered by poor bioavailability due to their light sensitivity, tight binding to soil particles and degradation by soil microorganisms (Lasota & Dybas (1990) *Acta Leiden* 59(1-2): 217-225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt delta endotoxins must be ingested to affect their target organ, the brush border of midgut epithelial cells (Marroquin et al. (2000) *Genetics*. 155(4): 1693-1699). Consequently they are not anticipated to be effective against the dispersal, non-feeding, juvenile stages of plant parasitic nematodes in the field. Because juvenile stages only commence feeding when a susceptible host has been infected, nematicides may need to penetrate the plant cuticle to be effective. Transcuticular uptake of a 65-130 kDa protein—the size of typical Bt delta ends toxins—is unlikely. Furthermore, soil mobility is expected to be relatively poor. Even transgenic approaches are hampered by the size of Bt delta toxins because delivery in planta is likely to be constrained by the exclusion of large particles by the feeding tubes of certain plant parasitic nematodes such as *Heterodera* (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Fatty acids are another class of natural compounds that have been investigated as alternatives to the toxic, non-specific organophosphate, carbamate and fumigant pesticides (Stadler et al. (1994) *Planta Medica* 60(2): 128-132; U.S. Pat. Nos. 5,192,546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S): 677-684). In view of this predicted mode of action it is not surprising that fatty acids are used in a variety of pesticidal applications including herbicides (e.g., SCYTHE by Dow Agrosciences is the C9 saturated fatty acid pelargonic acid), bactericides, fungicides (U.S. Pat. Nos. 4,771,571; 5,246,716), and insecticides (e.g., SAFER INSECTICIDAL SOAP by Safer, Inc.).

The phytotoxicity of fatty acids has been a major constraint on their general use in post-plant agricultural applications (U.S. Pat. No. 5,093,124) and the mitigation of these undesirable effects while preserving pesticidal activity is a major area of research. Post-plant applications are desirable because of the relatively short half-life of fatty acids under field conditions.

The esterification of fatty acids can significantly decrease their phytotoxicity (U.S. Pat. Nos. 5,674,897; 5,698,592; 6,124,359). Such modifications can however lead to loss of nematicidal activity as is seen for linoleic, linolenic and oleic acid (Stadler et al. (1994) *Planta Medica* 60(2): 128-132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J Nematol* 29(4S): 677-684). This is the expected result if both the phytotoxicity and the nematicidal activity derive from the non-specific disruption of plasma membrane integrity.

Ricinoleic acid, the major component of castor oil, has been shown to have an inhibitory effect on water and electrolyte absorption using everted hamster jejunal and ileal segments (Gaginella et al. (1975) *J Pharmacol Exp Ther* 195(2): 355-61) and to be cytotoxic to isolated intestinal epithelial cells (Gaginella et al. (1977) J Pharmacol Exp Ther 201(1): 259-66). These features are likely the source of the laxative properties of castor oil which is given as a purgative in humans and livestock (e.g., castor oil is a component of some de-worming protocols because of its laxative properties). In contrast, the methyl ester of ricinoleic acid is ineffective at suppressing water absorption in the hamster model (Gaginella et al. (1975) *J Pharmacol Exp Ther* 195(2): 355-61).

It has been reported that short- and medium-chain fatty acids and salts (e.g., C6 to C12) have superior fungicidal activity (U.S. Pat. Nos. 5,093,124 and 5,246,716). Not surprisingly, the commercial fungicidal and moss killing product De-Moss comprises mainly fatty acids and salts in this size range. The phytotoxicity of these shorter fatty acids also makes them suitable as broad-spectrum herbicides when used at higher concentrations as is exemplified by the commercial herbicide SCYTHE which comprises the C9 fatty acid pelargonic (nonanoic) acid. U.S. Pat. Nos. 5,093,124, 5,192, 546, 5,246,716 and 5,346,698 teach that C16 to C20 fatty acids and salts such as oleic acid (C18:1) are suitable insecticidal fatty acids. Insecticidal fatty acid products such as M-PEDE and SAFER Insecticidal Concentrate whose active ingredients comprise longer chain fatty acids rich in C16 and C18 components represent real world applications of this scientific information. In contrast, the prior art provides little guidance for the selection of suitable broad-spectrum nematicidal fatty acids and what information exists is often contradictory.

Stadler and colleagues (Stadler et al. (1994) *Planta Medica* 60(2): 128-132) tested a series of fatty acids against L4 and adult *C. elegans* and found that a number of common longer chain fatty acids such as linoleic (C18:2), myristic (C14:0), palmitoleic (C16:1) and oleic (C18:1) acids had significant nematicidal activity. *C. elegans* was not very sensitive to C6 to C10 (medium chain) fatty acids. Stadler et al. commented that their results contrasted with those of an earlier study on the plant parasite *Aphelenchoides besseyi* where C8 to C12 fatty acids were found to be highly active while linoleic acid—a C18 fatty acid—showed no activity. The differential sensitivity of specific nematodes to various fatty acids is again evident in the study of Djian and co-workers (Djian et al. (1994) *Pestic. Biochem. Physiol.* 50(3): 229-239) who demonstrate that the nematicidal potency of short volatile fatty acids such as pentanoic acid can vary between species (e.g., *Meloidogyne incognita* is over a hundred times more sensitive than *Panagrellus redivivus*). The recent finding by Momin and Nair (Momin & Nair (2002) *J. Agric. Food Chem.* 50(16): 4475-4478) that oleic acid at 100 µg/mL over 24 hours is not nematicidal to either *Panagrellus redivivus* or *Caenorhabditis elegans* further confuses the situation as it directly conflicts with the LD50 of 25 µg/mL (LD90 100 µg/mL) measured by Stadler and coworkers.

In summary, unlike the case for fungicides, herbicides and insecticides, the prior art provides no specific or credible guidance to aid in the selection of suitable nematicidal fatty acids. Moreover, whereas De-Moss, SCYTHE, M-PEDE and SAFER, are examples of successful pesticidal fatty acid products in these three areas respectively, there are currently no examples of commercial nematicidal fatty acid products in widespread use.

Many plant species are reported to be highly resistant to nematodes. The best documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family Asteraceae (family Compositae) (Hackney & Dickerson. (1975) *J Nematol* 7(1): 84-90). In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic. In many cases however, the active principle(s) for plant nematicidal activity has not been discovered and it therefore remains difficult to derive commercially successful nematicidal products from these resistant plants or to transfer the resistance to agronomically important crops such as soybeans and cotton.

Genetic resistance to certain nematodes is available in some commercial cultivars (e.g., soybeans), but these are restricted in number and the availability of cultivars with both desirable agronomic features and resistance is limited. The production of nematode resistant commercial varieties by conventional plant breeding based on genetic recombination through sexual crosses is a slow process and is often further hampered by a lack of appropriate germplasm.

Small chemical effectors can have significant advantages where size exclusion of larger molecules is a concern (e.g., with sedentary plant parasitic nematodes). However, unless the small molecule nematicidal active has high in planta mobility, or the chemical stimulates increased systemic resistance, a transgene encoding an enzyme must still be expressed in an appropriate spatial and temporal manner to be effective. With many plant parasitic nematodes this means that root expression of the nematicidal product is likely important for nematode control. It has been reported that when a constitutive promoter such as a Cauliflower Mosaic Virus (CaMV) 35S promoter is used to drive expression of certain hydroxylase enzymes, no significant amounts of protein production or hydroxylase activity is observed in non-seed tissues (e.g., roots or leaves), nor do hydroxylated fatty acids accumulate (van de Loo et al. (1995) *Proc Natl Acad Sci USA* 92(15): 6743-7; Broun & Sommerville (1997) *Plant Physiol.* 113(3): 933-942; Broun et al. (1998) *Plant J* 13(2): 201-210; U.S. Pat. No. 6,291,742; U.S. Pat. No. 6,310,194).

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

SUMMARY OF THE INVENTION

The invention concerns DNA constructs that include sequences encoding fatty acid hydroxylases or epoxygenases, transgenic plants harboring such constructs, and methods for making such transgenic plants. These transgenic plants can exhibit increased resistance to nematodes and can be useful for controlling nematodes in an environmentally safe manner. The invention is based in part on the surprising discovery that certain hydroxylated or epoxygenated fatty acids and methyl esters (e.g., ricinoleate, vernolate), exhibit nematicidal activity. These fatty acids show significantly enhanced nematicidal activity over other eighteen carbon free fatty acids such as oleate, elaidate and linoleate. Nucleic acids encoding hydroxylase or epoxygenase polypeptides can be introduced into plants in order to increase the levels of hydroxylated or epoxygenated fatty acids and thus aid in controlling nematode damage in commercially important plant species. These novel hydroxylase and epoxygenase constructs are also useful for increasing the accumulation of hydroxy and epoxy fatty acids for other industrial uses (e.g., providing safe sources of ricinoleic acid).

In one aspect, the invention features a transgenic plant containing at least one DNA construct. The construct comprises at least one regulatory element that confers expression in vegetative tissues of a plant. The regulatory element is operably linked to a nucleic acid encoding a polypeptide that is effective for catalysing the conversion of a substrate to a C16, C18, or C20 monounsaturated fatty acid product. The C16-C20 monounsaturated fatty acid product can be:

The C=C double bond can be cis or trans. The $R_3$ moiety of the C16-C20 monounsaturated fatty acid product can be C2 alkyl. A C16-C20 monounsaturated fatty acid product can have hydroxy, hydrogen, and C4 alkyl as the $R_1$, $R_2$ and $R_3$ moieties, respectively, e.g., a ricinoleate product. Alternatively, a C16-C20 monounsaturated fatty acid product can have an epoxy moiety at the $12^{th}$ and $13^{th}$ carbons counting from the carbonyl carbon and C4 alkyl at $R_3$, e.g., a vernolate product.

The plant can have an increased amount of a hydroxy-fatty acid, e.g., ricinoleic acid, in a vegetative tissue, relative to a corresponding plant that lacks the DNA construct. The hydroxy-fatty acid can constitute from about 0.01% to about 25% of the total fatty acid content of the tissue. In some embodiments, the plant has an increased amount of an epoxy-fatty acid, e.g., vernolic acid, in a vegetative tissue, relative to a corresponding plant that lacks the DNA construct. The epoxy-fatty acid can constitute from about 0.01% to about 25% of the total fatty acid content of the tissue.

The regulatory element can be a 5'-regulatory element or a 3'-regulatory element. The regulatory element can confer expression in root tissue, or in leaf tissue. For example, a 5'-regulatory element can be a CaMV35S promoter, a potato ribosomal protein S27a Ubi3 promoter, an alfalfa histone H3.2 promoter, an IRT2 promoter, an RB7 promoter, an *Arabidopsis* FAD2 5'-UTR, an *Arabidopsis* FAD3 5'-UTR, a Ubi3 5'-UTR, an alfalfa histone H3.2 5'-UTR, or a CaMV35S 5'-UTR.

There can be more than one regulatory element operably linked to the polypeptide coding sequence in the DNA construct. For example, a DNA construct can have two 5'-regulatory elements. The first 5'-regulatory element can be a Ubi3 promoter and the second 5'-regulatory element can be an *Arabidopsis* FAD2 5'-UTR, an *Arabidopsis* FAD3 5'-UTR, a potato ribosomal protein S27a Ubi3 5'-UTR, or a CaMV35S 5'-UTR. In some embodiments the DNA construct has a 5'-regulatory element and a 3'-regulatory element. The 3'-regulatory element can be a Ubi3 terminator or an E9 pea terminator. Alternatively, the 5'-regulatory element can be an *Arabidopsis* FAD2 5'-UTR or an *Arabidopsis*

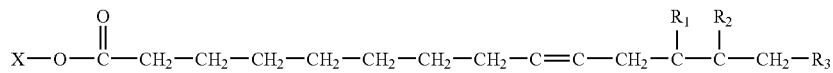

wherein X is hydrogen, CoA, glycerol, a monoglyceride, a diglyceride, ACP, methyl, Na+, phosphatidylcholine, or phosphatidylethanolamine, wherein both $R_1$ and $R_2$ are hydroxyl, one of $R_1$ and $R_2$ is hydroxyl and the other is hydrogen, or one of $R_1$ and $R_2$ is keto and the other is hydrogen, and wherein $R_3$ is C2, C4, or C6 alkyl. The C16-C20 monounsaturated fatty acid product can also be:

FAD3 5'-UTR and the 3'-regulatory element can be an *Arabidopsis* FAD2 3'-UTR or an *Arabidopsis* FAD3 3'-UTR.

The DNA construct in a plant can include a nucleic acid that encodes a PDAT or DAGAT or lipase polypeptide, operably linked to one or more regulatory elements that confer expression in vegetative tissues of a plant. Alternatively, the PDAT or DAGAT or lipase coding sequence and

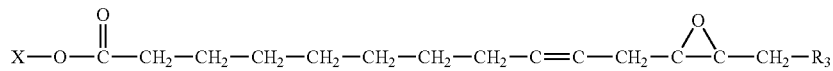

wherein X is hydrogen, CoA, glycerol, a monoglyceride, a diglyceride, ACP, methyl, Na+, phosphatidylcholine, or phosphatidylethanolamine, and wherein $R_3$ is C2, C4, or C6 alkyl.

regulatory element can be part of a separate DNA construct in the plant. In some embodiments, the plant contains a DNA construct encoding a delta-12 or delta-15 fatty acid desaturase.

The amino acid sequence of the polypeptide can be SEQ ID NO: 13, SEQ ID NO: 14, SEQ ID NO: 15, SEQ ID NO: 16, SEQ ID NO: 17, SEQ ID NO: 18, *C. palaestina* epoxygenase GenBank® No. CAA76156, SEQ ID NO: 19, SEQ ID NO: 20, SEQ ID NO: 21, SEQ ID NO: 22, SEQ ID NO: 23, SEQ ID NO: 24, a *C. palaestina* epoxygenase chimera, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 134, SEQ ID NO: 135, SEQ ID NO: 136, SEQ ID NO: 137 or SEQ ID NO: 138. The nucleic acid encoding the polypeptide can be SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 129, SEQ ID NO: 130, SEQ ID NO: 131, SEQ ID NO: 132 or SEQ ID NO: 133.

The plant can be a monocotyledonous or a dicotyledonous plant. For example, the plant can be a soybean, corn, cotton, rice, tobacco, tomato, wheat, banana, carrot, potato, strawberry or turf grass plant.

In another aspect, the invention features a method of making a transgenic plant. The method comprises obtaining a DNA construct as described herein, and introducing the construct into a plant. The DNA construct can include nucleic acids encoding the polypeptides described herein, and can include the regulatory elements described herein.

The invention also features a method of screening a transgenic plant for anthelmintic activity. The method comprises contacting a transgenic plant with a nematode under conditions effective to determine whether or not the plant has anthelmintic activity. For example, the nematodes can be contacted with one or more roots of the transgenic plant. The transgenic plant has a DNA construct that includes nucleic acids encoding a hydroxylase or epoxygenase polypeptide described herein, and can include the regulatory elements described herein. The method can also be carried out with plant tissue, e.g., root tissue, leaf tissue or stem tissue from such a transgenic plant.

In another aspect, the invention features an isolated nucleic acid. The nucleic acid can comprise the nucleotide sequence set forth in SEQ ID NO: 3, SEQ ID NO: 4, SEQ ID NO: 5, SEQ ID NO: 6, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 129, SEQ ID NO: 130, SEQ ID NO: 131, SEQ ID NO: 132 or SEQ ID NO: 133.

In another aspect, the invention features a recombinant nucleic acid construct. The construct comprises at least one regulatory element that confers expression in vegetative tissues of a plant. The regulatory element is operably linked to a nucleic acid having the nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 129, SEQ ID NO: 130, SEQ ID NO: 131, SEQ ID NO: 132 or SEQ ID NO: 133. The regulatory element can confer expression in, for example, roots or leaves. The regulatory element can be a 5'-regulatory element having the nucleotide sequence set forth in SEQ ID NO: 43 or SEQ ID NO: 44. The nucleic acid construct can further comprise a 3'-regulatory element having the nucleotide sequence set forth in SEQ ID NO: 45.

The invention also features a transgenic plant harboring a DNA construct. The construct comprises a nucleic acid encoding a fatty acid epoxygenase polypeptide or a fatty acid hydroxylase polypeptide, operably linked to a regulatory element conferring expression of the polypeptide in a vegetative tissue of the plant. The polypeptide can have the amino acid sequence of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, *C. palaestina* epoxygenase (GenBank® No. CAA76156), SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 134, SEQ ID NO: 135, SEQ ID NO: 136, SEQ ID NO: 137 or SEQ ID NO: 138.

The plant can have a significantly increased amount of a hydroxy-fatty acid, e.g., ricinoleic acid, in a vegetative tissue of the plant relative to a corresponding plant that lacks the DNA construct. The hydroxy-fatty acid can constitute from about 0.1% to about 10% of the total fatty acid content of the tissue. In some embodiments, the plant has a significantly increased amount of an epoxy-fatty acid, e.g., vernolic acid, in a vegetative tissue of the plant relative to a corresponding plant that lacks the DNA construct. The epoxy-fatty acid can constitute from about 0.1% to about 10% of the total fatty acid content of the tissue.

In another aspect, the invention features a transgenic plant containing at least one DNA construct. The construct comprises at least one regulatory element that confers expression in at least one tissue of seeds of a plant. The regulatory element is operably linked to a nucleic acid encoding a polypeptide that is effective for catalysing the conversion of a substrate to a C16, C18, or C20 monounsaturated fatty acid product. The C16-C20 monounsaturated fatty acid product can be:

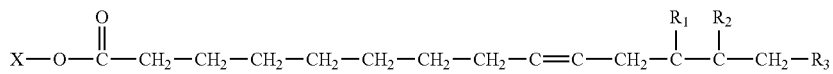

wherein X is hydrogen, CoA, glycerol, a monoglyceride, a diglyceride, ACP, methyl, Na+, phosphatidylcholine, or phosphatidylethanolamine, wherein both $R_1$ and $R_2$ are hydroxyl, one of $R_1$ and $R_2$ is hydroxyl and the other is hydrogen, or one of $R_1$ and $R_2$ is keto and the other is hydrogen, and wherein $R_3$ is C2, C4, or C6 alkyl. The C16-C20 monounsaturated fatty acid product can also be:

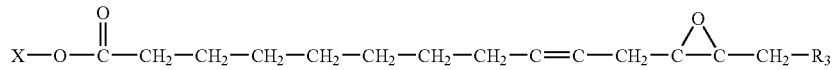

wherein X is hydrogen, CoA, glycerol, a monoglyceride, a diglyceride, ACP, methyl, Na+, phosphatidylcholine, or phosphatidylethanolamine, and wherein $R_3$ is C2, C4, or C6 alkyl.

The C=C double bond can be cis or trans. The $R_3$ moiety of the C16-C20 monounsaturated fatty acid product can be C2 alkyl. A C16-C20 monounsaturated fatty acid product can have hydroxy, hydrogen, and C4 alkyl as the $R_1$, $R_2$ and $R_3$ moieties, respectively, e.g., a ricinoleate product. Alternatively, a C16-C20 monounsaturated fatty acid product can have an epoxy moiety at the $12^{th}$ and $13^{th}$ carbons counting from the carbonyl carbon and C4 alkyl at $R_3$, e.g., a vernolate product.

The regulatory element can be a 5'-regulatory element. The plant can have an increased amount of a hydroxy-fatty acid, e.g., ricinoleic acid, in at least one tissue of seeds, relative to a corresponding plant that lacks the DNA construct. In some embodiments, the plant has an increased amount of an epoxy-fatty acid, e.g., vernolic acid, in at least one tissue of seeds, relative to a corresponding plant that lacks the DNA construct.

A "purified polypeptide", as used herein, refers to a polypeptide that has been separated from other proteins, lipids, and nucleic acids with which it is naturally associated. The polypeptide can constitute at least 10, 20, 50, 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic nucleic acid fragment, a fragment produced by polymerase chain reaction (PCR), or a restriction fragment; and (d) an engineered nucleic acid such as a recombinant DNA molecule that is part of a hybrid or fusion nucleic acid, (e.g., a gene encoding a fusion protein). Isolated nucleic acid molecules according to the present invention further include molecules produced synthetically, as well as any nucleic acids that have been altered chemically and/or that have modified backbones. Specifically excluded from this definition are nucleic acids present in mixtures of different (i) DNA molecules, (ii) transfected cells, or (iii) cell clones in a DNA library such as a cDNA or genomic DNA library, or other nucleic acid existing among hundreds to millions of other nucleic acids within, for example, gel slices containing a genomic DNA restriction digest. Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The term "ectopic expression" refers to a pattern of subcellular, cell-type, tissue-type and/or developmental or temporal expression that is not normal for the particular gene or enzyme in question. It also refers to expression of a heterologous gene; e.g. a gene not naturally occurring in the organism (also termed "transgene" as described below). Such ectopic expression does not necessarily exclude expression in normal tissues or developmental stages.

As used herein, the term "transgene" means a nucleic acid that is partly or entirely heterologous, i.e., foreign, to the transgenic plant, animal, or cell into which it is introduced, or, is homologous to an endogenous gene of the transgenic plant, animal, or cell into which it is introduced, but which is inserted into the plant's genome in such a way as to alter the genome of the cell into which it is inserted (e.g., it is inserted at a location which differs from that of the natural gene or its insertion results in a knockout). A transgene can include one or more regulatory elements operably linked to a polypeptide coding sequence.

As used herein, the term "transgenic cell" refers to a cell containing a transgene. As used herein, a "transgenic plant" is any plant in which one or more, or all, of the cells of the plant include a transgene. A transgene may be integrated within a chromosome, or it may be extrachromosomally replicating DNA.

The terms "operably linked", "operably inserted" or "operably associated" mean that a regulatory element is positioned in a DNA construct relative to a polypeptide coding sequence so as to effect expression of the polypeptide.

As used herein, the terms "hybridizes under stringent conditions" and "hybridizes under high stringency conditions" refers to conditions for hybridization in 6× sodium chloride/sodium citrate (SSC) buffer at about 45° C., followed by two washes in 0.2×SSC buffer, 0.1% SDS at 60° C. or 65° C. As used herein, the term "hybridizes under low stringency conditions" refers to conditions for hybridization in 6×SSC buffer at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, the term "binding" refers to the ability of a first compound and a second compound that are not covalently linked to physically interact. The apparent dissociation constant for a binding event can be 1 mM or less, for example, 10 nM, 1 nM, and 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in molar excess over the antibody.

As used herein, the term "altering an activity" refers to a change in level, either an increase or a decrease in the activity, (e.g., an increase or decrease in the ability of the polypeptide to bind or regulate other polypeptides or molecules) particularly a fatty acid desaturase-like or fatty acid desaturase activity (e.g., the ability to introduce a double bond at the delta-12 position of a fatty acid). The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is, for example, less than 0.05.

Unless otherwise specified, a "substituted" carbon, carbon chain, or methyl, alkyl can have one or more hydrogens replaced by another group, e.g., a halogen or a hydroxyl group.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, examples and from the claims.

BRIEF DESCRIPTION OF THE DRAWINGS

FIG. 1 is a set of drawings depicting the structures of ricinoleic acid, ricinelaidic acid, 12-oxo-9(Z)-octadecenoic acid, 12-oxo-9(E)-octadecenoic acid, (12,13)-epoxy-trans-9-octadecenoic acid and vernolic acid. The numbering of the carbons is indicated with the carbonyl (carboxyl) carbon being carbon 1. R=OH (acid); $OCH_3$ (methyl ester); $O^-Na^+$ (sodium salt).

FIG. 2 is an alignment of the sequences of the hydroxylase and epoxygenase polypeptides (SEQ ID NOs.: 13 to 24; 34 to 42) and A. thaliana (SEQ ID NO: 125), B. napus (SEQ ID NO: 126), G. max (SEQ ID NO: 127) and S. indicum (SEQ ID NO: 128) FAD2 delta-12 desaturase polypeptides (gi|15229956|ref|NP_187819.1, gi|8705229|gb|AAF78778.1, gi|904154|gb|AAB00860.1 and gi|8886726|gb|AAF80560.1 respectively).

DETAILED DESCRIPTION

Figure 3:
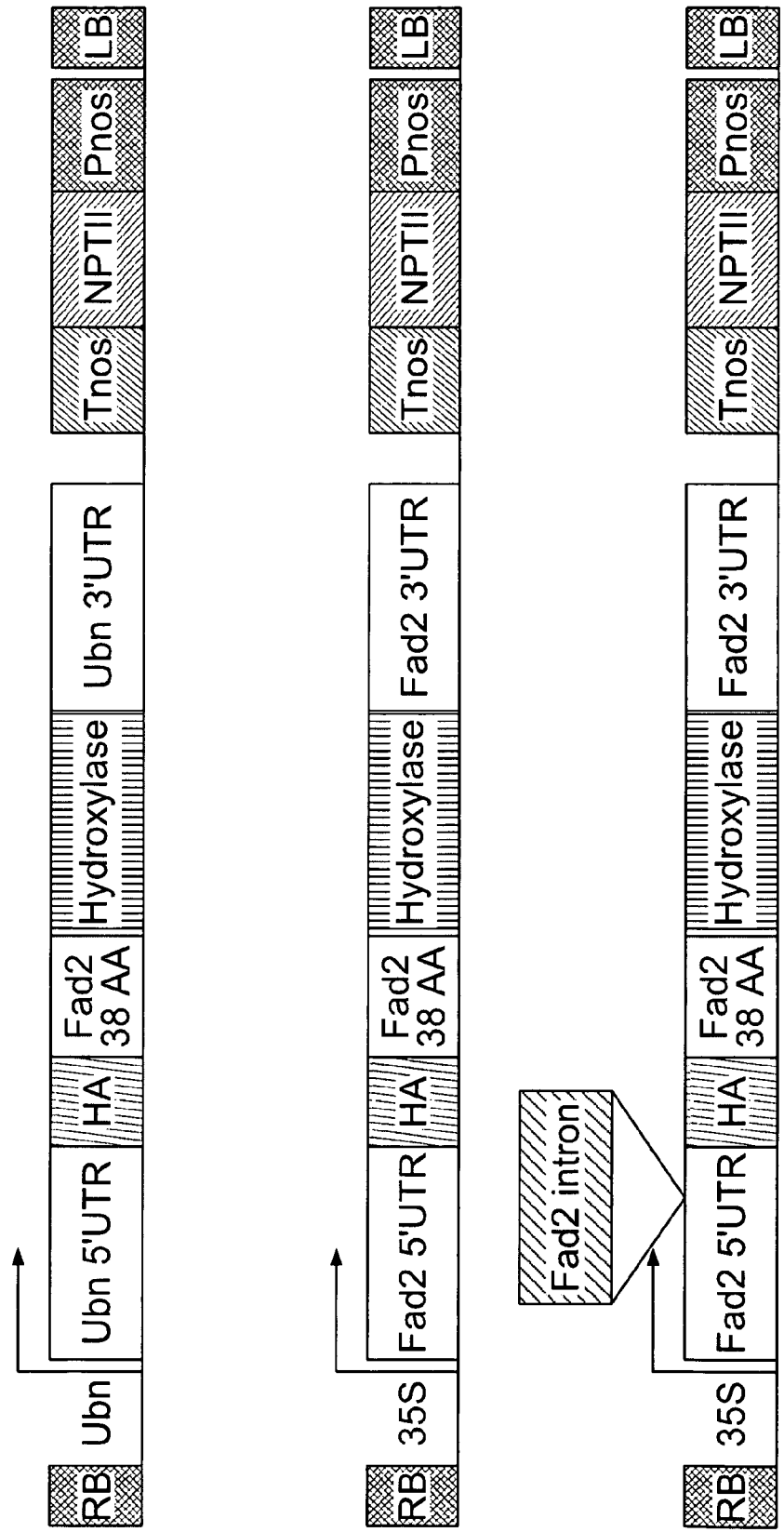
FIG. 3 is a schematic representation of transgenic epoxygenase and hydroxylase constructs. HA refers to the amino acid sequence YPYDVPDYA (SEQ ID NO: 139), which corresponds to residues 99-107 of human influenza virus hemagglutinin. LB and RB refer to the left and right borders, respectively, of an Agrobacterium T-DNA.

The present invention describes genes and genetic constructs encoding polypeptides effective for producing small molecule chemicals that show surprising nematicidal activity. The nematicidal activity is due in part to selective inhibition of metabolic processes that appear to be essential to nematodes and are either absent or non-essential in vertebrates and plants. The invention therefore provides urgently needed DNA constructs, transgenic plants and methods of making such plants for environmentally safe control of plant-parasitic nematodes.

Fatty Acids

Unsaturated fatty acids are essential to the proper functioning of biological membranes. At physiological temperatures, polar glycerolipids that contain only saturated fatty acids cannot form the liquid-crystalline bilayer that is the fundamental structure of biological membranes. The introduction of an appropriate number of double bonds (a process referred to as desaturation) into the fatty acids of membrane glycerolipids decreases the temperature of the transition from the gel to the liquid-crystalline phase and provides membranes with necessary fluidity. Fluidity of the membrane is important for maintaining the barrier properties of the lipid bilayer and for the activation and function of certain membrane bound enzymes. There is also evidence that unsaturation confers some protection to ethanol and oxidative stress, suggesting that the degree of unsaturation of membrane fatty acids has importance beyond temperature adaptation. Unsaturated fatty acids are also precursors of polyunsaturated acids (PUFAs) arachidonic and eicosapentaenoic acids in animals, which are important sources of prostaglandins. These molecules are local hormones that alter the activities of the cells in which they are synthesized and in adjoining cells, mediating processes in reproduction, immunity, neurophysiology, thermobiology, and ion and fluid transport.

The ability of cells to modulate the degree of unsaturation in their membranes is primarily determined by the action of fatty acid desaturases. Desaturase enzymes introduce unsaturated bonds at specific positions in their fatty acyl chain substrates, using molecular oxygen and reducing equivalents from NADH (or NADPH) to catalyze the insertion of double bonds. In many systems, the reaction uses a short electron transport chain consisting of NAD(P)H, cytochrome b5 reductase, and cytochrome b5, to shuttle electrons from NAD(P)H and the carbon-carbon single bond to oxygen, forming water and a double bond (C=C). Many eukaryotic desaturases are endoplasmic reticulum (ER) bound non-heme diiron-oxo proteins that contain three conserved histidine-rich motifs and two long stretches of hydrophobic residues. These hydrophobic alpha helical domains are thought to position the protein with its bulk exposed to the cytosolic face of the ER and to organize the active site histidines to appropriately coordinate the active diiron-oxo moiety.

While most eukaryotic organisms, including mammals, can introduce a double bond into an 18-carbon fatty acid at the Δ9 position, mammals are incapable of inserting double bonds at the Δ12 or Δ15 positions. For this reason, linoleate (18:2 Δ9,12) and linolenate (18:3 Δ9,12,15) must be obtained from the diet and, thus, are termed essential fatty acids. These dietary fatty acids come predominately from plant sources, since flowering plants readily desaturate the Δ12 and the Δ15 positions. Certain invertebrate animals, including some insects and nematodes, can synthesize de novo all of their component fatty acids, including linoleate and linolenate. The nematode *C. elegans*, for example, can synthesize de novo a broad range of polyunsaturated fatty acids including arachidonic acid and eicosapentaenoic acids, a feature not shared by either mammals or flowering plants (Spychalla et al. (1997) *Proc. Natl. Acad. Sci USA* 94(4): 1142-7).

The *C. elegans* desaturase gene fat2 has been expressed in *S. cerevisiae* and shown to be a delta-12 fatty acid desaturase (Peyou-Ndi et al. (2000) *Arch. Biochem. Biophys.* 376(2): 399-408). This enzyme introduces a double bond between the 12th and the 13th carbons (from the carboxylate end) and can convert the mono-unsaturated oleate (18:1 Δ9) and palmitoleate (16:1 Δ9) to the di-unsaturated linoleate (18:2 Δ9,12) and 16:2 Δ9,12 fatty acids, respectively.

The nematode delta-12 enzymes are potentially good targets for anti-nematode compounds for several reasons. Firstly, as mentioned above, mammals are thought not to have delta-12 fatty acid desaturases. In addition, the nematode enzymes appear to be phylogenetically distinct from their homologs in plants, having less than 40% pairwise sequence identity at the amino acid level and phylogenetic analyses demonstrate clustering of nematode delta-12 and ω-3 desaturases away from homologs in plants. Experiments with both transgenic *Arabidopsis* and soybeans reveal that plants can tolerate significant reductions in linoleate or linolenate, suggesting that inhibitors of delta-12 desaturases would likely not be toxic to plants (Miquel & Browse (1992) *J. Biol. Chem.* 267(3): 1502-9; Singh et al. (2000) *Biochem. Society Trans.* 28: 940-942; Lee et al. (1998) *Science* 280: 915-918). Thus, inhibitors of the enzyme are likely to be non-toxic to mammals.

We made the surprising discovery that the parent fatty acids and methyl esters of certain fatty acid analogs (e.g., ricinoleate, vemolate) are nematicidal and have activity consistent with that of specific inhibitors of nematode delta-12 desaturases. The fatty acids and methyl esters show significantly increased anthelmintic activity compared to eighteen carbon free fatty acids and esters such as oleate, elaidate and linoleate. In contrast to short chain fatty acids and esters such as pelargonate (pelargonic acid or methyl pelargonate), fatty acid analogs that are predicted delta-12 desaturase inhibitors show reduced phytotoxicity and can therefore be used effectively while minimizing undesirable damage to non-target organisms. Suitable nematode-inhibitory compounds include compounds having the following fatty acids in free or esterified form: ricinoleic acid (12-hydroxyoctadec-cis-9-enoic acid), hydroxypalmitoleic acid (12-hydroxyhexadec-cis-9-enoic acid), ricinelaidic acid, vernolic acid ((12,13)-epoxy-octadec-cis-9-enoic acid), and 12-oxo-9(Z)-octadecenoic acid.

Polypeptides

A polypeptide suitable for use in the invention is effective for catalysing the conversion of a substrate to a C16, C18, or C20 monounsaturated fatty acid product, e.g., a hydroxylated fatty acid or an epoxygenated fatty acid. The enzymatic products of hydroxylase or epoxygenase enzymes useful in the invention typically are fatty acids 16, 18, or 20 carbons in length, or analogs thereof. Such products typically have a cis (Z) or a trans (E) carbon double bond at the delta-9 position, between C9 and C10 counting from the carbonyl (carboxyl) carbon. Such products also have hydroxy or epoxy modifications at C12, C13 or both C12 and C13. A fatty acid hydroxylase or epoxygenase of this invention includes a polypeptide that demonstrates the ability to catalyze the production of ricinoleic, lesquerolic, hydroxyerucic (16-hydroxydocos-cis-13-enoic acid) or hydroxypalmitoleic (12-hydroxyhexadec-cis-9-enoic) from Coenzyme A, acyl carrier protein (ACP) or lipid-linked monoenoic fatty acid substrates under suitable conditions.

In some embodiments, the product is a C16-C20 monounsaturated oxo-fatty acid that has the following structure:

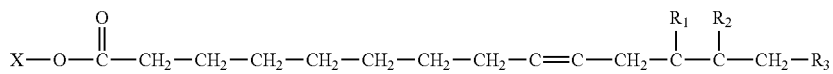

One or both of $R_1$ and $R_2$ can be hydroxyl, e.g., $R_1$ is hydrogen and $R_2$ is hydroxyl, $R_1$ is hydroxyl and $R_2$ is hydrogen, or both $R_1$ and $R_2$ are hydroxyl. Alternatively, $R_1$ can be keto and $R_2$ hydrogen, or $R_1$ can be hydrogen and $R_2$ keto. $R_3$ can be C2 alkyl, C4 alkyl, or C6 alkyl.

In other embodiments, the product is a C16-C20 epoxy monounsaturated fatty acid product that has the following structure:

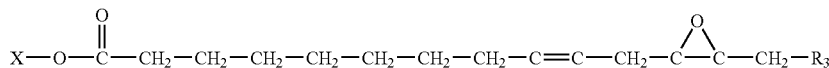

If X is hydrogen in the structures given above, the product is a free fatty acid. However, X can also be CoA, ACP, phosphatidylcholine, or phosphatidylethanolamine. X can also be glycerol, a glyceride, methyl, or Na+. In both of the structures given above, the double bond between the $9^{th}$ and $10^{th}$ carbons can be cis or can be trans.

Whether a polypeptide exhibits hydroxylase activity or epoxygenase activity can be determined by testing the polypeptide e.g., in a hydroxylase assay described in U.S. Pat. No. 6,310,194, or an epoxygenase assay described in U.S. Pat. No. 6,329,518. A rapid and efficient method to identify suitable polypeptides is an analysis of fatty acid production in yeast that express the polypeptide to be tested. Since *Saccharomyces cerevisiae* does not produce linoleic acid (the substrate of delta-12 desaturase-like epoxygenases), linoleic acid or methyl linoleate is provided exogenously as a substrate. Any conversion of the substrate to a hydroxylated or epoxygenated product can be measured by, for example, gas chromatography-mass spectrometry (GC-MS) of total fatty acids after hydrolysis and conversion to methyl esters. A polypeptide is considered to have hydroxylase activity or epoxygenase activity when it produces an amount of hydroxy- or epoxy-fatty acid that is statistically significantly greater in *Saccharomyces cerevisiae* that express the polypeptide, relative to the amount produced in corresponding control *S. cerevisiae* that lack or do not express the polypeptide. An alternative technique for identifying suitable polypeptides is an analysis of fatty acid content in vegetative tissues or at least one tissue of seeds of *Arabidopsis* plants, e.g., leaf tissue, root tissue, or endosperm or embryo tissue.

Typically, a difference is considered statistically significant a $p \leq 0.05$ with an appropriate parametric or non-parametric statistic, e.g., Chi-square test, Student's t-test, Mann-Whitney test, or F-test. In some embodiments, a difference is statistically significant at $p<0.01$, $p<0.005$, or $p<0.001$. A statistically significant difference in, for example, the level of ricinoleic acid in seeds from a transgenic *Arabidopsis* plant that expresses a hydroxylase polypeptide, compared to the level in a control *Arabidopsis* plant, indicates that expression of the polypeptide results in an increase in the level of ricinoleic acid. The significantly increased amount of a hydroxy-fatty acid can constitute from about 0.01% to about 25% by weight of the total fatty acid content of a sample, e.g., from about 0.03% to about 20%, about 0.05% to about 20%, about 0.1% to about 10%, about 0.1% to about 5%, about 0.2% to about 3%, about 0.5% to about 5.0%, about 0.5% to about 10%, about 2.0% to about 15%, about 1.0% to about 5.0%, about 1.0% to about 10%, about 3% to about 8%, about 3% to about 10%, about 4% to about 9%, about 4% to about 13%, about 5% to about 20%, about 5% to about 15%, or about 5% to about 10%. The significantly increased amount of an epoxy-fatty acid can constitute from about 0.01% to about 35% by weight of the total fatty acid content of a sample, e.g., from about 0.03% to about 25%, about 0.05% to about 20%, about 0.1% to about 5%, about 0.2% to about 3%, about 0.5% to about 5.0%, about 0.5% to about 10%, about 2.0% to about 15%, about 1.0% to about 5.0%, about 1.0% to about 10%, about 3% to about 8%, about 3% to about 10%, about 4% to about 9%, about 4% to about 13%, about 5% to about 20%, about 5% to about 15%, or about 5% to about 10%.

In some embodiments, the polypeptide is a hydroxylase encoded by a gene isolated from *Lesquerella* or *Ricinus* plants. In other embodiments, the polypeptide is an epoxygenase encoded by a gene isolated from *Stokesia*, *Crepis* or *Vernonia* plants. Examples of these enzymes include the oleate hydroxylases from *Ricinus communis*, *Lesquerella fendleri*, *Lesquerella lindheimeri*, *Lesquerella gracilis* and linoleate epoxygenases from *Stokesia laevis*, *Crepis biennis*, *Crepis palaestina* and *Vernonia galamensis*.

In some embodiments, a polypeptide suitable for use in the invention is a fusion of two or more naturally-occurring amino acid sequences. For example, a naturally occurring oleate hydroxylase polypeptide derived from *Ricinus communis*, *Lesquerella fendleri*, *Lesquerella lindheimeri*, or *Lesquerella gracilis* can have approximately thirty amino acids at the N-terminus replaced by N-terminal amino acids from the *Arabidopsis thaliana* FAD2 gene. See, e.g., SEQ ID NOs: 19 through 23. Alternatively, a fusion polypeptide can be a naturally occurring linoleate epoxygenase derived from Stokesia laevis or Crepis biennis (e.g., SEQ ID NO: 24) where amino acids at the N-terminus are replaced by N-terminal amino acids from the *Arabidopsis thaliana* FAD2 gene.

Other naturally occurring hydroxylases and epoxygenases are obtainable using the specific exemplified sequences provided herein. Furthermore, it will be apparent that one can make synthetic hydroxylases having modified amino acid sequences. Modified amino acid sequences include sequences which have been mutated, truncated, increased and the like, whether such sequences were partially or wholly synthesized.

In some embodiments, a hydroxylase or epoxygenase suitable for use in the invention has at least 60% overall amino acid sequence identity with a target polypeptide, e.g., 75%, 80%, 85%, 90%, 95%, 96%, 98%, or 99% sequence identity.

A percent sequence identity for any subject nucleic acid or amino acid sequence (e.g., any of the hydroxylase polypeptides described herein) relative to another "target" nucleic acid or amino acid sequence can be determined as follows. Such identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the B12seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\B12seq-i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (i) a 500 amino acid target sequence is compared to a subject amino acid sequence, (ii) the B12seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180 200×100=90). In some embodiments, the amino acid sequence of a polypeptide suitable for use in the invention has 40% sequence identity to the amino acid sequence of SEQ ID NOS: 13, 14, 15, 16, 17, 18, 36, 134, 135, 136, 137, or 138. In other embodiments, the amino acid sequence of a polypeptide suitable for use in the invention has greater than 40% sequence identity (e.g., >40%, >50%, >60%, >70%, >80%, >90%, or >95%) to the amino acid sequence of SEQ ID NOS: 13, 14, 15, 16, 17, 18, 36, 134, 135, 136, 137, or 138.

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

The identification of conserved regions in a template, or subject, polypeptide can facilitate homologous polypeptide sequence analysis. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam/ on the World Wide Web and genome.wustl.edu/Pfam/ on the World Wide Web. A description of the information included at the Pfam database is described in Sonnhammer et al. (1998) *Nucl. Acids Res.* 26: 320-322; Sonnhammer et al. (1997) *Proteins* 28:405-420; and Bateman et al. (1999) *Nuci. Acids Res.* 27:260-262. From the Pfam database, consensus sequences of protein motifs and domains can be aligned with the template polypeptide sequence to determine conserved region(s).

Conserved regions also can be determined by aligning sequences of the same or related polypeptides from closely related plant species. Closely related plant species preferably are from the same family. Alternatively, alignments are performed using sequences from plant species that are all monocots or are all dicots. In some embodiments, alignment of sequences from two different plant species is adequate. For example, sequences from canola and *Arabidopsis* can be used to identify one or more conserved regions.

Typically, polypeptides that exhibit at least about 35% amino acid sequence identity are useful to identify conserved regions. Conserved regions of related proteins sometimes exhibit at least 40% amino acid sequence identity (e.g., at least 50%, at least 60%; or at least 70%, at least 80%, or at least 90% amino acid sequence identity). In some embodiments, a conserved region of target and template polypeptides exhibit at least 92, 94, 96, 98, or 99% amino acid sequence identity. Amino acid sequence identity can be deduced from amino acid or nucleotide sequence.

A polypeptide useful in the invention optionally can possess additional amino acid residues at the amino-terminus or the carboxy-terminus. For example, 6× His-tag or FLAG™ residues can be linked to a polypeptide at the amino-terminus. See, e.g., U.S. Pat. Nos. 4,851,341 and 5,001,912. As another example, a reporter polypeptide such as green fluorescent protein (GFP) can be fused to the carboxy-terminus of the polypeptide. See, for example, U.S. Pat. No. 5,491,084.

Nucleic Acids

Among the nucleic acids suitable for the invention are those that encode a polypeptide described herein. Typically, such a nucleic acid is incorporated into a DNA construct suitable for introduction into a plant and integration into a plant genome. A DNA construct comprising a nucleic acid encoding a hydroxylase or epoxygenase polypeptide is operably linked to one or more regulatory elements that confer expression in vegetative tissues or at least one tissue of seeds of a plant. Typically, a DNA construct includes a 5'-regulatory element and a 3'-regulatory element for expression in transformed plants. In some embodiments, such constructs are chimeric, i.e., the coding sequence and one or more of the regulatory sequences are from different sources. For example, a polypeptide coding sequence can be a *Ricinus communis* hydroxylase and a 5'-regulatory element can be a potato S27a promoter. However, non-chimeric DNA constructs also can be used. DNA constructs can also include cloning vector nucleic acids. Cloning vectors suitable for use in the present invention are commercially available and are used routinely by those of ordinary skill in the art.

Regulatory elements typically do not themselves code for a gene product. Instead, regulatory elements affect expression of the coding sequence, i.e., transcription of the coding sequence, and processing and translation of the resulting mRNA. Examples of regulatory elements suitable for use in a DNA construct include promoter sequences, enhancer sequences, response elements or inducible elements that modulate expression of a nucleic acid sequence. As used herein, "operably linked" refers to positioning of a regulatory element in a construct relative to a nucleic acid coding sequence in such a way as to permit or facilitate expression of the encoded polypeptide. The choice of element(s) that are included in a construct depends upon several factors, including, but not limited to, replication efficiency, selectability, inducibility, desired expression level, and cell or tissue specificity.

Suitable regulatory elements include promoters that initiate transcription only, or predominantly, in certain cell types. For example, promoters specific to vegetative tissues such as ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory elements. A cell type or tissue-specific promoter can drive expression of operably linked sequences in tissues other than vegetative tissue. Thus, as used herein a cell type or tissue-specific promoter is one that drives expression preferentially in the target tissue, but can also lead to some expression in other cell types or tissues as well. Methods for identifying and characterizing promoter regions in plant genomic DNA include, for example, those described in the following references: Jordano et al. (1989) *Plant Cell*, 1: 855-866; Bustos et al. (1989) *Plant Cell*, 1: 839-854;

Green et al. (1988) *EMBO J.* 7: 4035-4044; Meier et al. (1991) *Plant Cell*, 3: 309-316; and Zhang et al. (1996) *Plant Physio.* 110: 1069-1079.

Other suitable regulatory elements can be found in 5'-untranslated regions (5'-UTR) and 3'-untranslated regions (3'-UTR). The terms 5'-UTR and 3'-UTR refer to nucleic acids that are positioned 5' and 3' to a coding sequence, respectively, in a DNA construct and that can be found in mRNA 5' to the initiation codon and 3' to the stop codon, respectively. A 5'-UTR and a 3'-UTR can include elements that affect transcription of the coding sequence, as well as elements that affect processing of mRNA and translation of the coding sequence.

Regulatory elements suitable for use in plants include nopaline and mannopine synthase regulatory elements, cauliflower mosaic virus 35S promoters, *Arabidopsis* root periphery IRT2 promoter, *Solanum tuberosum* (potato) ribosomal S27a Ubi3 promoter, rice Actin I gene promoter and Ubiquitin I gene promoter from maize (McElroy et al. (1995) *Mol. Breed.* 1: 27-37). Inducible nematode responsive promoters of interest include the tobacco tobRB7 (Yamamoto et al. (1991) *Plant Cell*, 3(4): 371-382), sunflower Sun-RB7 (Sarda et al. (1999) *Plant Mol. Biol.* 40(1): 179-191) and potato potRB7 (Heinrich et al. (1996) *Plant Physiol.* 112(2): 861-864) promoters. Other exemplary promoter-5'-UTR constructs which can be used in applications requiring root expression are listed in Table 8.

For embodiments where expression of a polypeptide is desired in vegetative plant tissues such as leaves or roots, the use of all or part of the 5' upstream non-coding regions (5'-UTR) and 3' downstream non-coding regions (3'-UTR) of a *Arabidopsis* FAD2 or FAD3 gene are contemplated. Also suitable is the construction of chimeric hydroxylases and epoxygenases by swapping approximately the first 30 amino acids from a desaturase such as the FAD2 or FAD3 desaturases for the equivalent N-terminal region of the hydroxylase or epoxygenase as in the nucleic acids of SEQ ID NOs: 7 to 12 and the amino acid sequences of SEQ ID NOs.: 19 to 24. Particularly desirable are the use of chimeric desaturase-like epoxygenases or hydroxylases with non-seed specific UTRs.

Regulatory elements such as transcript termination regions may be provided in DNA constructs. If the coding sequence and the transcript termination region in a DNA construct are derived from different naturally occurring sources, the transcript termination region typically contains at least about 0.5 kb, preferably about 1-3 kb of sequence 3' to the structural gene from which the termination region is derived.

DNA constructs also can contain sequences encoding other polypeptides. Such polypeptides can, for example, facilitate the introduction or maintenance of the nucleic acid construct in a host organism. Potential host cells include both prokaryotic and eukaryotic cells. A host cell may be unicellular or found in a multicellular differentiated or undifferentiated organism depending upon the intended use. Depending upon the host, regulatory elements can include elements from viral, plasmid or chromosomal genes, or the like. For expression in prokaryotic or eukaryotic microorganisms, particularly unicellular hosts, a wide variety of constitutive or inducible promoters may be employed. Expression in a microorganism can provide a ready source of a desired polypeptide. Among transcriptional initiation regions which have been described are regions from bacterial and yeast hosts, such as *Escherichia coli, Bacillus subtilis, Saccharomyces cerevisiae*, including genes such as beta-galactosidase, T7 polymerase, tryptophan E and the like.

DNA constructs can also include sequences encoding other polypeptides that can affect the expression, activity, biochemical activity or physiological activity of a hydroxylase or epoxygenase polypeptide. For example, a DNA construct can include a nucleic acid encoding a PDAT, DAGAT, lipase, FAD2 or FAD3 polypeptide, operably linked to at least one regulatory element that confers expression in vegetative tissues or at least one tissue of seeds of a plant. In some embodiments, a DNA construct includes a nucleic acid that encodes a PDAT polypeptide and a nucleic acid that encodes a FAD2 polypeptide. Alternatively, such other polypeptide coding sequences can be provided on a separate DNA construct(s).

Suitable phospholipid:diacylglycerol acyltransferase (PDAT) polypeptides and diacylglycerol acyltransferase (DAGAT) polypeptides include *A. thaliana* DAGAT or *C. elegans* DAGAT. Coding sequences for suitable PDAT and DAGAT polypeptides include GenBank® Accession Nos. AAF19262, AAF19345, AAF82410 and P40345.

DAGAT and PDAT enzymes are important determinants of both the amounts (Bouvier-Nave et al. (2000) *Biochem. Soc. Trans.* 28(6): 692-695; Jako et al. (2001) 126(2): 861-874) and types (Banas et al. (2000) *Biochem. Soc. Trans.* 28(6): 703-705; Dahlqvist et al. (2000) *Proc. Natl. Acad. Sci USA*, 97(12): 6487-6492) of fatty acids found in the triacylglycerol (TAG) fraction. Furthermore, the triacylglycerol (TAG) fraction is the predominant repository of novel fatty acids like ricinoleic acid and vernolic acid in seeds and it is thought that this minimizes the disruptive effects of these unusual fatty acids on plant cell membranes (Millar et al. (2000) *Trends Plant Sci.* 5(3): 95-101). In most plants, roots, leaves, and other non-seed tissues are not usually sites of major triacylglycerol accumulation. It is therefore likely that in non-seed tissues the activity of key enzymes in the TAG synthesis pathway such as PDATs and DAGATs are suboptimal for the contemplated application and can be improved by overexpression of these enzymes which can result in significant enhancement of fatty acid accumulation in the TAG fraction (Bouvier-Nave et al. (2000) *Eur J. Biochem.* 267(1): 85-96).

A DNA construct that encodes one or more desaturases includes constructs that encode delta-12 fatty acid desaturases or delta-15 fatty acid desaturases. For example, an *Arabidopsis thaliana* FAD2 or an *Arabidopsis thaliana* FAD3 polypeptide can be operably linked to a suitable promoter that confers expression in non-seed tissues such as roots and/or leaves. The expression of a delta-12 desaturase and an epoxygenases can be useful, since linoleic acid, the product of the desaturase, is the substrate converted to vernolic acid by the epoxygenase.

Nucleic acids described herein can be used to identify homologous plant hydroxylase or epoxygenase coding sequences and the resulting sequences may provide further plant hydroxylases or epoxygenases. In particular, PCR may be a useful technique to obtain related nucleic acids from sequence data provided herein. One skilled in the art will be able to design oligonucleotide probes based upon sequence comparisons or regions of typically highly conserved sequence. Of special interest are polymerase chain reaction primers based on the conserved regions of amino acid sequence between the hydroxylases and epoxygenases in FIG. 2 (SEQ ID NOs: 13 to 24 and 34 to 42). Details relating to the design and methods for a PCR reaction using these probes are described more fully in the examples. If nucleic acid probes are used, they can be shorter than the entire coding sequence. Oligonucleotides may be used, for example, that are 10, 15, 20, or 25 nucleotides or more in length.

Hydroxylated fatty acids are found in large quantities in some natural plant species, which suggests several possibilities for plant enzyme sources. For example, hydroxy fatty acids related to ricinoleate occur in major amounts in seed oils from various *Lesquerella* species. Of particular interest, lesquerolic acid is a 20-carbon homolog of ricinoleate with two additional carbons at the carboxyl end of the chain. Other natural plant sources of hydroxylated fatty acids include seeds of the *Linum* genus, seeds of *Wrightia* species, *Lycopodium* species, *Strophanthus* species, *Convulvaces* species, *Calendula* species and many others (van de Loo et al. (1993). For example, *Lesquerella densipila* contains a diunsaturated 18 carbon fatty acid with a hydroxyl group (van de Loo et al. (1993) *Lipid Metabolism in Plants* CRC Press, Boca Raton, p. 99-126) that is thought to be produced by an enzyme that is closely related to the castor and *Lesquerella fendleri* hydroxylases. Similarly, epoxygenated fatty acids are found in a variety of plants including *Vernonia* genus, *Crepis* genus, *Euphorbia* genus and *Stokesia laevis*.

In addition, nucleic acids encoding a polypeptide modified from a naturally occurring sequence can be made by mutagenesis. A delta-12 desaturase can for example be converted to an oleate hydroxylase by targeted mutagenesis (Broun et al. (1998) *Science*, 282(5392): 1315-1317; Broadwater et al. (2002) *J Biol. Chem.* 277(18): 15613-15620.). Similar changes in coding sequences such as delta-15 (omega-3) desaturases can be carried out to produce novel hydroxylases. As is well known in the art, once a cDNA clone encoding a plant hydroxylase or epoxygenase is obtained, it may be used to obtain its corresponding genomic nucleic acid. Thus, one skilled in the art will recognize that antibody preparations, nucleic acid probes and the like may be prepared and used to screen and recover homologous or related hydroxylases and epoxygenases from a variety of sources.

Typically, a nucleic acid of the invention has 70% or greater sequence identity, e.g., 80%, 85%, 90%, 95%, 96%, 97%, 98%, or 99% or greater sequence identity to a target nucleic acid. Sequence identity is determined as described herein. In some embodiments, nucleic acids are from 20 to 30 nucleotides, or 20 to 50 nucleotides, or 25 to 100 nucleotides, or 500 to 1500 nucleotides, or 900 to 2,000 nucleotides in length. Specific embodiments of nucleic acids include nucleotide sequences set forth in the sequence listings. It is noted that the degeneracy of the genetic code permits codon modification without a corresponding modification of the amino acid sequence. Thus, codons in a nucleic acid can be modified if desired, which may optimize expression of a polypeptide. For example, codons with 80,4 or lower percentage occurrence in a selected plant species genome can be replaced with a more frequently occurring codon, e.g., the most frequent or second most frequent codon for that particular amino acid. As another alternative, one member of a contiguous pair of codons can be modified if both codons have an occurrence of 12% or lower in known sequences of the genome of a selected plant species. Data relating to codon usage database can be found, for example, at kazusa.or.jp/codon/ on the World Wide Web.

Codons can also be changed to remove ATTTA (i.e., AUUUA) elements which may contribute to mRNA instability, and codons may be changed to ablate potential polyadenylation sites. Codons can also be modified to break up runs of five or greater contiguous nucleotides of A, C, C or I (e.g., TTTTTT). Codons can also be modified to reduce the likelihood of aberrant splicing. Splicing potential can be assessed and donor (GT) or acceptor (AG) splice sites ablated in order to diminish splicing potential, using predictive algorithms such as algorithms at cbs.dtu.dk/services/NetPGene on the World Wide Web. In addition, codons near the N-terminus of the polypeptide can be changed to codons preferred by a selected plant species, e.g., soybean (*Glycine max*). It will be appreciated that one or more codon modifications, including but not limited to the modifications discussed above can be made to a nucleic acid coding sequence. Examples of sequences that have one or more codon modification(s) to improve plant expression and have slight changes to the amino acid sequences relative to the wild-type sequence include SEQ ID NOs: 28 through 33 and 129 through 133.

A nucleic acid encoding a polypeptide can have a genomic coding sequence, a cDNA coding sequence, or an mRNA coding sequence. A cDNA coding sequence may or may not have pre-processing sequences, such as transit or signal peptide sequences. Transit or signal peptide sequences facilitate the delivery of the protein to a given organelle and are frequently cleaved from the polypeptide upon entry into the organelle, releasing the "mature" sequence. The use of the precursor DNA sequence can be useful in plant cell expression cassettes.

Transgenic Plants

According to another aspect of the invention, transgenic plants are provided. Such plants typically express the polypeptide coding sequence of a DNA construct described herein, resulting in an increase in the amount of a hydroxylated or epoxygenated fatty acid in vegetative plant tissues or at least one tissue of seeds of such plants. A plant species or cultivar may be transformed with a DNA construct that encodes a polypeptide from a different plant species or cultivar (e.g., soybean transformed with a gene encoding a castor enzyme). Alternatively, a plant species or cultivar may be transformed with a DNA construct that encodes a polypeptide from the same plant species or cultivar.

Accordingly, a method according to the invention comprises introducing a DNA construct as described herein into a plant. Techniques for introducing exogenous nucleic acids into monocotyledonous and dicotyledonous plants are known in the art, and include, without limitation, *Agrobacterium*-mediated transformation, liposome fusion, microinjection, viral vector-mediated transformation, infiltration, imbibition, electroporation and particle gun transformation, e.g., U.S. Pat. Nos. 5,204,253 and 6,013,863. If a cell or tissue culture is used as the recipient tissue for transformation, plants can be regenerated from transformed cultures by techniques known to those skilled in the art. Any method that provides for transformation may be employed.

Where *Agrobacterium* is used for plant cell transformation, a vector may be used which may be introduced into the *Agrobacterium* host for homologous recombination with the Ti- or $R_1$-plasmid present in the *Agrobacterium* host. The Ti- or $R_1$-plasmid containing the T-DNA for recombination may be armed (capable of causing gall formation) or disarmed (incapable of causing gall), the latter being permissible, so long as the vir genes are present in the transformed *Agrobacterium* host. The armed plasmid can give a mixture of normal plant cells and gall.

In some instances where *Agrobacterium* is used as the vehicle for transforming plant cells, the DNA construct, bordered by the T-DNA border(s), will be inserted into a broad host spectrum vector, there being broad host spectrum vectors described in the literature. Commonly used is pRK2 or derivatives thereof. Included with the expression construct and the T-DNA will be one or more markers, which allow for selection of transformed *Agrobacterium* and transformed plant cells. A number of markers have been developed for use with plant cells, such as resistance to kanamycin, the aminoglycoside G418, hygromycin, or the like.

A number of genes that confer herbicide resistance can be used as markers. Genes conferring resistance to a herbicide that inhibits the growing point or meristem can be suitable. Exemplary genes in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase(ACCase). Genes for resistance to glyphosate (sold under the trade name Roundup®) are also suitable. See, for example, U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase gene. Genes for resistance to phosphono compounds such as glufosinate ammonium or phosphinothricin, and pyridinoxy or phenoxy propionic acids and cyclohexones are also suitable. See European application No. 0 242 246. Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Patent Application No. 20010016956, and U.S. Pat. No. 6,084,155. The particular marker employed is not essential to this invention, one or another marker being suitable depending on the particular host and the manner of construction.

Transgenic plants typically contain a DNA construct integrated into their genome and typically exhibit Mendelian inheritance patterns. Transgenic plants can be entered into a breeding program, e.g., to introduce a nucleic acid encoding a polypeptide into other lines, to transfer the nucleic acid to other species or for further selection of other desirable traits. Alternatively, transgenic plants can be propagated vegetatively for those species amenable to such techniques. Progeny includes descendants of a particular plant or plant line. Progeny of an instant plant include seeds formed on $F_1$, $F_2$, $F_3$, and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

Plants which may be employed in practicing the present invention include, but are not limited to, tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Suitable grasses include Kentucky bluegrass (*Poa pratensis*) and creeping bentgrass (*Agrostris palustris*).

It is understood that hydroxylated or epoxygenated fatty acids produced by a polypeptide of the invention in planta may be subject to further enzymatic modification by other enzymes which are normally present in a plant or are introduced by genetic engineering methods into a plant. For example, lesquerolic acid, which is present in many *Lesquerella* species, is thought to be produced by elongation of ricinoleic acid (Moon et al. (2001) *Plant Physiol.* 127(4): 1635-1643). Thus, the presence of a *Ricinus communis* hydroxylase construct in a transgenic plant may be sufficient to produce lesquerolic acid in the same plant, via production of ricinoleic acid by the hydroxylase polypeptide and elongation of ricinoleic acid by an endogenous polypeptide.

Nematode Resistance

Transgenic plants may be tested for hydroxy- and epoxy-fatty acid production in non-seed tissues. Such plants may also be tested for nematicidal activity. Similar tests for hydroxylated and epoxygenated fatty acid production and nematicidal activity may be carried out on hairy root cultures formed by transformation with *A. rhizogenes*. Accordingly, the invention features a method of screening a transgenic plant for anthelmintic activity, comprising contacting the plant with a nematode under conditions effective to determine whether or not the plant has anthelmintic activity. The transgenic plant has a nucleic acid encoding a hydroxylase or epoxygenase polypeptide described herein. Suitable conditions for determining anthelmintic activity are described herein. The method can also be carried out with plant tissue, e.g., root tissue, leaf tissue or stem tissue from a transgenic plant.

In another aspect, the invention features a method for making a plant having anthelmintic activity. As discussed herein, techniques for introducing exogenous nucleic acids into monocotyledonous and dicotyledonous plants are known in the art. In some embodiments, for example, a method of making a plant having anthelmintic activity comprises (1) transforming regenerable cells of a plant species with a DNA construct described herein; and (2) regenerating one or more transgenic plants from the cells. The resulting transgenic plant can have a statistically significant increase in the amount of hydroxylated or epoxygenated fatty acid in non-seed tissues compared to a corresponding untransformed counterpart. The increased level of hydroxy- or epoxy-fatty acids can result in plants that have anthelmintic activity. Nematodes that parasitize plant roots, stems, bulbs, or leaves can be controlled using the method of this invention.

As used herein, a fatty acid compound has anthelmintic activity when, tested in planta, the compound has a statistically significant increase in nematode-killing activity, a statistically significant reduction in nematode fertility, a statistically significant increase in nematode sterility, a statistically significant reduction in the ability of a nematode to infect or reproduce in its host, a statistically significant reduction in nematode growth or development, relative to a control treatment in the absence of the compound. A compound having anthelmintic activity can, for example, reduce the survival time of adult nematodes relative to unexposed similarly staged adults, e.g., by about 20%, 40%, 60%, 80%, or more. In some embodiments, a compound having anthelmintic activity may also cause the nematodes to cease replicating, regenerating, and/or producing viable progeny, e.g., by about 20%, 40%, 60%, 80%, or more, compared to a control treatment in the absence of the compound.

A compound having anthelmintic activity can result in a statistically significant increase in nematode repellant properties relative to a control treatment in the absence of the compound. In the assay, the compound is combined with nematodes, e.g., in a well of microtiter dish, in liquid or solid media or in the soil containing the compound. Staged adult nematodes are placed on the media. The time of survival, viability of offspring, and/or the movement of the nematodes are measured.

Exemplary plants-parasitic nematodes from which plants may be protected by the present invention, and their corresponding plants, are as follows: alfalfa: *Ditylenchus dipsaci, Meloidogyne hapla, Meloidogyne incognita, Meloidogyne-javanica, Pratylenchus* spp., *Paratylenchus* spp., *Xiphinema* spp.; banana: *Radopholus similis, Helicotylenchus multicinctus, Meloidogyne incognita, M. arenaria, M. javanica, Pratylenchus coffeae, Rotylenchulus reniformis*; beans and peas: *Meloidogyne* spp., *Heterodera* spp., *Belonolaimus* spp., *Helicotylenchus* spp., *Rotylenchulus reniformis, Paratrichodorus anemones, Trichodorus* spp.; cassaya: *Rotylenchulus reniformis, Meloidogyne* spp.; cereals: *Anguina tritici* (Emmer, rye, spelt wheat), *Bidera avenae* (oat, wheat), *Ditylenchus dipsaci* (rye, oat), *Subanguina radicicola* (oat, barley, wheat, rye), *Meloidogyne naasi* (barley, wheat, rye), *Pratylenchus* spp. (oat, wheat, barley, rye), *Paratylenchus* spp. (wheat), *Tylenchorhynchus* spp. (wheat, oat); chickpea: *Heterodera cajani, Rotylenchulus reniformis, Hoplolaimus seinhorsti, Meloidogyne* spp., *Pratylenchus* spp.; citrus: *Tylenchulus semipenetrans, Radopholus similis, Radopholus citrophilus* (Florida only), *Hemicycliophora arenaria, Pratylenchus* spp., *Meloidogyne* spp., *Bolonolaimus longicaudatus* (Florida only), *Trichodorus, Paratrichodorus, Xiphinema* spp.; clover: *Meloidogyne* spp., *Heterodera trifolii*; coconut: *Rhadinaphelenchus cocophilus*; coffee: *Meloidogyne incognita* (most important in Brazil), *Meloidogyne exigua* (widespread), *Pratylenchus coffeae, Pratylenchus brachyurus, Radopholus similis, Rotylenchulus reniformis, Helicotylenchus* spp.; corn: *Pratylenchus* spp., *Paratrichodorus minor, Longidorus* spp., *Hoplolaimus columbus*; cotton: *Meloidogyne incognita, Belonolaimus longicaudatus, Rotylenchulus reniformis, Hoplolaimus galeatus, Pratylenchus* spp., *Tylenchorhynchus* spp., *Paratrichodorus minor*; grapes: *Xiphinema* spp., *Pratylenchus vulnus, Meloidogyne* spp., *Tylenchulus semipenetrans, Rotylenchulus reniformis*; grasses: *Pratylenchus* spp., *Longidorus* spp., *Paratrichodorus christiei, Xiphinema* spp., *Ditylenchus* spp.; peanut: *Pratylenchus* spp., *Meloidogyne hapla., Meloidogyne arenaria, Criconemella* spp., *Belonolaimus longicaudatus* (in Eastern United States); pigeon pea: *Heterodera cajani, Rotylenchulus reniformis, Hoplolaimus seinhorsti, Meloidogyne* spp., *Pratylenchus* spp.; pineapple: *Paratrichodorus christiei, Criconemella* spp., *Meloidogyne* spp., *Rotylenchulus reniformis, Helicotylenchus* spp., *Pratylenchus* spp., *Paratylenchus* spp.; potato: *Globodera rostochiensis, Globodera pallida, Meloidogyne* spp., *Pratylenchus* spp., *Trichodorus primitivus, Ditylenchus* spp., *Paratrichodorus* spp., *Nacoabbus aberrans*; rice: *Aphelenchiodes besseyi, Ditylenchus angustus, Hirchmanniella* spp., *Heterodera oryzae, Meloidogyne* spp.; small fruits: *Meloidogyne* spp.; *Pratylenchus* spp., *Xiphinema* spp., *Longidorus* spp., *Paratrichodorus christiei, Aphelenchoides* spp. (strawberry); soybean: *Heterodera glycines, Meloidogyne incognita, Meloidogyne javanica, Belonolaimus* spp., *Hoplolaimus columbus*; sugar beet: *Heterodera schachtii, Ditylenchus dipsaci, Meloidogyne* spp., *Nacobbus aberrans, Trichodorus* spp., *Longidorus* spp., *Paratrichodorus* spp.; sugar cane: *Meloidogyne* spp., *Pratylenchus* spp., *Radopholus* spp., *Heterodera* spp., *Hoplolaimus* spp., *Helicotylenchus* spp., *Scutellonema* spp., *Belonolaimus* spp., *Tylenchorhynchus* spp., *Xiphinema* spp., *Longidorus* spp., *Paratrichodorus* spp.; tea: *Meloidogyne* spp., *Pratylenchus* spp., *Radopholus similis, Hemicriconemoides kanayaensis, Helicotylenchus* spp., *Paratylenchus curvitatus*; tobacco: *Meloidogyne* spp., *Pratylenchus* spp., *Tylenchorhynchus claytoni, Globodera tabacum, Trichodorus* spp., *Xiphinema americanum, Ditylenchus dipsaci* (Europe only), *Paratrichodorus* spp.; tomato: *Pratylenchus* spp., *Meloidogyne* spp.; tree fruits: *Pratylenchus* spp. (apple, pear, stone fruits), *Paratylenchus* spp. (apple, pear), *Xiphinema* spp. (pear, cherry, peach), *Cacopaurus pestis* (walnut), *Meloidogyne* spp. (stone fruits, apple, etc.), *Longidorus* spp. (cherry), *Criconemella* spp. (peach), and *Tylenchulus* spp. (olive).

Transgenic plants described herein can provide an effective, environmentally safe means of inhibiting nematode metabolism, growth, viability, fecundity, development, infectivity and/or the nematode life-cycle. The plants may be used alone or in combination with chemical nematicides or as part of an integrated pest management strategy. Transgenic plants can afford season-long nematode control and thereby provide labor savings, by reducing the need for and frequency of chemical control.

Described below are experiments demonstrating that delta-12 fatty acid desaturase activity is essential for nematode viability. Also described are certain nematicidal fatty acids and analogs, including nematicidal fatty acids and esters that have activity consistent with that of delta-12 fatty acid desaturase inhibitors. The cloning, modification, introduction into plants and expression in non-seed tissues (e.g., roots) of DNA sequences encoding enzymes that produce these fatty acids is also described, as are tests of regenerated plant cells, roots and plants. The following examples are to be construed as merely illustrative, and not limiting in any way whatsoever.

EXAMPLE 1

RNA Mediated Interference (RNAi)

A double stranded RNA (dsRNA) molecule can be used to inactivate a delta-12 fatty acid desaturase (delta-12 fat2) gene in a cell by a process known as RNA mediated-interference (Fire et al. (1998) Nature 391: 806-811, and Gonczy et al. (2000) Nature 408: 331-336). The dsRNA molecule can have the nucleotide sequence of a delta-12 fat2 nucleic acid (preferably exonic) or a fragment thereof. The dsRNA molecule can be delivered to nematodes via direct injection, or by soaking nematodes in aqueous solution containing concentrated dsRNA, or by raising bacteriovorous nematodes on E. coli genetically engineered to produce the dsRNA molecule.

RNAi by injection: To examine the effect of inhibiting delta-12 fat2 activity, a dsRNA corresponding to the C. elegans delta-12 fat2 gene was injected into the nematode, basically as described in Mello et al. (1991) EMBO J. 10: 3959-3970. Briefly, a plasmid was constructed that contains a portion of the C. elegans delta-12 fat2 sequence, specifically a fragment 651 nucleotides long, containing the entire first exon and terminating just before the conserved intron splice junction between the first exon and first intron. This construct encodes approximately the first 217 amino acids of the C. elegans delta-12 fat2 gene. Primers were used to specifically amplify this sequence as a linear dsDNA. Single-stranded RNAs were transcribed from these fragments using T7 RNA polymerase and SP6 RNA polymerase (the RNAs correspond to the sense and antisense RNA strands). RNA was precipitated and resuspended in RNAse free water. For annealing of ssRNAs to form dsRNAs, ssRNAs were combined, heated to 95° C. for two minutes then allowed to cool from 70° C. to room temperature over 1.5-2.5 hours.

DsRNA was injected into the body cavity of 15-20 young adult C. elegans hermaphrodites. Worms were immobilized on an agarose pad and typically injected at a concentration of 1 mg/mL. Injections were performed with visual observation using a Zeiss Axiovert compound microscope equipped with 10× and 40× DIC objectives, for example. Needles for microinjection were prepared using a Narishige needle puller, stage micromanipulator (Leitz) and an N2-powered injector (Narishige) set at 10-20 p.s.i. After injection, 200 µl of recovery buffer (0.1% salmon sperm DNA, 4% glucose, 2.4 mM KCl, 66 mM NaCl, 3 mM CaCl2, 3 mM HEPES, pH 7.2) were added to the agarose pad and the worms were allowed to recover on the agarose pad for 0.5-4 hours. After recovery, the worms were transferred to NGM agar plates seeded with a lawn of E. coli strain OP50 as a food source. The following day and for 3 successive days thereafter, 7 individual healthy injected worms were transferred to new NGM plates seeded with OP50. The number of eggs laid per worm per day and the number of those eggs that hatched and reached fertile adulthood were determined. As a control, Green Fluorescent Protein (GFP) dsRNA was produced and injected using similar methods. GFP is a commonly used reporter gene originally isolated from jellyfish and is widely used in both prokaryotic and eukaryotic systems. The GFP gene is not present in the wild-type C. elegans genome and, therefore, GFP dsRNA does not trigger an RNAi phenotype in wild-type C. elegans. The C. elegans delta-12 fat2 RNAi injection phenotype presented as a strongly reduced F1 hatch-rate, with the few surviving individuals arrested in an early larval stage.

RNAi by feeding: C. elegans can be grown on lawns of E. coli genetically engineered to produce double stranded RNA (dsRNA) designed to inhibit delta-12 fat2 expression. Briefly, E. coli were transformed with a genomic fragment of a portion of the C. elegans fat2 gene sequence, specifically a fragment 651 nucleotides long, containing the entire first exon and terminating just before the conserved intron splice junction between the first exon and first intron. This construct encodes approximately the first 217 amino acids of the C. elegans delta-12 fat2 gene. The 651 nucleotide genomic fragment was cloned into an E. coli expression vector between opposing T7 polymerase promoters. The clone was then transformed into a strain of E. coli that carries an IPTG-inducible T7 polymerase. As a control, E. coli was transformed with a gene encoding the Green Fluorescent Protein (GFP). Feeding RNAi was initiated from C. elegans eggs or from C. elegans L4s. When feeding RNAi was started from C. elegans eggs at 23° C. on NGM plates containing IPTG and E. coli expressing the C. elegans delta-12 fat2 or GFP dsRNA, the C. elegans delta-12 fat2 RNAi feeding phenotype presented as partially sterile F1 individuals and dead F2 embryos. When feeding RNAi was started from C. elegans L4 larvae at 23° C. on NGM plates containing IPTG and E. coli expressing the C. elegans DELTA-12 fat2 or GFP dsRNA, the C. elegans RNAi feeding phenotype presented as partially sterile P0 individuals (i.e., the individuals exposed initially) with developmentally arrested, sterile F1 nematodes. The sequence of the fat2 gene is of sufficiently high complexity (i.e., unique) such that the RNAi is not likely to represent cross reactivity with other genes.

C. elegans cultures grown in the presence of E. coli expressing dsRNA and those injected with dsRNA from the delta-12 fat2 gene were strongly impaired indicating that the fatty acid desaturase-like gene provides an essential function in nematodes and that dsRNA from the fatty acid desaturase-like gene is lethal when ingested by or injected into C. elegans.

EXAMPLE 2

Rescue of C. elegans Delta-12 fat2 RNAi Feeding Phenotype by Linoleic Acid Methyl Ester The C. elegans delta-12 fatty acid desaturase (FAT-2 protein) converts the mono-unsaturated oleic acid to the di-unsaturated fatty acid linoleic acid. The delta-12 fat2 RNAi prevents expression of the delta-12 fatty acid desaturase, which is predicted to cause a decrease in levels of linoleic acid in the nematode, leading to arrested development and death. Addition of 3 mM linoleic acid methyl ester to the NGM media used for the RNAi experiment brings about a partial rescue of the delta-12 fat2 RNAi feeding phenotype. Addition of 3 mM oleic acid methyl ester does not rescue the delta-12 fat2 RNAi feeding phenotype (see Table 1 below).

TABLE 1

C. elegans delta-12 fat2 RNAi feeding phenotypes (starting with C. elegans L4 larvae as the P0 animal)

| Fatty Acid Added | P0 phenotype | F1 phenotype | F2 phenotype |
|---|---|---|---|
| None | Reduced egg laying (partial sterility) | Developmentally arrested and sterile | NA |
| Oleic Acid Methyl Ester | Reduced egg laying (partial sterility) | Developmentally arrested and sterile | NA |
| Linoleic Acid Methyl Ester | Reduced egg laying | Moderately delayed development and moderately reduced egg laying | Slightly delayed development |

EXAMPLE 3

Preparation of *Caenorhabditis elegans* and Fatty Acids

Mixed stage *C. elegans* were washed off plates seeded with OP50 bacteria using M9 solution. 250 μl of the M9 solution, which contained about 50-100 worms, was pipetted into each well of a 24-well plate.

With the exceptions of the fatty acid salts and the free acid of ricinelaidic acid, all other fatty acid emulsions were prepared following the teachings of Kim et al (U.S. Pat. No. 5,698,592). Briefly, 1 mL 1% stock solution emulsions were prepared by mixing 10 μl of fatty acid with 20 μl of the surfactant Igepal CO 630 in a 1.5 mL eppendorf tube. After careful mixing of fatty acid and Igepal CO 630, 850 μl of ddH$_2$0 was added and mixed by gentle pipetting until a homogeneous solution was obtained. Finally, 120 μl of pure isopropanol was added and mixed by gentle pipetting. 1% stock emulsions were also prepared for the potassium salt of ricinoleic acid, the sodium salt of ricinelaidic acid, and ricinelaidic free acid. For the potassium salt of ricinoleic acid, 0.01 grams were dissolved in 100 μl of ddH$_2$O, and combined with 20 μl of the surfactant Igepal CO 630 in a 1.5 mL eppendorf tube. After careful mixing of fatty acid and Igepal CO 630, 760 μl of ddH$_2$O was added and mixed by gentle pipetting until a homogeneous solution was obtained. Finally, 120 μl of pure isopropanol was added and mixed by gentle pipetting. For the sodium salt and free acid of ricinelaidic acid, 0.01 grams were dissolved in 100 μl of acetone, and combined with 20 μl of the surfactant Igepal CO 630 in a 1.5 mL eppendorf tube. After careful mixing of fatty acid and Igepal CO 630, 760 μl of ddH$_2$0 was added and mixed by gentle pipetting until a homogeneous solution was obtained. Finally, 120 μl of pure isopropanol was added and mixed by gentle pipetting. These stock solutions were then used to produce various fatty acid dilution emulsions in 24-well plate assays. An "acetone control" emulsion was prepared by combining 100 μl of acetone, 20 μl of the surfactant Igepal CO 630, 760 μl of ddH$_2$0, and 120 μl of pure isopropanol in a 1.5 mL eppendorf tube and mixing to homogeneity.

EXAMPLE 4

Nematicidal Activity of Single Fatty Acid Methyl Ester Emulsions Against *Caenorhabditis elegans*

To each well, fatty acid emulsions or control emulsions were added and rapidly mixed by swirling. Nematode viability was scored by visual observation and motility assays at various time points 24 hours following addition of emulsions or controls. The fatty acid emulsions tested were methyl esters of nonanoic (pelargonic) acid, ricinoleic acid, vernolic acid, linoleic acid, oleic acid, and control emulsions lacking fatty acids.

The structures of ricinoleic acid methyl ester, ricinelaidic acid methyl ester (not included in this table) and vernolic acid methyl ester are depicted in FIG. 1.

TABLE 2

Nematicidal activity of fatty acid methyl ester emulsions against *C. elegans*

| Fatty Acid | Concentration | Percentage of Worm Death | | |
|---|---|---|---|---|
| | | 1 hr | 6 hr | 24 hr |
| Nonanoic | 0.1% | 100% | 100% | 100% |
| (C9-methyl ester) | 0.003% | 50% | 50% | 50% |
| Ricinoleic Acid | 0.1% | 80% | 80% | 90% |
| (C18-methyl ester) | 0.003% | 40% | 40% | 40% |
| Vernolic Acid | 0.1% | 65% | 65% | 75% |
| (C18-methyl ester) | 0.003% | 20% | 20% | 20% |
| Linoleic Acid | 0.1% | 0-5% | 0-5% | 0-5% |
| (C18-methyl ester) | 0.003% | 0-5% | 0-5% | 0-5% |
| Oleic Acid | 0.1% | 0-5% | 0-5% | 0-5% |
| (C18-methyl ester) | 0.003% | 0-5% | 0-5% | 0-5% |
| Control | 0.1% | 0-5% | 0-5% | 0-5% |
| (no methyl ester) | 0.003% | 0-5% | 0-5% | 0-5% |

Both nonanoic and ricinoleic acid methyl ester emulsions are strongly nematicidal at a concentration of 0.1%. Nonanoic methyl ester emulsions cause an almost immediate cessation of nematode movement and subsequent death whereas ricinoleic methyl ester emulsions require up to 30 minutes before strong killing effects are apparent. However, at 0.003%, nonanoic acid methyl ester emulsions temporarily "stunned" *C. elegans*, initially giving the appearance of a 100% death phenotype. Several hours post inoculation, many nematodes recover and start moving again. This "stun" effect was not observed with the other fatty acid emulsions.

EXAMPLE 5

Nematicidal Activity of Single Fatty Acid Methyl Ester, Salt and Free Fatty Acid Emulsions Against *Caenorhabditis elegans* N2s and Dauers L: linoleic acid, R: ricinoleic acid, Re: ricinelaidic; V-trans: (12,13)-epoxy-trans-9-octadecenoic acid; ME: methyl ester

TABLE 3

Results vs. *C. elegans* (worm death)

| Fatty Acid | 0.1% | 0.01% | 0.001% |
|---|---|---|---|
| Castor Oil | 10% | <5% | NA |
| Pelargonic ME | 100% | 100% | 30% |
| L ME | <5% | <5% | <5% |
| L free acid | 10% | <5% | <5% |
| R ME | 90% | 40% | 20% |
| R free acid | 95% | 50% | <5% |
| Re ME | 100% | 100% | 80% |
| Re free acid* | 100% | 98% | 40% |
| Potassium R | 90% | 15% | 5% |
| Sodium Re* | 100% | 100% | NA |
| Acetone control | 10% | 5% | 5% |

TABLE 4

Results vs. *C. elegans* dauers (worm death)

| Fatty Acid | 0.1% | 0.01% | 0.001% |
|---|---|---|---|
| Castor Oil | NA | NA | NA |
| Pelargonic ME | NA | NA | NA |
| L ME | 40% | 20% | NA |
| L free acid | 50% | 40% | NA |
| R ME | 70% | 30% | NA |
| R free acid | 90% | 75% | NA |
| Re ME | 100% | 100% | NA |
| Re free acid* | 75% | 75% | NA |
| Potassium R | 75% | 20% | NA |
| Sodium Re* | NA | NA | NA |
| Acetone control | 35% | 20% | NA |
| V-trans ME | 90% | 50% | NA |

EXAMPLE 6

Preparation of Root Knot Nematode J2 Larvae (*Meloidogyne* spp.)

*M. incognita* and *M. javanica* were prepared from tomato roots. The roots were bleached and the debris was separated from the J2 larvae and eggs by filtration followed by sucrose density gradient centrifugation. Eggs were hatched over 4 days at 15° C. and the J2 larvae were collected by passage though a filter, followed by centrifugation.

EXAMPLE 7

Nematicidal Activity of Fatty Acid Methyl Ester Emulsions Against Root Knot Nematodes (*Meloidogyne* spp.)

Nematodes and emulsions were incubated with shaking at room temperature for 48 hours. The contents of each well were transferred to a small spot on individual NGM plates lacking bacteria. About 24 hours after the transfer to plates, worms on and off the inoculation spot were counted as not viable or viable, respectively. Worms were considered viable if they had crawled away from the inoculation spot, or if they were moving. Worms were considered non-viable if they remained at the inoculation spot.

TABLE 5

Nematicidal activity of fatty acid methyl ester emulsions against *M. javanica* and *M. incognita*

| Fatty acid (0.1%) | *M. javanica* (% not viable) | *M. incognita* (% not viable) |
|---|---|---|
| Vernolic Acid (C18-methyl ester) | 90% | 100% |
| Nonanoic (C9-methyl ester) | 100% | 100% |
| Ricinoleic Acid (C18-methyl ester) | 60% | 95% |
| Oleic Acid (C18-methyl ester) | 20% | 25% |

Nonanoic, vernolic and ricinoleic acid methyl ester emulsions have significant nematicidal activity against root knot nematodes (*Meloidogyne* spp.) at a concentration of 0.1%.

EXAMPLE 8

Phytotoxicity Evaluations of Fatty Acid Methyl Esters

Sterilized tomato seeds were germinated in magenta jars containing Gamborg's agar media. After two weeks of growth, seedlings were treated with 250 μl of 1% fatty acid methyl ester emulsion (nonanoic acid, ricinoleic acid, ricinelaidic acid, oleic acid, or a control emulsion lacking any fatty acid), applied directly to the stem-media interface. Tomato seedlings were scored at various times after application of emulsions. Of the fatty acids tested, only 1% nonanoic acid methyl ester emulsion showed obvious phytotoxic effects on the tomatoes. Within 18 hours of nonanoic acid emulsion application, those tomatoes showed a distinct loss of turgor pressure (wilting phenotype) and had become noticeably less green in appearance. Within 24 hours, nonanoic acid treated tomatoes were almost entirely bleached to a pale white color and had nearly totally collapsed with most leaves lying directly on the agar media surface. Importantly, none of the tomatoes treated with the other fatty acid methyl ester emulsions showed visible effects. Therefore, ricinoleic and ricinelaidic acid methyl esters show excellent potential as anthelmintic chemicals based on their combination of high nematicidal properties and with favorable low phytotoxicity.

EXAMPLE 9

Nematicidal Activity of Single Fatty Acid Methyl Ester Emulsions Against a Spectrum of Free-Living, Animal Parasitic, and Plant Parasitic Nematodes Briefly, the indicated fatty acid emulsions were added to nematodes in wells of a 24-well plate and rapidly mixed by swirling. Nematode viability was scored by visual observation and motility assays 24 hours following addition of emulsions (48 hours for plant parasitic nematodes *Meloidogyne* and *Heterodera* species). The fatty acid emulsions tested were methyl esters of nonanoic (pelargonic) acid, ricinelaidic acid, ricinoleic acid, vernolic acid, linoleic acid, and oleic acid. Results for fatty acid emulsions against free-living, animal parasitic, and plant parasitic nematodes are combined in one table to facilitate comparison of different emulsion activities against nematodes exhibiting diverse lifestyles. Results shown are mean % values obtained from multiple independent experiments

TABLE 6

Nematicidal activity of various fatty acid methyl esters against various free-living, animal parasitic, and plant parasitic nematodes

| | % Worm Death (24 hr) | | | | | |
|---|---|---|---|---|---|---|
| | −control | | Inhibitors | | | +control |
| Worm (% solution) | Oleic | Linoleic | Vernolic | Ricinoleic | Ricinelaidic | Nonanoic |
| C. elegans (0.1%) | <10 | <10 | 80 | 90 | 100 | 100 |
| C. elegans (0.01%) | <10 | <10 | 50 | 50 | 100 | 100 |
| C. elegans (0.001%) | | <10 | 30 | 30 | 75 | 30 |
| P. trichosuri (0.1%) | ~10 | ~25 | ~95 | ~50 | 100 | |
| P. trichosuri (0.01%) | ~10 | ~25 | ~90 | ~60 | 100 | |
| P. trichosuri (0.001%) | | | | | | |
| M. incognita (0.1%) | | 20 | 98 | 95 | ~99 | 100 |
| M. incognita (0.01%) | | 20 | 73 | 83 | ~99 | |
| M. incognita (0.001%) | | | | | 97 | |
| M. javanica (0.1%) | | 20 | 90 | 60 | 100 | 100 |
| M. javanica (0.01%) | | 0-5 | 60 | 5 | 100 | |
| M. javanica (0.001%) | | | | | ~60 | |
| H. glycines (0.1%) | <10 | <20 | 30 | ~60 | 100 | 100 |
| H. glycines (0.01%) | <10 | <20 | 20 | ~60 | 100 | >95 |
| H. glycines (0.001%) | <10 | <20 | 18 | ~40 | 100 | |
| P. scribneri (0.1%) | <20 | <20 | <20 | <20 | ~70 | <20 |
| P. scribneri (0.01%) | <20 | <20 | <20 | <20 | ~40 | <20 |
| P. scribneri (0.001%) | | | | | | |

The *Caenorhabditis elegans* were mixed stage populations. Similar effects were seen on several other free-living nematode species. The *Parastrongyloides trichosuri* (parasite of Australian bushtail possum) were dauer-like infective $3^{rd}$ stage larva. Similar effects are also seen against free-living stages. The *Meloidogyne incognita* and *Meloidogyne javanica* (root knot nematode) were $2^{nd}$ stage juveniles (dauer-like infective stage). The *Heterodera glycines* (soybean cyst nematode) were $2^{nd}$ stage juveniles (dauer-like infective stage). Finally, the *Pratylenchus scribneri* (corn lesion nematode) were mixed stage populations.

As the data in the table above demonstrate, both ricinelaidic and ricinoleic acid methyl ester emulsions are strongly nematicidal at concentrations of 0.1% and 0.01%. Ricinelaidic acid methyl ester in particular showed favorable nematicidal activity against a wide spectrum of divergent nematode genera.

EXAMPLE 10

The following table lists primers used in the cloning and preparation of various nucleic acids constructs including hydroxylases, epoxygenases, 5'-UTRs and 3'-UTRs.

TABLE 7

Sequence primers used in cloning

| Name | Sequence | SEQ ID NO | Homology to |
|---|---|---|---|
| Hyd1 | atgggaggtggtggtcgcatg | 46 | first 7 codons of R. communis |
| Hyd2 | ttaatacttgttccggtacca | 47 | last 7 codons of R. communis |
| Les1 | atgggtgctggtggaagaataatg | 48 | first 8 codons of L. fendleri |
| Les10 | tcataacttattgaagtaatagtagacacctttt | 49 | last 11 codons of L. fendleri |
| les6 | tcataacttattgttgtaata | 50 | last 7 codons of L. fendleri |
| Ecrep2 | gcaatccctccccattg | 51 | codons 33-38 of C. biennis |
| Ecrep8 | tcacaatttatcataccaataaacacc | 52 | last 9 codons of C. biennis |
| 5'UTR-HIIIF | atacaaaagcttagagagagagattctgcgga | 53 | first 20 nt of A. thaliana Fad2 5' UTR |
| 3'UTR-SphIR | attcaatgcatgcaacataatgagcagccaaaa | 54 | last 20 nt of A. thaliana Fad2 3' UTR |

TABLE 7-continued

Sequence primers used in cloning

| Name | Sequence | SEQ ID NO | Homology to |
|---|---|---|---|
| Fad-HIIIF | attcaataagcttatgggtgcaggtggaagaat | 55 | first 7 codons of *A. thaliana* Fad2 |
| Fad-SphIR | atacaagcatgctcataacttattgttgtacc | 56 | last 7 codons of *A. thaliana* Fad2 |
| 3'Fad/cas | aagcaatggggtgggatggctttcttcagatctcccaccg | 57 | codons 31-38 Fad2/codons 43-49 *R. communis* |
| 5'Fad/cas | cggtgggagatctgaagaaagccatcccaccccattgctt | 58 | codons 31-47 Fad2/codons 43-49 *R. communis* |
| Cas-SalR | gtcgacatacttgttccggtaccaga | 59 | last 7 codons of *R. communis* |
| 3'Fad/les | cgattgctttcttcagatctcccaccgagaaaggcggtt | 60 | codons 28-33 Fad2/codons 35-41 *L. fendleri* |
| 5'Fad/les | aaccgcctttctcggtgggagatctgaagaaagcaatcc | 61 | codons 28-33 Fad2/codons 35-41 *L. fendleri* |
| Les-SalIR | gtcgactaacttattgttgtaatagt | 62 | last 7AA of *L. fendleri* |
| 3'Fad/lind | gggattgctttccttagatctcccaccgagaaaggcggtt | 63 | codons 28-33 Fad2/ codons 35-41 *L. lindheimeri* |
| 5'Fad/lind | aaccgcctttctcggtgggagatctaaggaaagcaatccc | 64 | codons 28-33 Fad2/ codons 35-41 *L. lindheimeri* |
| Lind-SalIR | gtcgactaacttattgttgtaatagt | 65 | last 7 codons of *L. lindheimeri* |
| 3'Fad/grac | aaccgcctttctcggtgggagatctgaagaaagcaatccc | 66 | codons 28-33 Fad2/ codons 35-41 *L. gracilis* |
| 5'Fad/grac | gggattgctttcttcagatctcccaccgagaaaggcggtt | 67 | codons 28-33 Fad2/ codons 35-41 *L. gracilis* |
| Grac-SalIR | gtcgactcataacttattgttgtaat | 68 | last 7 codons of *L. gracilis* |
| 3'Fad/crep | cggtgggagatctgaagaaagcaatccctcccccattgctt | 69 | codons 32-38 Fad2/first 7 codons of partial *C. biennis* |
| 5'Fad/crep | aagcaatggggagggattgctttcttcagatctcccaccg | 70 | codons 32-38 Fad2/first 7 codons of partial *C. biennis* clone |
| Crep-SalIR | gtcgaccaatttatgataccaataaa | 71 | last 7 codons of partial *C. biennis* clone |
| 5'CastorhindIII-k | atacaaaagcttataatgggaggtggtggtcgcat | 72 | first 7 codons of *R. communis* |
| 3' CastorBamH1 | atacaaggatcctaatacttgttccggtacc | 73 | last 7 codons of *R. communis* |
| Castor-HANOTI | atacaagcggccgcagcgtaatctggaacatcgt | 74 | last 7 codons of *R. communis* |
| 5'fendhindIII-K | atacaaaagcttataatgggtgctggtggaagaat | 75 | first 7 codons of *L. fendleri* |
| 3' fendBamHI | atacaaggatcctcataacttattgttgtaat | 76 | first 7 codons of *L. fendleri* |
| 5'HindIIIK/HA/fend | atacaaaagcttataatgtacccatacgatgttcc | 77 | first 7 codons of *L. fendleri* |
| UT3 | atgagagctcgtttaaacgattttaatgtttagc | 78 | first 24 nt of UBI3 term |

TABLE 7-continued

Sequence primers used in cloning

| Name | Sequence | SEQ ID NO | Homology to |
|---|---|---|---|
| UT4 | atgagaattcggccggccaatagtctcgac | 79 | last 20 nt of UBI3 term |
| UP1 | tcatgaggcgcgccaaagcacatacttatcg | 80 | first 17 nt of UBI3 promoter |
| UP2 | atgagcatgcaagcttcttcgcctggaggagag | 81 | last 23 nt of UBI3 promoter |
| HA5 | agctatgtacccatacgatgttccagattacgctg | 82 | HA tag |
| HA6 | tcgacagcgtaatctggaacatcgtatgggtacat | 83 | HA tag |
| CHA1 | gatccatgtacccaatacgatgttccagattacgctctcgaggagct | 84 | HA tag |
| CHA2 | ctcgagagcgtaatctggaacatcgtatgggtacatg | 85 | HA tag |
| IRT1 | atgaggcgcgccctttctctgacttttaacatcc | 86 | first 22 nt of IRT2 promoter |
| IRT2 | actggcatgcgtattgagattgttttataatatatg | 87 | last 26 nt of IRT2 promoter |
| Castor 5'HindIII | atacaaaagcttatgggaggtggtggtcgcat | 88 | first 6 codons of *R. communis* |
| Casotr 3'BamHI | atacaaggatccatacttgttccggtaccaga | 89 | last 6 codons of *R. communis* |
| fend F SalI | atacaaaagcttatgggtgctggtggaagaat | 90 | first 6 codons of *L. fendleri* |
| Fend R B-stop | atacaaggatcctaacttattgttgtaatagt | 91 | last 6 codons of *L. fendleri* |
| Castor 5' SalI | atacaagtcgacatgggaggtggtggtcgcat | 92 | first 6 codons of *R. communis* |
| Castor 3' BamH1 | atacaaggatccatacttgttccggtaccaga | 93 | last 6 codons of *R. communis* |
| 5'ΔKKGG2 | ataaccagcaacaacagtgagagcagccaccttaagcgagc | 94 | codons 11-17, codons 22-27 of *R. communis* |
| 3'ΔKKGG2 | gctcgcttaaggtggctgctctcactgttgttgctggttat | 95 | codons 11-17, codons 22-27 of *R. communis* |
| 5'ΔT | ttcttcctcagcctctctcttacctagcttggcctctctat | 96 | codons 76-82, codons 84-90 of *L. gracilis* |
| 3'ΔT | atagagaggccaagctaggtaagagagaggctgaggaagaa | 97 | codons 76-82, codons 84-90 of *L. gracilis* |
| castor XbaI MfeI R | caattgtctagattaatacttgttccggtaccag | 98 | last 22 nt of *R. communis* |
| HIII NcoI castor F | aagcttaccatgggaggtggtggtcg | 99 | first 17 nt of *R. communis* |
| M13 Reverse | gaaacagctatgaccatg | 100 | M13 bacteriophage (M13/pUC plasmids) |
| *gracilis* XbaI MfeI R | caattgtctagatcataacttattgttgtaatag | 101 | last 22 nt of *L. gracilis* |
| HIII NcoI *gracilis* F | aagcttaccatgggtgctggtggaagaat | 102 | first 20 nt of *L. gracilis* |
| Crepis XbaI MfeI R | caattgtctagatcacaatttatgataccaataaa | 103 | last 23 nt of *C. biennis* |
| BamHI castor F | atacaaggatccaaatgggaggtggtggtcgcat | 104 | first 20 nt of *R. communis* |
| BamHI *gracilis* F | atacaaggatccaaatgggtgctggtggaagaat | 105 | first 20 nt of *L. gracilis* |
| BamHI NcoI *S. epoxygenase* F | aggatccctaccatgggtgcaggtggtcggat | 106 | first 20 nt of *S. laevis* |

TABLE 7-continued

Sequence primers used in cloning

| Name | Sequence | SEQ ID NO | Homology to |
|---|---|---|---|
| S. epoxygenase XbaI R | tctagattacattttatggtaccagtaaa | 107 | last 20 nt of S. laevis |
| BglII NcoI C. biennis F | agatctctaccatgggtgcccacggccatgg | 108 | first 20 nt of C. biennis |
| HA-tag-F | agcttctcgagaccatggcgtacccgtacgacgtgcccgactacgccag | 109 | HA tag |
| HA-tag-R | gatcctggcgtagtcgggcacgtcgtacgggtacgccatggtctcgaga | 110 | HA tag |
| Fad5'UTR-F | atcctcgagagagattctgcggaggagcttc | 111 | Fad2 5' UTR of A. thaliana |
| Fad5'UTR-R | atcggatccatggttctgcagaaaaccaaaagca | 112 | Fad2 5' UTR of A. thaliana |
| Fad3'UTR-F | atctctagatgaggatgatggtgaagaaattg | 113 | Fad2 3' UTR of A. thaliana |
| Fad3'UTR-R | atcaagcttactgtccgaaggtcacatttc | 114 | Fad2 3' UTR of A. thaliana |
| Crep12F | ggaatgcatgtacatcgagcc | 115 | codons 355-360 of C. biennis |
| Crep13R | ggaacttgtgttggcatggtg | 116 | codons 138-144 of C. biennis |
| Estok-14 | tggccngtntaytggttytg | 117 | codons 81-87 of S. laevis |
| Estok-17 | tcyttngcytcyctccacat | 118 | codons 350-356 of S. laevis |
| Sl-1 | atgggtgctggtggtcggatg | 119 | codons 1-7 of S. laevis |
| Stok-1R | gaacacgcttacacctaggac | 120 | codons 254-260 of S. laevis |
| Stok12R | atcaatccactggtattcac | 121 | codons 109-114 of S. laevis |
| Stok14F | gtcctaggtgtaagcgtg | 122 | codons 254-259 of S. laevis |
| HIII NcoI C. biennis F | aagcttaccatgggtgcccacggccatgg | 123 | first 20 nt of C. biennis |
| Asc1 Nco1 C. biennis F | ggcgcgccaccatgggtgcccacggccatgg | 124 | first 20 nt of C. biennis |

EXAMPLE 11

The table below lists promoters and UTRs that can be used to achieve expression of polypeptides in plant vegetative tissue.

TABLE 8

Promoter-UTR sequences for genes strongly expressed in plant roots

| Element | Species - Gene | Accession | Nucleotides |
|---|---|---|---|
| TobRB7 | Nicotiana tabacum (common tobacco) - aquaporin | S45406 | 1 to 1953 |
| TUB-1 | Arabidopsis thaliana (thale cress) - beta 1-tubulin | M20405 | 1 to 569 |
| PsMTA | Pisum sativum (pea) - metallothionein-like protein | Z23097 | 1 to 804 |
| RPL16A | Arabidopsis thaliana (thale cress) - ribosomal protein L16 | X81799 | 1 to 1014 |
| ARSK1 | Arabidopsis thaliana (thale cress) - serine/threonine protein kinase | L22302 | 1 to 807 |
| AKT1 | Arabidopsis thaliana (thale cress) - potassium transporter | U06745 | 1 to 231 |
| LJAS2 | Lotus japonicus - asparagine synthetase | X89410 | 1 to 144 |
| MsH3g1 | Medicago sativa - cultivar chief histone H3.2 | U09458 | 1 to 482 |

EXAMPLE 12

This example describes the cloning of delta-12 desaturase-like hydroxylases and epoxygenases (SEQ ID NOs: 1 to 6 and 27 in the sequence listings).

Cloning of Castor Oleate Hydroxylase Gene

Genomic DNA was isolated from *Ricinus communis* leaf tissue. The sense primer Hyd1 (SEQ ID NO: 46) and antisense primer Hyd2 (SEQ ID NO: 47) were used to amplify a genomic copy of the castor hydroxylase gene in a Gradient PCR reaction [30 thermal cycles (1 min 95° C., 30 sec 48-63° C., 2 min 68° C.)] with KTLA DNA polymerase under standard conditions. The PCR product was fractionated in a 1% agarose gel. Bands approximately 1100 bp long were excised and gel purified (QIAquick Gel Extraction). DNA was cloned using a TOPO TA kit (Invitrogen). Candidate clones were sequenced in their entirety with an automated DNA sequencer (such as model 373 from Applied Biosystems, Inc.)

Cloning of *Lesquerella lindheimeri* and *Lesquerella gracilis* Bifunctional Hydroxylase Genes Genomic DNA was isolated from *L. lindheimeri* and *L. gracilis* leaf tissue. Sense primer Les1 (SEQ ID NO: 48) and antisense primer Les10 (SEQ ID NO: 49) were used to amplify genomic copies of both *Lesquerella* bifunctional hydroxylase genes in a PCR reaction [30 thermal cycles (2 min 94° C., 1 min 55° C., 2 min 68° C.)] with KTLA DNA polymerase under standard conditions. The PCR product was fractionated in a 1% agarose gel. Bands approximately 1100 bp long were excised and gel purified (QIAquick Gel Extraction). DNA was cloned using a TOPO TA kit (Invitrogen). Candidate clones were sequenced in their entirety with an automated DNA sequencer (such as model 373 from Applied Biosystems, Inc.)

Cloning of *Lesquerella fendleri* Bifunctional Hydroxylase Gene

Genomic DNA was isolated from *L. fendleri*. Sense primer Les1 (SEQ ID NO: 48) and antisense primer Les6 (SEQ ID NO: 50) were used to amplify a genomic copy of the *L. fendleri* bifunctional hydroxylase gene in a Gradient PCR reaction [30 thermal cycles (1 min 95° C., 30 sec 45-63° C., 2 min 68° C.)] with KTLA DNA polymerase under standard conditions. The PCR product was fractionated in a 1% agarose gel. Bands approximately 1100 bp long were excised and gel purified (QIAquick Gel Extraction). DNA was cloned using a TOPO TA kit (Invitrogen). Candidate clones were sequenced in their entirety with an automated DNA sequencer (such as model 373 from Applied Biosystems, Inc.)

Cloning of *Crepis biennis* Epoxygenase Gene

Genomic DNA was isolated from *C. biennis*. The sense primer Ecrep2 (SEQ ID NO: 51) and antisense primer Ecrep8 (SEQ ID NO: 52) were used to amplify a partial genomic clone of the *C. biennis* epoxygenase gene in a Gradient PCR reaction [30 thermal cycles (1 min 95° C., 30 sec 45-63° C., 2 min 68° C.) with KTLA DNA polymerase under the standard conditions]. The PCR product was fractionated on a 1% agarose gel and a band approximately 1100 bp long was excised and gel purified (QIAquick Gel Extraction). The gene fragment was then cloned using a TOPO TA cloning kit (Invitrogen). Candidate clones were sequenced in their entirety with an automated DNA sequencer (such as model 373 from Applied Biosystems, Inc.) to yield plasmid clone, Div2966. Partial sequence data for the *C. biennis* epoxygenase was obtained from Div2966, including nucleotide sequence for codons 33-374 and the 3' stop codon. The clone lacked the first 32 codons of the *C. biennis* epoxygenase, as well as the 5' untranslated region. To obtain the missing 5' sequence of the *C. biennis* epoxygenase gene, the inverse PCR technique was applied. Inverse PCR permits the rapid amplification of unknown segments of DNA that immediately flank a target sequence. Briefly, *C. biennis* genomic DNA is digested with a selected restriction enzyme, then ligated to circularize smaller segments of genomic DNA. These circularized segments are then used as templates for PCR with primers directing DNA amplification outward away from the known region of the gene of interest to amplify the missing flanking sequences. Inverse PCR can be used to amplify missing 5' or 3' sequences. The digested, ligated, and circularized genomic DNA was directly PCR amplified using gene-specific primers (Crep12F; SEQ ID NO: 115 and Crep13R; SEQ ID NO: 116) designed from the known sequence that anneal within the gene of interest. This procedure was performed to generate clone Div4373, which contains codons 1-137 and 355-374. Taken together, clone Div2966 and Div4373 contain sequences comprising the complete open reading frame of the epoxygenase gene of *C. biennis*.

Cloning of *Stokesia leavis* Epoxygenase Gene

Genomic DNA was isolated from *S. laevis*. Degenerate primers were designed to anneal to regions within the *S. leavis* epoxygenase gene which were predicted to exhibit a high degree of sequence conservation across many plant epoxygenases. The sense primer Estok14 (SEQ ID NO: 117) and antisense primer Estok17 (SEQ ID NO: 118) were used to amplify a genomic fragment of the *S. laevis* epoxygenase gene. Amplified PCR products were then cloned into a suitable vector for DNA analysis. This procedure was performed to obtain clone Div4023. This clone contained codons 88-356. To obtain the 5'end sequence of the gene, gene-specific primers were designed from known sequence that anneal within the gene of interest, and a sense primer S1-1 (SEQ ID NO: 119) and an antisense primer Stok1R (SEQ ID NO: 120), were used to amplify the rest of the epoxygenase gene. This yielded plasmid clone Div4172. This clone contained codons 1-260. To obtain the 3' end of the *S. laevis* epoxygenase gene, the inverse PCR technique was applied. Inverse PCR permits the rapid amplification of unknown segments of DNA that immediately flank a target sequence. Briefly, *S. laevis* genomic DNA is digested with a selected restriction enzyme, then ligated to circularize smaller segments of genomic DNA. These circularized segments are then used as templates for PCR with primers directing DNA amplification outward away from the known region of the gene of interest to amplify the missing flanking sequences. Inverse PCR can be used to amplify missing 5' or 3' sequences. The digested, ligated, and circularized genomic DNA was directly PCR amplified using the gene-specific primers Stok12R (SEQ ID NO: 121) and Stok14F (SEQ ID NO: 122), which were designed from the known sequence that anneal within the gene of interest. This procedure was performed to generate clone Div4324, which contains codons 1-108 and 254-377. Taken together, clone Div4023, Div4172 and Div4324 contain sequences comprising the complete open reading frame of the epoxygenase gene of *S. laevis*.

Cloning of ΔT *L. gracilis* Bifunctional Hydroxylase Construct:

Specific primers were designed to remove nucleotides 245-247 (CTA) from the full length *R. communis* hydroxylase gene. A two-round PCR based subcloning strategy was used to generate the ΔT *L. gracilis* bifunctional hydroxylase. The first round of PCR primers were as follows; to amplify 5' end of the bifunctional hydroxylase excluding nucleotides 245-247, the sense primer M13 Reverse (SEQ ID NO: 100) and antisense primer 3'ΔT (SEQ ID NO: 97) were used in a PCR reaction using a copy of the *L. gracilis* bifunctional hydroxylase gene contained in the cloning vector pCR2.1 as a template. To amplify the 3' end of the bifunctional hydroxylase gene excluding nucleotides 245-247, the sense primer 5'ΔT (SEQ ID NO: 96) and antisense primer gracilis XbaI MfeI R (SEQ ID NO: 101) were used. For the second round of PCR, the sense primer HIII NcoI gracilis F (SEQ ID NO: 102) and antisense primer gracilis XbaI Mfe R (SEQ ID NO: 101) were used to generate the final PCR product ΔT *L. gracilis* hydroxylase. PCR products were amplified using 5 thermal cycles (1 min, 94 C, 30 sec 50° C., 1.5 min 68° C.) and then 15 thermal cycles (1 min, 94° C., 30 sec 57° C., 1.5 min 68° C.) with KTLA DNA polymerase under standard conditions. The construct was then subcloned into a plant expression vector using the NcoI and XbaI restriction enzymes sites.

Cloning of the ΔKKGG *Ricinus communis* Hydroxylase Construct:

Specific primers were designed to remove nucleotides 53-64 (AGAAAGGAGGAA, SEQ ID NO: 140) from the full length *R. communis* hydroxylase gene. A two-round PCR based subcloning strategy was used to generate the ΔKKGG *Ricinus communis* hydroxylase gene. The first round of PCR primers were as follows; to amplify 5' end of the *Ricinus* hydroxylase gene excluding nucleotides 53-64, the sense primer M13 Reverse (SEQ ID NO: 100) and antisense primer 3'ΔKKGG2 (SEQ ID NO: 95) were used in a PCR reaction using a copy of the *R. communis* hydroxylase gene contained in the cloning vector pCR2.1 as a template. To amplify the 3' end of the *Ricinus* hydroxylase gene excluding nucleotides 53-64, the sense primer 5'ΔKKGG2 (SEQ ID NO: 94) and antisense primer castor XbaI MfeI R (SEQ ID NO: 98) were used. For the second round of PCR, the sense primer HIII NcoI castor F (SEQ ID NO: 99) and castor XbaI Mfe R (SEQ ID NO: 98) were used to generate the final PCR product AKKGG *Ricinus communis* hydroxylase. PCR products were amplified using 5 thermal cycles (1 min, 94° C., 30 sec 50° C., 1.5 min 68° C.) and then 15 thermal cycles (1 min, 94° C., 30 sec 57° C., 1.5 min 68° C.) with KTLA DNA polymerase under standard conditions. The construct was then subcloned into a plant expression vector using the NcoI and XbaI restriction enzymes sites.

EXAMPLE 13

This example describes the isolation of the *Arabidopsis thaliana* fad2 regulatory and coding sequences and the construction of fad2/hydroxylase and fad2/epoxygenase fusion polypeptides. See SEQ ID NO: 7 to 12 in the sequence listings.

Isolation of the *A. thaliana* fad2 Desaturase cDNA Clone

Total RNA was isolated from *A. thaliana* leaf tissue (Qiagen RNeasy). RT-PCR was performed using the Roche Titan One Tube RT-PCR system with the sense primer 5'UTR-HIIIF (SEQ ID NO: 53) and antisense primer 3'UTR-SphIR (SEQ ID NO: 54). RT-PCR was set up following the kit directions [1 cycle (30 minutes 50° C.), 1 cycle (2 minutes 94° C.), 10 cycles (10 seconds 94° C., 30 seconds 60° C., 1 minute 68° C.), 25 cycles (10 seconds 94° C., 30 sec 60° C., 1 min 68° C.+cycle elongation of 5 seconds for each cycle), 1 cycle (7 min 68° C.)]. Bands approximately 1100 bp long were excised and gel purified (QIAquick Gel Extraction). DNA was cloned using a TOPO TA kit (Invitrogen). Candidate clones were sequenced in their entirety with an automated DNA sequencer (Model 373 from Applied Biosystems, Inc.)

Isolation of the *A. thaliana* fad2 Desaturase Genomic DNA Clone

Genomic DNA was isolated from *A. thaliana* leaf tissue. The sense primer 5'UTR-HIIIF (SEQ ID NO: 53) and antisense primer 3'UTR-SphIR (SEQ ID NO: 54) were used to amplify genomic fad2 DNA in a PCR reaction [5 thermal cycles (1 min 95° C., 30 sec 54° C., 2 min 68° C.), 25 thermal cycles (1 min 95° C., 30 sec 62° C., 2 min 68° C.)] with KTLA DNA polymerase under the standard conditions. The PCR product was fractionated in a 1% agarose gel. Bands approximately 2400 bp long were excised and gel purified (QIAquick Gel Extraction). DNA was cloned using a TOPO TA kit (Invitrogen). Candidate clones were sequenced in their entirety with an automated DNA sequencer (such as model 373 from Applied Biosystems, Inc.)

Generation of fad2/*Ricinus communis* Hydroxylase Chimeric cDNA

A two-round PCR based subcloning strategy was used to generate all of the chimeric cDNAs. In the first round of PCR, the sense primer Fad-HIIIF (SEQ ID NO: 55) and antisense primer 3'Fad/cas (SEQ ID NO: 57) were used to amplify the first 114 bases from the fad2 cDNA clone. The sense primer 5'-Fad/cas (SEQ ID NO: 58) and antisense primer Cas-SalR (SEQ ID NO: 59) were used to amplify the last 1034 bases (excluding TAA) of the *Ricinus communis* hydroxylase cDNA clone by PCR [1 thermal cycle (4 min 94° C.), 5 thermal cycles (45 sec 94° C., 45 sec 50° C., 60 sec 68° C.), 25 thermal cycles (45 sec 94° C., 45 sec 57° C., 60 sec 68° C.) with KTLA DNA polymerase under the standard conditions. The PCR products were fractionated on a 1% agarose gels. The bands were excised and cleaned (QIAquick Gel Extraction—final volume 50 uL). The clean product was diluted 1:100 (TE) and both DNAs were used as the template (1 μL each) in the second round of PCR. In the second round of PCR sense primer Fad-HIIIF (SEQ ID NO: 55) and antisense primer Cas-SalR (SEQ ID NO: 59) were used to generate the final PCR product fad2/*Ricinus communis* chimeric cDNA [1 thermal cycle (4 min 94° C.), 5 thermal cycles (45 sec 94° C., 45 sec 50° C., 60 sec 68° C.), 25 thermal cycles (45 sec 94° C., 45 sec 57° C., 60 sec 68° C.) with KTLA DNA polymerase under standard conditions]. A band approximately 1300 bp long was excised and gel purified (QIAquick Gel Extraction). DNA was cloned using a TOPO TA kit (Invitrogen). Candidate clones were sequenced in their entirety with an automated DNA sequencer (such as model 373 from Applied Biosystems, Inc.)

Generation of fad2/*Lesquerella fendleri* Hydroxylase Chimeric cDNA

The same two-round PCR based subcloning strategy was used to generate the fad2/*Lesquerella fendleri* chimeric cDNA. The first round PCR primers were as follows; to amplify the 5' end of the *A. thaliana* fad2, the sense primer Fad-HIIIF (SEQ ID NO: 55) and antisense primer 3'-Fad/les (SEQ ID NO: 60) were used. To amplify the 3' end of the *L. fendleri* bifunctional hydroxylase gene, the sense primer 5'Fad/les primer (SEQ ID NO: 61) and antisense primer Les-SalIR (SEQ ID NO: 62) were used. In the second round of PCR, the sense primer Fad-HIIIF (SEQ ID NO: 55) and antisense primer Les-SalIR (SEQ ID NO: 62) were used to generate the final PCR product fad2/*Lesquerella fendleri* chimeric cDNA.

Generation of fad22/*Lesquerella lindheimeri* Hydroxylase Chimeric cDNA

The same two-round PCR based subcloning strategy was used to generate the fad2/*Lesquerella* lindheimeri chimeric cDNA. The first round of PCR primers were as follows; to amplify the 5' end of the *A. thaliana* fad2, the sense primer Fad-HIIIF (SEQ ID NO: 55) and antisense primer 3'-Fad/lind (SEQ ID NO: 63) were used. To amplify the 3' end of the *L. lindheimeri* bifunctional hydroxylase gene, the sense primer 5'Fad/lind primer (SEQ ID NO: 64) and antisense primer Lind-SalIR (SEQ ID NO: 65) were used. In the second round of PCR, the sense primer Fad-HIIIF (SEQ ID NO: 55) and antisense primer Lind-SalIR (SEQ ID NO: 65) were used to generate the final PCR product fad2/*Lesquerella lindheimeri* chimeric cDNA.

Generation of fad2/*Lesquerella gracilis* A Hydroxylase Chimeric cDNA

The same two-round PCR based subcloning strategy was used to generate the fad2/*Lesquerella* gracilis A chimeric cDNA. The first round of PCR primers were as follows; to amplify the 5' end of the *A. thaliana* fad2, the sense primer Fad-HIIIF (SEQ ID NO: 55) and antisense primer 3'-Fad/grac (SEQ ID NO: 66) were used. To amplify the 3' end of the *L. gracilis* bifunctional hydroxylase gene, the sense primer 5'-Fad/grac primer (SEQ ID NO: 67) and antisense primer Grac-SalIR (SEQ ID NO: 68) were used. In the second round of PCR, the sense primer Fad-HIIIF (SEQ ID NO: 55) and antisense primer Grac-SalIR (SEQ ID NO: 68) were used to generate the final PCR product fad2/*Lesquerella gracilis* A chimeric cDNA.

Generation of fad2/*Crepis biennis* Epoxygenase Chimeric cDNA

The same two-round PCR based subcloning strategy was used to generate the fad2/*Crepis biennis* chimeric cDNA. The first round of PCR primers were as follows; to amplify the 5' end of the *A. thaliana* fad2, the sense primer Fad-HIIIF (SEQ ID NO: 55) and antisense primer 3'-Fad/crep (SEQ ID NO: 69) were used. To amplify the 3' end of the *C. biennis* epoxygenase, the sense primer 5'Fad/crep primer (SEQ ID NO: 70) and antisense primer Crep-SalIR (SEQ ID NO: 71) were used. In the second round of PCR, the sense primer Fad-HIIIF (SEQ ID NO: 55) and antisense primer Crep-SalIR (SEQ ID NO: 71) were used to generate the final PCR product fad2/*Crepis biennis* chimeric cDNA.

EXAMPLE 14

This example describes the construction of eleven (11) synthetic, optimized hydroxylase and epoxygenase sequences.

Five codon-optimized hydroxylase (*Ricinus communis*, HA-tagged *Ricinus communis* and *Lesquerella gracilis*) and epoxygenase (*Stokesia laevis* A and *Crepis biennis*) sequences were constructed as follows. First the 2nd, $3^{rd}$, and 4th codons downstream of the initiation methionine codon were changed to GCT, TCC, and TCC (encoding alanine, serine and serine). Secondly, codons with 8% or lower percentage occurrence in either the *Arabidopsis thaliana, Glycine max, Lycopersicon esculentum* or *Nicotiana tabacum* genomes (e.g., CGG for arginine) were replaced with the most frequent or second most frequent codon for that particular amino acid (e.g., AGA or AGG for arginine). Finally, one member of a contiguous pair of codons was optimized if both codons had an occurrence of 12% or lower in either the *Arabidopsis thaliana, Glycine max, Lycopersicon esculentum* or *Nicotiana tabacum* genomes. Data for the codon optimization process were taken from the codon usage database kazusa.or.jp/codon/ on the World Wide Web).

Codons were also changed to remove ATTTA (i.e., AUUUA) elements which may destabilize mRNAs, to ablate potential polyadenylation sites, and to break up runs of A, G, C or T of five or greater nucleotides (e.g., TTTTT). Codons were also modified to reduce the likelihood of aberrant splicing. Splicing potential was assessed with the NetPlantGene prediction server (http://www.cbs.dtu.dk/services/NetPGene/). Whenever a donor and acceptor existed where both were predicted with greater than 0.9 confidence a codon was mutated to ablate either the donor (GT) or acceptor (AG) sites and thus diminish splicing potential. SEQ ID NOS: 30, 31, 32 and 129 are examples of these optimized sequences.

Additional codon optimized variants of the *Ricinus communis* and *Lesquerella gracilis* hydroxylase and *Crepis biennis, Crepis palaestina* and a second *Stokesia laevis* (*Stokesia laevis* B) epoxgenase gene were made. These additional sequences contained modifications to more closely mimic the most common soybean (*Glycine max*) codons. The 2nd, $3^{rd}$, and 4th codons downstream of the initiation methionine codon were changed to GCT, TCC, and TCC (encoding alanine, serine and serine). Codons were also changed to remove ATTTA (i.e., AUUUA) elements which may destabilize mRNAs, to ablate potential polyadenylation sites, and to break up runs of A, G, C or T of five or greater nucleotides (e.g., TTTTT). Codons were also modified to reduce the likelihood of aberrant splicing. Splicing potential was assessed with the NetPlantGene prediction server cbs.dtu.dk/services/NetPGene/ on the World Wide Web). Whenever a donor and acceptor existed where both were predicted with greater than 0.9 confidence a codon was mutated to ablate either the donor (GT) or acceptor (AG) sites and thus diminish splicing potential. Data for codon optimization procedures were taken from the codon usage database kazusa.or.jp/codon/ on the World Wide web). SEQ ID Nos.: 28, 29, 130, 131, 132 and 133 are examples of such optimized *R. communis, S. laevis* A, *C. palaestina, S. laevis* B, *C. biennis* and *L. gracilis* genes, respectively.

EXAMPLE 15

This example describes the expression of hydroxylase, bifunctional hydroxylase and epoxygenase polypeptides in *Saccharomyces cerevisiae* and analysis of the fatty acid profiles in yeast by GC-MS.

Yeast Stains, Media, and Culture Conditions

*Saccharomyces cerevisiae* strains YPH499 (MATa ura3-52 lys2-801 ase2-101 trp1-Δ63 his3-Δ2000 leu2-Δ1) and INVsc1 (MATa his3-Δ1 leu2 trp1-289 ura3-52/MATα his3 μl leu2 trp1-289 ura3-52) were used throughout these studies.

Plasmid for Yeast Transformation

The plasmid pYES2 (Invitrogen) was used to transform yeast strains. The plasmid contains an *E. coli* replication origin, a yeast plasmid replication origin, an *E. coli* ampicillin resistance gene and the yeast gene URA3. It utilizes an expression cassette including a galactose-inducible promoter (GAL-1).

Cloning Genes of Interest into Yeast Expression Vector pYES2

Modification of the *R. communis* hydroxylase and *L. gracilis* bifunctional genomic clones were performed by PCR amplification using specific primers.

*Ricinus communis* hydroxylase: The following specific primers were designed to introduce a Kozak consensus sequence and a HindIII restriction site immediately upstream of the initiation codon and a BamH1 site immediately downstream of the stop codon: Direct primer: 5'-CastorhindIII-k (SEQ ID NO: 72) and Reverse primer: 3'CastorBamHI. (SEQ ID NO: 73). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII and BamH1 and subsequently cloned into HindIII, BamH1 of pYES2 yeast expression vector.

*Ricinus communis* hydroxylase with a C-terminal HA tag: The following specific primers were designed to introduce a Kozak consensus sequence and a HindIII site immediately upstream of the start codon and a NotI site and HA tag immediately before the stop codon: Direct primer: 5'-castorhindIII-k (SEQ ID NO: 72), and the Reverse primer: 5'-castor-HANOTI (SEQ ID NO: 74). The hydroxylase with a C-terminal HA tag was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII and NotI and subsequently cloned into the HindIII, NotI sites of the pYES2 expression vector.

*Ricinus communis* hydroxylase with a N-terminal HA tag: The following primers were designed for construction of a *Ricinus communis* hydroxylase with a N-terminal HA tag, Direct primer: BamHI castor F (SEQ ID NO: 104), and Reverse primer: castor XbaI MfeI R(SEQ ID NO: 98). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with BamHI/MfeI and subcloned into the BamHI/EcoRI sites of the pUC-HA vector. The hydroxylase plus the N-terminal HA tag was then subcloned (HindIII/XbaI) into the yeast expression vector pYES2.

*Lesquerella lindheimeri* bifunctional enzyme: The following specific primers were designed to introduce a Kozak consensus sequence and a HindIII restriction site immediately upstream of the initiation codon and a BamH1 site immediately downstream of the stop codon: Direct primer: 5'-fendhindIII-K (SEQ ID NO: 75), and Reverse primer: 3'-fendBamHI (SEQ ID NO: 76). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII, BamH1 and cloned into the HindIII, BamH1 of pYES2 yeast expression vector.

*Lesquerella lindheimeri* bifunctional enzyme with a N-terminal HA tag: The following specific primers were designed to introduce a Kozak consensus sequence and a HindIII site immediately upstream of the HA tag and a BamH1 site immediately before the stop codon: Direct primer 5'-HindIIIK/HA/fend (SEQ ID NO: 77), and Reverse primer: 3'-fendBamHI (SEQ ID NO: 76). The hydroxylase with a N-terminal HA tag was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII and BamH1 and subsequently cloned into HindIII, BamH1 of pYES2 expression vector.

*Lesquerella gracilis* bifunctional enzyme: The following specific primers were designed to introduce a Kozak consensus sequence: Direct primer: HIII NcoI gracilis F (SEQ ID NO: 102), and Reverse primer: gracilis XbaI MfeI R (SEQ ID NO: 101). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII, XbaI and cloned into the HindIII, XbaI of pYES2 yeast expression vector.

ΔT *Lesquerella gracilis* bifunctional enzyme: The following specific primers were designed to introduce a Kozak consensus sequence: Direct primer: HIII NcoI *gracilis* F (SEQ ID NO: 102), and Reverse primer: gracilis XbaI MfeI R (SEQ ID NO: 101). The ΔT*L.gracilis* hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII, XbaI and cloned into the HindIII, XbaI of pYES2 yeast expression vector.

ΔKKGG *Ricinus communis* hydroxylase: The following specific primers were designed to introduce a Kozak consensus sequence: Direct primer: HIII NcoI castor F (SEQ ID NO: 99), and Reverse primer: castor XbaI MfeI R (SEQ ID NO: 98). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII, XbaI and cloned into the HindIII, XbaI of pYES2 yeast expression vector.

*Crepis biennis* epoxygenase enzyme: The following specific primers were designed to introduce a Kozak consensus sequence: Direct primer: HIII NcoI *C. biennis* F (SEQ ID NO: 123), and Reverse primer: *Crepis* XbaI MfeI R (SEQ ID NO: 103). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with HindIII, XbaI and cloned into the HindIII, XbaI of pYES2 yeast expression vector.

*Stokesia laevis* epoxygenase enzyme: The following Specific primers were designed to introduce a Kozak consensus sequence: Direct primer: BamHI NcoI S. epoxygenase F (SEQ ID NO: 106), and Reverse primer: S. epoxygenase XbaI R (SEQ ID NO: 107). The hydroxylase was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with BamHI, XbaI and cloned into the BamHI, XbaI of pYES2 yeast expression vector.

Nucleotide Sequence Determination

Sequencing of the *R. communis* hydroxylase, *R. communis* hydroxylase with N-terminal HA tag, *R. communis* hydroxylase with C-terminal HA tag, *L. lindheimeri* bifunctional enzyme, L. lindheimeri bifunctional enzyme with N-terminal HA tag, ΔT *L. gracilis*, and ΔKKGG *R. communis* hydroxylase were performed using an automated sequencer (such as model 373 from Applied Biosystems, Inc.) using processes well known to those skilled in the art.

Transformation of Yeast

Transformation was preformed according to the Invitrogen pYES2 kit (V825-20). A fresh yeast culture (initial absorbance=0.4) was grown in YPD medium for 4 hours. The cells were collected and washed once in 1×TE and resuspended in 2 mL of 1× LiAc/0.5× TE (100 mm lithium acetate pH 7.5, 5 nm tris-HCL pH 7.5, 0.5 mm EDTA). 100 μg of denatured herring sperm DNA was added as a DNA carrier to 1 μg of the plasmid DNA. 100 μL of competent yeast and 700 μL of 1XliAc/40% PEG-3350/1×TE (100 mM lithium acetate pH 7.5, 40% PEG-3350, 10 mM tris-HCL pH 7.5, 1 mM EDTA) were added. The mixture was incubated at 30° C. for 30 min. 88 μL of DMSO was added and the mixture was incubated at 42° C. for 7 min. After centrifugation, the cells were resuspended in 1×TE (100 uL) and plated on minimum medium containing suitable supplements.

Over Expression of Genes of Interest in Yeast

Yeast strains transformed with pYES2 plasmid, harboring either no insert or the genes for hydroxylase or bifunctional enzymes were grown at the same time. For ricinoleic acid analysis, transformed cells were grown in SC-URA (yeast synthetic complete media devoid uracil, Sigma) supplemented with 2% glucose and 1% casamino acids at 30° C. to an optical density (600 nm) of 2.5. Cells were then centrifuged, washed 3 times in SC-URA media containing no glucose and cultured for 48 hours at 30° C. on SC-URA media (yeast synthetic complete media devoid of uracil, Sigma) supplemented with 2% galactose and 1% casamino acids. Cultures were centrifuged and dried.

Fatty Acid Analysis of Yeast Extracts

Dried yeast pellets were methylated with (400 μL 1% sodium methoxide in methanol), extracted with hexane, and trimethylsilylated (100 μL BSTAFA-TMCS, Supelco, 90° C. for 45 minutes). Samples were analyzed on an Agilent 6890 GC-5973 Mass Selective Detector (GC/MS) and an Agilent DB-23 capillary column (0.25 mm×30 m×0.25 um). The injector was held at 250° C., the oven temperature was 235° C., and a helium flow of 1.0 mL/min was maintained.

Table 9 shows examples of MS data from yeast expressing some of the enzymes described in Example 13.

TABLE 9

*Ricinus communis* hydroxylase with or without an N-terminal HA tag:

| Construct | % R |
|---|---|
| 3522 | 6.7 |
| 3522 | 4.1 |
| 3522 | 4.8 |
| 3522 | 9.5 |
| 3522 | 4.6 |
| 4074* | 2.1 |
| 4074* | 3.0 |
| 4074* | 5.3 |
| 4074* | 3.2 |

*Designates a construct carrying an N-terminal HA tag.

These GC/MS data indicate that the hydroxylase from *R. communis* (3522 or 4074*) was functional when expressed in yeast. The percentages of ricinoleic acid (% R) listed in the table are percentages of the total fatty acid.

TABLE 10

*L. gracilis* bifunctional hydroxylase expressed in yeast

| Construct | % R |
|---|---|
| 3958 | 8.0 |
| 3958 | 8.2 |
| 3958 | 13.1 |
| 3958 | 12.2 |
| 3958 | 10.7 |
| 3958 | 9.2 |
| 3958 | 6.3 |

These GC/MC data indicate that the hydroxylase from *L. gracilus* (3958) was functional when expressed in yeast. The percentages of ricinoleic acid (% R) listed in the table are percentages of the total fatty acid.

TABLE 11

ΔT *Lesquerella gracilis* bifunctional hydroxylase expressed in yeast

| Construct | % R |
|---|---|
| 4323 | 5.9 |
| 4323 | 5.9 |
| 4323 | 8.2 |
| 4323 | 7.2 |
| 4323 | 7.4 |

These GC/MS data indicate that the hydroxylase from *L. gracilis* was functional when expressed in yeast despite the deletion of amino acid 83. The percentages of ricinoleic acid (% R) listed in the table are percentages of the total fatty acid.

TABLE 12

ΔKKGG castor hydroxylase expressed in yeast

| Construct | % R |
|---|---|
| 4303 | 0.7 |
| 4303 | 1.4 |
| 4303 | 1.5 |
| 4303 | 1.3 |
| 4303 | 1.5 |

These GC/MS data indicate that the deletion mutant hydroxylase (ΔKKGG) from *R. communis* was functional when expressed in yeast despite the amino acid deletions at positions 18-21. The percentages of ricinoleic acid (% R) listed in the table are a percentage of the total fatty acid.

TABLE 13

Negative Control

| Construct | % R | % O |
|---|---|---|
| 3677 | 0 | 35.8 |
| 3677 | 0 | 34.71 |
| 3677 | 0 | 36.34 |
| 3677 | 0 | 30.87 |
| 3677 | 0 | 30.16 |

These GC/MS data indicate that no detectable amounts of ricinoleic acid were produced when the vector with no insert was expressed in yeast. The percentages of ricinoleic (% R) and oleic acid (% O) listed in the table are percentage of the total fatty acid.

EXAMPLE 16

Figure 4:
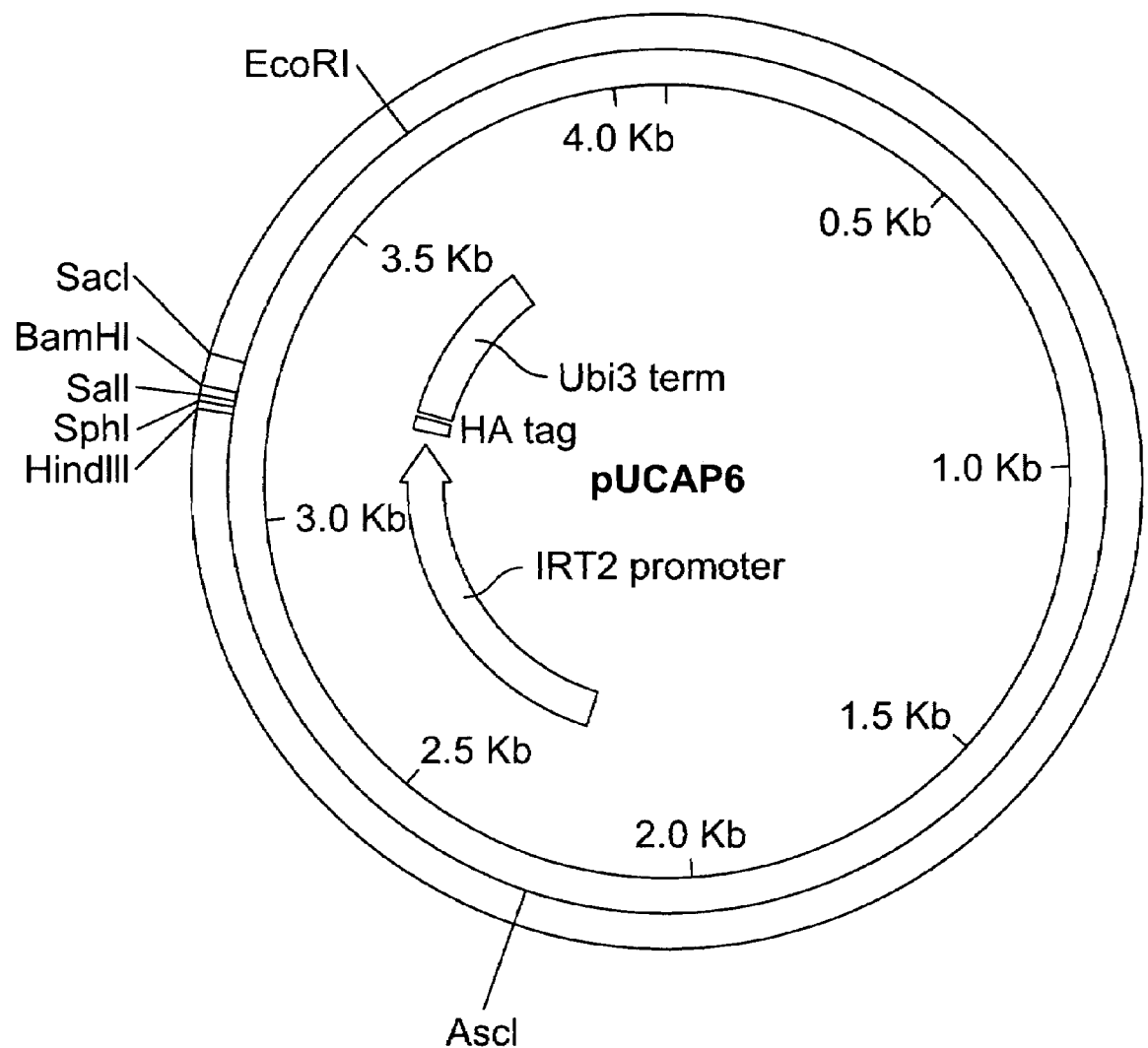
FIG. 4 is a schematic representation of the plasmid pUCAP6.
Figure 5:
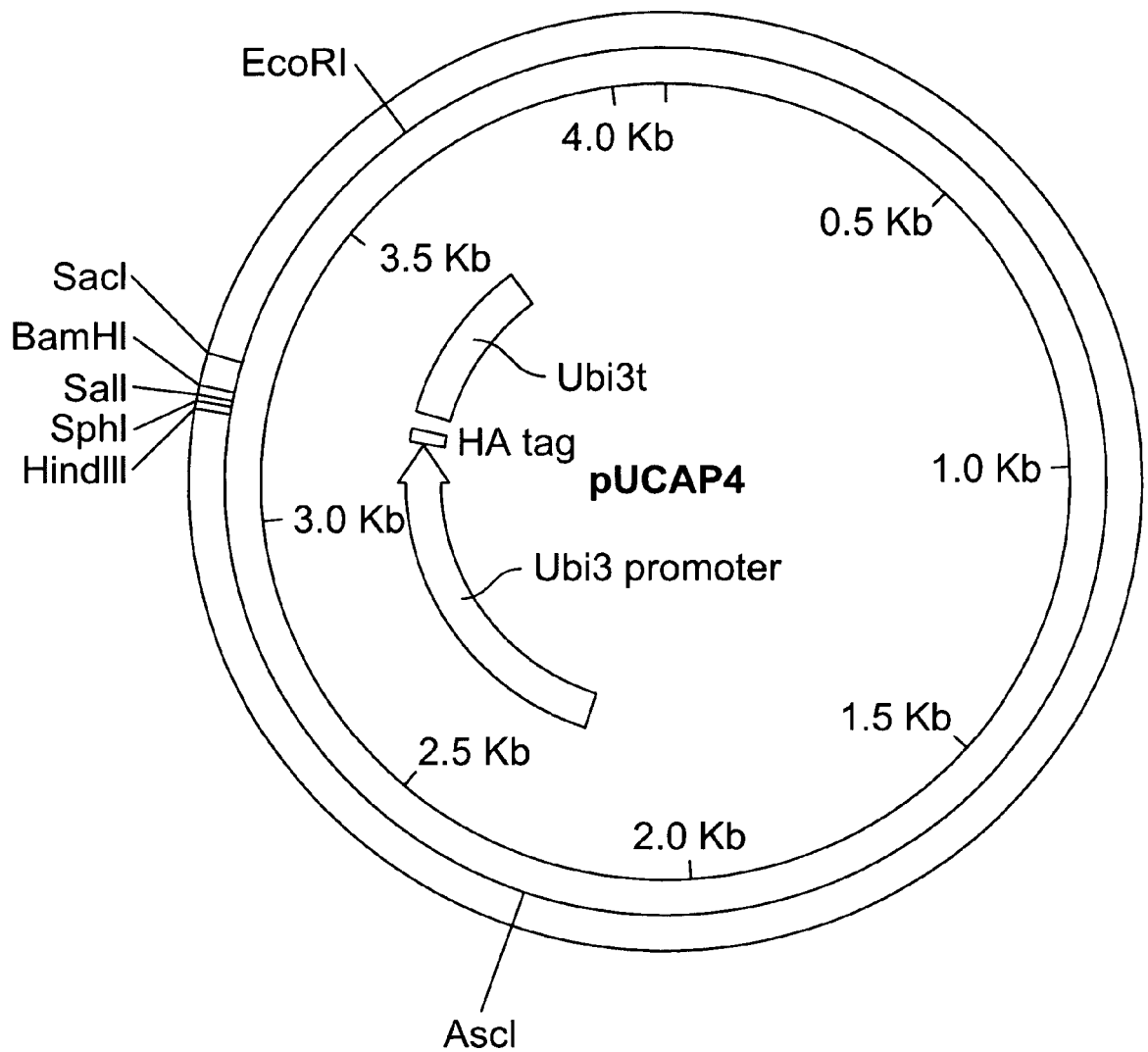
FIG. 5 is a schematic representation of the plasmid pUCAP4.
Figure 6:
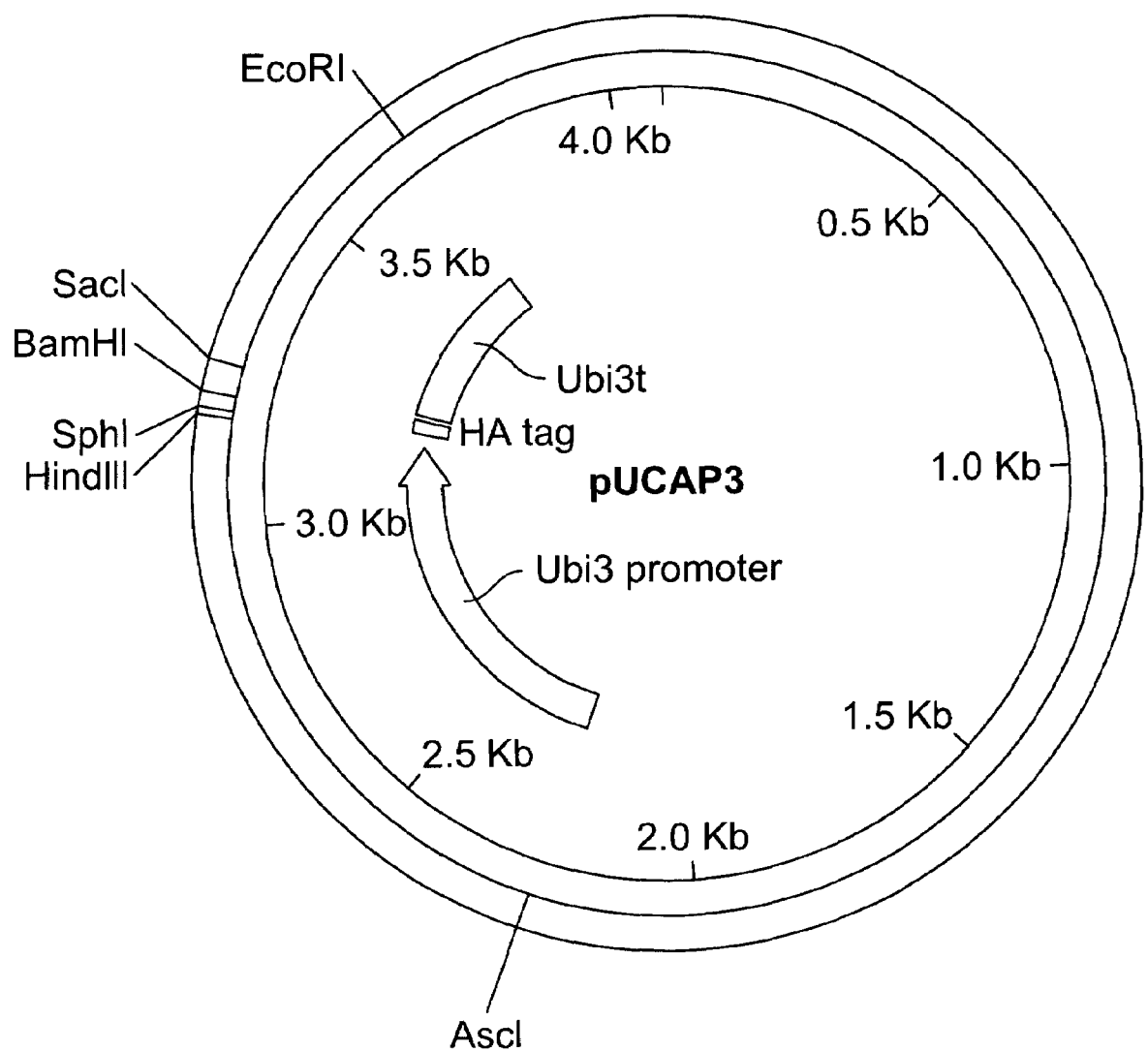
FIG. 6 is a schematic representation of the plasmid pUCAP3.

This example describes the construction of vectors suitable for expression in plants. Schematic diagrams of the vectors are shown in FIGS. 4-6.

Generation of Transgenic Vectors: Building Modified pUCAP Vectors

The pUCAP vector [Engelen et al. (1995) *Transgenic Res.* 4(4): 288-290] was modified to create pUCAP2, pUCAP3, pUCAP4, pUCAP5, and pUCAP6.

The following specific primers were designed to introduce a 5'-SacI and a 3'-EcoRI site flanking the Ubi3 terminator: Direct primer: UT3 (SEQ ID NO: 78), and Reverse primer: UT4 (SEQ ID NO: 79). The Ubi3 terminator was amplified from pBinplus [Engelen et al. (1995) *Transgenic Res.* 4(4): 288-290] by PCR [25 cycles (4 min 94° C., 30 sec 60° C., 1 min 68° C.) with KTLA DNA polymerase under standard conditions]. The PCR product was digested with SacI and EcoRI and subsequently cloned into pUCAP to give pUCAP1.

The following specific primers were designed to introduce a 5'-AscI and a 3'-SphI site flanking the Ubi 3 promoter: Direct primer: UP1 (SEQ ID NO: 80), and Reverse primer: UP2 (SEQ ID NO: 81). The Ubi3 promoter was amplified from pBinplus [Engelen et al. (1995) *Transgenic Res.* 4(4): 288-290] by PCR [25 cycles (4 min 94° C., 30 sec 60° C., 1 min 68° C.) with KTLA DNA polymerase under standard conditions]. The PCR product was digested with AscI and SphI and subsequently cloned into the AscI/SphI sites of pUCAP1 giving pUCAP2.

The following specific oligos were designed to create an HA tag with a BamH1 overhang immediately before the initiation codon and a SacI overhang immediately after the last codon of the tag: Direct oligo: CHA1 (SEQ ID NO: 84), and Reverse oligo: CHA2 (SEQ ID NO: 85). The HA tag was created by annealing oligos (0.1 pg/uL) at 92° C. for 3 minutes and slowly bringing to room temperature. The HA tag was cloned into the BamHI/SacI sites of pUCAP2 to create pUCAP3. DNA cloned into the MCS of pUCAP3 will have the HA tag at the C-terminus.

The following specific oligos were designed to create an HA tag with a HindIII overhang immediately before the initiation codon and a SalI overhang immediately after the last codon of the tag: Direct oligo: HA5 (SEQ ID NO: 82), and Reverse oligo: HA6 (SEQ ID NO: 83). The HA tag was created by annealing oligos (0.1 pg/uL) at 92° C. for 3 minutes and slowly bringing to room temperature. The HA tag was cloned into the HindIII/SalI site of pUCAP2 to create pUCAP4. DNA cloned into the MCS of pUCAP4 will have the HA tag at the N-terminus.

The following specific primers were designed to add a 5'-AscI site and a 3'-SphI site flanking the *A. thaliana* IRT2 promoter to AscI and SphI of pUCAP1: Direct primer: IRT1 (SEQ ID NO: 86), and Reverse primer: IRT2 (SEQ ID NO: 87). The IRT2 promoter was amplified from *Arabidopsis thaliana* using a 30 cycle Gradient PCR [(4 min 95° C., 30 sec 48-63° C., 2 min 68° C.) with KTLA DNA polymerase under standard conditions]. The PCR product was digested with AscI/SphI and AscI/SphI cloned into of pUCAP1 giving pUCAP5.

pUCAP6 was created by replacing the Ubi3 promoter of pUCAP3 with the IRT2 promoter, using the AscI/SphI sites.

Generation of a Vector Containing the HA-tag for N-terminal Fusions.

The oligonucleotides HA-tag-F (SEQ ID NO: 109) and HA-tag-R (SEQ ID NO: 110) were mixed and annealed using standard procedures. The annealed product generates compatible ends for HindIII and BamHI restriction sites and was cloned into the plasmid vector pUC 118, generating the plasmid pUC-HA.

Plant Transformation Vector Containing the 5' UTR and 3' UTR Regions of the fad2 Gene from *A. thaliana*.

*A. thaliana* genomic DNA was used as template and KTLA was the DNA polymerase of choice For PCR. Primers Fad5'UTR-F (SEQ ID NO: 111) and Fad5'UTR-R (SEQ ID NO: 112) were used to PCR amplify the 5' UTR, first intron and first codon of fad2, flanked by the restriction sites XhoI at the 5' end and NcoI, BamHI at the 3' end. PCR reactions were performed under standard conditions as follow: 97° C. for 30 sec, 35 cycles of amplification (45 sec at 94° C., 1 min at 55° C., 90 sec at 72° C.) and a final extension of 5 min at 72° C. The PCR product was cloned into the plasmid vector pCR2.1 (Invitrogen).

Primers Fad3'UTR-F (SEQ ID NO: 113) and Fad3'UTR-R (SEQ ID NO: 114) were used to PCR amplify the 3' UTR of fad2. Reactions were performed as follow: 97 C for 10 sec and 35 cycles of amplification (30 sec at 94° C., 1 min at 60° C., 2.5 min at 72° C.). The PCR product was cloned into the plasmid vector pCR2.1. The identities of both PCR products, fad2 5' UTR (SEQ ID NO: 44) and Fad2 3' UTR (SEQ ID NO: 45) were confirmed by DNA sequencing.

The plant transformation vector containing both fad2 UTR regions was constructed in two steps: first, the fad2 5' UTR fragment was subcloned immediately downstream of the CaMV35S promoter of a binary vector as a XhoI/BamHI insert. Then, the *A. tumefaciens* NOS 3' UTR present in the plasmid between the XbaI and HindIII restriction sites was replaced with the *A. thaliana* fad2 3'UTR fragment, between the same sites, generating a plasmid called pFADUTR.

Cloning Hydroxylase and Bifunctional Hydroxylase Genes into pUCAP3, pUCAP4 and pUCAP6

*R. communis* hydroxylase and *L. lindheimeri* bifunctional hydroxylase genomic clones were generated by PCR amplification using specific primers.

*Ricinus communis* hydroxylase with a C-terminal HA tag: The following specific primers were designed to introduce a HindIII site immediately upstream of the initiation codon and a BamHI site immediately before stop codon: Direct primer: Castor 5'-HindIII (SEQ ID NO: 88), and Reverse primer: Castor 3'-BamHI (SEQ ID NO: 89). The hydroxylase was amplified by PCR [5 cycles (4 min 94° C., 45 sec 94° C., 50° C. 45 sec, 72° C.) and then 25 cycles (45 sec 94° C., 45 sec 58° C., 2 min 72° C.) with KTLA under standard conditions]. The PCR product was digested with HindIII and BamH1 and subsequently cloned into HindIII, BamH1 of pUCAP3 expression vector giving Rc-pUCAP3.

*Ricinus communis* hydroxylase with a N-terminal HA tag: The following primers were designed in order to tag the *Ricinus communis* hydroxylase with a N-terminal HA tag: Direct primer: BamHI castor F (SEQ ID NO: 104), and Reverse primer: castor XbaI MfeI R (SEQ ID NO: 98). The hydroxylase gene was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with BamHI/MfeI and subcloned into the BamHI/EcoRI sites of the pUC-HA vector.

*Lesquerella lindheimeri* bifunctional enzyme with an N-terminal HA tag: The following specific primers were designed to introduce a SalI site immediately upstream of the start codon and BamH1 site immediately after the stop codon: Direct primer fend F SalI (SEQ ID NO: 90), and Reverse primer: Fend R B-stop. (SEQ ID NO: 91). The bi-functional hydroxylase gene was amplified by PCR [5 cycles (4 min 94° C., 45 sec 94° C., 45 sec 50° C., 2 min 72° C.) and then 25 cycles (45 sec 94° C., 45 sec 58° C., 2 min 72° C.) with KTLA DNA polymerase under standard conditions]. The PCR product was digested with SalI and BamH1 subsequently cloned into SalI/BamH1 of pUCAP4 giving Rc-pUCAP4.

*L. gracilis* bifunctional hydroxylase with a N-terminal HA tag: The following primers were designed in order to tag the *L. gracilis* bifunctional hydroxylase with a N-terminal HA tag, Direct primer: BamHI gracilis F (SEQ ID NO: 105), and Reverse primer: gracilis XbaI MfeI R (SEQ ID NO: 101). The hydroxylase gene was amplified by PCR [5 thermal cycles (1 min, 92° C., 30 sec 50° C., 1.5 min 68° C.) and then 25 thermal cycles (1 min, 92° C., 30 sec 57° C., 1.5 min 68° C.) with KTLA DNA polymerase under standard conditions]. The PCR product was digested with BamHI/MfeI and subcloned into the BamHI/EcoRI sites of the pUC-HA vector.

The *Crepis biennis* and *Stokesia laevis* epoxygenase genes were subcloned as described above into the pUC-HA vector using BglII NcoI *C. biennis* F (SEQ ID NO: 108)/Crepis XbaI MfeI R (SEQ ID NO: 103) and BamHI NcoI S. epoxygenase F (SEQ ID NO: 106)/S. epoxygenase XbaI R (SEQ ID NO:107).

The *Crepis biennis* and *Stokesia laevis* epoxygenase genes lacking the HA sequence were subcloned as described above into a plant expression vector using AscI NcoI *C. biennis* F (SEQ ID NO: 124)/Crepis XbaI MfeI R (SEQ ID NO: 103) and BamHI NcoI S. epoxygenase F (SEQ ID NO: 106)/S. epoxygenase XbaI R (SEQ ID NO:107).

Plant Expression Vectors

Constructs Rc-pUCAP3, L1-pUCAP4, and Rc-pUCAP6 were digested with AscI and PacI to release the inserts and inserts were subsequently sub-cloned into the AscI/PacI sites of pBinPlusARS binary vector engineered as described by [Engelen et al. (1995) *Transgenic Res.* 4(4): 288-290] giving Rc-3pBinPlusARS, L14-pBinPlusARS and Rc6-pBinPlusARS.

ΔKKGG castor, ΔT gracilis, *R. communis* hydroxylase, chimeric fad2/*R. communis* hydroxylase, *L. gracilis* bifunctional hydroxylase, chimeric fad2/*L. gracilis* bifunctional hydroxylase, *C. biennis* epoxygenase, and *S. laevis* epoxygenase genes were subcloned into a plant expression vector using NcoI/XbaI restriction enzyme sites. N-terminal HA tagged chimeric fad2/*R. communis* hydroxylase and N-terminal chimeric fad2/*R. communis* hydroxylase were removed from pUC-HA and subcloned into a plant expression vector using NcoI/XbaI restriction enzyme sites. The above constructs were also subcloned into a plant expression vector containing the fad2 5'UTR and fad2 3'UTR (pFADUTR), using the NcoI/XbaI restriction sites.

EXAMPLE 17

This example describes the production of transgenic *Arabidopsis* plants, transgenic tomato callus, transgenic tomato hairy roots, *Arabidopsis* hairy root, soybean hairy root, and soybean composite plants using the plasmid vectors described in Example 16.

Transformation of *Agrobacterium tumefaciens* and *Agrobacterium rhizogenes*

Plant expression vectors harboring genes encoding hydroxylases, epoxygenases or chimeric fad2 constructs were transformed into *Agrobacterium tumefaciens* LB4404 as follows. *Agrobacterium* was grown overnight in 100 mL of LB [(1% bacto tryptone, 0.5% sodium chloride and 0.5% bacto-yeast extract) supplemented with kanamycin (50 ug/mL), rifampicin (10 ug/mL), and streptomycin (150 ug/mL)]. 100 mL of LB supplemented in the same manner was inoculated with 1 mL of the overnight culture and grown at 30° C. for 4 hrs. The culture was chilled for 10 minutes and cells were harvested by centrifugation. Cells were resuspended in 1 mL of ice cold $CaCl_2$ (20 mM) and dispensed into 100 µL aliquots. 1 µg of plasmid DNA was added to the cells, frozen on dry ice, put at 37° C. for 5 minutes, and shaken for 90 minutes at 30° C. in 1 mL LB. Cells were pelleted and resuspended in 100 µL of LB and plated on LB plates [(1% bacto tryptone, 0.5% sodium chloride, 0.5% bacto-yeast extract, and 0.15% agar) supplemented with kanamycin (50 ug/mL), rifampicin (10 ug/mL), and streptomycin (150 ug/mL)].

Transformation of *Agrobacterium rhizogenes* strain A4 was performed in the same manner as *Agrobacterium tumefaciens* strain LB4404 with the following exceptions: Media used was MGL [extract (2.5 g/L), tryptone (5 g/L), sodium chloride (5 g/L), L-glutamic acid (1 g/L), mannitol (5 g/L), potassium phosphate (0.26 g/L), magnesium sulfate heptahydrate (100 mg/L), and biotin (1 mg/L)] and MGL plates [yeast extract (2.5 g/L), tryptone (5 g/L), sodium chloride (5 g/L), L-glutamic acid (1 g/L), mannitol (5 g/L), potassium phosphate (0.26 g/L), magnesium sulfate heptahydrate (100 mg/L), biotin (1 mg/L), and bacto-agar (14 g/L)].

Plant Transformation

*Arabidopsis thaliana* was transformed via *Agrobacterium tumefaciens* following Clough and Bent [Clough & Bent (1998) *Plant J* 19(3): 249-257]. Briefly, 5 mL overnight cultures of transformed LB4404 (LB-10 ug/mL rifampicin, 50 ug/mL kanamycin, 150 µg/mL streptomycin) were grown at 30° C. The 5 mL cultures were used to inoculate 500 mL LB (10 µg/mL rifampicin, 50 µg/mL kanamycin, 150 ug/mL streptomycin) and grown overnight at 30° C. Cultures were spun down (5K, 5 min). Pellets were resuspended in 5% glucose+0.02% Silwet L-77. The above ground parts of the plant were submerged into *Agrobacterium* solution for 5 min with gentle agitation. Plants were covered under a dome overnight.

Fatty Acid Analysis of *Arabidopsis thaliana* Leaf and Root Tissue

Generation of Plant Material

Seed sterilization: Approximately 200 second generation seeds from transformed plants were placed in an eppendorf tube. 1 mL of 20% bleach in ethanol was added and the tubes were left at room temperature for 15 minutes. The seeds were then washed 2× with 100% ethanol and opened tubes were left in the laminar flow hood to dry overnight.

Seed Germination: Approximately 50 seeds were placed on 0.5×MS plates, wrapped in parafilm, and kept at room temperature until germination.

Approximately 0.10 g of root tissue or leaf tissue was put in a 1.5 mL eppendorf tube and frozen on dry ice and subsequently ground with a pestle. The ground root tissue was then methylated with (500 µL 1% sodium methoxide in methanol), extracted with hexane, and trimethylsilylated (100 µL BSTAFA-TMCS, Supelco, 90° C. for 45 minutes). Samples were analyzed on an Agilent 6890 GC-5973 Mass Selective Detector (GC/MS) and an Agilent DB-23 capillary column (0.25 mm×30 m×0.25 um). The injector was held at 250° C., the oven temperature was 235° C., and a helium flow of 1.0 mL/min was maintained.

TABLE 14

Fatty Acid Analysis of extracts from *Arabidopsis thaliana* harboring a chimeric fad2/*R. communis* hydroxylase

| Tissue | Construct | Line | % R | % L | % O |
|---|---|---|---|---|---|
| Leaves | 4028* | 6 | 1.19 | 15.82 | 1.87 |
| Leaves | 4028* | 6 | 1.11 | 15.22 | 2.02 |
| Roots | 4028* | 6 | 0.54 | 25.52 | 0.61 |
| Roots | 4028* | 6 | 0.10 | 22.24 | 0.73 |
| Roots | 4062 | 3 | 1.44 | 21.18 | 5.09 |
| Roots | 3819 | — | 0 | 21.54 | 1.96 |

*Designates constructs with a HA tag on the N-terminus.

These GC/MS data indicate that a chimeric fad2/*R. communis* hydroxylase (4062 or 4028*) operably linked to 5' and 3' fad2 UTRs was functional when expressed in *A. thaliana*. The percentages of ricinoleic acid listed in the table are a percentage of the total fatty acid. *A. thaliana* transformed with a vector containing no insert (3819), did not accumulate ricinoleic acid (R).

Hairy Root Transformation Protocol for Tomato

Plant material preparation: This protocol can be used for tomato root transformation. Numerous strains of *A. rhizogenes* may be used as the transforming agent, however, strain A4 (ATCC number 43057) was used in this case. *Lycopersicon esculentum* cv. Rutgers, Money Maker or Mountain Spring, were used, although other varieties that are susceptible to *Meloidogyne incognita* (*M. incognita*) infection may be used. As a control, the resistant cultivar Motelle was used [Vos et al. (1998) *Nat. Biotechnol.* 16: 1365-1369]. This protocol can also be used to generate hairy root cultures from *Arabidopsis thaliana*, ecotype Columbia.

The transformation protocol is similar to that described previously [McCormick (1991) Transformation of tomato with *Agrobacterium tumefaciens*. in Plant Tissue Culture Manual, Fundamentals and Applications, K. Lindsey (ed), Kluwer, Vol. B6: 1-9]. Briefly, tomato seeds were sterilized with hypochlorite and grown in magenta boxes containing Gamborg's synthetic medium [Gamborg et al. (1968) *Exp. Cell Res.* 50: 151-158] in daylight for 7 days, until cotyledons are completely unfolded. Cotyledons were removed sterilely and wounded in MSO medium (MS salts, 3% sucrose, Gamborg's B5 vitamins, pH 5.8) by removing both the proximal and distal tips with a razor blade. Wounded cotyledons were incubated for 1-2 days, adaxial side up, on filter paper placed on 150 mm² plates made with D1 medium (MS salts, 3% glucose, Gamborg's B5 vitamins, 1 mg/L zeatin, 0.8% Gel-rite agar). After this incubation period, cotyledons were cocultured with a suspension of *A. rhizogenes* to initiate transformation.

*A. rhizozenes* culture preparation: A glycerol stock of *A. rhizogenes* A4 was streaked onto MGL medium [McCormick (1991) Transformation of tomato with *Agrobacterium tumefaciens*. in Plant Tissue Culture Manual, Fundamentals and Applications, K. Lindsey (ed), Kluwer, Volume B6: 1-9] and grown at 29° C. until individual colonies appeared. A single colony was used to inoculate a 15 mL culture of MGL medium, which was grown for one day in a shaking incubator at 29° C., 100 rpm. On the following day, the bacteria were harvested by centrifugation at 3800×g for 10 minutes. The resulting pellet was washed twice, without disturbing the pellet, with 15 mL of MSO medium and centrifuging at 3800×g for 5 minutes. The final pellet was resuspended in 15 mL MSO medium and the optical density of the culture at 550 nm was determined. The density was adjusted to 0.4 with MSO medium. 10 mL of this culture was used for cocultivation after the addition of 50 μL of 0.074 M acetosyringone. Cocultivation was performed within one hour of the addition of acetosyringone.

Cocultivation of tomato cotyledons and *A. rhizogenes*: Onto each plate of cotyledons, 5 mL of *A. rhizogenes* culture was pipetted over the preincubated cotyledons using sterile technique. The plates were incubated at room temperature for 10 minutes, with occasional swirling of plates during this time. The bacterial suspension was then removed with a sterile pipette. The cotyledons were transferred gently, abaxial side up, using a scalpel or razor blade, to a new 100×20 mm Petri plate containing a Whatman filter paper disk on D1 medium. The plates were sealed with micropore tape and incubated for 2 days at room temperature near a south facing window.

Selection of transgenic roots: After cocultivation, the cotyledons were transferred, abaxial side up onto Gamborg's medium containing 200 mg/L cefotaxime at a density of 20-30 cotyledons per plate. The plates were sealed with micropore tape and incubated at room temperature in the dark for 10 days. On the 10$^{th}$ day, the cotyledons were transferred to fresh selective media plate. After an additional 10 day period, hairy root initials were removed from the cotyledons using a sterile razor blade and incubated on selective medium with transfer to fresh plates after 10 days. To assess whether the hairy roots were cured of infection by *A. rhizogenes*, the roots were transferred to Gamborg's medium without cefotaxime and allowed to grow for 10 days. Any plates showing bacterial growth around the roots were discarded.

Root cultures were maintained on Gamborg's medium lacking selection by serial transfer every 20-30 days.

Fatty Acid Analysis of Tomato Hairy Root Extracts

Approximately 0.25 g of root tissue was placed in a 1.5 mL eppendorf tube and frozen on dry ice and subsequently ground with a pestle. The ground root tissue was then methylated with (500 μL 1% sodium methoxide in methanol), extracted with hexane, and trimethylsilylated (100 μL BSTAFA-TMCS, Supelco, 90° C. for 45 minutes). Samples were analyzed on an Agilent 6890 GC-5973 Mass Selective Detector (GC/MS) and an Agilent DB-23 capillary column (0.25 mm×30 m×0.25 um). The injector was held at 250° C., the oven temperature was 235° C., and a helium flow of 1.0 mL/min was maintained.

TABLE 15

Fatty Acid Analysis of tomato roots harboring a *R. communis* hydroxylase

| Construct | Line | % R | % L | % O | Temp | Cultivar |
|---|---|---|---|---|---|---|
| 4203 | 7 | 1.637 | 50.54 | 0.94 | 23 | Money Maker |
| 4203 | 7 | 1.17 | 50.48 | 1.20 | 23 | Money Maker |
| 4203 | 16 | 1.29 | 55.67 | 0.00 | 23 | Money Maker |
| 4203 | 16 | 1.07 | 52.04 | 1.89 | 23 | Money Maker |
| 4203 | 15 | 1.21 | 53.66 | 1.25 | 23 | Money Maker |
| 4203 | 15 | 0.91 | 51.57 | 1.63 | 23 | Money Maker |
| 3677 | 19 | 0 | 47.06 | 0.00 | 23 | Money Maker |

These GC/MS data indicate that a *R. communis* (4203) hydroxylase was functional when expressed in tomato hairy root tissue. The percentages of ricinoleic acid (% R) listed in the table are percentages of the total fatty acid. Tomato hairy roots transformed with a vector containing no insert (3677), did not accumulate ricinoleic acid (R). Linoleic and oleic acid percentages are listed under the columns % L and % O, respectively.

TABLE 16

Fatty Acid Analysis of tomato roots harboring a chimeric fad2/R. communis hydroxylase

| Construct | Line | % R | % L | % O | Temp | Cultivar |
|---|---|---|---|---|---|---|
| 3927 | 7 | 2.81 | 49.02 | 2.05 | 23 | Rutgers |
| 3927 | 7 | 1.97 | 51.78 | 2.22 | 23 | Rutgers |
| 3927 | 7 | 1.67 | 55 | 2.17 | 23 | Rutgers |
| 3927 | 20 | 1.03 | 52.38 | 1.04 | 15 | Rutgers |
| 3927 | 20 | 0.98 | 51.08 | 1.59 | 15 | Rutgers |
| 3927 | 20 | 0.75 | 50.89 | 1.14 | 23 | Rutgers |
| 3938* | 14 | 1.02 | 47.92 | 1.25 | 23 | Rutgers |
| 3938* | 14 | 0.973 | 48.57 | 2.25 | 23 | Rutgers |
| 3938* | 18 | 0.49 | 49.45 | 1.45 | 23 | Rutgers |
| 3938* | 18 | 0.86 | 47.98 | 2.16 | 23 | Rutgers |
| 3677 |  | 0 | 52.05 | 2.51 | 23 | Rutgers |

*Designates HA on N terminus

These GC/MS data indicate that a chimeric fad2/R. communis hydroxylase (3927 or 3938*) was functional when expressed in tomato hairy root. The percentages of ricinoleic acid (% R) listed in the table are percentages of the total fatty acid. Tomato hairy roots transformed with a vector containing no insert (3677) did not accumulate ricinoleic acid (R). Linoleic acid percentages are listed under the columns % L and % O, respectively.

TABLE 17

Chimeric fad2/R. communis hydroxylase with 5' and 3' fad2 UTRs

| Construct | Line | % R | % L | % O | Temp | Cultivar |
|---|---|---|---|---|---|---|
| 4062 | 19 | 1.26 | 48.04 | 6.99 | 23 | Rutgers |
| 4062 | 19 | 2.25 | 48.22 | 4.59 | 23 | Rutgers |
| 4062 | 19 | 1.97 | 50.19 | 3.60 | 23 | Rutgers |
| 4028* | 12 | 2.38 | 50.54 | 2.43 | 15 | Rutgers |
| 4028* | 12 | 2.36 | 52.64 | 2.70 | 15 | Rutgers |
| 4028* | 12 | 1.13 | 51.34 | 4.19 | 23 | Rutgers |
| 3677 | 2 | 0 | 53.32 | 0.84 | RT | Rutgers |
| 4028* | 5 | 0.95 | 53.15 | 2.49 | RT | Mountain Spring |
| 4028* | 5 | 1.3 | 54.8 | 1.55 | RT | Mountain Spring |
| 4028* | 5 | 0.58 | 47.61 | 2.56 | RT | Mountain Spring |
| 3677 | 2 | 0 | 57.94 | 0.87 | RT | Mountain Spring |

*Designates HA on N terminus.
RT = room temperature

These GC/MS data indicate that a chimeric Fad2/R. communis hydroxylase (4062 or 4028*) operably linked to 5' and 3'fad2 UTRs was functional when expressed in tomato hairy root. The percentages of ricinoleic acid listed in the table are percentages of the total fatty acid. Tomato hairy roots transformed with a vector containing no insert (3677) did not accumulate ricinoleic acid (R).

Hairy Root Transformation Protocol for Soybean

Seed sterilization: Approximately 250 seeds were placed in a 100×25 mm plate and placed in a desicator in a fume hood. Using a 350 mL beaker, 2 mL of concentrated HCl was carefully added to 200 mL of 100% bleach and the beaker was placed inside the desicator to expose the seeds to sterilizing gas. After 24 hours, the procedure was repeated. This was done 3 times for total of 3 sterilizations. To test for sterility, 10 seeds were placed in LB and put in a shaker at 37° C. for 24 hour. If the LB was clear, indicating no bacterial growth, the seeds were sealed in the Petri dish and germinated at a later date. If there was bacterial growth, the sterilization procedure was performed again.

Seed Germination: 9 seeds were placed on 0.25× solid MS plates, wrapped in parafilm, and kept at room temperature for 7 days.

A. rhizogenes culture preparation: A glycerol stock of A. rhizogenes A4 was streaked onto MGL medium [McCormick (1991) Transformation of tomato with Agrobacterium tumefaciens. in Plant Tissue Culture Manual, Fundamentals and Applications, K. Lindsey (ed), Kluwer, Volume B6: 1-9] and grown at 29° C. until individual colonies appeared. A single colony was used to inoculate a 15 mL culture of LB+Kanamycin medium, which was grown for one day in a shaking incubator at 29° C., 100 rpm. On the following day, the bacteria were harvested by centrifugation at 3800×g for 10 minutes. The resulting pellet was resuspended in MSO to a final optical density of 0.2-0.3. Acetosyringone was then added to a final concentration of 375 um. Cocultivation was performed within one hour of the addition of acetosyringone.

Explant Excision: The cotyledons were cut from the main axis making sure that the axillary bud was removed.

Cocultivation of soybean cotyledons and A. rhizogenes: Soybean cotyledons were added to the culture using sterile technique. The cultures were then vacuum infiltrated for 2 minutes and incubated at room temperature for 20 minutes. The bacterial suspension was then removed with a sterile pipette. The cotyledons were transferred gently, abaxial side up, using tweezers, to a 100×20 mm Petri plate containing a Whatman filter paper disk soaked in MSO. The plates were sealed with micropore tape and incubated for 2 days at room temperature near a south facing window.

Selection of transgenic roots: After cocultivation, the cotyledons were transferred, abaxial side up onto MS solid medium containing 500 mg/L carbenicillin at a density of 10 cotyledons per plate. The plates were sealed with micropore tape and incubated at room temperature. About 28 days post-inoculation, hairy roots were removed from the cotyledons using a sterile razor blade and incubated on Gamborgs medium plus selection.

Hairy Root Transformation Protocol for Arabidopsis thaliana

Seed sterilization: Approximately 200 seeds were placed in an eppendorf tube. 1 mL of 20% bleach in ethanol was added and the tubes were left at room temperature for 15 minutes. The seeds were then washed 2× with 100% ethanol and opened tubes were left in the laminar flow hood to dry overnight.

Seed Germination: Approximately 50 seeds were placed on 0.5× solid MS plates, wrapped in parafilm, and kept at room temperature until germination.

A. rhizozenes culture preparation: A glycerol stock of A. rhizogenes A4 was streaked onto MGL medium [McCormick (1991) Transformation of tomato with Agrobacterium tumefaciens. in Plant Tissue Culture Manual, Fundamentals and Applications, K. Lindsey (ed), Kluwer, Volume B6: 1-9] and grown at 29° C. until individual colonies appeared. A single colony was used to inoculate a 15 mL culture of LB+Kanamycin medium, which was grown for one day in a shaking incubator at 29° C., 100 rpm. On the following day, the bacteria were harvested by centrifugation at 3800×g for 10 minutes. The resulting pellet was resuspended in MSO to a final optical density of 0.2-0.3. Acetosyringone was then added to a final concentration of 375 um. Cocultivation was performed within one hour of the addition of acetosyringone.

Explant Excision: *A. thaliana* cotyledons were removed sterilely and wounded in MSO medium (MS salts, 3% sucrose, Gamborg's B5 vitamins, pH 5.8) by removing both the proximal and distal tips with a razor blade. Wounded cotyledons were incubated for 1-2 days, adaxial side up, on filter paper placed on 150 $mm^2$ plates made with D1 medium (MS salts, 3% glucose, Gamborg's B5 vitamins, 1 mg/L zeatin, 0.8% Gel-rite agar). After this incubation period, cotyledons were cocultured with a suspension of *A. rhizogenes* to initiate transformation.

Cocultivation of *A. thaliana* cotyledons and *A. rhizogenes*: *A. thaliana* cotyledons were added to the *A. rhizogenes* culture using sterile technique and left at room temperature for 10 minutes. The bacterial suspension was then removed with a sterile pipette. The cotyledons were transferred gently, abaxial side up, using a sterile spatula, to a Whatman filter paper disk in a 100×20 mm Petri plate containing solid Gamborgs medium plus 500 mg/L carbenicillin. The plates were sealed with micropore tape and incubated for at room temperature near a south facing window.

Selection of transgenic roots: About 10 days post-inoculation, hairy roots were removed from the cotyledons using a sterile razor blade and placed on Gamborgs medium plus selection.

Callus Transformation Protocol

Plant material preparation: This protocol can be used to generate transgenic tomato callus. All transformations carried out used *Agrobacterium tumefaciens* strain LB4404 and the tomato cultivar *Lycopersicon esculentum* cv. Rutgers, Money Maker, or Mountain Spring. Tomato cotyledons were grown as described in the hairy root transformation section.

*A. tumefaciens* culture preparation: A glycerol stock of *A. tumefaciens* LB4404 was streaked onto LB medium (rifampicin 10 mg/L, streptomycin 150 mg/L, kanamycin 50 mg/L) (McCormick, 1991) and grown at 29° C. until individual colonies appeared. A single colony was used to inoculate a 15 mL culture of LB medium, which was grown for one day in a shaking incubator at 29° C., 100 rpm. On the following day, the bacteria were harvested by centrifugation at 3800×g for 10 minutes. The resulting pellet was washed twice, without disturbing the pellet, with 15 mL of MSO medium and centrifuging at 3800×g for 5 minutes. The final pellet was resuspended in 15 mL MSO medium and the optical density of the culture at 550 nm was determined. The density was adjusted to 0.4 with MSO medium. 10 mL of this culture was used for cocultivation after the addition of 50 μL of 0.074 M acetosyringone. Cocultivation was performed within one hour of the addition of acetosyringone.

Cocultivation of tomato cotyledons and *A. tumefaciens*: Cocultivation was carried out as described in the hairy root transformation section with the exception of using *A. tumefaciens*.

Selection of transgenic callus: After cocultivation, the cotyledons were transferred, abaxial side up onto 2Z medium (4.3 g MS salt/L, 20% sucrose, 1 mg zeatin/L, 100 mg/L inositol, 1× Nitsch vitamin, 1× folic acid, 8 g/L tissue culture agar) containing 200 mg/L cefotaxime and 100 mg/L kanamycin at a density of 20-30 cotyledons per plate. The plates were sealed with micropore tape and incubated at room temperature in the dark for 10 days. Every 10 days, the cotyledons were transferred to fresh selective media plate. Explants started to grow green or white callus after two to three weeks. Explants that were dying (turning brown) were removed. Callus was excised from explants that contained dying tissue. The callus was maintained on Gamborg's medium.

Composite Plant Protocol for Soybean:

*Agrobacterium rhizogenes* A4 cultures were grown overnight at 30° C. in Luria Broth with the appropriate antibiotics. Cultures were spun down at 4,000 g for 10 minutes. Cells were suspended with ¼ MS to a final $O.D._{600\ nm}$ between 0.2-0.5.

Sterile soybean seeds ($Cl_2$ gas treated seeds) were planted in soil. Young shoots lacking any inflorescences were cut in the middle of the internode region. Shoots were transplanted into one $cm^2$ FibrGro® cubes. Each transplant was inoculated with 4 mL of suspended *A. rhizogenes*, placed in a flat, covered with a clear lid, and left on the bench top for one day to allow for acclimation. On the second day the lid was removed to let the cubes dry out. Transplants were then watered and covered. Roots appeared between two and four weeks. Transformed roots can be identified by a visible marker. The untransformed roots should be excised. After several weeks, shoots can be transplanted to sand for nematode infection assays.

EXAMPLE 18

This example describes assays to measure anthelmintic activity of transgenic plants.

Infection of hairy roots: Plates for assays were prepared by transferring one growing hairy root tip, 1-2 cm long, from a stock root plate onto 100×15 cm Petri dishes containing approximately 30 mL of Gamborg's media in which the Gel-rite agar had been replaced by 3.0% Phytagel (Sigma catalog P-8169). At least two plates were used per transgenic line per assay. As a control, we used a hairy root line that was generated using *A. rhizogenes* that had been transformed with a plant transformation plasmid that does not carry any coding sequence after the promoter. Assay plates were sealed with micropore tape and incubated at 28° C. for 4-7 days prior to infection with *Meloidogyne incognita* eggs.

Preparation of *Meloidogyne incognita* inoculum: *M. incognita* eggs were harvested from a greenhouse-grown tomato plant (*Lycopersicon esculentum* cv. Mountain Spring) that had been infected 28-42 days previously with 5000 *M. incognita* eggs using a protocol described previously [Hussey & Barker (1973) *Plant Disease Reporter* 57: 1025-1028]. Aerial tissues of the tomato plant were removed and the root mass was freed from soil by gentle agitation in a bucket filled with tap water. The root mass was transferred to a household blender with the addition of 500 mL 10% bleach solution (Clorox bleach in tap water) and chopped into fine pieces using the puree setting. The root slurry was transferred to a 200 mesh sieve seated on top of a 500 mesh sieve (VWR catalog numbers 57334-480 and 57334-492, respectively) and eggs were collected on the 500 mesh sieve by rinsing vigorously with tap water. Eggs were further cleaned and concentrated by sucrose density centrifugation. Eggs were collected in approximately 30 mL of water and were pipetted on top of 30 mL of 30% sucrose solution in a 50 mL centrifuge tube and banded by centrifugation in a swinging bucket rotor at 1000×g for 10 minutes. The eggs were collected using a Pasteur pipette and rinsed extensively to remove sucrose on a small 500 mesh sieve using tap water. Eggs were collected in a small amount of water and stored at 4° C. until use.

Sterilization of inoculum: Approximately 100,000 stored *M. incognita* eggs were placed in a 15 mL centrifuge tube and brought to 10 mL volume with a 10% bleach solution. The tube was agitated for 5 minutes and eggs were collected by centrifugation as described above. The supernatant was removed and the eggs were rinsed 3 times with sterile water. Eggs were resuspended in 1 mL of water and counted using a McMaster worm egg counting chamber. Only eggs containing vermiform larvae were counted.

Alternatively, if hatched J2 larvae were to be used as inoculum, eggs were hatched using a standard protocol. Larvae were collected by centrifugation as above and sterilized as described in Atkins, 1996 [Atkinson et al. (1996) *J Nematol*. 28: 209-215], using sequential incubations in penicillin, streptomycin sulfate, and chlorhexidine solutions, followed by rinsing in sterile water.

Inoculation and monitoring of assay: Hairy root infections were initiated by adding either 300 eggs or 100 J2 larvae per plate in 10 µL, using sterile technique. Plates were resealed with parafilm after inoculum addition and monitored at 2, 7, 14, 21, 28 and 35 days. Plates that showed contamination with bacteria or fungi were discarded. Nematode-induced infection galls were visible under low-power magnification at 7 days, and adult females were visible at 25-30 days.

Scoring of Infection Assays

Gall number: The number of galls per plate was determined after 30-35 days by counting under low-power magnification. Total number of galls, as well as the number of adult and gravid females, was recorded. Alternatively, total number of *M. incognita* at all stages was determined by fuchsin staining of the roots [Eisenback (2000) Techniques for measuring nematode development and egg production in Laboratory Techniques in Nematode Ecology. Wheeler et al., eds. Society of Nematologists: Hyattsville, Md. p. 1-4].

Brood size: Gravid females were excised from each separate assay plate and placed in microcentrifuge tubes. 1 mL of 10% bleach was added to each tube and the tubes were agitated for 3 minutes. Freed eggs were collected by microcentrifugation (1000×g, 2 minutes), rinsed three times with sterile water, and counted as described above. Brood size was recorded as eggs/female:

Brood viability: After counting, eggs from individual plates were transferred in 500 µL water to wells of a 24-well plate and incubated at room temperature in the dark for 7 days. The number of newly hatched J2 larvae visible after this period was determined and recorded. Ability of eggs or larvae to re-infect hairy roots was determined by inoculating control roots with eggs or J2's as described.

Scoring system based on root galling: A relatively higher throughput scoring system can be utilized when the number of plates becomes difficult to score by the methods listed above. The following table is an example of a rating system based on visual estimation of root damaged caused by *Meloidogyne* spp:

| Damage Score | Description |
| --- | --- |
| 0 | No galls |
| 1 | 1-2 small galls |
| 3 | 3-5 small galls |
| 5 | >5 small galls, but no multiple galls |
| 10 | Several small galls and at least one multiple gall |
| 25 | About 25% of the roots with multiple galls; many small galls |
| 50 | About 50% of the roots with multiple galls |
| 75 | About 75% of the roots with multiple galls |
| 90 | Entire root system is galled and stunted |

Soybean Cyst Nematode Pot Assay

This assay is used to evaluate the resistance of soybean plants to infection by and reproduction of the soybean cyst nematode (*Heterodera glycines*) on roots. Three or four inch diameter square pots were filled with clean sand and watered thoroughly. Soybean seeds, or alternatively any rooted plant parts, were planted one per pot in the center of the pot and watered well to remove air pockets. The pots were incubated in the greenhouse or growth chamber at 20° C. to 30° C. until the plants reached a suitable age for inoculation. Soybeans started from seed were typically inoculated 2-3 weeks after planting, while transplants were inoculated 1-3 days after planting. The test inoculum consisted of eggs from ripe *H. glycines* cysts collected from the soil and roots of infested soybean plants. A 250 micron mesh sieve was used to collect the cysts, which were then crushed in a Tenbroeck glass tissue homogenizer to release the eggs. The eggs were further purified by sieving and centrifugation over 40% sucrose solution at 4000 RPM for 5 minutes. Inoculum for an experiment consisted of water containing 500 vermiform eggs per mL. Five mL of the egg suspension was pipetted over the surface of the sand containing the test plants and the eggs were lightly watered in. The test plants were then returned to the greenhouse or growth chamber and incubated for 3-4 weeks to allow for root infection and cyst formation. The roots were then harvested by gently removing the pot and sand and rinsing in water. The severity of nematode infection was measured by counting the number of white nematode cysts adhering to the root system. Alternatively, the sand and roots could be diluted in water and passed over a 250 micron sieve to collect and concentrate the cysts for storage or counting.

Use of tomato hairy roots for assay of cyst nematode infections: The assay described above can also be used to determine the ability of cyst nematode to infect tomato roots using the cyst nematode strain TN2.

EXAMPLE 19

TABLE 18

Sequence ID numbers for hydroxylase and epoxygenase genes

| Construct | cDNA | Amino acid |
| --- | --- | --- |
| *Ricinus communis* | SEQ ID NO: 1 | SEQ ID NO: 13 |
| *Lesquerella fendleri* | SEQ ID NO: 2 | SEQ ID NO: 14 |
| *Lesquerella lindheimeri* | SEQ ID NO: 3 | SEQ ID NO: 15 |
| *Lesquerella gracilis* A | SEQ ID NO: 4 | SEQ ID NO: 16 |
| *Lesquerella gracilis* B | SEQ ID NO: 5 | SEQ ID NO: 17 |
| *Crepis biennis* | SEQ ID NO: 6 | SEQ ID NO: 18 |
| fad2/*R. communis* | SEQ ID NO: 7 | SEQ ID NO: 19 |
| fad2/*L. fendleri* | SEQ ID NO: 8 | SEQ ID NO: 20 |
| fad2/*L. lindheimeri* | SEQ ID NO: 9 | SEQ ID NO: 21 |
| fad2/*L. gracilis* A | SEQ ID NO: 10 | SEQ ID NO: 22 |
| fad2/*L. gracilis* B | SEQ ID NO: 11 | SEQ ID NO: 23 |
| fad2/*C. biennis* | SEQ ID NO: 12 | SEQ ID NO: 24 |
| *R. communis* ΔKKGG | SEQ ID NO: 25 | SEQ ID NO: 34 |
| *L. gracilis* B ΔT | SEQ ID NO: 26 | SEQ ID NO: 35 |
| *Stokesia laevis* | SEQ ID NO: 27 | SEQ ID NO: 36 |
| *R. communis* optimization 2 | SEQ ID NO: 28 | SEQ ID NO: 37 |

TABLE 18-continued

Sequence ID numbers for hydroxylase and epoxygenase genes

| Construct | cDNA | Amino acid |
|---|---|---|
| S. laevis A optimization 2 | SEQ ID NO: 29 | SEQ ID NO: 38 |
| R. communis optimization 1 | SEQ ID NO: 30 | SEQ ID NO: 39 |
| L. gracilis B optimization 1 | SEQ ID NO: 31 | SEQ ID NO: 40 |
| C. biennis optimization 1 | SEQ ID NO: 32 | SEQ ID NO: 41 |
| S. laevis A optimization 1 | SEQ ID NO: 33 | SEQ ID NO: 42 |
| HA R. communis optimization | SEQ ID NO: 129 | SEQ ID NO: 134 |
| C. palaestina optimization | SEQ ID NO: 130 | SEQ ID NO: 135 |
| S. laevis B optimization | SEQ ID NO: 131 | SEQ ID NO: 136 |
| C. biennis optimization 2 | SEQ ID NO: 132 | SEQ ID NO: 137 |
| L. gracilis B optimization 2 | SEQ ID NO: 133 | SEQ ID NO: 138 |

*Arabidopsis thaliana* FAD2 5'-untranslated regin (SEQ ID NO: 43 and 44) and *Arabidopsis thaliana* FAD2 3'-untanslated region (SEQ ID NO: 45).

EXAMPLE 20

This example describes the results of fatty acid analyses for tomato hairy roots and *Arabidopsis thaliana* seeds expressing various codon-optimized *Ricinus communis* constructs.

The fatty acid analysis of tomato hairy roots was carried out with the basic derivatization method. Results of the analysis of tomato hairy roots expressing the SID 129 gene (the HA-tagged *R. communes* sequence—SEQ ID NO: 129) are presented in Table 19. Results of the analysis of tomato hairy roots expressing the SID 30 gene (of *R. communis*—SEQ ID NO: 30) or the SID 28 gene (of *R. communis*—SEQ ID NO: 28) are presented in Table 20. Roots utilized in the analysis were grown under light and temperature cycling conditions (12 hours at 23° C. in the light alternating with 12 hours at 20° C. in the dark). A basic derivatization method was performed essentially as described by Cahoon et al. (Plant Physiol. 2002, 128: 615-624). Ground root tissue was methylated with 500 μL 1% sodium methoxide in methanol, extracted with hexane, and trimethylsilylated (100 μL BSTAFA-TMCS, Supelco, 90° C. for 45 minutes). Samples were analyzed on an Agilent 6890 GC-5973 Mass Selective Detector (GC/MS) and an Agilent DB-23 capillary column (0.25 mm×30 m×0.25 um). The injector was held at 250° C., the oven temperature was 235° C., and a helium flow of 1.0 mL/min was maintained.

The fatty acid analysis of *A. thaliana* seeds was carried out with either the basic or the acidic derivatization method. Results of the analysis of *A. thaliana* seeds expressing the SID 129 gene (the HA-tagged *R. communis* sequence—SEQ ID NO: 129) are presented in Table 21. *Arabidopsis* plants were grown in 3-inch pots under controlled environment in growth chambers. A temperature of 23° C. was maintained, with a 12 hour light: 12 hour dark cycle. Plants were watered daily with tap water and fertilized once a week. The basic derivatization method was performed essentially as described by Cahoon et al. (Plant Physiol. 2002, 128: 615-624). The acidic derivatization protocol is the same as the basic derivatization method, except that 500 μL 2.5% sulfuric acid in methanol is used in place of the sodium methoxide in methanol.

TABLE 19

Fatty acid analysis of tomato hairy roots

| Gene | Line | 18:1-OH | 18:2 | 18:1 | 16:0 | 18:0 | 18:3 |
|---|---|---|---|---|---|---|---|
| SID 129 | A | .91 | 52.81 | 1.04 | 15.30 | 1.47 | 21.88 |
| SID 129 | A | 1.29 | 54.23 | 1.28 | 16.35 | 3.34 | 16.19 |
| SID 129 | B | 0.92 | 54.00 | 4.62 | 14.05 | 2.62 | 18.28 |
| SID 129 | B | 1.71 | 53.76 | 4.35 | 12.87 | 1.24 | 17.83 |
| SID 129 | C | 1.24 | 48.96 | 1.53 | 15.75 | 2.98 | 22.07 |
| SID 129 | C | 2.5 | 54.69 | 2.2 | 15.11 | 2.51 | 17.60 |
| SID 129 | D | 3.03 | 51.41 | 1.74 | 14.90 | 4.46 | 15.96 |
| SID 129 | E | 0.79 | 53.30 | 1.18 | 13.82 | 2.79 | 22.46 |
| SID 129 | F | 0.93 | 57.49 | 2.3 | 14.22 | 2.42 | 18.51 |
| EV | G | 0 | 58.01 | 1.16 | 14.85 | 2.48 | 18.14 |
| EV | H | 0 | 58.29 | .60 | 15.81 | 2.35 | 18.03 |

SID 129: HA-tagged *R. communis* (SEQ ID NO: 129) basic derivatization method;
EV: empty vector;
18:1-OH - ricinoleic acid,
18:2 - linoleic acid;
18:1 - oleic acid;
16:0 - palmitic acid;
18:0 - stearic acid;
18:3 - alpha linolenic acid.

TABLE 20

Fatty acid analysis of tomato hairy roots

| Gene | Line | 18:1-OH | 18:2 | 18:1 | 16:0 | 18:0 | 18:3 |
|---|---|---|---|---|---|---|---|
| SID 30 | A | 2.76 | 50.95 | 5.10 | 16.17 | 3.06 | 14.39 |
| SID 30 | B | 1.34 | 54.78 | 4.53 | 14.26 | 1.25 | 14.99 |
| SID 30 | C | 3.21 | 51.75 | 3.89 | 14.03 | 2.07 | 16.41 |
| SID 30 | C | 2.215 | 50.24 | 3.45 | 15.51 | 2.86 | 15.81 |
| SID 30 | D | 3.04 | 51.71 | 8.89 | 14.26 | 2.33 | 11.71 |
| SID 28 | A | 3.23 | 48.70 | 1.70 | 12.92 | 3.40 | 17.22 |
| SID 28 | A | 3.65 | 51.59 | 2.79 | 11.23 | 1.48 | 21.54 |
| SID 28 | B | 2.98 | 51.38 | 2.97 | 12.89 | 2.97 | 19.48 |
| SID 28 | B | 1.56 | 51.37 | 1.96 | 14.33 | 2.78 | 19.95 |
| SID 28 | C | 2.48 | 54.40 | 4.36 | 14.20 | 1.19 | 17.22 |
| SID 28 | D | 4.73 | 54.69 | 2.22 | 10.05 | 2.83 | 18.04 |
| SID 28 | D | 3.32 | 55.17 | 2.49 | 12.89 | 3.29 | 16.07 |
| SID 28 | E | 2.847 | 52.46 | 2.25 | 12.05 | 2.61 | 19.06 |
| SID 28 | F | 1.96 | 55.91 | 2.55 | 14.50 | 2.88 | 15.81 |
| EV | G | 0 | 56.31 | 0.964 | 15.94 | 1.61 | 19.48 |
| EV | G | 0 | 56.3 | 1.6 | 15.96 | 1.61 | 19.45 |

SID 30: *R. communis* (SEQ ID NO: 30) basic derivatization method;
SID 28: *R. communis* (SEQ ID NO: 28) basic derivatization method

TABLE 21

Fatty acid analysis of *A. thaliana* seeds

| Gene | 18:1 | 18:2 | 16:0 | 18:0 | 18:3 | 20:0 | 18:1-OH | 18:2-OH | 20:1-OH |
|---|---|---|---|---|---|---|---|---|---|
| SID 129 A | 21.19 | 20.04 | 7.99 | 4.2 | 12.01 | 4.39 | 3.78 | 1.15 | 1.02 |
| SID 129 A | 21.16 | 21.97 | 9.15 | 3.79 | 13.81 | 2.47 | 2.29 | 1.42 | 0.81 |
| EV A | 20.95 | 27.25 | 6.41 | 3.53 | 14.56 | 1.89 | 0 | 0 | 0 |

TABLE 21-continued

| | Fatty acid analysis of *A. thaliana* seeds | | | | | | | | |
|---|---|---|---|---|---|---|---|---|---|
| Gene | 18:1 | 18:2 | 16:0 | 18:0 | 18:3 | 20:0 | 18:1-OH | 18:2-OH | 20:1-OH |
| SID 129 B | 21.45 | 20.82 | 9.68 | 3.76 | 13.2 | 2.64 | 2.64 | 1.7 | 0.84 |
| SID 129 B | 20.51 | 22.97 | 7.62 | 3.01 | 14.05 | 1.67 | 1.75 | 1.65 | 0.66 |
| SID 129 B | 20.43 | 23.07 | 7.78 | 2.99 | 13.97 | 1.66 | 1.6 | 1.64 | 0.62 |
| EV B | 22.67 | 28.43 | 6.13 | 2.61 | 14.56 | 1.9 | 0 | 0 | 0 |

SID 129 A or B: HA-tagged *R. communis* (SEQ ID NO: 129) acidic or basic derivatization methods, respectively;
EV A or B: empty vector acidic or basic derivatization methods, respectively;
18:1 - oleic acid,
18:2 - linoleic acid,
16:0 - palmitic acid,
18:0 - stearic acid,
18:3 - alpha linolenic acid;
20:0 - arachidic acid,
18:1-OH - ricinoleic acid,
18:2-OH - densipolic acid,
20:0-OH - lesquerolic acid.

Tables 19 and 20 show that codon optimization of castor genes allows for an accumulation of ricinoleic acid (18:1-OH) in vegetative tissues of plants expressing such genes, as compared to no accumulation in plants transformed with an empty vector. Table 21 shows that the ricinoleic acid accumulation is detected in *A. thaliana* seeds, even though the CaMV 35S promoter is not a seed specific promoter. Taken together, the results of these and the experiments described above suggest that an increased accumulation of novel fatty acids in transgenic plants is useful for both nematode control as well as for non-pesticidal industrial uses (e.g., in oil seed engineering).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic plant containing at least one DNA construct, said construct comprising:
   a) a nucleic acid encoding a polypeptide effective for catalysing the conversion of a substrate to a C16, C18, or C20 monounsaturated fatty acid product, wherein said polypeptide has at least 95% sequence identity to the amino acid sequence shown in SEQ ID NO:137, wherein said fatty acid product has the following structure:

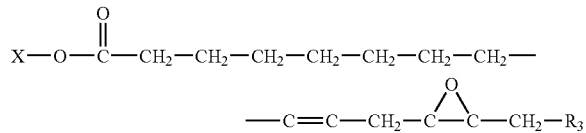

wherein X is hydrogen, CoA, glycerol, a monoglyceride, a diglyceride, ACP, methyl, Na+, phosphatidylcholine, or phosphatidylethanolamine, and wherein R3 is C2, C4, or C6 alkyl; and
   (b) a regulatory element operably linked to said nucleic acid encoding said polypeptide, wherein said regulatory element confers expression in a vegetative tissue of said plant; wherein the transpenic Dlant has anthelmintic activity.

2. The plant according to claim 1, wherein the double bond between the 9$^{th}$ and 10$^{th}$ carbons is cis.

3. The plant according to claim 1, wherein the double bond between the 9$^{th}$ and 10$^{th}$ carbons is trans.

4. The plant according to claim 1, wherein said regulatory element is a 5'-regulatory element.

5. The plant of claim 4, wherein said 5'-regulatory element confers expression in root tissue.

6. The plant of claim 5, said plant having a significantly increased amount of a epoxy-fatty acid in roots of said plant relative to a corresponding plant that lacks said DNA construct.

7. The plant of claim 6, wherein said epoxy-fatty acid is vernolic acid.

8. The plant of claim 7, wherein said vernolic acid constitutes from about 0.1% to about 25% of the total fatty acid content of said roots.

9. The plant of claim 4, wherein said 5'-regulatory element is selected from the group consisting of a potato ribosomal protein S27a Ubi3 promoter, a RB7 promoter, an alfalfa histone H3.2 promoter, an IRT2 promoter, an Arabidopsis FAD2 5'-UTR, an Arabidopsis FAD3 5'-UTR, a Ubi3 5'-UTR, an alfalfa histone H3.2 5'-UTR, and a CaMV35S 5'-UTR.

10. The plant of claim 1, wherein said regulatory element comprises a first 5'-regulatory element operably linked to a second 5'-regulatory element, wherein said first 5'-regulatory element is an Ubi3 promoter and said second 5'-regulatory element is selected from the group consisting of an Arabidopsis FAD2 5'-UTR, an Arabidopsis FAD3 5'-UTR, a potato ribosomal protein S27a 5'-UTR, a Ubi3 5'-UTR, and a CaMV35S 5'-UTR.

11. The plant of claim 4, wherein said DNA construct further comprises a 3'-regulatory element.

12. The plant of claim 11, wherein said 3'-regulatory element comprises a Ubi3 terminator or an E9 pea terminator.

13. The plant of claim 11, wherein said 5'-regulatory element is selected from the group consisting of an Arabidopsis FAD2 5'-UTR and an Arabidopsis FAD3 5'-UTR and said 3'-regulatory element is selected from the group consisting of an Arabidopsis FAD2 3'-UTR and an Arabidopsis FAD3 3'-UTR.

14. The plant of claim 13, wherein said 5'-regulatory element comprises SEQ ID NOS: 43 or 44 and said 3'-regulatory element comprises SEQ ID NO: 45.

15. The plant of claim 1, wherein said at least one DNA construct further comprises at least one regulatory element that confers expression in vegetative tissues of a plant operably linked to a nucleic acid that encodes a PDAT or DAGAT polypeptide.

16. The plant of claim 1, said plant further comprising a second DNA construct, said second DNA construct comprising at least one regulatory element that confers expression in vegetative tissues of a plant operably linked to a nucleic acid that encodes a PDAT or DAGAT polypeptide.

17. The plant of claim 1, wherein $R_3$ is C2 alkyl or C4 alkyl.

18. The plant of claim 1, where said plant is selected from the group consisting of tobacco, tomato, soybean, corn, cotton, rice, wheat, banana, carrot, potato, strawberry and turf grass.

19. A method of making a transgenic plant having anthelmintic activity, said method comprising introducing a construct into a plant, wherein said construct comprises:
  a) a nucleic acid encoding a polypeptide effective for catalysing the conversion of a substrate to a C16, C18, or C20 monounsaturated fatty acid product, wherein said polypeptide has the amino acid sequence shown in SEQ ID NO:137, wherein said fatty acid product has the following structure:

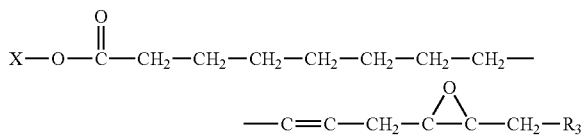

wherein X is hydrogen, CoA, glycerol, a monoglyceride, a diglyceride, ACP, methyl, Na+, phosphatidylcholine, or phosphatidylethanolamine, and wherein $R_3$ is C2, C4, or C6 alkyl; and
  (b) a regulatory element operably linked to said nucleic acid encoding said polypeptide, wherein said regulatory element confers expression in a vegetative tissue of said plant.

20. The method of claim 19, wherein said regulatory element of said construct is a 5'-regulatory element.

21. The method of claim 20, wherein said 5'-regulatory element comprises a potato ribosomal protein S27a Ubi3 promoter, a RB7 promoter, an alfalfa histone H3.2 promoter, an IRT2 promoter, an *Arabidopsis* FAD2 5'-UTR, an *Arabidopsis* FAD3 5'-UTR, a Ubi3 5'-UTR, an alfalfa histone H3.2 5'-UTR, and a CaMV35S 5'-UTR.

22. The method of claim 20, wherein said regulatory element comprises a first 5'-regulatory element operably linked to a second 5'-regulatory element, wherein said first 5'-regulatory element is an Ubi3 promoter and said second 5'-regulatory element is selected from the group consisting of an *Arabidopsis* FAD2 5'-UTR, an *Arabidopsis* FAD3 5'-UTR, a potato ribosomal protein S27a 5'-UTR, a Ubi3 5'-UTR, and a CaMV35S 5'-UTR.

23. The method of claim 20, wherein said DNA construct further comprises a 3'-regulatory element.

24. The method of claim 23, wherein said 5'-regulatory element comprises SEQ ID NO: 43 or SEQ ID NO: 44 and said 3'-UTR comprises SEQ ID NO: 45.

25. An isolated nucleic acid comprising the nucleotide sequence set forth in SEQ ID NO:132.

26. A recombinant nucleic acid construct comprising at least one regulatory element that confers expression in a vegetative tissue of a plant, said regulatory element operably linked to a nucleic acid having the nucleotide sequence set forth in SEQ ID NO: 132.

27. The nucleic acid construct of claim 26, wherein said at least one regulatory element comprises a 5'-regulatory element having the nucleotide sequence set forth in SEQ ID NO: 43 or SEQ ID NO: 44.

28. The nucleic acid construct of claim 27, wherein said construct further comprises a 3'-regulatory element having the nucleotide sequence set forth in SEQ ID NO: 45.

29. A transgenic plant harboring a DNA construct comprising a nucleic acid encoding a fatty acid epoxygenase polypeptide operably linked to a regulatory element conferring expression of said polypeptide in a vegetative tissue of said plant, wherein said polypeptide has the amino acid sequence shown in SEQ ID NO:137.

30. The plant of claim 29, said plant having a significantly increased amount of a epoxy-fatty acid in roots of said plant relative to a corresponding plant that lacks said DNA construct.

31. The plant of claim 30, wherein said epoxy-fatty acid is vernolic acid.

32. The plant of claim 31, wherein said vernolic acid constitutes from about 0.1% to about 25% of the total fatty acid content of said roots.

33. A transgenic plant containing at least one DNA construct, said construct comprising:
  a) a nucleic acid encoding a polypeptide effective for catalysing the conversion of a substrate to a C16, C18, or C20 monounsaturated fatty acid product, wherein said polypeptide has at least 95% sequence identity to the amino acid sequence shown in SEQ ID NO:137, wherein said fatty acid product has the following structure:

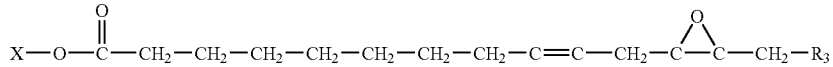

wherein X is hydrogen, CoA, glycerol, a monoglyceride, a diglyceride, ACP, methyl, Na+, phosphatidylcholine, or phosphatidylethanolamine, and wherein R3 is C2, C4, or C6 alkyl; and
  (b) a regulatory element operably linked to said nucleic acid encoding said polypeptide, wherein said regulatory element confers expression in a vegetative tissue of said plant; wherein the transgenic plant has anthelmintic activity.

34. The plant according to claim 33, wherein said regulatory element is a 5'-regulatory element.

35. The plant of claim 34, said plant having a significantly increased amount of an epoxy-fatty acid in at least one tissue of seeds of said plant relative to a corresponding plant that lacks said DNA construct.

36. The plant of claim 35, wherein said epoxy-fatty acid is vernolic acid.

37. A method of making a transgenic plant having anthelmintic activity, said method comprising introducing a construct into a plant, wherein said construct comprises:

a) a nucleic acid encoding a polypeptide effective for catalysing the conversion of a substrate to a C16, C18, or C20 monounsaturated fatty acid product, wherein said polypeptide has the amino acid sequence shown in SEQ ID NO:137, wherein said fatty acid product has the following structure:

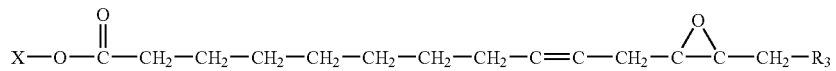

wherein X is hydrogen, CoA, glycerol, a monoglyceride, a diglyceride, ACP, methyl, Na+, phosphatidylcholine, or phosphatidylethanolamine, and wherein $R_3$ is C2, C4, or C6 alkyl; and (b) a regulatory element operably linked to said nucleic acid encoding said polypeptide, wherein said regulatory element confers expression in a vegetative tissue of said plant.

* * * * *

UNITED STATES PATENT AND TRADEMARK OFFICE
CERTIFICATE OF CORRECTION

PATENT NO. : 7,368,629 B2 Page 1 of 1
APPLICATION NO. : 10/912534
DATED : May 6, 2008
INVENTOR(S) : Michelle L. Verbsky et al.

It is certified that error appears in the above-identified patent and that said Letters Patent is hereby corrected as shown below:

Title Page, Item [75] Inventors, Rodolfo Zentella, please delete "St. Louis, MO" and insert --Durham, NC-- therefor;

Column 225, line 48 (Claim 1), please delete "R3" and insert --$R_3$-- therefor;

Column 225, line 53 (Claim 1), please delete "transpenic Dlant" and insert --transgenic plant-- therefor;

Column 228, line 49 (Claim 33), please delete "R3" and insert --$R_3$-- therefor.

Signed and Sealed this

Ninth Day of September, 2008

JON W. DUDAS
*Director of the United States Patent and Trademark Office*

```
                        SEQUENCE LISTING

<160> NUMBER OF SEQ ID NOS: 140

<210> SEQ ID NO 1
<211> LENGTH: 1164
<212> TYPE: DNA
<213> ORGANISM: Ricinus communis
<220> FEATURE:
<221> NAME/KEY: CDS
<222> LOCATION: (1)...(1161)

<400> SEQUENCE: 1 atg gga ggt ggt ggt cgc atg tct act gtc ata acc agc aac aac agt      48
Met Gly Gly Gly Gly Arg Met Ser Thr Val Ile Thr Ser Asn Asn Ser
1               5                   10                  15 gag aag aaa gga gga agc agc cac ctt aag cga gcg ccg cac acg aag      96
Glu Lys Lys Gly Gly Ser Ser His Leu Lys Arg Ala Pro His Thr Lys
            20                  25                  30 cct cct ttc aca ctt ggt gac ctc aag aga gcc atc cca ccc cat tgc     144
Pro Pro Phe Thr Leu Gly Asp Leu Lys Arg Ala Ile Pro Pro His Cys
        35                  40                  45 ttt gaa cgc tct ttt gtg cgc tca ttc tcc tat gtt gcc tat gat gtc     192
Phe Glu Arg Ser Phe Val Arg Ser Phe Ser Tyr Val Ala Tyr Asp Val
    50                  55                  60 tgc tta agt ttt ctt ttc tac tcg atc gcc acc aac ttc ttc cct tac     240
Cys Leu Ser Phe Leu Phe Tyr Ser Ile Ala Thr Asn Phe Phe Pro Tyr
65                  70                  75                  80 atc tct tct ccg ctc tcg tat gtc gct tgg ctg gtt tac tgg ctc ttc     288
Ile Ser Ser Pro Leu Ser Tyr Val Ala Trp Leu Val Tyr Trp Leu Phe
```

-continued

```
                         85                    90                    95
caa ggc tgc att ctc act ggt ctt tgg gtc atc ggc cat gaa tgt ggc         336
Gln Gly Cys Ile Leu Thr Gly Leu Trp Val Ile Gly His Glu Cys Gly
            100                 105                 110 cat cat gct ttt agt gag tat cag ctg gct gat gac att gtt ggc cta         384
His His Ala Phe Ser Glu Tyr Gln Leu Ala Asp Asp Ile Val Gly Leu
                115                 120                 125 att gtc cat tct gca ctt ctg gtt cca tat ttt tca tgg aaa tat agc         432
Ile Val His Ser Ala Leu Leu Val Pro Tyr Phe Ser Trp Lys Tyr Ser
    130                 135                 140 cat cgc cgc cac cat tct aac ata gga tct ctc gag cga gac gaa gtg         480
His Arg Arg His His Ser Asn Ile Gly Ser Leu Glu Arg Asp Glu Val
145                 150                 155                 160 ttc gtc ccg aaa tca aag tcg aaa att tca tgg tat tct aag tac tta         528
Phe Val Pro Lys Ser Lys Ser Lys Ile Ser Trp Tyr Ser Lys Tyr Leu
                165                 170                 175 aac aac ccg cca ggt cga gtt ttg aca ctt gct gcc acg ctc ctc ctt         576
Asn Asn Pro Pro Gly Arg Val Leu Thr Leu Ala Ala Thr Leu Leu Leu
            180                 185                 190 ggc tgg cct tta tac tta gct ttc aat gtc tct ggt aga cct tac gat         624
Gly Trp Pro Leu Tyr Leu Ala Phe Asn Val Ser Gly Arg Pro Tyr Asp
        195                 200                 205 cgc ttt gct tgc cat tat gat ccc tat ggc cca ata ttt tcc gaa aga         672
Arg Phe Ala Cys His Tyr Asp Pro Tyr Gly Pro Ile Phe Ser Glu Arg
    210                 215                 220 gaa agg ctt cag att tac att gct gac ctc gga atc ttt gcc aca acg         720
Glu Arg Leu Gln Ile Tyr Ile Ala Asp Leu Gly Ile Phe Ala Thr Thr
225                 230                 235                 240 ttt gtg ctt tat cag gct aca atg gca aaa ggg ttg gct tgg gta atg         768
Phe Val Leu Tyr Gln Ala Thr Met Ala Lys Gly Leu Ala Trp Val Met
                245                 250                 255 cgt atc tat ggg gtg cca ttg ctt att gtt aac tgt ttc ctt gtt atg         816
Arg Ile Tyr Gly Val Pro Leu Leu Ile Val Asn Cys Phe Leu Val Met
            260                 265                 270 atc aca tac ttg cag cac act cac cca gct att cca cgc tat ggc tca         864
Ile Thr Tyr Leu Gln His Thr His Pro Ala Ile Pro Arg Tyr Gly Ser
        275                 280                 285 tcg gaa tgg gat tgg ctc cgg gga gca atg gtg act gtc gat aga gat         912
Ser Glu Trp Asp Trp Leu Arg Gly Ala Met Val Thr Val Asp Arg Asp
    290                 295                 300 tat ggg gtg ttg aat aaa gta ttc cat aac att gca gac act cat gta         960
Tyr Gly Val Leu Asn Lys Val Phe His Asn Ile Ala Asp Thr His Val
305                 310                 315                 320 gct cat cat ctc ttt gct aca gtg cca cat tac cat gca atg gag gcc        1008
Ala His His Leu Phe Ala Thr Val Pro His Tyr His Ala Met Glu Ala
                325                 330                 335 act aaa gca atc aag cct ata atg ggt gag tat tac cgg tat gat ggt        1056
Thr Lys Ala Ile Lys Pro Ile Met Gly Glu Tyr Tyr Arg Tyr Asp Gly
            340                 345                 350 acc cca ttt tac aag gca ttg tgg agg gag gca aag gag tgc ttg ttc        1104
Thr Pro Phe Tyr Lys Ala Leu Trp Arg Glu Ala Lys Glu Cys Leu Phe
        355                 360                 365 gtc gag cca gat gaa gga gct cct aca caa ggc gtt ttc tgg tac cgg        1152
Val Glu Pro Asp Glu Gly Ala Pro Thr Gln Gly Val Phe Trp Tyr Arg
    370                 375                 380 aac aag tat taa                                                         1164
Asn Lys Tyr
385
```

<210> SEQ ID NO 2
<211> LENGTH: 1155
<212> TYPE: DNA
<213> ORGANISM: Lesquerella fendleri
<220> FEATURE:
<221> NAME/KEY: CDS
<222> LOCATION: (1)...(1152)

<400> SEQUENCE: 2

| | | | | | | | | | | | | | | | | |
|---|---|---|---|---|---|---|---|---|---|---|---|---|---|---|---|---|
| atg | ggt | gct | ggt | gga | aga | ata | atg | gtt | acc | ccc | tct | tcc | aag | aaa | tca | 48 |
| Met | Gly | Ala | Gly | Gly | Arg | Ile | Met | Val | Thr | Pro | Ser | Ser | Lys | Lys | Ser | |
| 1 | | | | 5 | | | | | 10 | | | | | 15 | | |
| gaa | act | gaa | gcc | cta | aaa | cgt | gga | cca | tgt | gag | aaa | cca | cca | ttc | act | 96 |
| Glu | Thr | Glu | Ala | Leu | Lys | Arg | Gly | Pro | Cys | Glu | Lys | Pro | Pro | Phe | Thr | |
| | | | 20 | | | | | 25 | | | | | 30 | | | |
| gtt | aaa | gat | ctg | aag | aaa | gca | atc | cca | cag | cat | tgt | ttt | cag | cgc | tct | 144 |
| Val | Lys | Asp | Leu | Lys | Lys | Ala | Ile | Pro | Gln | His | Cys | Phe | Gln | Arg | Ser | |
| | | 35 | | | | | 40 | | | | | 45 | | | | |
| atc | cct | cgt | tct | ttc | tcc | tac | ctt | ctc | aca | gat | atc | act | tta | gtt | tct | 192 |
| Ile | Pro | Arg | Ser | Phe | Ser | Tyr | Leu | Leu | Thr | Asp | Ile | Thr | Leu | Val | Ser | |
| | 50 | | | | | 55 | | | | | 60 | | | | | |
| tgc | ttc | tac | tac | gtt | gcc | aca | aat | tac | ttc | tct | ctt | ctt | cct | cag | cct | 240 |
| Cys | Phe | Tyr | Tyr | Val | Ala | Thr | Asn | Tyr | Phe | Ser | Leu | Leu | Pro | Gln | Pro | |
| 65 | | | | | 70 | | | | | 75 | | | | | 80 | |
| ctc | tct | act | tac | cta | gct | tgg | cct | ctc | tat | tgg | gta | tgt | caa | ggc | tgt | 288 |
| Leu | Ser | Thr | Tyr | Leu | Ala | Trp | Pro | Leu | Tyr | Trp | Val | Cys | Gln | Gly | Cys | |
| | | | | 85 | | | | | 90 | | | | | 95 | | |
| gtc | tta | aca | ggt | atc | tgg | gtc | att | ggc | cat | gaa | tgt | ggt | cac | cat | gca | 336 |
| Val | Leu | Thr | Gly | Ile | Trp | Val | Ile | Gly | His | Glu | Cys | Gly | His | His | Ala | |
| | | | 100 | | | | | 105 | | | | | 110 | | | |
| ttc | agt | gac | tat | caa | tgg | gta | gat | gac | act | gtt | ggt | ttt | atc | ttc | cat | 384 |
| Phe | Ser | Asp | Tyr | Gln | Trp | Val | Asp | Asp | Thr | Val | Gly | Phe | Ile | Phe | His | |
| | | 115 | | | | | 120 | | | | | 125 | | | | |
| tcc | ttc | ctt | ctc | gtc | cct | tac | ttc | tcc | tgg | aaa | tac | agt | cat | cgt | cgt | 432 |
| Ser | Phe | Leu | Leu | Val | Pro | Tyr | Phe | Ser | Trp | Lys | Tyr | Ser | His | Arg | Arg | |
| | 130 | | | | | 135 | | | | | 140 | | | | | |
| cac | cat | tcc | aac | aat | gga | tct | ctc | gag | aaa | gat | gaa | gtc | ttt | gtc | cca | 480 |
| His | His | Ser | Asn | Asn | Gly | Ser | Leu | Glu | Lys | Asp | Glu | Val | Phe | Val | Pro | |
| 145 | | | | | 150 | | | | | 155 | | | | | 160 | |
| ccg | aaa | aaa | gct | gca | gtc | aaa | tgg | tat | gtt | aaa | tac | ctc | aac | aac | cct | 528 |
| Pro | Lys | Lys | Ala | Ala | Val | Lys | Trp | Tyr | Val | Lys | Tyr | Leu | Asn | Asn | Pro | |
| | | | | 165 | | | | | 170 | | | | | 175 | | |
| ctt | gga | cgc | att | ctg | gtg | tta | aca | gtt | cag | ttt | atc | ctc | ggg | tgg | cct | 576 |
| Leu | Gly | Arg | Ile | Leu | Val | Leu | Thr | Val | Gln | Phe | Ile | Leu | Gly | Trp | Pro | |
| | | | 180 | | | | | 185 | | | | | 190 | | | |
| ttg | tat | cta | ccc | ttt | aat | gta | tca | ggt | aga | cct | tat | gat | ggt | ttc | gct | 624 |
| Leu | Tyr | Leu | Pro | Phe | Asn | Val | Ser | Gly | Arg | Pro | Tyr | Asp | Gly | Phe | Ala | |
| | | 195 | | | | | 200 | | | | | 205 | | | | |
| tca | cat | ttc | ttc | cct | cat | gca | cct | atc | ttt | aaa | gac | cgc | gaa | cgt | ctc | 672 |
| Ser | His | Phe | Phe | Pro | His | Ala | Pro | Ile | Phe | Lys | Asp | Arg | Glu | Arg | Leu | |
| | 210 | | | | | 215 | | | | | 220 | | | | | |
| cag | ata | tac | atc | tca | gat | gct | ggt | att | cta | gct | gtc | tgt | tat | ggt | ctt | 720 |
| Gln | Ile | Tyr | Ile | Ser | Asp | Ala | Gly | Ile | Leu | Ala | Val | Cys | Tyr | Gly | Leu | |
| 225 | | | | | 230 | | | | | 235 | | | | | 240 | |
| tac | cgt | tac | gct | gct | tca | caa | gga | ttg | act | gct | atg | atc | tgc | gtc | tat | 768 |
| Tyr | Arg | Tyr | Ala | Ala | Ser | Gln | Gly | Leu | Thr | Ala | Met | Ile | Cys | Val | Tyr | |
| | | | | 245 | | | | | 250 | | | | | 255 | | |
| gga | gta | ccg | ctt | ttg | ata | gtg | aac | ttt | ttc | ctt | gtc | ttg | gta | act | ttc | 816 |
| Gly | Val | Pro | Leu | Leu | Ile | Val | Asn | Phe | Phe | Leu | Val | Leu | Val | Thr | Phe | |
| | | | 260 | | | | | 265 | | | | | 270 | | | |
| ttg | cag | cac | act | cat | cct | tcg | tta | cct | cac | tat | gat | tca | acc | gag | tgg | 864 |

```
Leu Gln His Thr His Pro Ser Leu Pro His Tyr Asp Ser Thr Glu Trp
            275                 280                 285 gaa tgg att aga gga gct ttg gtt acg gta gac aga gac tat gga atc       912
Glu Trp Ile Arg Gly Ala Leu Val Thr Val Asp Arg Asp Tyr Gly Ile
    290                 295                 300 ttg aac aag gtg ttt cac aac ata aca gac aca cat gtg gct cat cat       960
Leu Asn Lys Val Phe His Asn Ile Thr Asp Thr His Val Ala His His
305                 310                 315                 320 ctc ttt gca act ata ccg cat tat aac gca atg gaa gct aca gag gcg      1008
Leu Phe Ala Thr Ile Pro His Tyr Asn Ala Met Glu Ala Thr Glu Ala
                325                 330                 335 ata aag cca ata ctt ggt gat tac tac cac ttc gat gga aca ccg tgg      1056
Ile Lys Pro Ile Leu Gly Asp Tyr Tyr His Phe Asp Gly Thr Pro Trp
            340                 345                 350 tat gtg gcc atg tat agg gaa gca aag gag tgt ctc tat gta gaa ccg      1104
Tyr Val Ala Met Tyr Arg Glu Ala Lys Glu Cys Leu Tyr Val Glu Pro
        355                 360                 365 gat acg gaa cgt ggg aag aaa ggt gtg tac tat tac aac aat aag tta      1152
Asp Thr Glu Arg Gly Lys Lys Gly Val Tyr Tyr Tyr Asn Asn Lys Leu
370                 375                 380 tga                                                                  1155

<210> SEQ ID NO 3
<211> LENGTH: 1152
<212> TYPE: DNA
<213> ORGANISM: Lesquerella lindheimeri
<220> FEATURE:
<221> NAME/KEY: CDS
<222> LOCATION: (1)...(1149)

<400> SEQUENCE: 3 atg ggt gct ggt gga aga ata atg gtt acc ccc tct tcc aag aaa tcg        48
Met Gly Ala Gly Gly Arg Ile Met Val Thr Pro Ser Ser Lys Lys Ser
1               5                  10                  15 aaa cct gaa gcc cta aga cgt ggg cca ggt gag aaa cca cca ttc act        96
Lys Pro Glu Ala Leu Arg Arg Gly Pro Gly Glu Lys Pro Pro Phe Thr
                20                  25                  30 gtt caa gat cta agg aaa gca atc cca cgg cat tgt ttc aaa cgc tct       144
Val Gln Asp Leu Arg Lys Ala Ile Pro Arg His Cys Phe Lys Arg Ser
            35                  40                  45 atc cct cgt tct ttc tcc tat ctt ctc aca gat atc att tta gct tct       192
Ile Pro Arg Ser Phe Ser Tyr Leu Leu Thr Asp Ile Ile Leu Ala Ser
    50                  55                  60 tgc ttc tac tac gtg gcc acc aat tac ttc tca ctt ctt cca cag cct       240
Cys Phe Tyr Tyr Val Ala Thr Asn Tyr Phe Ser Leu Leu Pro Gln Pro
65                  70                  75                  80 ctc tct act tac ttt gct tgg cct ctc tat tgg gta tgt caa ggc tgt       288
Leu Ser Thr Tyr Phe Ala Trp Pro Leu Tyr Trp Val Cys Gln Gly Cys
                85                  90                  95 gtc tta acc ggt gtt tgg gtc ctt ggc cat gaa tgt ggt cac caa gca       336
Val Leu Thr Gly Val Trp Val Leu Gly His Glu Cys Gly His Gln Ala
                100                 105                 110 ttt agt gac tat caa tgg gta gat gac act gtt ggt ttt atc atc cat       384
Phe Ser Asp Tyr Gln Trp Val Asp Asp Thr Val Gly Phe Ile Ile His
            115                 120                 125 acc ttc ctc ctc atc cct tac ttc tcc tgg aag tat agt cat cgt cgt       432
Thr Phe Leu Leu Ile Pro Tyr Phe Ser Trp Lys Tyr Ser His Arg Arg
    130                 135                 140 cac cat gcc aat aat gga tca ctc gag aga gat gaa gtc ttt gtc cca       480
His His Ala Asn Asn Gly Ser Leu Glu Arg Asp Glu Val Phe Val Pro
145                 150                 155                 160
```

```
ccg aag aaa gct gca gtc aaa tgg tat gtc aaa tac ctc aac aac cct      528
Pro Lys Lys Ala Ala Val Lys Trp Tyr Val Lys Tyr Leu Asn Asn Pro
            165                 170                 175 ctt gga cgc act gtg gtg tta ata gtc cag ttt gtc ctc gga tgg ccc      576
Leu Gly Arg Thr Val Val Leu Ile Val Gln Phe Val Leu Gly Trp Pro
        180                 185                 190 ttg tac cta gcc ttt aac gta tca ggt aga tcc tat gat ggt ttc gct      624
Leu Tyr Leu Ala Phe Asn Val Ser Gly Arg Ser Tyr Asp Gly Phe Ala
    195                 200                 205 tca cat ttc ttc cca cat gca ccc atc ttc aag gac cga gaa cgt ctc      672
Ser His Phe Phe Pro His Ala Pro Ile Phe Lys Asp Arg Glu Arg Leu
210                 215                 220 cat ata tac atc aca gat gct ggt att cta gct gtc tgt tat ggt ctt      720
His Ile Tyr Ile Thr Asp Ala Gly Ile Leu Ala Val Cys Tyr Gly Leu
225                 230                 235                 240 tac cgt tac gca gct aca aaa gga ttg acc gct atg atc tgc gtc tat      768
Tyr Arg Tyr Ala Ala Thr Lys Gly Leu Thr Ala Met Ile Cys Val Tyr
                245                 250                 255 ggg gta cct cct ctg gtt gta aac ttt ttc ctt gtc ttg gtc act ttc      816
Gly Val Pro Pro Leu Val Val Asn Phe Phe Leu Val Leu Val Thr Phe
            260                 265                 270 ttg cag cac act cat cct tca tta cct cac tat gat tca acc gag tgg      864
Leu Gln His Thr His Pro Ser Leu Pro His Tyr Asp Ser Thr Glu Trp
        275                 280                 285 gac tgg att aga gga gcc atg gtt aca gta gac aga gac tat ggg atc      912
Asp Trp Ile Arg Gly Ala Met Val Thr Val Asp Arg Asp Tyr Gly Ile
    290                 295                 300 ttg aac aag gtg ttc cac aac ata aca gac aca cat gtg gct cat cat      960
Leu Asn Lys Val Phe His Asn Ile Thr Asp Thr His Val Ala His His
305                 310                 315                 320 ctt ttc gca aca ata ccg cat tat aat gca atg gaa gct aca gag gcg     1008
Leu Phe Ala Thr Ile Pro His Tyr Asn Ala Met Glu Ala Thr Glu Ala
                325                 330                 335 ata aag cca ata ctc gga gac tac tac cat ttc gat gga aca ccc tgg     1056
Ile Lys Pro Ile Leu Gly Asp Tyr Tyr His Phe Asp Gly Thr Pro Trp
            340                 345                 350 tat gtg gct atg tat agg gaa gca aag cag tgt ctc tat gta gaa cag     1104
Tyr Val Ala Met Tyr Arg Glu Ala Lys Gln Cys Leu Tyr Val Glu Gln
        355                 360                 365 gat aca gaa aag aag aaa ggt gtc tac tat tac aac aat aag tta          1149
Asp Thr Glu Lys Lys Lys Gly Val Tyr Tyr Tyr Asn Asn Lys Leu
    370                 375                 380 tga                                                                   1152

<210> SEQ ID NO 4
<211> LENGTH: 1155
<212> TYPE: DNA
<213> ORGANISM: Lesquerella gracilis A
<220> FEATURE:
<221> NAME/KEY: CDS
<222> LOCATION: (1)...(1152)

<400> SEQUENCE: 4 atg ggt gct ggt gga aga ata atg gta acc ccc tct tcg aag aaa tcg       48
Met Gly Ala Gly Gly Arg Ile Met Val Thr Pro Ser Ser Lys Lys Ser
1               5                   10                  15 aaa cct caa gcc cta aga cgt gga cca tgt gag aaa cca cca ttc act       96
Lys Pro Gln Ala Leu Arg Arg Gly Pro Cys Glu Lys Pro Pro Phe Thr
            20                  25                  30 gtt aaa gat ctg aag aaa gca atc cca ccg cat tgt ttc aaa cgc tct      144
```

-continued

```
                Val Lys Asp Leu Lys Lys Ala Ile Pro Pro His Cys Phe Lys Arg Ser
                             35                  40                  45 atc cct cgc tct ttc tct tac ctt ctc aca gat ttc att cta gct tct       192
Ile Pro Arg Ser Phe Ser Tyr Leu Leu Thr Asp Phe Ile Leu Ala Ser
 50                  55                  60 tgc ttc tac tac gtg gct aca aat tac ttc tct ctt ctc cca cag cct       240
Cys Phe Tyr Tyr Val Ala Thr Asn Tyr Phe Ser Leu Leu Pro Gln Pro
 65                  70                  75                  80 gtc tct aat tac ctg gct tgg cct ctc tat tgg ata tgt caa ggc tgt       288
Val Ser Asn Tyr Leu Ala Trp Pro Leu Tyr Trp Ile Cys Gln Gly Cys
                 85                  90                  95 gtc tta acc ggt gtt tgg gtc ctt ggc cat gaa tgt ggt cac cat gca       336
Val Leu Thr Gly Val Trp Val Leu Gly His Glu Cys Gly His His Ala
                100                 105                 110 ttc agt gac tat caa tgg gta gat gac act gtt ggt ttt atc atc cat       384
Phe Ser Asp Tyr Gln Trp Val Asp Asp Thr Val Gly Phe Ile Ile His
                115                 120                 125 tcc ttc ctc ctt gtc cct tac ttc tcc tgg aag tac agt cat cgt cgt       432
Ser Phe Leu Leu Val Pro Tyr Phe Ser Trp Lys Tyr Ser His Arg Arg
130                 135                 140 cac cat tcc aac aat gga tcc ctc gag aaa gat gaa gtc ttt gtt cca       480
His His Ser Asn Asn Gly Ser Leu Glu Lys Asp Glu Val Phe Val Pro
145                 150                 155                 160 cct aag aaa gct gca gtc aaa tgg tat gtt aag tac ctc aac aac cct       528
Pro Lys Lys Ala Ala Val Lys Trp Tyr Val Lys Tyr Leu Asn Asn Pro
                165                 170                 175 ctt gga cgc act gtg gtg tta ata gtc cag ttt gtc ctc ggg tgg cct       576
Leu Gly Arg Thr Val Val Leu Ile Val Gln Phe Val Leu Gly Trp Pro
                180                 185                 190 ttg tat cta gcc ttt aac gta tca ggt aga ccc tat gat ggg ttc gct       624
Leu Tyr Leu Ala Phe Asn Val Ser Gly Arg Pro Tyr Asp Gly Phe Ala
                195                 200                 205 tca cac ttc ttt cct cat gca ccc atc ttc agg gac cgt gaa cgc ctc       672
Ser His Phe Phe Pro His Ala Pro Ile Phe Arg Asp Arg Glu Arg Leu
                210                 215                 220 cat ata tac atc aca gat gct ggt att cta gct gtc tgt tat ggt ctt       720
His Ile Tyr Ile Thr Asp Ala Gly Ile Leu Ala Val Cys Tyr Gly Leu
225                 230                 235                 240 tac cgt tac gct gct tca aaa gga ttg acc gct atg atc tgc gtc tac       768
Tyr Arg Tyr Ala Ala Ser Lys Gly Leu Thr Ala Met Ile Cys Val Tyr
                245                 250                 255 gga gta ccg ctt ttg ata gtg aac ttt ttc ctc gtg ttg gtc act ttc       816
Gly Val Pro Leu Leu Ile Val Asn Phe Phe Leu Val Leu Val Thr Phe
                260                 265                 270 ttg cag cac act cat cct tca tta cct cac tat gat tca acc gag tgg       864
Leu Gln His Thr His Pro Ser Leu Pro His Tyr Asp Ser Thr Glu Trp
                275                 280                 285 gaa tgg att aga gga gcc ttg gtt aca gta gac aga gac tat gga atc       912
Glu Trp Ile Arg Gly Ala Leu Val Thr Val Asp Arg Asp Tyr Gly Ile
                290                 295                 300 ttg aac aag gtg ttc cac aac ata aca gac aca cat gtg gct cat cat       960
Leu Asn Lys Val Phe His Asn Ile Thr Asp Thr His Val Ala His His
305                 310                 315                 320 att ttc gca aca ata ccg cat tat aat gca atg gaa gct aca gag gcg      1008
Ile Phe Ala Thr Ile Pro His Tyr Asn Ala Met Glu Ala Thr Glu Ala
                325                 330                 335 ata aag cca ata ctc gga gac tac tac cat ttc gat gga aca ccg tgg      1056
Ile Lys Pro Ile Leu Gly Asp Tyr Tyr His Phe Asp Gly Thr Pro Trp
                340                 345                 350
```

```
tat gtg gcc atg tac agg gaa gca aag gag tgt ctc tat gta gaa cag      1104
Tyr Val Ala Met Tyr Arg Glu Ala Lys Glu Cys Leu Tyr Val Glu Gln
            355                 360                 365 gat aca gaa cgt ggg aag aaa ggt gtc tac tat tac aac aat aag tta      1152
Asp Thr Glu Arg Gly Lys Lys Gly Val Tyr Tyr Tyr Asn Asn Lys Leu
    370                 375                 380 tga                                                                  1155

<210> SEQ ID NO 5
<211> LENGTH: 1155
<212> TYPE: DNA
<213> ORGANISM: Lesquerella gracilis B
<220> FEATURE:
<221> NAME/KEY: CDS
<222> LOCATION: (1)...(1152)

<400> SEQUENCE: 5 atg ggt gct ggt gga aga ata atg gtt acc cct tct tcc aag aaa tca        48
Met Gly Ala Gly Gly Arg Ile Met Val Thr Pro Ser Ser Lys Lys Ser
1               5                  10                  15 gaa act gaa gcc cta aaa cgt gga cca tgt gag aaa cca cca ttc act        96
Glu Thr Glu Ala Leu Lys Arg Gly Pro Cys Glu Lys Pro Pro Phe Thr
            20                  25                  30 gtt aaa gat ctg aag aaa gca atc cca cag cat tgt ttt caa cgc tct       144
Val Lys Asp Leu Lys Lys Ala Ile Pro Gln His Cys Phe Gln Arg Ser
        35                  40                  45 atc cct cgt tct ttc tcc tac ctt ctc aca gat atc act tta gtt tct       192
Ile Pro Arg Ser Phe Ser Tyr Leu Leu Thr Asp Ile Thr Leu Val Ser
    50                  55                  60 tgc ttc tac tac gtt gcc aca aat tac ttc tct ctt ctt cct cag cct       240
Cys Phe Tyr Tyr Val Ala Thr Asn Tyr Phe Ser Leu Leu Pro Gln Pro
65                  70                  75                  80 ctc tct act tac cta gct tgg cct ctc tat tgg gta tgt caa ggc tgt       288
Leu Ser Thr Tyr Leu Ala Trp Pro Leu Tyr Trp Val Cys Gln Gly Cys
                85                  90                  95 gtc cta aca ggt atc tgg gtc ctt ggc cat gaa tgt ggt cac cat gca       336
Val Leu Thr Gly Ile Trp Val Leu Gly His Glu Cys Gly His His Ala
            100                 105                 110 ttc agt gac tat caa tgg cta gat gac act gtt ggt ttt atc ttc cat       384
Phe Ser Asp Tyr Gln Trp Leu Asp Asp Thr Val Gly Phe Ile Phe His
        115                 120                 125 tcc tta ctt ctc gtc cct tac ttc tcc tgg aaa tac agt cat cgt cgt       432
Ser Leu Leu Leu Val Pro Tyr Phe Ser Trp Lys Tyr Ser His Arg Arg
    130                 135                 140 cac cat tcc aac aat gga tct ctc gag aaa gat gaa gtc ttt gtc cca       480
His His Ser Asn Asn Gly Ser Leu Glu Lys Asp Glu Val Phe Val Pro
145                 150                 155                 160 ccg aaa aaa gct gca gtc aaa tgg tat gtt aaa tac ctc aac aac cct       528
Pro Lys Lys Ala Ala Val Lys Trp Tyr Val Lys Tyr Leu Asn Asn Pro
                165                 170                 175 ctt gga cgc att ctg gtg tta aca gtt cgg ttt atc ctc ggg tgg cct       576
Leu Gly Arg Ile Leu Val Leu Thr Val Arg Phe Ile Leu Gly Trp Pro
            180                 185                 190 ttg tat cta gcc ttt aat gta tca ggt aga cct tat gat ggt ttc gct       624
Leu Tyr Leu Ala Phe Asn Val Ser Gly Arg Pro Tyr Asp Gly Phe Ala
        195                 200                 205 tca cat ttc ttc cct cat gca cct atc ttt aaa gac cgc gaa cgt ctc       672
Ser His Phe Phe Pro His Ala Pro Ile Phe Lys Asp Arg Glu Arg Leu
    210                 215                 220 cag ata tac atc tca gat gct ggt att cta gct gtc tgt tat ggt ctt       720
Gln Ile Tyr Ile Ser Asp Ala Gly Ile Leu Ala Val Cys Tyr Gly Leu
```

```
                    225                 230                 235                 240
tac cgt tac gct gct tca caa gga ttg acc gct atg atc tgc gtc tat      768
Tyr Arg Tyr Ala Ala Ser Gln Gly Leu Thr Ala Met Ile Cys Val Tyr
                    245                 250                 255 gga gta ccg ctt ttg ata gtg aac ttt ttc ctt gtc ttg gta act ttc      816
Gly Val Pro Leu Leu Ile Val Asn Phe Phe Leu Val Leu Val Thr Phe
                260                 265                 270 ttg cag cac act cat cct tcg tta cct cac tat gat tca acc gag tgg      864
Leu Gln His Thr His Pro Ser Leu Pro His Tyr Asp Ser Thr Glu Trp
                275                 280                 285 gaa tgg att aga gga gct ttg gtt acg gta gac aga gac tac gga atc      912
Glu Trp Ile Arg Gly Ala Leu Val Thr Val Asp Arg Asp Tyr Gly Ile
                290                 295                 300 ttg aac aag gtg ttt cac aac ata aca gac aca cat gtg gct cat cat      960
Leu Asn Lys Val Phe His Asn Ile Thr Asp Thr His Val Ala His His
305                 310                 315                 320 ctt ttc gca act ata ccg cat tat aac gca atg gaa gct aca gag gcg     1008
Leu Phe Ala Thr Ile Pro His Tyr Asn Ala Met Glu Ala Thr Glu Ala
                325                 330                 335 ata aag cca ata ctt ggt gat tac tac cat ttc gat gga aca ccg tgg     1056
Ile Lys Pro Ile Leu Gly Asp Tyr Tyr His Phe Asp Gly Thr Pro Trp
                340                 345                 350 tat gtg gct atg tat agg gaa gca aag gag tgt ctc tat gta gaa ccg     1104
Tyr Val Ala Met Tyr Arg Glu Ala Lys Glu Cys Leu Tyr Val Glu Pro
                355                 360                 365 gat acg gaa cgt ggg aag aaa ggt gtc tac tat tac aac aat aag tta     1152
Asp Thr Glu Arg Gly Lys Lys Gly Val Tyr Tyr Tyr Asn Asn Lys Leu
                370                 375                 380 tga                                                                  1155

<210> SEQ ID NO 6
<211> LENGTH: 1125
<212> TYPE: DNA
<213> ORGANISM: Crepis biennis
<220> FEATURE:
<221> NAME/KEY: CDS
<222> LOCATION: (1)...(1122)

<400> SEQUENCE: 6 atg ggt gcc cac ggc cat ggt cga aca tcg aaa aaa tcg gtc atg gaa       48
Met Gly Ala His Gly His Gly Arg Thr Ser Lys Lys Ser Val Met Glu
1               5                   10                  15 cgt gtc tcg gtt gat cca gta ccc ttc tcg cta agt gat tta aag caa       96
Arg Val Ser Val Asp Pro Val Pro Phe Ser Leu Ser Asp Leu Lys Gln
                20                  25                  30 gca atc cct ccc cat tgc ttc cag cga tct gtc atc cgt tca tct tac      144
Ala Ile Pro Pro His Cys Phe Gln Arg Ser Val Ile Arg Ser Ser Tyr
            35                  40                  45 tat gta gtt cac gat ctc att att gcc tac atc ttc tac ttc ctt gcc      192
Tyr Val Val His Asp Leu Ile Ile Ala Tyr Ile Phe Tyr Phe Leu Ala
        50                  55                  60 gat aaa tat att ccg att ctc cct gct cct cta gcc tac tta gct tgg      240
Asp Lys Tyr Ile Pro Ile Leu Pro Ala Pro Leu Ala Tyr Leu Ala Trp
65                  70                  75                  80 ccc ctt tac tgg ttc tgt caa gct agc atc ctc act ggt tta tgg atc      288
Pro Leu Tyr Trp Phe Cys Gln Ala Ser Ile Leu Thr Gly Leu Trp Ile
                85                  90                  95 ctc ggt cat gaa tgc ggt cac cat gcc ttt agc gag tac caa tgg gtt      336
Leu Gly His Glu Cys Gly His His Ala Phe Ser Glu Tyr Gln Trp Val
                100                 105                 110
```

| | | |
|---|---|---|
| gac gac act gtg ggc ttc atg gtc cac tca ttt ctc ctc acc ccg tat<br>Asp Asp Thr Val Gly Phe Met Val His Ser Phe Leu Leu Thr Pro Tyr<br>115                        120                     125 | | 384 |
| ttc tcg tgg aaa tac agt cac cgg aat cac cat gcc aac aca agt tcc<br>Phe Ser Trp Lys Tyr Ser His Arg Asn His His Ala Asn Thr Ser Ser<br>    130                   135                    140 | | 432 |
| atc gat aac gat gaa gtt tac att ccg aaa agc aag tcc aaa ctc gcg<br>Ile Asp Asn Asp Glu Val Tyr Ile Pro Lys Ser Lys Ser Lys Leu Ala<br>145                       150                   155               160 | | 480 |
| ctt acc tat aaa ctt ctt aac aac ccg cct ggt cga ctg tta gtt atg<br>Leu Thr Tyr Lys Leu Leu Asn Asn Pro Pro Gly Arg Leu Leu Val Met<br>                  165                    170                 175 | | 528 |
| gtt atc atg ttc acc cta gga ttt cct tta tac ctc ttg aca aat att<br>Val Ile Met Phe Thr Leu Gly Phe Pro Leu Tyr Leu Leu Thr Asn Ile<br>              180                      185                190 | | 576 |
| tcc ggc aag aag tac gac agg ttt gcc aac cac ttc gac ccc atg agt<br>Ser Gly Lys Lys Tyr Asp Arg Phe Ala Asn His Phe Asp Pro Met Ser<br>         195                    200                   205 | | 624 |
| cca att ttc aag gaa cgt gag cgg ttt cag gtc ttg ctt tcg gat ctt<br>Pro Ile Phe Lys Glu Arg Glu Arg Phe Gln Val Leu Leu Ser Asp Leu<br>210                       215                   220 | | 672 |
| ggc ctt ctt gct gtg ttt tat gga att aaa gtt gct gta gca aag aaa<br>Gly Leu Leu Ala Val Phe Tyr Gly Ile Lys Val Ala Val Ala Lys Lys<br>225                       230                   235               240 | | 720 |
| gga gct gcg tgg gtg gcg tgt atg tat gga gtt ccg atg cta ggc gta<br>Gly Ala Ala Trp Val Ala Cys Met Tyr Gly Val Pro Met Leu Gly Val<br>                  245                    250                255 | | 768 |
| ttt acc ctt ttc gat atc atc acg tac ttg cac cac acc cat cag tcg<br>Phe Thr Leu Phe Asp Ile Ile Thr Tyr Leu His His Thr His Gln Ser<br>                  260                    265                270 | | 816 |
| tct cct cat tat gac tca act gaa tgg aac tgg atc aga ggg gcg ttg<br>Ser Pro His Tyr Asp Ser Thr Glu Trp Asn Trp Ile Arg Gly Ala Leu<br>         275                    280                   285 | | 864 |
| tca gca atc gat agg gac ttt ggg ttc atg aat agt gtt ttc cat gat<br>Ser Ala Ile Asp Arg Asp Phe Gly Phe Met Asn Ser Val Phe His Asp<br>290                       295                   300 | | 912 |
| gtt aca cac act cac gtc atg cat cat atg ttt tca tac att cca cac<br>Val Thr His Thr His Val Met His His Met Phe Ser Tyr Ile Pro His<br>305                       310                   315               320 | | 960 |
| tat cat gcg aaa gag gca agg gat gca atc aat aca atc ata ggc gac<br>Tyr His Ala Lys Glu Ala Arg Asp Ala Ile Asn Thr Ile Ile Gly Asp<br>                  325                    330                335 | | 1008 |
| tat tat atg atc gat agg act cca att ttg aaa gca ctg tgg aga gag<br>Tyr Tyr Met Ile Asp Arg Thr Pro Ile Leu Lys Ala Leu Trp Arg Glu<br>              340                      345                350 | | 1056 |
| gcc aag gaa tgc atg tac atc gag cct gat agc aag cgc aaa ggt gta<br>Ala Lys Glu Cys Met Tyr Ile Glu Pro Asp Ser Lys Arg Lys Gly Val<br>         355                    360                   365 | | 1104 |
| tat tgg tac cat aaa ttg tga<br>Tyr Trp Tyr His Lys Leu<br>    370 | | 1125 |

```
<210> SEQ ID NO 7
<211> LENGTH: 1152
<212> TYPE: DNA
<213> ORGANISM: Ricinus communis
<220> FEATURE:
<221> NAME/KEY: CDS
<222> LOCATION: (1)...(1149)

<400> SEQUENCE: 7
```

-continued

| | |
|---|---|
| atg ggt gca ggt gga aga atg ccg gtt cct act tct tcc aag aaa tcg<br>Met Gly Ala Gly Gly Arg Met Pro Val Pro Thr Ser Ser Lys Lys Ser<br>1               5                   10                  15 | 48 |
| gaa acc gac acc aca aag cgt gtg ccg tgc gag aaa ccg cct ttc tcg<br>Glu Thr Asp Thr Thr Lys Arg Val Pro Cys Glu Lys Pro Pro Phe Ser<br>            20                  25                  30 | 96 |
| gtg gga gat ctg aag aaa gcc atc cca ccc cat tgc ttt gaa cgc tct<br>Val Gly Asp Leu Lys Lys Ala Ile Pro Pro His Cys Phe Glu Arg Ser<br>        35                  40                  45 | 144 |
| ttt gtg cgc tca ttc tcc tat gtt gcc tat gat gtc tgc tta agt ttt<br>Phe Val Arg Ser Phe Ser Tyr Val Ala Tyr Asp Val Cys Leu Ser Phe<br>    50                  55                  60 | 192 |
| ctt ttc tac tcg atc gcc acc aac ttc ttc cct tac atc tct tct ccg<br>Leu Phe Tyr Ser Ile Ala Thr Asn Phe Phe Pro Tyr Ile Ser Ser Pro<br>65                  70                  75                  80 | 240 |
| ctc tcg tat gtc gct tgg ctg gtt tac tgg ctc ttc caa ggc tgc att<br>Leu Ser Tyr Val Ala Trp Leu Val Tyr Trp Leu Phe Gln Gly Cys Ile<br>                85                  90                  95 | 288 |
| ctc act ggt ctt tgg gtc atc ggc cat gaa tgt ggc cat cat gct ttt<br>Leu Thr Gly Leu Trp Val Ile Gly His Glu Cys Gly His His Ala Phe<br>            100                 105                 110 | 336 |
| agt gag tat cag ctg gct gat gac att gtt ggc cta att gtc cat tct<br>Ser Glu Tyr Gln Leu Ala Asp Asp Ile Val Gly Leu Ile Val His Ser<br>        115                 120                 125 | 384 |
| gca ctt ctg gtt cca tat ttt tca tgg aaa tat agc cat cgc cgc cac<br>Ala Leu Leu Val Pro Tyr Phe Ser Trp Lys Tyr Ser His Arg Arg His<br>    130                 135                 140 | 432 |
| cat tct aac ata gga tct ctc gag cga gac gaa gtg ttc gtc ccg aaa<br>His Ser Asn Ile Gly Ser Leu Glu Arg Asp Glu Val Phe Val Pro Lys<br>145                 150                 155                 160 | 480 |
| tca aag tcg aaa att tca tgg tat tct aag tac tta aac aac ccg cca<br>Ser Lys Ser Lys Ile Ser Trp Tyr Ser Lys Tyr Leu Asn Asn Pro Pro<br>                165                 170                 175 | 528 |
| ggt cga gtt ttg aca ctt gct gcc acg ctc ctc ctt ggc tgg cct tta<br>Gly Arg Val Leu Thr Leu Ala Ala Thr Leu Leu Leu Gly Trp Pro Leu<br>            180                 185                 190 | 576 |
| tac tta gct ttc aat gtc tct ggt aga cct tac gat cgc ttt gct tgc<br>Tyr Leu Ala Phe Asn Val Ser Gly Arg Pro Tyr Asp Arg Phe Ala Cys<br>        195                 200                 205 | 624 |
| cat tat gat ccc tat ggc cca ata ttt tcc gaa aga gaa agg ctt cag<br>His Tyr Asp Pro Tyr Gly Pro Ile Phe Ser Glu Arg Glu Arg Leu Gln<br>    210                 215                 220 | 672 |
| att tac att gct gac ctc gga atc ttt gcc aca acg ttt gtg ctt tat<br>Ile Tyr Ile Ala Asp Leu Gly Ile Phe Ala Thr Thr Phe Val Leu Tyr<br>225                 230                 235                 240 | 720 |
| cag gct aca atg gca aaa ggg ttg gct tgg gta atg cgt atc tat ggg<br>Gln Ala Thr Met Ala Lys Gly Leu Ala Trp Val Met Arg Ile Tyr Gly<br>                245                 250                 255 | 768 |
| gtg cca ttg ctt att gtt aac tgt ttc ctt gtt atg atc aca tac ttg<br>Val Pro Leu Leu Ile Val Asn Cys Phe Leu Val Met Ile Thr Tyr Leu<br>            260                 265                 270 | 816 |
| cag cac act cac cca gct att cca cgc tat ggc tca tcg gaa tgg gat<br>Gln His Thr His Pro Ala Ile Pro Arg Tyr Gly Ser Ser Glu Trp Asp<br>        275                 280                 285 | 864 |
| tgg ctc cgg gga gca atg gtg act gtc gat aga gat tat ggg gtg ttg<br>Trp Leu Arg Gly Ala Met Val Thr Val Asp Arg Asp Tyr Gly Val Leu<br>    290                 295                 300 | 912 |
| aat aaa gta ttc cat aac att gca gac act cat gta gct cat cat ctc<br>Asn Lys Val Phe His Asn Ile Ala Asp Thr His Val Ala His His Leu<br>305                 310                 315                 320 | 960 |

```
ttt gct aca gtg cca cat tac cat gca atg gag gcc act aaa gca atc         1008
Phe Ala Thr Val Pro His Tyr His Ala Met Glu Ala Thr Lys Ala Ile
                325                 330                 335 aag cct ata atg ggt gag tat tac cgg tat gat ggt acc cca ttt tac         1056
Lys Pro Ile Met Gly Glu Tyr Tyr Arg Tyr Asp Gly Thr Pro Phe Tyr
            340                 345                 350 aag gca ttg tgg agg gag gca aag gag tgc ttg ttc gtc gag cca gat         1104
Lys Ala Leu Trp Arg Glu Ala Lys Glu Cys Leu Phe Val Glu Pro Asp
        355                 360                 365 gaa gga gct cct aca caa ggc gtt ttc tgg tac cgg aac aag tat             1149
Glu Gly Ala Pro Thr Gln Gly Val Phe Trp Tyr Arg Asn Lys Tyr
    370                 375                 380 taa                                                                     1152

<210> SEQ ID NO 8
<211> LENGTH: 1155
<212> TYPE: DNA
<213> ORGANISM: Lesquerella fendleri
<220> FEATURE:
<221> NAME/KEY: CDS
<222> LOCATION: (1)...(1152)

<400> SEQUENCE: 8 atg ggt gca ggt gga aga atg ccg gtt cct act tct tcc aag aaa tcg         48
Met Gly Ala Gly Gly Arg Met Pro Val Pro Thr Ser Ser Lys Lys Ser
1               5                   10                  15 gaa acc gac acc aca aag cgt gtg ccg tgc gag aaa ccg cct ttc tcg         96
Glu Thr Asp Thr Thr Lys Arg Val Pro Cys Glu Lys Pro Pro Phe Ser
            20                  25                  30 gtg gga gat ctg aag aaa gca atc cca cag cat tgt ttt cag cgc tct         144
Val Gly Asp Leu Lys Lys Ala Ile Pro Gln His Cys Phe Gln Arg Ser
        35                  40                  45 atc cct cgt tct ttc tcc tac ctt ctc aca gat atc act tta gtt tct         192
Ile Pro Arg Ser Phe Ser Tyr Leu Leu Thr Asp Ile Thr Leu Val Ser
    50                  55                  60 tgc ttc tac tac gtt gcc aca aat tac ttc tct ctt ctt cct cag cct         240
Cys Phe Tyr Tyr Val Ala Thr Asn Tyr Phe Ser Leu Leu Pro Gln Pro
65                  70                  75                  80 ctc tct act tac cta gct tgg cct ctc tat tgg gta tgt caa ggc tgt         288
Leu Ser Thr Tyr Leu Ala Trp Pro Leu Tyr Trp Val Cys Gln Gly Cys
                85                  90                  95 gtc tta aca ggt atc tgg gtc att ggc cat gaa tgt ggt cac cat gca         336
Val Leu Thr Gly Ile Trp Val Ile Gly His Glu Cys Gly His His Ala
            100                 105                 110 ttc agt gac tat caa tgg gta gat gac act gtt ggt ttt atc ttc cat         384
Phe Ser Asp Tyr Gln Trp Val Asp Asp Thr Val Gly Phe Ile Phe His
        115                 120                 125 tcc ttc ctt ctc gtc cct tac ttc tcc tgg aaa tac agt cat cgt cgt         432
Ser Phe Leu Leu Val Pro Tyr Phe Ser Trp Lys Tyr Ser His Arg Arg
    130                 135                 140 cac cat tcc aac aat gga tct ctc gag aaa gat gaa gtc ttt gtc cca         480
His His Ser Asn Asn Gly Ser Leu Glu Lys Asp Glu Val Phe Val Pro
145                 150                 155                 160 ccg aaa aaa gct gca gtc aaa tgg tat gtt aaa tac ctc aac aac cct         528
Pro Lys Lys Ala Ala Val Lys Trp Tyr Val Lys Tyr Leu Asn Asn Pro
                165                 170                 175 ctt gga cgc att ctg gtg tta aca gtt cag ttt atc ctc ggg tgg cct         576
Leu Gly Arg Ile Leu Val Leu Thr Val Gln Phe Ile Leu Gly Trp Pro
            180                 185                 190 ttg tat cta ccc ttt aat gta tca ggt aga cct tat gat ggt ttc gct         624
```

-continued

```
Leu Tyr Leu Pro Phe Asn Val Ser Gly Arg Pro Tyr Asp Gly Phe Ala
        195                 200                 205 tca cat ttc ttc cct cat gca cct atc ttt aaa gac cgc gaa cgt ctc      672
Ser His Phe Phe Pro His Ala Pro Ile Phe Lys Asp Arg Glu Arg Leu
    210                 215                 220 cag ata tac atc tca gat gct ggt att cta gct gtc tgt tat ggt ctt      720
Gln Ile Tyr Ile Ser Asp Ala Gly Ile Leu Ala Val Cys Tyr Gly Leu
225                 230                 235                 240 tac cgt tac gct gct tca caa gga ttg act gct atg atc tgc gtc tat      768
Tyr Arg Tyr Ala Ala Ser Gln Gly Leu Thr Ala Met Ile Cys Val Tyr
                245                 250                 255 gga gta ccg ctt ttg ata gtg aac ttt ttc ctt gtc ttg gta act ttc      816
Gly Val Pro Leu Leu Ile Val Asn Phe Phe Leu Val Leu Val Thr Phe
        260                 265                 270 ttg cag cac act cat cct tcg tta cct cac tat gat tca acc gag tgg      864
Leu Gln His Thr His Pro Ser Leu Pro His Tyr Asp Ser Thr Glu Trp
    275                 280                 285 gaa tgg att aga gga gct ttg gtt acg gta gac aga gac tat gga atc      912
Glu Trp Ile Arg Gly Ala Leu Val Thr Val Asp Arg Asp Tyr Gly Ile
290                 295                 300 ttg aac aag gtg ttt cac aac ata aca gac aca cat gtg gct cat cat      960
Leu Asn Lys Val Phe His Asn Ile Thr Asp Thr His Val Ala His His
305                 310                 315                 320 ctc ttt gca act ata ccg cat tat aac gca atg gaa gct aca gag gcg     1008
Leu Phe Ala Thr Ile Pro His Tyr Asn Ala Met Glu Ala Thr Glu Ala
                325                 330                 335 ata aag cca ata ctt ggt gat tac tac cac ttc gat gga aca ccg tgg     1056
Ile Lys Pro Ile Leu Gly Asp Tyr Tyr His Phe Asp Gly Thr Pro Trp
        340                 345                 350 tat gtg gcc atg tat agg gaa gca aag gag tgt ctc tat gta gaa ccg     1104
Tyr Val Ala Met Tyr Arg Glu Ala Lys Glu Cys Leu Tyr Val Glu Pro
    355                 360                 365 gat acg gaa cgt ggg aag aaa ggt gtg tac tat tac aac aat aag tta     1152
Asp Thr Glu Arg Gly Lys Lys Gly Val Tyr Tyr Tyr Asn Asn Lys Leu
370                 375                 380 tga                                                                  1155
```

<210> SEQ ID NO 9
<211> LENGTH: 1152
<212> TYPE: DNA
<213> ORGANISM: Lesquerella lindheimeri
<220> FEATURE:
<221> NAME/KEY: CDS
<222> LOCATION: (1)...(1149)

<400> SEQUENCE: 9

```
atg ggt gca ggt gga aga atg ccg gtt cct act tct tcc aag aaa tcg       48
Met Gly Ala Gly Gly Arg Met Pro Val Pro Thr Ser Ser Lys Lys Ser
1               5                  10                  15 gaa acc gac acc aca aag cgt gtg ccg tgc gag aaa ccg cct ttc tcg       96
Glu Thr Asp Thr Thr Lys Arg Val Pro Cys Glu Lys Pro Pro Phe Ser
                20                  25                  30 gtg gga gat cta agg aaa gca atc cca cgg cat tgt ttc aaa cgc tct      144
Val Gly Asp Leu Arg Lys Ala Ile Pro Arg His Cys Phe Lys Arg Ser
            35                  40                  45 atc cct cgt tct ttc tcc tat ctt ctc aca gat atc att tta gct tct      192
Ile Pro Arg Ser Phe Ser Tyr Leu Leu Thr Asp Ile Ile Leu Ala Ser
        50                  55                  60 tgc ttc tac tac gtg gcc acc aat tac ttc tca ctt ctt cca cag cct      240
Cys Phe Tyr Tyr Val Ala Thr Asn Tyr Phe Ser Leu Leu Pro Gln Pro
65                  70                  75                  80
```

```
ctc tct act tac ttt gct tgg cct ctc tat tgg gta tgt caa ggc tgt         288
Leu Ser Thr Tyr Phe Ala Trp Pro Leu Tyr Trp Val Cys Gln Gly Cys
                85                  90                  95 gtc tta acc ggt gtt tgg gtc ctt ggc cat gaa tgt ggt cac caa gca         336
Val Leu Thr Gly Val Trp Val Leu Gly His Glu Cys Gly His Gln Ala
            100                 105                 110 ttt agt gac tat caa tgg gta gat gac act gtt ggt ttt atc atc cat         384
Phe Ser Asp Tyr Gln Trp Val Asp Asp Thr Val Gly Phe Ile Ile His
        115                 120                 125 acc ttc ctc ctc atc cct tac ttc tcc tgg aag tat agt cat cgt cgt         432
Thr Phe Leu Leu Ile Pro Tyr Phe Ser Trp Lys Tyr Ser His Arg Arg
    130                 135                 140 cac cat gcc aat aat gga tca ctc gag aga gat gaa gtc ttt gtc cca         480
His His Ala Asn Asn Gly Ser Leu Glu Arg Asp Glu Val Phe Val Pro
145                 150                 155                 160 ccg aag aaa gct gca gtc aaa tgg tat gtc aaa tac ctc aac aac cct         528
Pro Lys Lys Ala Ala Val Lys Trp Tyr Val Lys Tyr Leu Asn Asn Pro
                165                 170                 175 ctt gga cgc act gtg gtg tta ata gtc cag ttt gtc ctc gga tgg ccc         576
Leu Gly Arg Thr Val Val Leu Ile Val Gln Phe Val Leu Gly Trp Pro
            180                 185                 190 ttg tac cta gcc ttt aac gta tca ggt aga tcc tat gat ggt ttc gct         624
Leu Tyr Leu Ala Phe Asn Val Ser Gly Arg Ser Tyr Asp Gly Phe Ala
        195                 200                 205 tca cat ttc ttc cca cat gca ccc atc ttc aag gac cga gaa cgt ctc         672
Ser His Phe Phe Pro His Ala Pro Ile Phe Lys Asp Arg Glu Arg Leu
    210                 215                 220 cat ata tac atc aca gat gct ggt att cta gct gtc tgt tat ggt ctt         720
His Ile Tyr Ile Thr Asp Ala Gly Ile Leu Ala Val Cys Tyr Gly Leu
225                 230                 235                 240 tac cgt tac gca gct aca aaa gga ttg acc gct atg atc tgc gtc tat         768
Tyr Arg Tyr Ala Ala Thr Lys Gly Leu Thr Ala Met Ile Cys Val Tyr
                245                 250                 255 ggg gta cct cct ctg gtt gta aac ttt ttc ctt gtc ttg gtc act ttc         816
Gly Val Pro Pro Leu Val Val Asn Phe Phe Leu Val Leu Val Thr Phe
            260                 265                 270 ttg cag cac act cat cct tca tta cct cac tat gat tca acc gag tgg         864
Leu Gln His Thr His Pro Ser Leu Pro His Tyr Asp Ser Thr Glu Trp
        275                 280                 285 gac tgg att aga gga gcc atg gtt aca gta gac aga gac tat ggg atc         912
Asp Trp Ile Arg Gly Ala Met Val Thr Val Asp Arg Asp Tyr Gly Ile
    290                 295                 300 ttg aac aag gtg ttc cac aac ata aca gac aca cat gtg gct cat cat         960
Leu Asn Lys Val Phe His Asn Ile Thr Asp Thr His Val Ala His His
305                 310                 315                 320 ctt ttc gca aca ata ccg cat tat aat gca atg gaa gct aca gag gcg        1008
Leu Phe Ala Thr Ile Pro His Tyr Asn Ala Met Glu Ala Thr Glu Ala
                325                 330                 335 ata aag cca ata ctc gga gac tac tac cat ttc gat gga aca ccc tgg        1056
Ile Lys Pro Ile Leu Gly Asp Tyr Tyr His Phe Asp Gly Thr Pro Trp
            340                 345                 350 tat gtg gct atg tat agg gaa gca aag cag tgt ctc tat gta gaa cag        1104
Tyr Val Ala Met Tyr Arg Glu Ala Lys Gln Cys Leu Tyr Val Glu Gln
        355                 360                 365 gat aca gaa aag aag aaa ggt gtc tac tat tac aac aat aag tta             1149
Asp Thr Glu Lys Lys Lys Gly Val Tyr Tyr Tyr Asn Asn Lys Leu
    370                 375                 380 tga                                                                     1152
```

<210> SEQ ID NO 10
<211> LENGTH: 1155
<212> TYPE: DNA
<213> ORGANISM: Lesquerella gracilis A
<220> FEATURE:
<221> NAME/KEY: CDS
<222> LOCATION: (1)...(1152)

<400> SEQUENCE: 10

```
atg ggt gca ggt gga aga atg ccg gtt cct act tct tcc aag aaa tcg      48
Met Gly Ala Gly Gly Arg Met Pro Val Pro Thr Ser Ser Lys Lys Ser
 1               5                  10                  15 gaa acc gac acc aca aag cgt gtg ccg tgc gag aaa ccg cct ttc tcg      96
Glu Thr Asp Thr Thr Lys Arg Val Pro Cys Glu Lys Pro Pro Phe Ser
                20                  25                  30 gtg gga gat ctg aag aaa gca atc cca ccg cat tgt ttc aaa cgc tct     144
Val Gly Asp Leu Lys Lys Ala Ile Pro Pro His Cys Phe Lys Arg Ser
            35                  40                  45 atc cct cgc tct ttc tct tac ctt ctc aca gat ttc att cta gct tct     192
Ile Pro Arg Ser Phe Ser Tyr Leu Leu Thr Asp Phe Ile Leu Ala Ser
        50                  55                  60 tgc ttc tac tac gtg gct aca aat tac ttc tct ctt ctc cca cag cct     240
Cys Phe Tyr Tyr Val Ala Thr Asn Tyr Phe Ser Leu Leu Pro Gln Pro
 65                  70                  75                  80 gtc tct aat tac ctg gct tgg cct ctc tat tgg ata tgt caa ggc tgt     288
Val Ser Asn Tyr Leu Ala Trp Pro Leu Tyr Trp Ile Cys Gln Gly Cys
                85                  90                  95 gtc tta acc ggt gtt tgg gtc ctt ggc cat gaa tgt ggt cac cat gca     336
Val Leu Thr Gly Val Trp Val Leu Gly His Glu Cys Gly His His Ala
                100                 105                 110 ttc agt gac tat caa tgg gta gat gac act gtt ggt ttt atc atc cat     384
Phe Ser Asp Tyr Gln Trp Val Asp Asp Thr Val Gly Phe Ile Ile His
            115                 120                 125 tcc ttc ctc ctt gtc cct tac ttc tcc tgg aag tac agt cat cgt cgt     432
Ser Phe Leu Leu Val Pro Tyr Phe Ser Trp Lys Tyr Ser His Arg Arg
        130                 135                 140 cac cat tcc aac aat gga tcc ctc gag aaa gat gaa gtc ttt gtt cca     480
His His Ser Asn Asn Gly Ser Leu Glu Lys Asp Glu Val Phe Val Pro
145                 150                 155                 160 cct aag aaa gct gca gtc aaa tgg tat gtt aag tac ctc aac aac cct     528
Pro Lys Lys Ala Ala Val Lys Trp Tyr Val Lys Tyr Leu Asn Asn Pro
                165                 170                 175 ctt gga cgc act gtg gtg tta ata gtc cag ttt gtc ctc ggg tgg cct     576
Leu Gly Arg Thr Val Val Leu Ile Val Gln Phe Val Leu Gly Trp Pro
                180                 185                 190 ttg tat cta gcc ttt aac gta tca ggt aga ccc tat gat ggg ttc gct     624
Leu Tyr Leu Ala Phe Asn Val Ser Gly Arg Pro Tyr Asp Gly Phe Ala
            195                 200                 205 tca cac ttc ttt cct cat gca ccc atc ttc agg gac cgt gaa cgc ctc     672
Ser His Phe Phe Pro His Ala Pro Ile Phe Arg Asp Arg Glu Arg Leu
        210                 215                 220 cat ata tac atc aca gat gct ggt att cta gct gtc tgt tat ggt ctt     720
His Ile Tyr Ile Thr Asp Ala Gly Ile Leu Ala Val Cys Tyr Gly Leu
225                 230                 235                 240 tac cgt tac gct gct tca aaa gga ttg acc gct atg atc tgc gtc tac     768
Tyr Arg Tyr Ala Ala Ser Lys Gly Leu Thr Ala Met Ile Cys Val Tyr
                245                 250                 255 gga gta ccg ctt ttg ata gtg aac ttt ttc ctc gtg ttg gtc act ttc     816
Gly Val Pro Leu Leu Ile Val Asn Phe Phe Leu Val Leu Val Thr Phe
                260                 265                 270
```

```
ttg cag cac act cat cct tca tta cct cac tat gat tca acc gag tgg      864
Leu Gln His Thr His Pro Ser Leu Pro His Tyr Asp Ser Thr Glu Trp
        275                 280                 285 gaa tgg att aga gga gcc ttg gtt aca gta gac aga gac tat gga atc      912
Glu Trp Ile Arg Gly Ala Leu Val Thr Val Asp Arg Asp Tyr Gly Ile
    290                 295                 300 ttg aac aag gtg ttc cac aac ata aca gac aca cat gtg gct cat cat      960
Leu Asn Lys Val Phe His Asn Ile Thr Asp Thr His Val Ala His His
305                 310                 315                 320 att ttc gca aca ata ccg cat tat aat gca atg gaa gct aca gag gcg     1008
Ile Phe Ala Thr Ile Pro His Tyr Asn Ala Met Glu Ala Thr Glu Ala
                325                 330                 335 ata aag cca ata ctc gga gac tac tac cat ttc gat gga aca ccg tgg     1056
Ile Lys Pro Ile Leu Gly Asp Tyr Tyr His Phe Asp Gly Thr Pro Trp
            340                 345                 350 tat gtg gcc atg tac agg gaa gca aag gag tgt ctc tat gta gaa cag     1104
Tyr Val Ala Met Tyr Arg Glu Ala Lys Glu Cys Leu Tyr Val Glu Gln
        355                 360                 365 gat aca gaa cgt ggg aag aaa ggt gtc tac tat tac aac aat aag tta     1152
Asp Thr Glu Arg Gly Lys Lys Gly Val Tyr Tyr Tyr Asn Asn Lys Leu
    370                 375                 380 tga                                                                 1155
```

<210> SEQ ID NO 11
<211> LENGTH: 1155
<212> TYPE: DNA
<213> ORGANISM: Lesquerella gracilis B
<220> FEATURE:
<221> NAME/KEY: CDS
<222> LOCATION: (1)...(1152)

<400> SEQUENCE: 11

```
atg ggt gca ggt gga aga atg ccg gtt cct act tct tcc aag aaa tcg       48
Met Gly Ala Gly Gly Arg Met Pro Val Pro Thr Ser Ser Lys Lys Ser
1               5                  10                  15 gaa acc gac acc aca aag cgt gtg ccg tgc gag aaa ccg cct ttc tcg       96
Glu Thr Asp Thr Thr Lys Arg Val Pro Cys Glu Lys Pro Pro Phe Ser
            20                  25                  30 gtg gga gat ctg aag aaa gca atc cca cag cat tgt ttt caa cgc tct      144
Val Gly Asp Leu Lys Lys Ala Ile Pro Gln His Cys Phe Gln Arg Ser
        35                  40                  45 atc cct cgt tct ttc tcc tac ctt ctc aca gat atc act tta gtt tct      192
Ile Pro Arg Ser Phe Ser Tyr Leu Leu Thr Asp Ile Thr Leu Val Ser
    50                  55                  60 tgc ttc tac tac gtt gcc aca aat tac ttc tct ctt ctt cct cag cct      240
Cys Phe Tyr Tyr Val Ala Thr Asn Tyr Phe Ser Leu Leu Pro Gln Pro
65                  70                  75                  80 ctc tct act tac cta gct tgg cct ctc tat tgg gta tgt caa ggc tgt      288
Leu Ser Thr Tyr Leu Ala Trp Pro Leu Tyr Trp Val Cys Gln Gly Cys
                85                  90                  95 gtc cta aca ggt atc tgg gtc ctt ggc cat gaa tgt ggt cac cat gca      336
Val Leu Thr Gly Ile Trp Val Leu Gly His Glu Cys Gly His His Ala
            100                 105                 110 ttc agt gac tat caa tgg cta gat gac act gtt ggt ttt atc ttc cat      384
Phe Ser Asp Tyr Gln Trp Leu Asp Asp Thr Val Gly Phe Ile Phe His
        115                 120                 125 tcc tta ctt ctc gtc cct tac ttc tcc tgg aaa tac agt cat cgt cgt      432
Ser Leu Leu Leu Val Pro Tyr Phe Ser Trp Lys Tyr Ser His Arg Arg
    130                 135                 140 cac cat tcc aac aat gga tct ctc gag aaa gat gaa gtc ttt gtc cca      480
His His Ser Asn Asn Gly Ser Leu Glu Lys Asp Glu Val Phe Val Pro
```

```
ccg aaa aaa gct gca gtc aaa tgg tat gtt aaa tac ctc aac aac cct      528
Pro Lys Lys Ala Ala Val Lys Trp Tyr Val Lys Tyr Leu Asn Asn Pro
            165                 170                 175 ctt gga cgc att ctg gtg tta aca gtt cgg ttt atc ctc ggg tgg cct      576
Leu Gly Arg Ile Leu Val Leu Thr Val Arg Phe Ile Leu Gly Trp Pro
        180                 185                 190 ttg tat cta gcc ttt aat gta tca ggt aga cct tat gat ggt ttc gct      624
Leu Tyr Leu Ala Phe Asn Val Ser Gly Arg Pro Tyr Asp Gly Phe Ala
    195                 200                 205 tca cat ttc ttc cct cat gca cct atc ttt aaa gac cgc gaa cgt ctc      672
Ser His Phe Phe Pro His Ala Pro Ile Phe Lys Asp Arg Glu Arg Leu
210                 215                 220 cag ata tac atc tca gat gct ggt att cta gct gtc tgt tat ggt ctt      720
Gln Ile Tyr Ile Ser Asp Ala Gly Ile Leu Ala Val Cys Tyr Gly Leu
225                 230                 235                 240 tac cgt tac gct gct tca caa gga ttg acc gct atg atc tgc gtc tat      768
Tyr Arg Tyr Ala Ala Ser Gln Gly Leu Thr Ala Met Ile Cys Val Tyr
                245                 250                 255 gga gta ccg ctt ttg ata gtg aac ttt ttc ctt gtc ttg gta act ttc      816
Gly Val Pro Leu Leu Ile Val Asn Phe Phe Leu Val Leu Val Thr Phe
            260                 265                 270 ttg cag cac act cat cct tcg tta cct cac tat gat tca acc gag tgg      864
Leu Gln His Thr His Pro Ser Leu Pro His Tyr Asp Ser Thr Glu Trp
        275                 280                 285 gaa tgg att aga gga gct ttg gtt acg gta gac aga gac tac gga atc      912
Glu Trp Ile Arg Gly Ala Leu Val Thr Val Asp Arg Asp Tyr Gly Ile
    290                 295                 300 ttg aac aag gtg ttt cac aac ata aca gac aca cat gtg gct cat cat      960
Leu Asn Lys Val Phe His Asn Ile Thr Asp Thr His Val Ala His His
305                 310                 315                 320 ctt ttc gca act ata ccg cat tat aac gca atg gaa gct aca gag gcg     1008
Leu Phe Ala Thr Ile Pro His Tyr Asn Ala Met Glu Ala Thr Glu Ala
                325                 330                 335 ata aag cca ata ctt ggt gat tac tac cat ttc gat gga aca ccg tgg     1056
Ile Lys Pro Ile Leu Gly Asp Tyr Tyr His Phe Asp Gly Thr Pro Trp
            340                 345                 350 tat gtg gct atg tat agg gaa gca aag gag tgt ctc tat gta gaa ccg     1104
Tyr Val Ala Met Tyr Arg Glu Ala Lys Glu Cys Leu Tyr Val Glu Pro
        355                 360                 365 gat acg gaa cgt ggg aag aaa ggt gtc tac tat tac aac aat aag tta     1152
Asp Thr Glu Arg Gly Lys Lys Gly Val Tyr Tyr Tyr Asn Asn Lys Leu
    370                 375                 380 tga                                                                  1155

<210> SEQ ID NO 12
<211> LENGTH: 1143
<212> TYPE: DNA
<213> ORGANISM: Crepis biennis
<220> FEATURE:
<221> NAME/KEY: CDS
<222> LOCATION: (1)...(1140)

<400> SEQUENCE: 12 atg ggt gca ggt gga aga atg ccg gtt cct act tct tcc aag aaa tcg       48
Met Gly Ala Gly Gly Arg Met Pro Val Pro Thr Ser Ser Lys Lys Ser
1               5                   10                  15 gaa acc gac acc aca aag cgt gtg ccg tgc gag aaa ccg cct ttc tcg       96
Glu Thr Asp Thr Thr Lys Arg Val Pro Cys Glu Lys Pro Pro Phe Ser
            20                  25                  30
```

```
gtg gga gat ctg aag aaa gca atc cct ccc cat tgc ttc cag cga tct      144
Val Gly Asp Leu Lys Lys Ala Ile Pro Pro His Cys Phe Gln Arg Ser
         35                  40                  45 gta atc cgt tca tct tac tat gta gtt cac gat ctc att att gcc tac      192
Val Ile Arg Ser Ser Tyr Tyr Val Val His Asp Leu Ile Ile Ala Tyr
 50                  55                  60 atc ttc tac ttc ctt gcc gat aaa tat att ccg att ctc cct gct cct      240
Ile Phe Tyr Phe Leu Ala Asp Lys Tyr Ile Pro Ile Leu Pro Ala Pro
 65                  70                  75                  80 cta gcc tac tta gct tgg ccc ctt tac tgg ttc tgt caa gct agc atc      288
Leu Ala Tyr Leu Ala Trp Pro Leu Tyr Trp Phe Cys Gln Ala Ser Ile
                 85                  90                  95 ctc act ggt tta tgg atc ctc ggt cat gaa tgc ggt cac cat gcc ttt      336
Leu Thr Gly Leu Trp Ile Leu Gly His Glu Cys Gly His His Ala Phe
             100                 105                 110 agc gag cac caa tgg gtt gac gac act gtg ggc ttc atg gtc cac tca      384
Ser Glu His Gln Trp Val Asp Asp Thr Val Gly Phe Met Val His Ser
         115                 120                 125 ttt ctc ctc acc ccg tat ttc tcg tgg aaa tac agt cac cgg aat cac      432
Phe Leu Leu Thr Pro Tyr Phe Ser Trp Lys Tyr Ser His Arg Asn His
130                 135                 140 cat gcc aac aca agt tcc att gat aac gat gaa gtt tac att ccg aaa      480
His Ala Asn Thr Ser Ser Ile Asp Asn Asp Glu Val Tyr Ile Pro Lys
145                 150                 155                 160 agc aag tcc aaa ctc gcg ctt acc tat aaa ctt ctt aac aac ccg cct      528
Ser Lys Ser Lys Leu Ala Leu Thr Tyr Lys Leu Leu Asn Asn Pro Pro
                 165                 170                 175 ggt cga ctg tta gtt atg gtt atc atg ttc acc cta gga ttt cct tta      576
Gly Arg Leu Leu Val Met Val Ile Met Phe Thr Leu Gly Phe Pro Leu
             180                 185                 190 tac ctc ttg aca aat att tcc ggc aag aag tac gac agg ttt gcc aac      624
Tyr Leu Leu Thr Asn Ile Ser Gly Lys Lys Tyr Asp Arg Phe Ala Asn
         195                 200                 205 cac ttc gac ccc atg agt cca att ttc aag gaa cgt gag cgg ttt cag      672
His Phe Asp Pro Met Ser Pro Ile Phe Lys Glu Arg Glu Arg Phe Gln
     210                 215                 220 gtc ttg ctt tcg gat ctt ggc ctt ctt gct gtg ttt tat gga att aaa      720
Val Leu Leu Ser Asp Leu Gly Leu Leu Ala Val Phe Tyr Gly Ile Lys
225                 230                 235                 240 gtt gct gta gca aag aaa gga gct gcg tgg gtg gcg tgt atg tat gga      768
Val Ala Val Ala Lys Lys Gly Ala Ala Trp Val Ala Cys Met Tyr Gly
                 245                 250                 255 gtt ccg atg cta ggc gta ttt acc ctt ttc gat atc atc acg tac ttg      816
Val Pro Met Leu Gly Val Phe Thr Leu Phe Asp Ile Ile Thr Tyr Leu
             260                 265                 270 cac cac acc cat cag tcg tct cct cat tat gac tca act gaa tgg aac      864
His His Thr His Gln Ser Ser Pro His Tyr Asp Ser Thr Glu Trp Asn
         275                 280                 285 tgg atc aga ggg gcg ttg tca gca atc gat agg gac ttt ggg ttc atg      912
Trp Ile Arg Gly Ala Leu Ser Ala Ile Asp Arg Asp Phe Gly Phe Met
     290                 295                 300 aat agt gtt ttc cat gat gtt aca cac act cac gtc atg cat cat atg      960
Asn Ser Val Phe His Asp Val Thr His Thr His Val Met His His Met
305                 310                 315                 320 ttt tca tac att cca cac tat cat gcg aaa gag gca agg gat gca atc     1008
Phe Ser Tyr Ile Pro His Tyr His Ala Lys Glu Ala Arg Asp Ala Ile
                 325                 330                 335 aat aca atc ata ggc gac tat tat atg atc gat agg act cca att ttg     1056
Asn Thr Ile Ile Gly Asp Tyr Tyr Met Ile Asp Arg Thr Pro Ile Leu
             340                 345                 350
```

-continued

```
aaa gca ctg tgg aga gag gcc aag gaa tgc atg tac atc gag cct gat      1104
Lys Ala Leu Trp Arg Glu Ala Lys Glu Cys Met Tyr Ile Glu Pro Asp
        355                 360                 365 agc aag cgc aaa ggt gtt tat tgg tat cat aaa ttg tga                  1143
Ser Lys Arg Lys Gly Val Tyr Trp Tyr His Lys Leu
    370                 375                 380

<210> SEQ ID NO 13
<211> LENGTH: 387
<212> TYPE: PRT
<213> ORGANISM: Ricinus communis

<400> SEQUENCE: 13

Met Gly Gly Gly Gly Arg Met Ser Thr Val Ile Thr Ser Asn Asn Ser
 1               5                  10                  15

Glu Lys Lys Gly Gly Ser Ser His Leu Lys Arg Ala Pro His Thr Lys
            20                  25                  30

Pro Pro Phe Thr Leu Gly Asp Leu Lys Arg Ala Ile Pro Pro His Cys
        35                  40                  45

Phe Glu Arg Ser Phe Val Arg Ser Phe Ser Tyr Val Ala Tyr Asp Val
    50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Leu
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335
```

```
Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
            355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 14
<211> LENGTH: 384
<212> TYPE: PRT
<213> ORGANISM: Lesquerella fendleri

<400> SEQUENCE: 14

Met Gly Ala Gly Gly Arg Ile Met Val Thr Pro Ser Ser Lys Lys Ser
 1               5                  10                  15

Glu Thr Glu Ala Leu Lys Arg Gly Pro Cys Glu Lys Pro Pro Phe Thr
            20                  25                  30

Val Lys Asp Leu Lys Lys Ala Ile Pro Gln His Cys Phe Gln Arg Ser
        35                  40                  45

Ile Pro Arg Ser Phe Ser Tyr Leu Leu Thr Asp Ile Thr Leu Val Ser
    50                  55                  60

Cys Phe Tyr Tyr Val Ala Thr Asn Tyr Phe Ser Leu Leu Pro Gln Pro
65                  70                  75                  80

Leu Ser Thr Tyr Leu Ala Trp Pro Leu Tyr Trp Val Cys Gln Gly Cys
                85                  90                  95

Val Leu Thr Gly Ile Trp Val Ile Gly His Glu Cys Gly His His Ala
            100                 105                 110

Phe Ser Asp Tyr Gln Trp Val Asp Asp Thr Val Gly Phe Ile Phe His
        115                 120                 125

Ser Phe Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Gln Phe Ile Leu Gly Trp Pro
            180                 185                 190

Leu Tyr Leu Pro Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
        275                 280                 285

Glu Trp Ile Arg Gly Ala Leu Val Thr Val Asp Arg Asp Tyr Gly Ile
    290                 295                 300

Leu Asn Lys Val Phe His Asn Ile Thr Asp Thr His Val Ala His His
```

```
                    305                 310                 315                 320
Leu Phe Ala Thr Ile Pro His Tyr Asn Ala Met Glu Ala Thr Glu Ala
                325                 330                 335
Ile Lys Pro Ile Leu Gly Asp Tyr Tyr His Phe Asp Gly Thr Pro Trp
                340                 345                 350
Tyr Val Ala Met Tyr Arg Glu Ala Lys Glu Cys Leu Tyr Val Glu Pro
                355                 360                 365
Asp Thr Glu Arg Gly Lys Lys Gly Val Tyr Tyr Asn Asn Lys Leu
                370                 375                 380

<210> SEQ ID NO 15
<211> LENGTH: 383
<212> TYPE: PRT
<213> ORGANISM: Lesquerella lindheimeri

<400> SEQUENCE: 15

Met Gly Ala Gly Gly Arg Ile Met Val Thr Pro Ser Ser Lys Lys Ser
  1               5                  10                  15
Lys Pro Glu Ala Leu Arg Arg Gly Pro Gly Glu Lys Pro Pro Phe Thr
               20                  25                  30
Val Gln Asp Leu Arg Lys Ala Ile Pro Arg His Cys Phe Lys Arg Ser
            35                  40                  45
Ile Pro Arg Ser Phe Ser Tyr Leu Leu Thr Asp Ile Ile Leu Ala Ser
     50                  55                  60
Cys Phe Tyr Tyr Val Ala Thr Asn Tyr Phe Ser Leu Leu Pro Gln Pro
 65                  70                  75                  80
Leu Ser Thr Tyr Phe Ala Trp Pro Leu Tyr Trp Val Cys Gln Gly Cys
                 85                  90                  95
Val Leu Thr Gly Val Trp Val Leu Gly His Glu Cys Gly His Gln Ala
              100                 105                 110
Phe Ser Asp Tyr Gln Trp Val Asp Asp Thr Val Gly Phe Ile Ile His
            115                 120                 125
Thr Phe Leu Leu Ile Pro Tyr Phe Ser Trp Lys Tyr Ser His Arg Arg
    130                 135                 140
His His Ala Asn Asn Gly Ser Leu Glu Arg Asp Glu Val Phe Val Pro
145                 150                 155                 160
Pro Lys Lys Ala Ala Val Lys Trp Tyr Val Lys Tyr Leu Asn Asn Pro
                165                 170                 175
Leu Gly Arg Thr Val Val Leu Ile Val Gln Phe Val Leu Gly Trp Pro
            180                 185                 190
Leu Tyr Leu Ala Phe Asn Val Ser Gly Arg Ser Tyr Asp Gly Phe Ala
        195                 200                 205
Ser His Phe Phe Pro His Ala Pro Ile Phe Lys Asp Arg Glu Arg Leu
    210                 215                 220
His Ile Tyr Ile Thr Asp Ala Gly Ile Leu Ala Val Cys Tyr Gly Leu
225                 230                 235                 240
Tyr Arg Tyr Ala Ala Thr Lys Gly Leu Thr Ala Met Ile Cys Val Tyr
                245                 250                 255
Gly Val Pro Pro Leu Val Val Asn Phe Phe Leu Val Leu Val Thr Phe
            260                 265                 270
Leu Gln His Thr His Pro Ser Leu Pro His Tyr Asp Ser Thr Glu Trp
        275                 280                 285
Asp Trp Ile Arg Gly Ala Met Val Thr Val Asp Arg Asp Tyr Gly Ile
    290                 295                 300
```

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
            340                 345                 350

Tyr Val Ala Met Tyr Arg Glu Ala Lys Gln Cys Leu Tyr Val Glu Gln
        355                 360                 365

Asp Thr Glu Lys Lys Gly Val Tyr Tyr Asn Asn Lys Leu
    370                 375                 380

<210> SEQ ID NO 16
<211> LENGTH: 384
<212> TYPE: PRT
<213> ORGANISM: Lesquerella gracilis A

<400> SEQUENCE: 16

Met Gly Ala Gly Gly Arg Ile Met Val Thr Pro Ser Ser Lys Lys Ser
1               5                   10                  15

Lys Pro Gln Ala Leu Arg Arg Gly Pro Cys Glu Lys Pro Pro Phe Thr
                20                  25                  30

Val Lys Asp Leu Lys Lys Ala Ile Pro Pro His Cys Phe Lys Arg Ser
            35                  40                  45

Ile Pro Arg Ser Phe Ser Tyr Leu Leu Thr Asp Phe Ile Leu Ala Ser
    50                  55                  60

Cys Phe Tyr Tyr Val Ala Thr Asn Tyr Phe Ser Leu Leu Pro Gln Pro
65                  70                  75                  80

Val Ser Asn Tyr Leu Ala Trp Pro Leu Tyr Trp Ile Cys Gln Gly Cys
                85                  90                  95

Val Leu Thr Gly Val Trp Val Leu Gly His Glu Cys Gly His His Ala
            100                 105                 110

Phe Ser Asp Tyr Gln Trp Val Asp Asp Thr Val Gly Phe Ile Ile His
        115                 120                 125

Ser Phe Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Thr Val Val Leu Ile Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Arg Asp Arg Glu Arg Leu
    210                 215                 220

His Ile Tyr Ile Thr Asp Ala Gly Ile Leu Ala Val Cys Tyr Gly Leu
225                 230                 235                 240

Tyr Arg Tyr Ala Ala Ser Lys Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
        275                 280                 285

Glu Trp Ile Arg Gly Ala Leu Val Thr Val Asp Arg Asp Tyr Gly Ile
    290                 295                 300

```
Leu Asn Lys Val Phe His Asn Ile Thr Asp Thr His Val Ala His His
305                 310                 315                 320

Ile Phe Ala Thr Ile Pro His Tyr Asn Ala Met Glu Ala Thr Glu Ala
            325                 330                 335

Ile Lys Pro Ile Leu Gly Asp Tyr Tyr His Phe Asp Gly Thr Pro Trp
            340                 345                 350

Tyr Val Ala Met Tyr Arg Glu Ala Lys Glu Cys Leu Tyr Val Glu Gln
        355                 360                 365

Asp Thr Glu Arg Gly Lys Lys Gly Val Tyr Tyr Asn Asn Lys Leu
    370                 375                 380

<210> SEQ ID NO 17
<211> LENGTH: 384
<212> TYPE: PRT
<213> ORGANISM: Lesquerella gracilis B

<400> SEQUENCE: 17

Met Gly Ala Gly Gly Arg Ile Met Val Thr Pro Ser Ser Lys Lys Ser
1               5                   10                  15

Glu Thr Glu Ala Leu Lys Arg Gly Pro Cys Glu Lys Pro Pro Phe Thr
            20                  25                  30

Val Lys Asp Leu Lys Lys Ala Ile Pro Gln His Cys Phe Gln Arg Ser
        35                  40                  45

Ile Pro Arg Ser Phe Ser Tyr Leu Leu Thr Asp Ile Thr Leu Val Ser
    50                  55                  60

Cys Phe Tyr Tyr Val Ala Thr Asn Tyr Phe Ser Leu Leu Pro Gln Pro
65                  70                  75                  80

Leu Ser Thr Tyr Leu Ala Trp Pro Leu Tyr Trp Val Cys Gln Gly Cys
                85                  90                  95

Val Leu Thr Gly Ile Trp Val Leu Gly His Glu Cys Gly His His Ala
            100                 105                 110

Phe Ser Asp Tyr Gln Trp Leu Asp Asp Thr Val Gly Phe Ile Phe His
        115                 120                 125

Ser Leu Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Arg Phe Ile Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
        275                 280                 285

Glu Trp Ile Arg Gly Ala Leu Val Thr Val Asp Arg Asp Tyr Gly Ile
```

```
            290                 295                 300
Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
                340                 345                 350

Tyr Val Ala Met Tyr Arg Glu Ala Lys Glu Cys Leu Tyr Val Glu Pro
                355                 360                 365

Asp Thr Glu Arg Gly Lys Lys Gly Val Tyr Tyr Asn Asn Lys Leu
                370                 375                 380

<210> SEQ ID NO 18
<211> LENGTH: 374
<212> TYPE: PRT
<213> ORGANISM: Crepis biennis

<400> SEQUENCE: 18

Met Gly Ala His Gly His Gly Arg Thr Ser Lys Lys Ser Val Met Glu
1               5                   10                  15

Arg Val Ser Val Asp Pro Val Pro Phe Ser Leu Ser Asp Leu Lys Gln
                20                  25                  30

Ala Ile Pro Pro His Cys Phe Gln Arg Ser Val Ile Arg Ser Ser Tyr
            35                  40                  45

Tyr Val Val His Asp Leu Ile Ile Ala Tyr Ile Phe Tyr Phe Leu Ala
        50                  55                  60

Asp Lys Tyr Ile Pro Ile Leu Pro Ala Pro Leu Ala Tyr Leu Ala Trp
65                  70                  75                  80

Pro Leu Tyr Trp Phe Cys Gln Ala Ser Ile Leu Thr Gly Leu Trp Ile
                85                  90                  95

Leu Gly His Glu Cys Gly His His Ala Phe Ser Glu Tyr Gln Trp Val
                100                 105                 110

Asp Asp Thr Val Gly Phe Met Val His Ser Phe Leu Leu Thr Pro Tyr
            115                 120                 125

Phe Ser Trp Lys Tyr Ser His Arg Asn His His Ala Asn Thr Ser Ser
130                 135                 140

Ile Asp Asn Asp Glu Val Tyr Ile Pro Lys Ser Lys Ser Lys Leu Ala
145                 150                 155                 160

Leu Thr Tyr Lys Leu Leu Asn Asn Pro Pro Gly Arg Leu Leu Val Met
                165                 170                 175

Val Ile Met Phe Thr Leu Gly Phe Pro Leu Tyr Leu Leu Thr Asn Ile
            180                 185                 190

Ser Gly Lys Lys Tyr Asp Arg Phe Ala Asn His Phe Asp Pro Met Ser
                195                 200                 205

Pro Ile Phe Lys Glu Arg Glu Arg Phe Gln Val Leu Leu Ser Asp Leu
            210                 215                 220

Gly Leu Leu Ala Val Phe Tyr Gly Ile Lys Val Ala Val Ala Lys Lys
225                 230                 235                 240

Gly Ala Ala Trp Val Ala Cys Met Tyr Gly Val Pro Met Leu Gly Val
                245                 250                 255

Phe Thr Leu Phe Asp Ile Ile Thr Tyr Leu His His Thr His Gln Ser
            260                 265                 270

Ser Pro His Tyr Asp Ser Thr Glu Trp Asn Trp Ile Arg Gly Ala Leu
        275                 280                 285
```

```
Ser Ala Ile Asp Arg Asp Phe Gly Phe Met Asn Ser Val Phe His Asp
    290                 295                 300

Val Thr His Thr His Val Met His His Met Phe Ser Tyr Ile Pro His
305                 310                 315                 320

Tyr His Ala Lys Glu Ala Arg Asp Ala Ile Asn Thr Ile Ile Gly Asp
                325                 330                 335

Tyr Tyr Met Ile Asp Arg Thr Pro Ile Leu Lys Ala Leu Trp Arg Glu
                340                 345                 350

Ala Lys Glu Cys Met Tyr Ile Glu Pro Asp Ser Lys Arg Lys Gly Val
            355                 360                 365

Tyr Trp Tyr His Lys Leu
    370

<210> SEQ ID NO 19
<211> LENGTH: 383
<212> TYPE: PRT
<213> ORGANISM: Ricinus communis

<400> SEQUENCE: 19

Met Gly Ala Gly Gly Arg Met Pro Val Pro Thr Ser Ser Lys Lys Ser
  1               5                  10                  15

Glu Thr Asp Thr Thr Lys Arg Val Pro Cys Glu Lys Pro Pro Phe Ser
                 20                  25                  30

Val Gly Asp Leu Lys Lys Ala Ile Pro Pro His Cys Phe Glu Arg Ser
             35                  40                  45

Phe Val Arg Ser Phe Ser Tyr Val Ala Tyr Asp Val Cys Leu Ser Phe
         50                  55                  60

Leu Phe Tyr Ser Ile Ala Thr Asn Phe Phe Pro Tyr Ile Ser Ser Pro
 65                  70                  75                  80

Leu Ser Tyr Val Ala Trp Leu Val Tyr Trp Leu Phe Gln Gly Cys Ile
                 85                  90                  95

Leu Thr Gly Leu Trp Val Ile Gly His Glu Cys Gly His His Ala Phe
            100                 105                 110

Ser Glu Tyr Gln Leu Ala Asp Asp Ile Val Gly Leu Ile Val His Ser
        115                 120                 125

Ala Leu Leu Val Pro Tyr Phe Ser Trp Lys Tyr Ser His Arg Arg His
    130                 135                 140

His Ser Asn Ile Gly Ser Leu Glu Arg Asp Glu Val Phe Val Pro Lys
145                 150                 155                 160

Ser Lys Ser Lys Ile Ser Trp Tyr Ser Lys Tyr Leu Asn Asn Pro Pro
                165                 170                 175

Gly Arg Val Leu Thr Leu Ala Thr Leu Leu Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Phe Ser Glu Arg Glu Arg Leu Gln
    210                 215                 220

Ile Tyr Ile Ala Asp Leu Gly Ile Phe Ala Thr Thr Phe Val Leu Tyr
225                 230                 235                 240

Gln Ala Thr Met Ala Lys Gly Leu Ala Trp Val Met Arg Ile Tyr Gly
                245                 250                 255

Val Pro Leu Leu Ile Val Asn Cys Phe Leu Val Met Ile Thr Tyr Leu
            260                 265                 270

Gln His Thr His Pro Ala Ile Pro Arg Tyr Gly Ser Ser Glu Trp Asp
        275                 280                 285
```

```
Trp Leu Arg Gly Ala Met Val Thr Val Asp Arg Asp Tyr Gly Val Leu
    290                 295                 300

Asn Lys Val Phe His Asn Ile Ala Asp Thr His Val Ala His His Leu
305                 310                 315                 320

Phe Ala Thr Val Pro His Tyr His Ala Met Glu Ala Thr Lys Ala Ile
                325                 330                 335

Lys Pro Ile Met Gly Glu Tyr Tyr Arg Tyr Asp Gly Thr Pro Phe Tyr
            340                 345                 350

Lys Ala Leu Trp Arg Glu Ala Lys Glu Cys Leu Phe Val Glu Pro Asp
        355                 360                 365

Glu Gly Ala Pro Thr Gln Gly Val Phe Trp Tyr Arg Asn Lys Tyr
    370                 375                 380

<210> SEQ ID NO 20
<211> LENGTH: 384
<212> TYPE: PRT
<213> ORGANISM: Lesquerella fendleri

<400> SEQUENCE: 20

Met Gly Ala Gly Gly Arg Met Pro Val Pro Thr Ser Ser Lys Lys Ser
  1               5                  10                  15

Glu Thr Asp Thr Thr Lys Arg Val Pro Cys Glu Lys Pro Pro Phe Ser
                 20                  25                  30

Val Gly Asp Leu Lys Lys Ala Ile Pro Gln His Cys Phe Gln Arg Ser
             35                  40                  45

Ile Pro Arg Ser Phe Ser Tyr Leu Leu Thr Asp Ile Thr Leu Val Ser
         50                  55                  60

Cys Phe Tyr Tyr Val Ala Thr Asn Tyr Phe Ser Leu Leu Pro Gln Pro
 65                  70                  75                  80

Leu Ser Thr Tyr Leu Ala Trp Pro Leu Tyr Trp Val Cys Gln Gly Cys
                 85                  90                  95

Val Leu Thr Gly Ile Trp Val Ile Gly His Glu Cys Gly His His Ala
            100                 105                 110

Phe Ser Asp Tyr Gln Trp Val Asp Asp Thr Val Gly Phe Ile Phe His
        115                 120                 125

Ser Phe Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Gln Phe Ile Leu Gly Trp Pro
            180                 185                 190

Leu Tyr Leu Pro Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
```

```
             275                 280                 285
Glu Trp Ile Arg Gly Ala Leu Val Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
                340                 345                 350

Tyr Val Ala Met Tyr Arg Glu Ala Lys Glu Cys Leu Tyr Val Glu Pro
                355                 360                 365

Asp Thr Glu Arg Gly Lys Lys Gly Val Tyr Tyr Asn Asn Lys Leu
            370                 375                 380

<210> SEQ ID NO 21
<211> LENGTH: 383
<212> TYPE: PRT
<213> ORGANISM: Lesquerella lindheimeri

<400> SEQUENCE: 21

Met Gly Ala Gly Gly Arg Met Pro Val Pro Thr Ser Ser Lys Lys Ser
  1               5                  10                  15

Glu Thr Asp Thr Thr Lys Arg Val Pro Cys Glu Lys Pro Pro Phe Ser
                20                  25                  30

Val Gly Asp Leu Arg Lys Ala Ile Pro Arg His Cys Phe Lys Arg Ser
            35                  40                  45

Ile Pro Arg Ser Phe Ser Tyr Leu Leu Thr Asp Ile Ile Leu Ala Ser
        50                  55                  60

Cys Phe Tyr Tyr Val Ala Thr Asn Tyr Phe Ser Leu Leu Pro Gln Pro
 65                  70                  75                  80

Leu Ser Thr Tyr Phe Ala Trp Pro Leu Tyr Trp Val Cys Gln Gly Cys
                85                  90                  95

Val Leu Thr Gly Val Trp Val Leu Gly His Glu Cys Gly His Gln Ala
            100                 105                 110

Phe Ser Asp Tyr Gln Trp Val Asp Asp Thr Val Gly Phe Ile Ile His
        115                 120                 125

Thr Phe Leu Leu Ile Pro Tyr Phe Ser Trp Lys Tyr Ser His Arg Arg
    130                 135                 140

His His Ala Asn Asn Gly Ser Leu Glu Arg Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Thr Val Val Leu Ile Val Gln Phe Val Leu Gly Trp Pro
            180                 185                 190

Leu Tyr Leu Ala Phe Asn Val Ser Gly Arg Ser Tyr Asp Gly Phe Ala
        195                 200                 205

Ser His Phe Phe Pro His Ala Pro Ile Phe Lys Asp Arg Glu Arg Leu
    210                 215                 220

His Ile Tyr Ile Thr Asp Ala Gly Ile Leu Ala Val Cys Tyr Gly Leu
225                 230                 235                 240

Tyr Arg Tyr Ala Ala Thr Lys Gly Leu Thr Ala Met Ile Cys Val Tyr
                245                 250                 255

Gly Val Pro Pro Leu Val Val Asn Phe Phe Leu Val Leu Val Thr Phe
            260                 265                 270
```

```
Leu Gln His Thr His Pro Ser Leu Pro His Tyr Asp Ser Thr Glu Trp
        275                 280                 285

Asp Trp Ile Arg Gly Ala Met Val Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
                340                 345                 350

Tyr Val Ala Met Tyr Arg Glu Ala Lys Gln Cys Leu Tyr Val Glu Gln
                355                 360                 365

Asp Thr Glu Lys Lys Lys Gly Val Tyr Tyr Asn Asn Lys Leu
        370                 375                 380

<210> SEQ ID NO 22
<211> LENGTH: 384
<212> TYPE: PRT
<213> ORGANISM: Lesquerella gracilis A

<400> SEQUENCE: 22

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Pro His Cys Phe Lys Arg Ser
        35                  40                  45

Ile Pro Arg Ser Phe Ser Tyr Leu Leu Thr Asp Phe Ile Leu Ala Ser
    50                  55                  60

Cys Phe Tyr Tyr Val Ala Thr Asn Tyr Phe Ser Leu Leu Pro Gln Pro
65                  70                  75                  80

Val Ser Asn Tyr Leu Ala Trp Pro Leu Tyr Trp Ile Cys Gln Gly Cys
                85                  90                  95

Val Leu Thr Gly Val Trp Val Leu Gly His Glu Cys Gly His His Ala
            100                 105                 110

Phe Ser Asp Tyr Gln Trp Val Asp Asp Thr Val Gly Phe Ile Ile His
        115                 120                 125

Ser Phe Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Thr Val Val Leu Ile Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Arg Asp Arg Glu Arg Leu
    210                 215                 220

His Ile Tyr Ile Thr Asp Ala Gly Ile Leu Ala Val Cys Tyr Gly Leu
225                 230                 235                 240

Tyr Arg Tyr Ala Ala Ser Lys Gly Leu Thr Ala Met Ile Cys Val Tyr
                245                 250                 255

Gly Val Pro Leu Leu Ile Val Asn Phe Phe Leu Val Leu Val Thr Phe
            260                 265                 270
```

```
Leu Gln His Thr His Pro Ser Leu Pro His Tyr Asp Ser Thr Glu Trp
            275                 280                 285

Glu Trp Ile Arg Gly Ala Leu Val Thr Val Asp Arg Asp Tyr Gly Ile
        290                 295                 300

Leu Asn Lys Val Phe His Asn Ile Thr Asp Thr His Val Ala His His
305                 310                 315                 320

Ile Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
                340                 345                 350

Tyr Val Ala Met Tyr Arg Glu Ala Lys Glu Cys Leu Tyr Val Glu Gln
            355                 360                 365

Asp Thr Glu Arg Gly Lys Lys Gly Val Tyr Tyr Asn Asn Lys Leu
            370                 375                 380

<210> SEQ ID NO 23
<211> LENGTH: 384
<212> TYPE: PRT
<213> ORGANISM: Lesquerella gracilis B

<400> SEQUENCE: 23

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Gln His Cys Phe Gln Arg Ser
        35                  40                  45

Ile Pro Arg Ser Phe Ser Tyr Leu Leu Thr Asp Ile Thr Leu Val Ser
    50                  55                  60

Cys Phe Tyr Tyr Val Ala Thr Asn Tyr Phe Ser Leu Leu Pro Gln Pro
65                  70                  75                  80

Leu Ser Thr Tyr Leu Ala Trp Pro Leu Tyr Trp Val Cys Gln Gly Cys
                85                  90                  95

Val Leu Thr Gly Ile Trp Val Leu Gly His Glu Cys Gly His His Ala
            100                 105                 110

Phe Ser Asp Tyr Gln Trp Leu Asp Asp Thr Val Gly Phe Ile Phe His
        115                 120                 125

Ser Leu Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Arg Phe Ile Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
```

-continued

```
                260                 265                 270
Leu Gln His Thr His Pro Ser Leu Pro His Tyr Asp Ser Thr Glu Trp
                275                 280                 285
Glu Trp Ile Arg Gly Ala Leu Val Thr Val Asp Arg Asp Tyr Gly Ile
            290                 295                 300
Leu Asn Lys Val Phe His Asn Ile Thr Asp Thr His Val Ala His His
305                 310                 315                 320
Leu Phe Ala Thr Ile Pro His Tyr Asn Ala Met Glu Ala Thr Glu Ala
                325                 330                 335
Ile Lys Pro Ile Leu Gly Asp Tyr Tyr His Phe Asp Gly Thr Pro Trp
            340                 345                 350
Tyr Val Ala Met Tyr Arg Glu Ala Lys Glu Cys Leu Tyr Val Glu Pro
                355                 360                 365
Asp Thr Glu Arg Gly Lys Lys Gly Val Tyr Tyr Asn Asn Lys Leu
            370                 375                 380
```

<210> SEQ ID NO 24
<211> LENGTH: 380
<212> TYPE: PRT
<213> ORGANISM: Crepis biennis

<400> SEQUENCE: 24

```
Met Gly Ala Gly Gly Arg Met Pro Val Pro Thr Ser Ser Lys Lys Ser
1               5                   10                  15
Glu Thr Asp Thr Thr Lys Arg Val Pro Cys Glu Lys Pro Pro Phe Ser
                20                  25                  30
Val Gly Asp Leu Lys Lys Ala Ile Pro Pro His Cys Phe Gln Arg Ser
            35                  40                  45
Val Ile Arg Ser Ser Tyr Tyr Val Val His Asp Leu Ile Ile Ala Tyr
        50                  55                  60
Ile Phe Tyr Phe Leu Ala Asp Lys Tyr Ile Pro Ile Leu Pro Ala Pro
65                  70                  75                  80
Leu Ala Tyr Leu Ala Trp Pro Leu Tyr Trp Phe Cys Gln Ala Ser Ile
                85                  90                  95
Leu Thr Gly Leu Trp Ile Leu Gly His Glu Cys Gly His His Ala Phe
                100                 105                 110
Ser Glu His Gln Trp Val Asp Asp Thr Val Gly Phe Met Val His Ser
            115                 120                 125
Phe Leu Leu Thr Pro Tyr Phe Ser Trp Lys Tyr Ser His Arg Asn His
        130                 135                 140
His Ala Asn Thr Ser Ser Ile Asp Asn Asp Glu Val Tyr Ile Pro Lys
145                 150                 155                 160
Ser Lys Ser Lys Leu Ala Leu Thr Tyr Lys Leu Leu Asn Asn Pro Pro
                165                 170                 175
Gly Arg Leu Leu Val Met Val Ile Met Phe Thr Leu Gly Phe Pro Leu
            180                 185                 190
Tyr Leu Leu Thr Asn Ile Ser Gly Lys Lys Tyr Asp Arg Phe Ala Asn
        195                 200                 205
His Phe Asp Pro Met Ser Pro Ile Phe Lys Glu Arg Glu Arg Phe Gln
    210                 215                 220
Val Leu Leu Ser Asp Leu Gly Leu Leu Ala Val Phe Tyr Gly Ile Lys
225                 230                 235                 240
Val Ala Val Ala Lys Lys Gly Ala Ala Trp Val Ala Cys Met Tyr Gly
                245                 250                 255
```

-continued

```
Val Pro Met Leu Gly Val Phe Thr Leu Phe Asp Ile Ile Thr Tyr Leu
            260                 265                 270

His His Thr His Gln Ser Ser Pro His Tyr Asp Ser Thr Glu Trp Asn
        275                 280                 285

Trp Ile Arg Gly Ala Leu Ser Ala Ile Asp Arg Asp Phe Gly Phe Met
    290                 295                 300

Asn Ser Val Phe His Asp Val Thr His Thr His Val Met His His Met
305                 310                 315                 320

Phe Ser Tyr Ile Pro His Tyr His Ala Lys Glu Ala Arg Asp Ala Ile
                325                 330                 335

Asn Thr Ile Ile Gly Asp Tyr Tyr Met Ile Asp Arg Thr Pro Ile Leu
            340                 345                 350

Lys Ala Leu Trp Arg Glu Ala Lys Glu Cys Met Tyr Ile Glu Pro Asp
        355                 360                 365

Ser Lys Arg Lys Gly Val Tyr Trp Tyr His Lys Leu
    370                 375                 380

<210> SEQ ID NO 25
<211> LENGTH: 1152
<212> TYPE: DNA
<213> ORGANISM: Ricinus communis
<220> FEATURE:
<221> NAME/KEY: CDS
<222> LOCATION: (1)...(1149)

<400> SEQUENCE: 25 atg gga ggt ggt ggt cgc atg tct act gtc ata acc agc aac aac agt      48
Met Gly Gly Gly Gly Arg Met Ser Thr Val Ile Thr Ser Asn Asn Ser
 1               5                  10                  15 gag agc agc cac ctt aag cga gcg ccg cac acg aag cct cct ttc aca      96
Glu Ser Ser His Leu Lys Arg Ala Pro His Thr Lys Pro Pro Phe Thr
                20                  25                  30 ctt ggt gac ctc aag aga gcc atc cca ccc cat tgc ttt gaa cgc tct     144
Leu Gly Asp Leu Lys Arg Ala Ile Pro Pro His Cys Phe Glu Arg Ser
            35                  40                  45 ttt gtg cgc tca ttc tcc tat gtt gcc tat gat gtc tgc tta agt ttt     192
Phe Val Arg Ser Phe Ser Tyr Val Ala Tyr Asp Val Cys Leu Ser Phe
        50                  55                  60 ctt ttc tac tcg atc gcc acc aac ttc ttc cct tac atc tct tct ccg     240
Leu Phe Tyr Ser Ile Ala Thr Asn Phe Phe Pro Tyr Ile Ser Ser Pro
65                  70                  75                  80 ctc tcg tat gtc gct tgg ctg gtt tac tgg ctc ttc caa ggc tgc att     288
Leu Ser Tyr Val Ala Trp Leu Val Tyr Trp Leu Phe Gln Gly Cys Ile
                85                  90                  95 ctc act ggt ctt tgg gtc atc ggc cat gaa tgt ggc cat cat gct ttt     336
Leu Thr Gly Leu Trp Val Ile Gly His Glu Cys Gly His His Ala Phe
                100                 105                 110 agt gag tat cag ctg gct gat gac att gtt ggc cta att gtc cat tct     384
Ser Glu Tyr Gln Leu Ala Asp Asp Ile Val Gly Leu Ile Val His Ser
            115                 120                 125 gca ctt ctg gtt cca tat ttt tca tgg aaa tat agc cat cgc cgc cac     432
Ala Leu Leu Val Pro Tyr Phe Ser Trp Lys Tyr Ser His Arg Arg His
        130                 135                 140 cat tct aac ata gga tct ctc gag cga gac gaa gtg ttc gtc ccg aaa     480
His Ser Asn Ile Gly Ser Leu Glu Arg Asp Glu Val Phe Val Pro Lys
145                 150                 155                 160 tca aag tcg aaa att tca tgg tat tct aag tac tta aac aac ccg cca     528
Ser Lys Ser Lys Ile Ser Trp Tyr Ser Lys Tyr Leu Asn Asn Pro Pro
                165                 170                 175
```

```
ggt cga gtt ttg aca ctt gct gcc acg ctc ctc ctt ggc tgg cct tta      576
Gly Arg Val Leu Thr Leu Ala Ala Thr Leu Leu Leu Gly Trp Pro Leu
            180                 185                 190 tac tta gct ttc aat gtc tct ggt aga cct tac gat cgc ttt gct tgc      624
Tyr Leu Ala Phe Asn Val Ser Gly Arg Pro Tyr Asp Arg Phe Ala Cys
        195                 200                 205 cat tat gat ccc tat ggc cca ata ttt tcc gaa aga gaa agg ctt cag      672
His Tyr Asp Pro Tyr Gly Pro Ile Phe Ser Glu Arg Glu Arg Leu Gln
    210                 215                 220 att tac att gct gac ctc gga atc ttt gcc aca acg ttt gtg ctt tat      720
Ile Tyr Ile Ala Asp Leu Gly Ile Phe Ala Thr Thr Phe Val Leu Tyr
225                 230                 235                 240 cag gct aca atg gca aaa ggg ttg gct tgg gta atg cgt atc tat ggg      768
Gln Ala Thr Met Ala Lys Gly Leu Ala Trp Val Met Arg Ile Tyr Gly
                245                 250                 255 gtg cca ttg ctt att gtt aac tgt ttc ctt gtt atg atc aca tac ttg      816
Val Pro Leu Leu Ile Val Asn Cys Phe Leu Val Met Ile Thr Tyr Leu
            260                 265                 270 cag cac act cac cca gct att cca cgc tat ggc tca tcg gaa tgg gat      864
Gln His Thr His Pro Ala Ile Pro Arg Tyr Gly Ser Ser Glu Trp Asp
        275                 280                 285 tgg ctc cgg gga gca atg gtg act gtc gat aga gat tat ggg gtg ttg      912
Trp Leu Arg Gly Ala Met Val Thr Val Asp Arg Asp Tyr Gly Val Leu
    290                 295                 300 aat aaa gta ttc cat aac att gca gac act cat gta gct cat cat ctc      960
Asn Lys Val Phe His Asn Ile Ala Asp Thr His Val Ala His His Leu
305                 310                 315                 320 ttt gct aca gtg cca cat tac cat gca atg gag gcc act aaa gca atc     1008
Phe Ala Thr Val Pro His Tyr His Ala Met Glu Ala Thr Lys Ala Ile
                325                 330                 335 aag cct ata atg ggt gag tat tac cgg tat gat ggt acc cca ttt tac     1056
Lys Pro Ile Met Gly Glu Tyr Tyr Arg Tyr Asp Gly Thr Pro Phe Tyr
            340                 345                 350 aag gca ttg tgg agg gag gca aag gag tgc ttg ttc gtc gag cca gat     1104
Lys Ala Leu Trp Arg Glu Ala Lys Glu Cys Leu Phe Val Glu Pro Asp
        355                 360                 365 gaa gga gct cct aca caa ggc gtt ttc tgg tac cgg aac aag tat         1149
Glu Gly Ala Pro Thr Gln Gly Val Phe Trp Tyr Arg Asn Lys Tyr
    370                 375                 380 taa                                                                 1152

<210> SEQ ID NO 26
<211> LENGTH: 1152
<212> TYPE: DNA
<213> ORGANISM: Lesquerella gracilis B
<220> FEATURE:
<221> NAME/KEY: CDS
<222> LOCATION: (1)...(1149)

<400> SEQUENCE: 26 atg ggt gct ggt gga aga ata atg gtt acc cct tct tcc aag aaa tca       48
Met Gly Ala Gly Gly Arg Ile Met Val Thr Pro Ser Ser Lys Lys Ser
1               5                   10                  15 gaa act gaa gcc cta aaa cgt gga cca tgt gag aaa cca cca ttc act       96
Glu Thr Glu Ala Leu Lys Arg Gly Pro Cys Glu Lys Pro Pro Phe Thr
            20                  25                  30 gtt aaa gat ctg aag aaa gca atc cca cag cat tgt ttt caa cgc tct      144
Val Lys Asp Leu Lys Lys Ala Ile Pro Gln His Cys Phe Gln Arg Ser
        35                  40                  45 atc cct cgt tct ttc tcc tac ctt ctc aca gat atc act tta gtt tct      192
Ile Pro Arg Ser Phe Ser Tyr Leu Leu Thr Asp Ile Thr Leu Val Ser
```

```
                50                      55                      60
tgc ttc tac tac gtt gcc aca aat tac ttc tct ctt ctt cct cag cct    240
Cys Phe Tyr Tyr Val Ala Thr Asn Tyr Phe Ser Leu Leu Pro Gln Pro
 65                  70                  75                  80 ctc tct tac cta gct tgg cct ctc tat tgg gta tgt caa ggc tgt gtc    288
Leu Ser Tyr Leu Ala Trp Pro Leu Tyr Trp Val Cys Gln Gly Cys Val
                 85                  90                  95 cta aca ggt atc tgg gtc ctt ggc cat gaa tgt ggt cac cat gca ttc    336
Leu Thr Gly Ile Trp Val Leu Gly His Glu Cys Gly His His Ala Phe
            100                 105                 110 agt gac tat caa tgg cta gat gac act gtt ggt ttt atc ttc cat tcc    384
Ser Asp Tyr Gln Trp Leu Asp Asp Thr Val Gly Phe Ile Phe His Ser
        115                 120                 125 tta ctt ctc gtc cct tac ttc tcc tgg aaa tac agt cat cgt cgt cac    432
Leu Leu Leu Val Pro Tyr Phe Ser Trp Lys Tyr Ser His Arg Arg His
    130                 135                 140 cat tcc aac aat gga tct ctc gag aaa gat gaa gtc ttt gtc cca ccg    480
His Ser Asn Asn Gly Ser Leu Glu Lys Asp Glu Val Phe Val Pro Pro
145                 150                 155                 160 aaa aaa gct gca gtc aaa tgg tat gtt aaa tac ctc aac aac cct ctt    528
Lys Lys Ala Ala Val Lys Trp Tyr Val Lys Tyr Leu Asn Asn Pro Leu
                165                 170                 175 gga cgc att ctg gtg tta aca gtt cgg ttt atc ctc ggg tgg cct ttg    576
Gly Arg Ile Leu Val Leu Thr Val Arg Phe Ile Leu Gly Trp Pro Leu
            180                 185                 190 tat cta gcc ttt aat gta tca ggt aga cct tat gat ggt ttc gct tca    624
Tyr Leu Ala Phe Asn Val Ser Gly Arg Pro Tyr Asp Gly Phe Ala Ser
        195                 200                 205 cat ttc ttc cct cat gca cct atc ttt aaa gac cgc gaa cgt ctc cag    672
His Phe Phe Pro His Ala Pro Ile Phe Lys Asp Arg Glu Arg Leu Gln
    210                 215                 220 ata tac atc tca gat gct ggt att cta gct gtc tgt tat ggt ctt tac    720
Ile Tyr Ile Ser Asp Ala Gly Ile Leu Ala Val Cys Tyr Gly Leu Tyr
225                 230                 235                 240 cgt tac gct gct tca caa gga ttg acc gct atg atc tgc gtc tat gga    768
Arg Tyr Ala Ala Ser Gln Gly Leu Thr Ala Met Ile Cys Val Tyr Gly
                245                 250                 255 gta ccg ctt ttg ata gtg aac ttt ttc ctt gtc ttg gta act ttc ttg    816
Val Pro Leu Leu Ile Val Asn Phe Phe Leu Val Leu Val Thr Phe Leu
            260                 265                 270 cag cac act cat cct tcg tta cct cac tat gat tca acc gag tgg gaa    864
Gln His Thr His Pro Ser Leu Pro His Tyr Asp Ser Thr Glu Trp Glu
        275                 280                 285 tgg att aga gga gct ttg gtt acg gta gac aga gac tac gga atc ttg    912
Trp Ile Arg Gly Ala Leu Val Thr Val Asp Arg Asp Tyr Gly Ile Leu
    290                 295                 300 aac aag gtg ttt cac aac ata aca gac aca cat gtg gct cat cat ctt    960
Asn Lys Val Phe His Asn Ile Thr Asp Thr His Val Ala His His Leu
305                 310                 315                 320 ttc gca act ata ccg cat tat aac gca atg gaa gct aca gag gcg ata   1008
Phe Ala Thr Ile Pro His Tyr Asn Ala Met Glu Ala Thr Glu Ala Ile
                325                 330                 335 aag cca ata ctt ggt gat tac tac cat ttc gat gga aca ccg tgg tat   1056
Lys Pro Ile Leu Gly Asp Tyr Tyr His Phe Asp Gly Thr Pro Trp Tyr
            340                 345                 350 gtg gct atg tat agg gaa gca aag gag tgt ctc tat gta gaa ccg gat   1104
Val Ala Met Tyr Arg Glu Ala Lys Glu Cys Leu Tyr Val Glu Pro Asp
        355                 360                 365 acg gaa cgt ggg aag aaa ggt gtc tac tat tac aac aat aag tta        1149
```

```
                Thr Glu Arg Gly Lys Lys Gly Val Tyr Tyr Tyr Asn Lys Leu
                    370                 375                 380 tga                                                                         1152

<210> SEQ ID NO 27
<211> LENGTH: 1134
<212> TYPE: DNA
<213> ORGANISM: Stokesia laevis
<220> FEATURE:
<221> NAME/KEY: CDS
<222> LOCATION: (1)...(1131)

<400> SEQUENCE: 27 atg ggt gca ggt ggt cgg atg tcg gat cta tct gac gga aaa aat ctc              48
Met Gly Ala Gly Gly Arg Met Ser Asp Leu Ser Asp Gly Lys Asn Leu
 1               5                  10                  15 ctc aaa cgt gtg cca gtt gat cca cct ttc aca tta agt gat ata aag              96
Leu Lys Arg Val Pro Val Asp Pro Pro Phe Thr Leu Ser Asp Ile Lys
                 20                  25                  30 aaa gca atc cct ccc cat tgc ttc aaa cga tct gtc ata cgt tcg tcc             144
Lys Ala Ile Pro Pro His Cys Phe Lys Arg Ser Val Ile Arg Ser Ser
             35                  40                  45 tac tat gtt gtt cat gat ctc atc gtc tcc tac gtc ttc ttc ttc ctc             192
Tyr Tyr Val Val His Asp Leu Ile Val Ser Tyr Val Phe Phe Phe Leu
         50                  55                  60 gca acg aca tat att act gtt ctt cct gct cct ctt gct tac ata gcg             240
Ala Thr Thr Tyr Ile Thr Val Leu Pro Ala Pro Leu Ala Tyr Ile Ala
 65                  70                  75                  80 tgg cca gtt tac tgg ttt tgc caa gca agt att ctc act ggg ttg tgg             288
Trp Pro Val Tyr Trp Phe Cys Gln Ala Ser Ile Leu Thr Gly Leu Trp
                 85                  90                  95 gtt atc ggc cat gaa tgt ggt cac cat gcc ttt agt gaa tac cag tgg             336
Val Ile Gly His Glu Cys Gly His His Ala Phe Ser Glu Tyr Gln Trp
                100                 105                 110 att gat gac aca gtt ggg ttc atc ctc cac tcg gct ctc ctc acc cct             384
Ile Asp Asp Thr Val Gly Phe Ile Leu His Ser Ala Leu Leu Thr Pro
            115                 120                 125 tac ttc tct tgg aaa tat agc cat cga aat cac cat gcg aac aca aat             432
Tyr Phe Ser Trp Lys Tyr Ser His Arg Asn His His Ala Asn Thr Asn
        130                 135                 140 tca ctc gac aac gac gaa gtt tac att cct aag cgc aag tcc aaa gtc             480
Ser Leu Asp Asn Asp Glu Val Tyr Ile Pro Lys Arg Lys Ser Lys Val
145                 150                 155                 160 aag att tac tcc aaa atc cta aac aac cca cct gga cga gtg ttc act             528
Lys Ile Tyr Ser Lys Ile Leu Asn Asn Pro Pro Gly Arg Val Phe Thr
                165                 170                 175 ttg gtt ttc agg ttg acg cta ggg ttt cct ttg tac ctg tta act aat             576
Leu Val Phe Arg Leu Thr Leu Gly Phe Pro Leu Tyr Leu Leu Thr Asn
            180                 185                 190 atc tct gga aag aaa tac caa cgg ttt gcc aac cac ttt gat cca ttg             624
Ile Ser Gly Lys Lys Tyr Gln Arg Phe Ala Asn His Phe Asp Pro Leu
        195                 200                 205 agt ccc atc ttc acc gag cgt gaa cga att cag gtt ctt gta tca gat             672
Ser Pro Ile Phe Thr Glu Arg Glu Arg Ile Gln Val Leu Val Ser Asp
    210                 215                 220 ctt ggt ctt cta gct gta atc tac gca atc aag ctt ctt gtt gct gca             720
Leu Gly Leu Leu Ala Val Ile Tyr Ala Ile Lys Leu Leu Val Ala Ala
225                 230                 235                 240 aaa gga gct gtc tgg gtg aca tgc atc tat gga gtt cca gtc cta ggt             768
Lys Gly Ala Val Trp Val Thr Cys Ile Tyr Gly Val Pro Val Leu Gly
                245                 250                 255
```

```
gta agc gtg ttc ttc gtt ttg atc acg tat tta cac cac acc cat ctc      816
Val Ser Val Phe Phe Val Leu Ile Thr Tyr Leu His His Thr His Leu
        260                 265                 270 tcc tta cct cat tac gat tcg act gag tgg aac tgg atc aga ggg gca      864
Ser Leu Pro His Tyr Asp Ser Thr Glu Trp Asn Trp Ile Arg Gly Ala
            275                 280                 285 ttg tca acc atc gat agg gat ttt ggg ttc cta aat agg gtt ttc cat      912
Leu Ser Thr Ile Asp Arg Asp Phe Gly Phe Leu Asn Arg Val Phe His
        290                 295                 300 gac gtt aca cac act cat gta ttg cat cat ttg atc tct tac att cca      960
Asp Val Thr His Thr His Val Leu His His Leu Ile Ser Tyr Ile Pro
305                 310                 315                 320 cac tat cat gca aag gag gca aga gat gca atc aaa cca gtt ttg ggt     1008
His Tyr His Ala Lys Glu Ala Arg Asp Ala Ile Lys Pro Val Leu Gly
                325                 330                 335 gat tat tat aag att gat agg act ccg ata ttc aaa gca atg tgg aga     1056
Asp Tyr Tyr Lys Ile Asp Arg Thr Pro Ile Phe Lys Ala Met Trp Arg
            340                 345                 350 gag gcc aag gaa tgc atc tat atc gag cca gat gaa gat act gaa cac     1104
Glu Ala Lys Glu Cys Ile Tyr Ile Glu Pro Asp Glu Asp Thr Glu His
        355                 360                 365 aag ggt gtt tac tgg tac cat aaa atg tga                             1134
Lys Gly Val Tyr Trp Tyr His Lys Met
        370                 375

<210> SEQ ID NO 28
<211> LENGTH: 1164
<212> TYPE: DNA
<213> ORGANISM: Ricinus communis
<220

```
cat aga aga cat cat tct aac att gga tct ctt gag aga gac gag gtg      480
His Arg Arg His His Ser Asn Ile Gly Ser Leu Glu Arg Asp Glu Val
145                 150                 155                 160 ttt gtg cct aag tct aag tct aag att tct tgg tat tct aag tat ctt      528
Phe Val Pro Lys Ser Lys Ser Lys Ile Ser Trp Tyr Ser Lys Tyr Leu
                165                 170                 175 aac aac cca cct gga aga gtg ctt act ctt gct gca act ctt ttg ctt      576
Asn Asn Pro Pro Gly Arg Val Leu Thr Leu Ala Ala Thr Leu Leu Leu
            180                 185                 190 gga tgg cca ctt tat ctt gct ttc aac gtg tct gga aga cca tat gac      624
Gly Trp Pro Leu Tyr Leu Ala Phe Asn Val Ser Gly Arg Pro Tyr Asp
        195                 200                 205 aga ttc gct tgt cat tat gac cca tat gga cca att ttc tct gag aga      672
Arg Phe Ala Cys His Tyr Asp Pro Tyr Gly Pro Ile Phe Ser Glu Arg
    210                 215                 220 gag aga ctt caa atc tat att gct gac ctt gga att ttc gct act act      720
Glu Arg Leu Gln Ile Tyr Ile Ala Asp Leu Gly Ile Phe Ala Thr Thr
225                 230                 235                 240 ttc gtg ctt tat caa gct act atg gct aag gga ctt gct tgg gtt atg      768
Phe Val Leu Tyr Gln Ala Thr Met Ala Lys Gly Leu Ala Trp Val Met
                245                 250                 255 aga atc tat gga gtg cca ctt ttg att gtg aac tgt ttc ctt gtg atg      816
Arg Ile Tyr Gly Val Pro Leu Leu Ile Val Asn Cys Phe Leu Val Met
            260                 265                 270 att act tat ctt caa cat act cat cca gct att cca aga tat gga tct      864
Ile Thr Tyr Leu Gln His Thr His Pro Ala Ile Pro Arg Tyr Gly Ser
        275                 280                 285 tct gaa tgg gat tgg ctt aga gga gct atg gtg act gtg gac aga gac      912
Ser Glu Trp Asp Trp Leu Arg Gly Ala Met Val Thr Val Asp Arg Asp
290                 295                 300 tat gga gtg ctt aac aag gtg ttc cat aac att gct gac act cat gtg      960
Tyr Gly Val Leu Asn Lys Val Phe His Asn Ile Ala Asp Thr His Val
305                 310                 315                 320 gct cat cat ctt ttc gct act gtg cca cat tat cat gct atg gag gct     1008
Ala His His Leu Phe Ala Thr Val Pro His Tyr His Ala Met Glu Ala
                325                 330                 335 act aag gct att aag cca att atg gga gag tat tat aga tat gac gga     1056
Thr Lys Ala Ile Lys Pro Ile Met Gly Glu Tyr Tyr Arg Tyr Asp Gly
            340                 345                 350 act cca ttc tat aag gct ctt tgg aga gag gct aag gag tgt ctt ttc     1104
Thr Pro Phe Tyr Lys Ala Leu Trp Arg Glu Ala Lys Glu Cys Leu Phe
        355                 360                 365 gtt gaa cca gat gaa gga gct cca act caa gga gtg ttc tgg tat aga     1152
Val Glu Pro Asp Glu Gly Ala Pro Thr Gln Gly Val Phe Trp Tyr Arg
370                 375                 380 aac aag tat taa                                                     1164
Asn Lys Tyr
385

<210> SEQ ID NO 29
<211> LENGTH: 1134
<212> TYPE: DNA
<213> ORGANISM: Stokesia laevis
<220> FEATURE:
<221> NAME/KEY: CDS
<222> LOCATION: (1)...(1131)

<400> SEQUENCE: 29 atg gct tcc tcc gga aga atg tct gac ctt tct gac gga aag aac ctt       48
Met Ala Ser Ser Gly Arg Met Ser Asp Leu Ser Asp Gly Lys Asn Leu
1               5                   10                  15
```

| | | |
|---|---|---|
| ttg aag aga gtg cca gtg gac cca cct ttc act ctt tct gac att aag<br>Leu Lys Arg Val Pro Val Asp Pro Pro Phe Thr Leu Ser Asp Ile Lys<br>20 25 30 | | 96 |
| aag gct att cca cct cat tgt ttc aag aga tct gtg att aga tct tct<br>Lys Ala Ile Pro Pro His Cys Phe Lys Arg Ser Val Ile Arg Ser Ser<br>35 40 45 | | 144 |
| tat tat gtg gtg cat gac ctt att gtg tct tat gtg ttc ttc ttc ctt<br>Tyr Tyr Val Val His Asp Leu Ile Val Ser Tyr Val Phe Phe Phe Leu<br>50 55 60 | | 192 |
| gct act act tat att act gtg ctt cca gct cca ctt gct tat att gct<br>Ala Thr Thr Tyr Ile Thr Val Leu Pro Ala Pro Leu Ala Tyr Ile Ala<br>65 70 75 80 | | 240 |
| tgg cca gtg tat tgg ttc tgt caa gct tct att ctt act gga ctt tgg<br>Trp Pro Val Tyr Trp Phe Cys Gln Ala Ser Ile Leu Thr Gly Leu Trp<br>85 90 95 | | 288 |
| gtt att gga cat gag tgt gga cat cat gct ttc tct gag tat caa tgg<br>Val Ile Gly His Glu Cys Gly His His Ala Phe Ser Glu Tyr Gln Trp<br>100 105 110 | | 336 |
| att gac gac act gtg gga ttc att ctt cat tct gct ctt ttg act cca<br>Ile Asp Asp Thr Val Gly Phe Ile Leu His Ser Ala Leu Leu Thr Pro<br>115 120 125 | | 384 |
| tat ttc tct tgg aag tat tct cat aga aac cat cat gct aac act aac<br>Tyr Phe Ser Trp Lys Tyr Ser His Arg Asn His His Ala Asn Thr Asn<br>130 135 140 | | 432 |
| tct ctt gac aac gac gag gtg tat att cca aag aga aag tct aag gtg<br>Ser Leu Asp Asn Asp Glu Val Tyr Ile Pro Lys Arg Lys Ser Lys Val<br>145 150 155 160 | | 480 |
| aag atc tat tct aag att ctt aac aac cca cct gga aga gtg ttc act<br>Lys Ile Tyr Ser Lys Ile Leu Asn Asn Pro Pro Gly Arg Val Phe Thr<br>165 170 175 | | 528 |
| ctt gtg ttc aga ctt act ctt gga ttc cca ctt tat ctt ttg act aac<br>Leu Val Phe Arg Leu Thr Leu Gly Phe Pro Leu Tyr Leu Leu Thr Asn<br>180 185 190 | | 576 |
| att tct gga aag aag tat caa aga ttc gct aac cat ttc gac cca ctt<br>Ile Ser Gly Lys Lys Tyr Gln Arg Phe Ala Asn His Phe Asp Pro Leu<br>195 200 205 | | 624 |
| tct cca att ttc act gag aga gag aga att caa gtg ctt gtg tct gac<br>Ser Pro Ile Phe Thr Glu Arg Glu Arg Ile Gln Val Leu Val Ser Asp<br>210 215 220 | | 672 |
| ctt gga ctt ttg gct gtg atc tat gct att aag ctt ttg gtt gct gca<br>Leu Gly Leu Leu Ala Val Ile Tyr Ala Ile Lys Leu Leu Val Ala Ala<br>225 230 235 240 | | 720 |
| aag gga gct gtg tgg gtg act tgt atc tat gga gtt cca gtt ctt gga<br>Lys Gly Ala Val Trp Val Thr Cys Ile Tyr Gly Val Pro Val Leu Gly<br>245 250 255 | | 768 |
| gtg tct gtg ttc ttc gtg ctt att act tat ctt cat cat act cat ctt<br>Val Ser Val Phe Phe Val Leu Ile Thr Tyr Leu His His Thr His Leu<br>260 265 270 | | 816 |
| tct ctt cca cat tat gac tct act gag tgg aac tgg att aga gga gct<br>Ser Leu Pro His Tyr Asp Ser Thr Glu Trp Asn Trp Ile Arg Gly Ala<br>275 280 285 | | 864 |
| ctt tct act att gac aga gac ttc gga ttc ctt aac aga gtg ttc cat<br>Leu Ser Thr Ile Asp Arg Asp Phe Gly Phe Leu Asn Arg Val Phe His<br>290 295 300 | | 912 |
| gac gtg act cat act cat gtg ctt cat cat ctt att tct tat att cca<br>Asp Val Thr His Thr His Val Leu His His Leu Ile Ser Tyr Ile Pro<br>305 310 315 320 | | 960 |
| cat tat cat gct aag gag gct aga gac gct att aag cca gtg ctt gga<br>His Tyr His Ala Lys Glu Ala Arg Asp Ala Ile Lys Pro Val Leu Gly | | 1008 |

-continued

```
                325                 330                 335
gac tat tat aag att gac aga act cca atc ttt aag gct atg tgg aga      1056
Asp Tyr Tyr Lys Ile Asp Arg Thr Pro Ile Phe Lys Ala Met Trp Arg
                340                 345                 350 gag gct aag gag tgt atc tat att gaa cca gac gaa gac act gag cat      1104
Glu Ala Lys Glu Cys Ile Tyr Ile Glu Pro Asp Glu Asp Thr Glu His
            355                 360                 365 aag gga gtg tat tgg tat cat aag atg taa                              1134
Lys Gly Val Tyr Trp Tyr His Lys Met
        370                 375

<210> SEQ ID NO 30
<211> LENGTH: 1164
<212> TYPE: DNA
<213> ORGANISM: Ricinus communis
<220> FEATURE:
<221> NAME/KEY: CDS
<222> LOCATION: (1)...(1161)

<400> SEQUENCE: 30 atg gct tcc tcc ggt agg atg tct act gtc ata acc agc aac aac agt       48
Met Ala Ser Ser Gly Arg Met Ser Thr Val Ile Thr Ser Asn Asn Ser
  1               5                  10                  15 gag aag aaa gga gga agc agt cac ctt aag agg gct cca cac act aag       96
Glu Lys Lys Gly Gly Ser Ser His Leu Lys Arg Ala Pro His Thr Lys
                 20                  25                  30 cct cct ttc aca ctt ggt gac ctc aag aga gcc atc cca ccc cat tgc      144
Pro Pro Phe Thr Leu Gly Asp Leu Lys Arg Ala Ile Pro Pro His Cys
             35                  40                  45 ttt gaa agg tct ttt gtg aga tca ttc tcc tat gtt gcc tat gat gtc      192
Phe Glu Arg Ser Phe Val Arg Ser Phe Ser Tyr Val Ala Tyr Asp Val
         50                  55                  60 tgc tta agt ttt ctt ttc tac tct atc gcc acc aac ttc ttc cct tac      240
Cys Leu Ser Phe Leu Phe Tyr Ser Ile Ala Thr Asn Phe Phe Pro Tyr
     65                  70                  75                  80 atc tct tct cca ctc tct tat gtc gct tgg ctg gtt tac tgg ctc ttc      288
Ile Ser Ser Pro Leu Ser Tyr Val Ala Trp Leu Val Tyr Trp Leu Phe
                 85                  90                  95 caa ggc tgc att ctc act ggt ctt tgg gtc atc ggc cat gaa tgt ggc      336
Gln Gly Cys Ile Leu Thr Gly Leu Trp Val Ile Gly His Glu Cys Gly
                100                 105                 110 cat cat gct ttt agt gag tat cag ctg gct gat gac att gtt ggc cta      384
His His Ala Phe Ser Glu Tyr Gln Leu Ala Asp Asp Ile Val Gly Leu
            115                 120                 125 att gtc cat tct gca ctt ctg gtt cca tac ttc tca tgg aaa tat agc      432
Ile Val His Ser Ala Leu Leu Val Pro Tyr Phe Ser Trp Lys Tyr Ser
        130                 135                 140 cat aga agg cac cat tct aac ata gga tct ctc gag agg gac gaa gtg      480
His Arg Arg His His Ser Asn Ile Gly Ser Leu Glu Arg Asp Glu Val
145                 150                 155                 160 ttc gtc cca aaa tca aag tct aaa att tca tgg tat tct aag tac tta      528
Phe Val Pro Lys Ser Lys Ser Lys Ile Ser Trp Tyr Ser Lys Tyr Leu
                165                 170                 175 aac aac cct cca ggt agg gtt ttg aca ctt gct gcc act ctt ctc ctt      576
Asn Asn Pro Pro Gly Arg Val Leu Thr Leu Ala Ala Thr Leu Leu Leu
            180                 185                 190 ggc tgg cct tta tac tta gct ttc aat gtc tct ggt aga cct tac gat      624
Gly Trp Pro Leu Tyr Leu Ala Phe Asn Val Ser Gly Arg Pro Tyr Asp
        195                 200                 205 agg ttt gct tgc cat tat gat ccc tat ggc cca ata ttt tcc gaa aga      672
Arg Phe Ala Cys His Tyr Asp Pro Tyr Gly Pro Ile Phe Ser Glu Arg
```

```
              210                 215                 220
gaa agg ctt cag atc tac att gct gac ctc gga atc ttt gcc aca act     720
Glu Arg Leu Gln Ile Tyr Ile Ala Asp Leu Gly Ile Phe Ala Thr Thr
225                 230                 235                 240 ttt gtg ctt tat cag gct aca atg gca aaa ggg ttg gct tgg gta atg     768
Phe Val Leu Tyr Gln Ala Thr Met Ala Lys Gly Leu Ala Trp Val Met
                245                 250                 255 agg atc tat ggg gtg cca ttg ctt att gtt aac tgt ttc ctt gtt atg     816
Arg Ile Tyr Gly Val Pro Leu Leu Ile Val Asn Cys Phe Leu Val Met
                260                 265                 270 atc aca tac ttg cag cac act cac cca gct att cca agg tat ggc tca     864
Ile Thr Tyr Leu Gln His Thr His Pro Ala Ile Pro Arg Tyr Gly Ser
                275                 280                 285 tct gaa tgg gat tgg ctc agg gga gca atg gtg act gtc gat aga gat     912
Ser Glu Trp Asp Trp Leu Arg Gly Ala Met Val Thr Val Asp Arg Asp
290                 295                 300 tat ggg gtg ttg aac aag gta ttc cat aac att gca gac act cat gta     960
Tyr Gly Val Leu Asn Lys Val Phe His Asn Ile Ala Asp Thr His Val
305                 310                 315                 320 gct cat cat ctc ttt gct aca gtg cca cat tac cat gca atg gag gcc    1008
Ala His His Leu Phe Ala Thr Val Pro His Tyr His Ala Met Glu Ala
                325                 330                 335 act aaa gca atc aag cct ata atg gga gag tat tac agg tat gat ggt    1056
Thr Lys Ala Ile Lys Pro Ile Met Gly Glu Tyr Tyr Arg Tyr Asp Gly
                340                 345                 350 acc cca ttt tac aag gca ttg tgg agg gag gca aag gag tgc ttg ttc    1104
Thr Pro Phe Tyr Lys Ala Leu Trp Arg Glu Ala Lys Glu Cys Leu Phe
                355                 360                 365 gtc gag cca gat gaa gga gct cct aca caa ggc gtt ttc tgg tac agg    1152
Val Glu Pro Asp Glu Gly Ala Pro Thr Gln Gly Val Phe Trp Tyr Arg
370                 375                 380 aac aag tat taa                                                    1164
Asn Lys Tyr
385

<210> SEQ ID NO 31
<211> LENGTH: 1155
<212> TYPE: DNA
<213> ORGANISM: Artificial Sequence
<220> FEATURE:
<223> OTHER INFORMATION: hypothetical sequence
<220> FEATURE:
<221> NAME/KEY: CDS
<222> LOCATION: (1)...(1152)

<400> SEQUENCE: 31 atg gct tcc tcc gga aga atc atg gtt act cct tct tcc aag aag tca      48
Met Ala Ser Ser Gly Arg Ile Met Val Thr Pro Ser Ser Lys Lys Ser
1               5                   10                  15 gaa act gaa gcc cta aag cgt gga cca tgt gag aaa cca cca ttc act      96
Glu Thr Glu Ala Leu Lys Arg Gly Pro Cys Glu Lys Pro Pro Phe Thr
                20                  25                  30 gtt aaa gat ctg aag aag gca atc cca cag cat tgt ttc caa aga tct     144
Val Lys Asp Leu Lys Lys Ala Ile Pro Gln His Cys Phe Gln Arg Ser
            35                  40                  45 atc cct cgt tct ttc tcc tac ctt ctc aca gat atc act tta gtt tct     192
Ile Pro Arg Ser Phe Ser Tyr Leu Leu Thr Asp Ile Thr Leu Val Ser
        50                  55                  60 tgc ttc tac tac gtt gcc aca aat tac ttc tct ctt ctt cct cag cct     240
Cys Phe Tyr Tyr Val Ala Thr Asn Tyr Phe Ser Leu Leu Pro Gln Pro
65                  70                  75                  80
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctc | tct | act | tac | cta | gct | tgg | cct | ctc | tat | tgg | gta | tgt | caa | ggc | tgt | 288  |
| Leu | Ser | Thr | Tyr | Leu | Ala | Trp | Pro | Leu | Tyr | Trp | Val | Cys | Gln | Gly | Cys |      |
|     |     |     |     | 85  |     |     |     |     | 90  |     |     |     |     | 95  |     |      |
| gtc | cta | aca | ggt | atc | tgg | gtc | ctt | ggc | cat | gaa | tgt | ggt | cac | cat | gca | 336  |
| Val | Leu | Thr | Gly | Ile | Trp | Val | Leu | Gly | His | Glu | Cys | Gly | His | His | Ala |      |
|     |     |     | 100 |     |     |     |     | 105 |     |     |     |     | 110 |     |     |      |
| ttc | agt | gac | tat | caa | tgg | cta | gat | gac | act | gtt | ggt | ttc | atc | ttc | cat | 384  |
| Phe | Ser | Asp | Tyr | Gln | Trp | Leu | Asp | Asp | Thr | Val | Gly | Phe | Ile | Phe | His |      |
|     |     | 115 |     |     |     |     | 120 |     |     |     |     | 125 |     |     |     |      |
| tcc | tta | ctt | ctc | gtc | cct | tac | ttc | tcc | tgg | aaa | tac | agt | cat | cgt | cgt | 432  |
| Ser | Leu | Leu | Leu | Val | Pro | Tyr | Phe | Ser | Trp | Lys | Tyr | Ser | His | Arg | Arg |      |
|     | 130 |     |     |     |     | 135 |     |     |     |     | 140 |     |     |     |     |      |
| cac | cat | tcc | aac | aat | gga | tct | ctc | gag | aaa | gat | gaa | gtc | ttt | gtc | cca | 480  |
| His | His | Ser | Asn | Asn | Gly | Ser | Leu | Glu | Lys | Asp | Glu | Val | Phe | Val | Pro |      |
| 145 |     |     |     |     | 150 |     |     |     |     | 155 |     |     |     |     | 160 |      |
| cca | aag | aag | gct | gca | gtc | aaa | tgg | tat | gtt | aaa | tac | ctc | aac | aac | cct | 528  |
| Pro | Lys | Lys | Ala | Ala | Val | Lys | Trp | Tyr | Val | Lys | Tyr | Leu | Asn | Asn | Pro |      |
|     |     |     |     | 165 |     |     |     |     | 170 |     |     |     |     | 175 |     |      |
| ctt | gga | agg | att | ctg | gtg | tta | aca | gtt | agg | ttt | atc | ctc | ggg | tgg | cct | 576  |
| Leu | Gly | Arg | Ile | Leu | Val | Leu | Thr | Val | Arg | Phe | Ile | Leu | Gly | Trp | Pro |      |
|     |     |     | 180 |     |     |     |     | 185 |     |     |     |     | 190 |     |     |      |
| ttg | tat | cta | gcc | ttt | aat | gta | tca | ggt | aga | cct | tat | gat | ggt | ttc | gct | 624  |
| Leu | Tyr | Leu | Ala | Phe | Asn | Val | Ser | Gly | Arg | Pro | Tyr | Asp | Gly | Phe | Ala |      |
|     |     | 195 |     |     |     |     | 200 |     |     |     |     | 205 |     |     |     |      |
| tca | cat | ttc | ttc | cct | cat | gca | cct | atc | ttt | aaa | gac | agg | gaa | cgt | ctc | 672  |
| Ser | His | Phe | Phe | Pro | His | Ala | Pro | Ile | Phe | Lys | Asp | Arg | Glu | Arg | Leu |      |
|     | 210 |     |     |     |     | 215 |     |     |     |     | 220 |     |     |     |     |      |
| cag | ata | tac | atc | tca | gat | gct | ggt | att | cta | gct | gtc | tgt | tat | ggt | ctt | 720  |
| Gln | Ile | Tyr | Ile | Ser | Asp | Ala | Gly | Ile | Leu | Ala | Val | Cys | Tyr | Gly | Leu |      |
| 225 |     |     |     |     | 230 |     |     |     |     | 235 |     |     |     |     | 240 |      |
| tac | cgt | tac | gct | gct | tca | caa | gga | ttg | acc | gct | atg | atc | tgc | gtc | tat | 768  |
| Tyr | Arg | Tyr | Ala | Ala | Ser | Gln | Gly | Leu | Thr | Ala | Met | Ile | Cys | Val | Tyr |      |
|     |     |     |     | 245 |     |     |     |     | 250 |     |     |     |     | 255 |     |      |
| gga | gta | cct | ctt | ttg | ata | gtg | aac | ttc | ttc | gtc | ttg | gta | act | ttc | | 816  |
| Gly | Val | Pro | Leu | Leu | Ile | Val | Asn | Phe | Phe | Leu | Val | Leu | Thr | Phe |     |      |
|     |     |     | 260 |     |     |     |     | 265 |     |     |     |     | 270 |     |     |      |
| ttg | cag | cac | act | cat | cct | tct | tta | cct | cac | tat | gat | tca | acc | gag | tgg | 864  |
| Leu | Gln | His | Thr | His | Pro | Ser | Leu | Pro | His | Tyr | Asp | Ser | Thr | Glu | Trp |      |
|     |     |     | 275 |     |     |     |     | 280 |     |     |     |     | 285 |     |     |      |
| gaa | tgg | att | aga | gga | gct | ttg | gtt | act | gta | gac | aga | gac | tac | gga | atc | 912  |
| Glu | Trp | Ile | Arg | Gly | Ala | Leu | Val | Thr | Val | Asp | Arg | Asp | Tyr | Gly | Ile |      |
|     |     | 290 |     |     |     |     | 295 |     |     |     |     | 300 |     |     |     |      |
| ttg | aac | aag | gtg | ttt | cac | aac | ata | aca | gac | aca | cat | gtg | gct | cat | cat | 960  |
| Leu | Asn | Lys | Val | Phe | His | Asn | Ile | Thr | Asp | Thr | His | Val | Ala | His | His |      |
| 305 |     |     |     |     | 310 |     |     |     |     | 315 |     |     |     |     | 320 |      |
| ttg | ttc | gca | act | ata | cct | cat | tat | aac | gca | atg | gaa | gct | aca | gag | gct | 1008 |
| Leu | Phe | Ala | Thr | Ile | Pro | His | Tyr | Asn | Ala | Met | Glu | Ala | Thr | Glu | Ala |      |
|     |     |     |     | 325 |     |     |     |     | 330 |     |     |     |     | 335 |     |      |
| atc | aag | cca | ata | ctt | ggt | gat | tac | tac | cat | ttc | gat | gga | aca | cct | tgg | 1056 |
| Ile | Lys | Pro | Ile | Leu | Gly | Asp | Tyr | Tyr | His | Phe | Asp | Gly | Thr | Pro | Trp |      |
|     |     |     | 340 |     |     |     |     | 345 |     |     |     |     | 350 |     |     |      |
| tat | gtg | gct | atg | tat | agg | gaa | gca | aag | gag | tgt | ctc | tat | gta | gaa | cct | 1104 |
| Tyr | Val | Ala | Met | Tyr | Arg | Glu | Ala | Lys | Glu | Cys | Leu | Tyr | Val | Glu | Pro |      |
|     |     |     | 355 |     |     |     |     | 360 |     |     |     |     | 365 |     |     |      |
| gat | act | gaa | cgt | ggg | aag | aag | ggt | gtc | tac | tat | tac | aac | aat | aag | tta | 1152 |
| Asp | Thr | Glu | Arg | Gly | Lys | Lys | Gly | Val | Tyr | Tyr | Tyr | Asn | Asn | Lys | Leu |      |
| 370 |     |     |     |     | 375 |     |     |     |     | 380 |     |     |     |     |     |      |
| taa |     |     |     |     |     |     |     |     |     |     |     |     |     |     |     | 1155 |

```
<210> SEQ ID NO 32
<211> LENGTH: 1125
<212> TYPE: DNA
<213> ORGANISM: Artificial Sequence
<220> FEATURE:
<223> OTHER INFORMATION: hypothetical sequence
<220> FEATURE:
<221> NAME/KEY: CDS
<222> LOCATION: (1)...(1122)

<400> SEQUENCE: 32 atg gct tcc tcc ggc cat agt cga aca tct aag aag tct gtc atg gaa      48
Met Ala Ser Ser Gly His Ser Arg Thr Ser Lys Lys Ser Val Met Glu
 1               5                  10                  15 cgt gtc tct gtt gat cca gta ccc ttc tct cta agt gat ttg aag caa      96
Arg Val Ser Val Asp Pro Val Pro Phe Ser Leu Ser Asp Leu Lys Gln
             20                  25                  30 gca atc cct ccc cat tgc ttc cag cga tct gtc atc cgt tca tct tac     144
Ala Ile Pro Pro His Cys Phe Gln Arg Ser Val Ile Arg Ser Ser Tyr
         35                  40                  45 tat gta gtt cac gat ctc att att gcc tac atc ttc tac ttc ctt gcc     192
Tyr Val Val His Asp Leu Ile Ile Ala Tyr Ile Phe Tyr Phe Leu Ala
     50                  55                  60 gac aaa tac att cca att ctc cct gct cct cta gcc tac tta gct tgg     240
Asp Lys Tyr Ile Pro Ile Leu Pro Ala Pro Leu Ala Tyr Leu Ala Trp
 65                  70                  75                  80 ccc ctt tac tgg ttc tgt caa gct agc atc ctc act ggt tta tgg atc     288
Pro Leu Tyr Trp Phe Cys Gln Ala Ser Ile Leu Thr Gly Leu Trp Ile
                 85                  90                  95 ctc ggt cat gaa tgc ggt cac cat gcc ttt agc gag tac caa tgg gtt     336
Leu Gly His Glu Cys Gly His His Ala Phe Ser Glu Tyr Gln Trp Val
            100                 105                 110 gac gac act gtg ggc ttc atg gtc cac tca ttt ctt ctc act cct tac     384
Asp Asp Thr Val Gly Phe Met Val His Ser Phe Leu Leu Thr Pro Tyr
        115                 120                 125 ttc tct tgg aaa tac agt cac agg aat cac cat gcc aac aca agt tcc     432
Phe Ser Trp Lys Tyr Ser His Arg Asn His His Ala Asn Thr Ser Ser
    130                 135                 140 att gat aac gat gaa gtt tac att cct aag agc aag tcc aaa ctc gct     480
Ile Asp Asn Asp Glu Val Tyr Ile Pro Lys Ser Lys Ser Lys Leu Ala
145                 150                 155                 160 ctt acc tat aag ctt ctt aac aac cct cca gga agg ctg tta gtt atg     528
Leu Thr Tyr Lys Leu Leu Asn Asn Pro Pro Gly Arg Leu Leu Val Met
                165                 170                 175 gtt atc atg ttc acc cta gga ttt cct tta tac ctc ttg aca aat att     576
Val Ile Met Phe Thr Leu Gly Phe Pro Leu Tyr Leu Leu Thr Asn Ile
            180                 185                 190 tcc ggc aag aag tac gac agg ttt gcc aac cac ttc gac ccc atg agt     624
Ser Gly Lys Lys Tyr Asp Arg Phe Ala Asn His Phe Asp Pro Met Ser
        195                 200                 205 cca att ttc aag gaa cgt gag agg ttt cag gtc ttg ctt tct gat ctt     672
Pro Ile Phe Lys Glu Arg Glu Arg Phe Gln Val Leu Leu Ser Asp Leu
    210                 215                 220 ggc ctt ctt gct gtg ttt tat gga atc aaa gtt gct gta gca aag aag     720
Gly Leu Leu Ala Val Phe Tyr Gly Ile Lys Val Ala Val Ala Lys Lys
225                 230                 235                 240 gga gct gct tgg gtg gct tgt atg tat gga gtt cca atg cta ggc gta     768
Gly Ala Ala Trp Val Ala Cys Met Tyr Gly Val Pro Met Leu Gly Val
                245                 250                 255 ttc acc ctt ttc gat atc atc act tac ttg cac cac acc cat cag tca     816
Phe Thr Leu Phe Asp Ile Ile Thr Tyr Leu His His Thr His Gln Ser
            260                 265                 270
```

-continued

```
tct cct cat tat gac tca act gaa tgg aac tgg atc aga gga gct ttg      864
Ser Pro His Tyr Asp Ser Thr Glu Trp Asn Trp Ile Arg Gly Ala Leu
        275                 280                 285 tca gca atc gat agg gac ttt ggg ttc atg aat agt gtc ttc cat gat      912
Ser Ala Ile Asp Arg Asp Phe Gly Phe Met Asn Ser Val Phe His Asp
    290                 295                 300 gtt aca cac act cac gtc atg cat cat atg ttc tca tac att cca cac      960
Val Thr His Thr His Val Met His His Met Phe Ser Tyr Ile Pro His
305                 310                 315                 320 tat cat gct aag gag gca agg gat gca atc aat aca atc ata ggc gac     1008
Tyr His Ala Lys Glu Ala Arg Asp Ala Ile Asn Thr Ile Ile Gly Asp
                325                 330                 335 tat tat atg atc gat agg act cca att ttg aaa gca ctg tgg aga gag     1056
Tyr Tyr Met Ile Asp Arg Thr Pro Ile Leu Lys Ala Leu Trp Arg Glu
            340                 345                 350 gcc aag gaa tgc atg tac atc gag cct gat agc aag agg aag ggt gta     1104
Ala Lys Glu Cys Met Tyr Ile Glu Pro Asp Ser Lys Arg Lys Gly Val
        355                 360                 365 tat tgg tac cat aaa ttg taa                                         1125
Tyr Trp Tyr His Lys Leu
    370

<210> SEQ ID NO 33
<211> LENGTH: 1134
<212> TYPE: DNA
<213> ORGANISM: Stokesia laevis
<220> FEATURE:
<221> NAME/KEY: CDS
<222> LOCATION: (1)...(1131)

<400> SEQUENCE: 33 atg gct tcc tcc ggt agg atg tct gat ctt tct gac ggt aag aat ctt       48
Met Ala Ser Ser Gly Arg Met Ser Asp Leu Ser Asp Gly Lys Asn Leu
1               5                  10                  15 ctc aaa agg gtg cca gtt gat cca cct ttc aca tta agt gat ata aag       96
Leu Lys Arg Val Pro Val Asp Pro Pro Phe Thr Leu Ser Asp Ile Lys
            20                  25                  30 aaa gca atc cct ccc cat tgc ttc aaa agg tct gtc ata agg tct tca      144
Lys Ala Ile Pro Pro His Cys Phe Lys Arg Ser Val Ile Arg Ser Ser
        35                  40                  45 tac tat gtt gtt cat gat ctc atc gtc tcc tac gtc ttc ttc ctc          192
Tyr Tyr Val Val His Asp Leu Ile Val Ser Tyr Val Phe Phe Phe Leu
    50                  55                  60 gca act aca tat att act gtt ctt cct gct cct ctt gct tac ata gct      240
Ala Thr Thr Tyr Ile Thr Val Leu Pro Ala Pro Leu Ala Tyr Ile Ala
65                  70                  75                  80 tgg cca gtt tac tgg ttt tgc caa gca agt att ctc act ggg ttg tgg      288
Trp Pro Val Tyr Trp Phe Cys Gln Ala Ser Ile Leu Thr Gly Leu Trp
                85                  90                  95 gtt atc ggc cat gaa tgt ggt cac cat gcc ttt agt gaa tac cag tgg      336
Val Ile Gly His Glu Cys Gly His His Ala Phe Ser Glu Tyr Gln Trp
            100                 105                 110 att gat gac aca gtt ggg ttc atc ctc cac tct gct ctt ctc acc cct      384
Ile Asp Asp Thr Val Gly Phe Ile Leu His Ser Ala Leu Leu Thr Pro
        115                 120                 125 tac ttc tct tgg aaa tat agc cat agg aat cac cat gct aac aca aat      432
Tyr Phe Ser Trp Lys Tyr Ser His Arg Asn His His Ala Asn Thr Asn
    130                 135                 140 tca ctc gac aac gac gaa gtt tac att cct aag agg aag tcc aaa gtc      480
Ser Leu Asp Asn Asp Glu Val Tyr Ile Pro Lys Arg Lys Ser Lys Val
145                 150                 155                 160
```

```
aag atc tac tcc aaa atc cta aac aac cca cct gga agg gtg ttc act    528
Lys Ile Tyr Ser Lys Ile Leu Asn Asn Pro Pro Gly Arg Val Phe Thr
                165                 170                 175 ttg gtt ttc agg ttg act cta ggg ttt cct ttg tac ctg tta act aat    576
Leu Val Phe Arg Leu Thr Leu Gly Phe Pro Leu Tyr Leu Leu Thr Asn
            180                 185                 190 atc tct gga aag aaa tac caa agg ttt gcc aac cac ttt gat cca ttg    624
Ile Ser Gly Lys Lys Tyr Gln Arg Phe Ala Asn His Phe Asp Pro Leu
        195                 200                 205 agt ccc atc ttc acc gag agg gaa agg att cag gtt ctt gta tca gat    672
Ser Pro Ile Phe Thr Glu Arg Glu Arg Ile Gln Val Leu Val Ser Asp
    210                 215                 220 ctt ggt ctt cta gct gta atc tac gca atc aag ctt ctt gtt gct gca    720
Leu Gly Leu Leu Ala Val Ile Tyr Ala Ile Lys Leu Leu Val Ala Ala
225                 230                 235                 240 aaa gga gct gtc tgg gtg aca tgc atc tat gga gtt cca gtc cta ggt    768
Lys Gly Ala Val Trp Val Thr Cys Ile Tyr Gly Val Pro Val Leu Gly
                245                 250                 255 gta agc gtg ttc ttc gtt ttg atc act tac ttg cac cac acc cat ctt    816
Val Ser Val Phe Phe Val Leu Ile Thr Tyr Leu His His Thr His Leu
            260                 265                 270 tcc ttg cct cat tac gat tct act gag tgg aac tgg atc aga ggg gca    864
Ser Leu Pro His Tyr Asp Ser Thr Glu Trp Asn Trp Ile Arg Gly Ala
        275                 280                 285 ttg tca acc atc gat agg gat ttt ggg ttc cta aat agg gtt ttc cat    912
Leu Ser Thr Ile Asp Arg Asp Phe Gly Phe Leu Asn Arg Val Phe His
    290                 295                 300 gac gtt aca cac act cat gta ttg cat cat ttg atc tct tac att cca    960
Asp Val Thr His Thr His Val Leu His His Leu Ile Ser Tyr Ile Pro
305                 310                 315                 320 cac tat cat gca aag gag gca aga gat gca atc aaa cca gtt ttg ggt   1008
His Tyr His Ala Lys Glu Ala Arg Asp Ala Ile Lys Pro Val Leu Gly
                325                 330                 335 gat tat tat aag att gat agg act cct ata ttc aaa gca atg tgg aga   1056
Asp Tyr Tyr Lys Ile Asp Arg Thr Pro Ile Phe Lys Ala Met Trp Arg
            340                 345                 350 gag gcc aag gaa tgc atc tat atc gag cca gat gaa gat act gaa cac   1104
Glu Ala Lys Glu Cys Ile Tyr Ile Glu Pro Asp Glu Asp Thr Glu His
        355                 360                 365 aag ggt gtt tac tgg tac cat aaa atg taa                           1134
Lys Gly Val Tyr Trp Tyr His Lys Met
    370                 375
```

<210> SEQ ID NO 34
<211> LENGTH: 383
<212> TYPE: PRT
<213> ORGANISM: Ricinus communis

<400> SEQUENCE: 34

```
Met Gly Gly Gly Gly Arg Met Ser Thr Val Ile Thr Ser Asn Asn Ser
 1               5                  10                  15

Glu Ser Ser His Leu Lys Arg Ala Pro His Thr Lys Pro Pro Phe Thr
            20                  25                  30

Leu Gly Asp Leu Lys Arg Ala Ile Pro Pro His Cys Phe Glu Arg Ser
        35                  40                  45

Phe Val Arg Ser Phe Ser Tyr Val Ala Tyr Asp Val Cys Leu Ser Phe
    50                  55                  60

Leu Phe Tyr Ser Ile Ala Thr Asn Phe Phe Pro Tyr Ile Ser Ser Pro
65                  70                  75                  80
```

```
Leu Ser Tyr Val Ala Trp Leu Val Tyr Trp Leu Phe Gln Gly Cys Ile
                85                  90                  95

Leu Thr Gly Leu Trp Val Ile Gly His Glu Cys Gly His His Ala Phe
            100                 105                 110

Ser Glu Tyr Gln Leu Ala Asp Asp Ile Val Gly Leu Ile Val His Ser
        115                 120                 125

Ala Leu Leu Val Pro Tyr Phe Ser Trp Lys Tyr Ser His Arg Arg His
130                 135                 140

His Ser Asn Ile Gly Ser Leu Glu Arg Asp Glu Val Phe Val Pro Lys
145                 150                 155                 160

Ser Lys Ser Lys Ile Ser Trp Tyr Ser Lys Tyr Leu Asn Asn Pro Pro
                165                 170                 175

Gly Arg Val Leu Thr Leu Ala Ala Thr Leu Leu Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Phe Ser Glu Arg Glu Arg Leu Gln
    210                 215                 220

Ile Tyr Ile Ala Asp Leu Gly Ile Phe Ala Thr Thr Phe Val Leu Tyr
225                 230                 235                 240

Gln Ala Thr Met Ala Lys Gly Leu Ala Trp Val Met Arg Ile Tyr Gly
                245                 250                 255

Val Pro Leu Leu Ile Val Asn Cys Phe Leu Val Met Ile Thr Tyr Leu
            260                 265                 270

Gln His Thr His Pro Ala Ile Pro Arg Tyr Gly Ser Ser Glu Trp Asp
        275                 280                 285

Trp Leu Arg Gly Ala Met Val Thr Val Asp Arg Asp Tyr Gly Val Leu
    290                 295                 300

Asn Lys Val Phe His Asn Ile Ala Asp Thr His Val Ala His His Leu
305                 310                 315                 320

Phe Ala Thr Val Pro His Tyr His Ala Met Glu Ala Thr Lys Ala Ile
                325                 330                 335

Lys Pro Ile Met Gly Glu Tyr Tyr Arg Tyr Asp Gly Thr Pro Phe Tyr
            340                 345                 350

Lys Ala Leu Trp Arg Glu Ala Lys Glu Cys Leu Phe Val Glu Pro Asp
        355                 360                 365

Glu Gly Ala Pro Thr Gln Gly Val Phe Trp Tyr Arg Asn Lys Tyr
    370                 375                 380

<210> SEQ ID NO 35
<211> LENGTH: 383
<212> TYPE: PRT
<213> ORGANISM: Lesquerella gracilis B

<400> SEQUENCE: 35

Met Gly Ala Gly Gly Arg Ile Met Val Thr Pro Ser Ser Lys Lys Ser
1               5                   10                  15

Glu Thr Glu Ala Leu Lys Arg Gly Pro Cys Glu Lys Pro Pro Phe Thr
            20                  25                  30

Val Lys Asp Leu Lys Lys Ala Ile Pro Gln His Cys Phe Gln Arg Ser
        35                  40                  45

Ile Pro Arg Ser Phe Ser Tyr Leu Leu Thr Asp Ile Thr Leu Val Ser
    50                  55                  60

Cys Phe Tyr Tyr Val Ala Thr Asn Tyr Phe Ser Leu Leu Pro Gln Pro
```

```
                 65                  70                  75                  80
Leu Ser Tyr Leu Ala Trp Pro Leu Tyr Trp Val Cys Gln Gly Cys Val
                         85                  90                  95
Leu Thr Gly Ile Trp Val Leu Gly His Glu Cys Gly His His Ala Phe
                100                 105                 110
Ser Asp Tyr Gln Trp Leu Asp Asp Thr Val Gly Phe Ile Phe His Ser
        115                 120                 125
Leu Leu Leu Val Pro Tyr Phe Ser Trp Lys Tyr Ser His Arg Arg His
    130                 135                 140
His Ser Asn Asn Gly Ser Leu Glu Lys Asp Glu Val Phe Val Pro Pro
145                 150                 155                 160
Lys Lys Ala Ala Val Lys Trp Tyr Val Lys Tyr Leu Asn Asn Pro Leu
                165                 170                 175
Gly Arg Ile Leu Val Leu Thr Val Arg Phe Ile Leu Gly Trp Pro Leu
                    180                 185                 190
Tyr Leu Ala Phe Asn Val Ser Gly Arg Pro Tyr Asp Gly Phe Ala Ser
            195                 200                 205
His Phe Phe Pro His Ala Pro Ile Phe Lys Asp Arg Glu Arg Leu Gln
        210                 215                 220
Ile Tyr Ile Ser Asp Ala Gly Ile Leu Ala Val Cys Tyr Gly Leu Tyr
225                 230                 235                 240
Arg Tyr Ala Ala Ser Gln Gly Leu Thr Ala Met Ile Cys Val Tyr Gly
                245                 250                 255
Val Pro Leu Leu Ile Val Asn Phe Phe Leu Val Leu Val Thr Phe Leu
                    260                 265                 270
Gln His Thr His Pro Ser Leu Pro His Tyr Asp Ser Thr Glu Trp Glu
            275                 280                 285
Trp Ile Arg Gly Ala Leu Val Thr Val Asp Arg Asp Tyr Gly Ile Leu
        290                 295                 300
Asn Lys Val Phe His Asn Ile Thr Asp Thr His Val Ala His His Leu
305                 310                 315                 320
Phe Ala Thr Ile Pro His Tyr Asn Ala Met Glu Ala Thr Glu Ala Ile
                325                 330                 335
Lys Pro Ile Leu Gly Asp Tyr His Phe Asp Gly Thr Pro Trp Tyr
                    340                 345                 350
Val Ala Met Tyr Arg Glu Ala Lys Glu Cys Leu Tyr Val Glu Pro Asp
            355                 360                 365
Thr Glu Arg Gly Lys Lys Gly Val Tyr Tyr Asn Asn Lys Leu
        370                 375                 380

<210> SEQ ID NO 36
<211> LENGTH: 377
<212> TYPE: PRT
<213> ORGANISM: Stokesia laevis

<400> SEQUENCE: 36

Met Gly Ala Gly Gly Arg Met Ser Asp Leu Ser Asp Gly Lys Asn Leu
1               5                   10                  15
Leu Lys Arg Val Pro Val Asp Pro Pro Phe Thr Leu Ser Asp Ile Lys
                20                  25                  30
Lys Ala Ile Pro Pro His Cys Phe Lys Arg Ser Val Ile Arg Ser Ser
            35                  40                  45
Tyr Tyr Val Val His Asp Leu Ile Val Ser Tyr Val Phe Phe Phe Leu
        50                  55                  60
```

Ala Thr Thr Tyr Ile Thr Val Leu Pro Ala Pro Leu Ala Tyr Ile Ala
 65                  70                  75                  80

Trp Pro Val Tyr Trp Phe Cys Gln Ala Ser Ile Leu Thr Gly Leu Trp
                 85                  90                  95

Val Ile Gly His Glu Cys Gly His His Ala Phe Ser Glu Tyr Gln Trp
            100                 105                 110

Ile Asp Asp Thr Val Gly Phe Ile Leu His Ser Ala Leu Leu Thr Pro
        115                 120                 125

Tyr Phe Ser Trp Lys Tyr Ser His Arg Asn His Ala Asn Thr Asn
    130                 135                 140

Ser Leu Asp Asn Asp Glu Val Tyr Ile Pro Lys Arg Lys Ser Lys Val
145                 150                 155                 160

Lys Ile Tyr Ser Lys Ile Leu Asn Asn Pro Pro Gly Arg Val Phe Thr
                165                 170                 175

Leu Val Phe Arg Leu Thr Leu Gly Phe Pro Leu Tyr Leu Leu Thr Asn
            180                 185                 190

Ile Ser Gly Lys Lys Tyr Gln Arg Phe Ala Asn His Phe Asp Pro Leu
        195                 200                 205

Ser Pro Ile Phe Thr Glu Arg Glu Arg Ile Gln Val Leu Val Ser Asp
    210                 215                 220

Leu Gly Leu Leu Ala Val Ile Tyr Ala Ile Lys Leu Leu Val Ala Ala
225                 230                 235                 240

Lys Gly Ala Val Trp Val Thr Cys Ile Tyr Gly Val Pro Val Leu Gly
                245                 250                 255

Val Ser Val Phe Phe Val Leu Ile Thr Tyr Leu His His Thr His Leu
            260                 265                 270

Ser Leu Pro His Tyr Asp Ser Thr Glu Trp Asn Trp Ile Arg Gly Ala
        275                 280                 285

Leu Ser Thr Ile Asp Arg Asp Phe Gly Phe Leu Asn Arg Val Phe His
    290                 295                 300

Asp Val Thr His Thr His Val Leu His His Leu Ile Ser Tyr Ile Pro
305                 310                 315                 320

His Tyr His Ala Lys Glu Ala Arg Asp Ala Ile Lys Pro Val Leu Gly
                325                 330                 335

Asp Tyr Tyr Lys Ile Asp Arg Thr Pro Ile Phe Lys Ala Met Trp Arg
            340                 345                 350

Glu Ala Lys Glu Cys Ile Tyr Ile Glu Pro Asp Glu Asp Thr Glu His
        355                 360                 365

Lys Gly Val Tyr Trp Tyr His Lys Met
    370                 375

<210> SEQ ID NO 37
<211> LENGTH: 387
<212> TYPE: PRT
<213> ORGANISM: Ricinus communis

<400> SEQUENCE: 37

Met Ala Ser Ser Gly Arg Met Ser Thr Val Ile Thr

-continued

```
            50                  55                  60
Cys Leu Ser Phe Leu Phe Tyr Ser Ile Ala Thr Asn Phe Phe Pro Tyr
 65                  70                  75                  80

Ile Ser Ser Pro Leu Ser Tyr Val Ala Trp Leu Val Tyr Trp Leu Phe
                 85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Leu
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 38
<211> LENGTH: 377
<212> TYPE: PRT
<213> ORGANISM: Stokesia laevis

<400> SEQUENCE: 38

Met Ala Ser Ser Gly Arg Met Ser Asp Leu Ser Asp Gly Lys Asn Leu
  1               5                  10                  15

Leu Lys Arg Val Pro Val Asp Pro Pro Phe Thr Leu Ser Asp Ile Lys
             20                  25                  30
```

```
Lys Ala Ile Pro Pro His Cys Phe Lys Arg Ser Val Ile Arg Ser Ser
            35                   40                   45

Tyr Tyr Val Val His Asp Leu Ile Val Ser Tyr Val Phe Phe Leu
        50                   55                   60

Ala Thr Thr Tyr Ile Thr Val Leu Pro Ala Pro Leu Ala Tyr Ile Ala
65                       70                   75                   80

Trp Pro Val Tyr Trp Phe Cys Gln Ala Ser Ile Leu Thr Gly Leu Trp
                    85                   90                   95

Val Ile Gly His Glu Cys Gly His His Ala Phe Ser Glu Tyr Gln Trp
                100                 105                 110

Ile Asp Asp Thr Val Gly Phe Ile Leu His Ser Ala Leu Leu Thr Pro
                115                 120                 125

Tyr Phe Ser Trp Lys Tyr Ser His Arg Asn His His Ala Asn Thr Asn
            130                 135                 140

Ser Leu Asp Asn Asp Glu Val Tyr Ile Pro Lys Arg Lys Ser Lys Val
145                 150                 155                 160

Lys Ile Tyr Ser Lys Ile Leu Asn Asn Pro Pro Gly Arg Val Phe Thr
                165                 170                 175

Leu Val Phe Arg Leu Thr Leu Gly Phe Pro Leu Tyr Leu Leu Thr Asn
                180                 185                 190

Ile Ser Gly Lys Lys Tyr Gln Arg Phe Ala Asn His Phe Asp Pro Leu
            195                 200                 205

Ser Pro Ile Phe Thr Glu Arg Glu Arg Ile Gln Val Leu Val Ser Asp
        210                 215                 220

Leu Gly Leu Leu Ala Val Ile Tyr Ala Ile Lys Leu Leu Val Ala Ala
225                 230                 235                 240

Lys Gly Ala Val Trp Val Thr Cys Ile Tyr Gly Val Pro Val Leu Gly
                245                 250                 255

Val Ser Val Phe Phe Val Leu Ile Thr Tyr Leu His His Thr His Leu
                260                 265                 270

Ser Leu Pro His Tyr Asp Ser Thr Glu Trp Asn Trp Ile Arg Gly Ala
            275                 280                 285

Leu Ser Thr Ile Asp Arg Asp Phe Gly Phe Leu Asn Arg Val Phe His
        290                 295                 300

Asp Val Thr His Thr His Val Leu His His Leu Ile Ser Tyr Ile Pro
305                 310                 315                 320

His Tyr His Ala Lys Glu Ala Arg Asp Ala Ile Lys Pro Val Leu Gly
                325                 330                 335

Asp Tyr Tyr Lys Ile Asp Arg Thr Pro Ile Phe Lys Ala Met Trp Arg
            340                 345                 350

Glu Ala Lys Glu Cys Ile Tyr Ile Glu Pro Asp Glu Asp Thr Glu His
        355                 360                 365

Lys Gly Val Tyr Trp Tyr His Lys Met
    370                 375

<210> SEQ ID NO 39
<211> LENGTH: 387
<212> TYPE: PRT
<213> ORGANISM: Ricinus communis

<400> SEQUENCE: 39

Met Ala Ser Ser Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
            20                  25                  30
```

Pro Pro Phe Thr Leu Gly Asp Leu Lys Arg Ala Ile Pro Pro His Cys
        35                  40                  45

Phe Glu Arg Ser Phe Val Arg Ser Phe Ser Tyr Val Ala Tyr Asp Val
 50                  55                  60

Cys Leu Ser Phe Leu Phe Tyr Ser Ile Ala Thr Asn Phe Phe Pro Tyr
 65                  70                  75                  80

Ile Ser Ser Pro Leu Ser Tyr Val Ala Trp Leu Val Tyr Trp Leu Phe
                 85                  90                  95

Gln Gly Cys Ile Leu Thr Gly Leu Trp Val Ile Gly His Glu Cys Gly
                100                 105                 110

His His Ala Phe Ser Glu Tyr Gln Leu Ala Asp Asp Ile Val Gly Leu
                115                 120                 125

Ile Val His Ser Ala Leu Leu Val Pro Tyr Phe Ser Trp Lys Tyr Ser
                130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Leu
                165                 170                 175

Asn Asn Pro Pro Gly Arg Val Leu Thr Leu Ala Ala Thr Leu Leu Leu
                180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
                260                 265                 270

Ile Thr Tyr Leu Gln His Thr His Pro Ala Ile Pro Arg Tyr Gly Ser
                275                 280                 285

Ser Glu Trp Asp Trp Leu Arg Gly Ala Met Val Thr Val Asp Arg Asp
        290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
                340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
        370                 375                 380

Asn Lys Tyr
385

<210> SEQ ID NO 40
<211> LENGTH: 384
<212> TYPE: PRT
<213> ORGANISM: Artificial Sequence
<220> FEATURE:
<223> OTHER INFORMATION: hypothetical sequence

<400> SEQUENCE: 40

```
Met Ala Ser Ser Gly Arg Ile Met Val Thr Pro Ser Ser Lys Lys Ser
 1               5                  10                  15

Glu Thr Glu Ala Leu Lys Arg Gly Pro Cys Glu Lys Pro Pro Phe Thr
             20                  25                  30

Val Lys Asp Leu Lys Lys Ala Ile Pro Gln His Cys Phe Gln Arg Ser
         35                  40                  45

Ile Pro Arg Ser Phe Ser Tyr Leu Leu Thr Asp Ile Thr Leu Val Ser
     50                  55                  60

Cys Phe Tyr Tyr Val Ala Thr Asn Tyr Phe Ser Leu Leu Pro Gln Pro
 65                  70                  75                  80

Leu Ser Thr Tyr Leu Ala Trp Pro Leu Tyr Trp Val Cys Gln Gly Cys
                 85                  90                  95

Val Leu Thr Gly Ile Trp Val Leu Gly His Glu Cys Gly His His Ala
            100                 105                 110

Phe Ser Asp Tyr Gln Trp Leu Asp Asp Thr Val Gly Phe Ile Phe His
            115                 120                 125

Ser Leu Leu Val Pro Tyr Phe Ser Trp Lys Tyr Ser His Arg Arg
130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Arg Phe Ile Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
        275                 280                 285

Glu Trp Ile Arg Gly Ala Leu Val Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
            340                 345                 350

Tyr Val Ala Met Tyr Arg Glu Ala Lys Glu Cys Leu Tyr Val Glu Pro
        355                 360                 365

Asp Thr Glu Arg Gly Lys Lys Gly Val Tyr Tyr Asn Asn Lys Leu
    370                 375                 380

<210> SEQ ID NO 41
<211> LENGTH: 374
<212> TYPE: PRT
<213> ORGANISM: Artificial Sequence
<220> FEATURE:
```

<223> OTHER INFORMATION: hypothetical sequence

<400> SEQUENCE: 41

```
Met Ala Ser Ser Gly His Ser Arg Thr Ser Lys Lys Ser Val Met Glu
 1               5                  10                  15

Arg Val Ser Val Asp Pro Val Pro Phe Ser Leu Ser Asp Leu Lys Gln
            20                  25                  30

Ala Ile Pro Pro His Cys Phe Gln Arg Ser Val Ile Arg Ser Ser Tyr
        35                  40                  45

Tyr Val Val His Asp Leu Ile Ile Ala Tyr Ile Phe Tyr Phe Leu Ala
 50                  55                  60

Asp Lys Tyr Ile Pro Ile Leu Pro Ala Pro Leu Ala Tyr Leu Ala Trp
 65                  70                  75                  80

Pro Leu Tyr Trp Phe Cys Gln Ala Ser Ile Leu Thr Gly Leu Trp Ile
            85                  90                  95

Leu Gly His Glu Cys Gly His His Ala Phe Ser Glu Tyr Gln Trp Val
            100                 105                 110

Asp Asp Thr Val Gly Phe Met Val His Ser Phe Leu Leu Thr Pro Tyr
            115                 120                 125

Phe Ser Trp Lys Tyr Ser His Arg Asn His His Ala Asn Thr Ser Ser
130                 135                 140

Ile Asp Asn Asp Glu Val Tyr Ile Pro Lys Ser Lys Ser Lys Leu Ala
145                 150                 155                 160

Leu Thr Tyr Lys Leu Leu Asn Asn Pro Pro Gly Arg Leu Leu Val Met
                165                 170                 175

Val Ile Met Phe Thr Leu Gly Phe Pro Leu Tyr Leu Leu Thr Asn Ile
            180                 185                 190

Ser Gly Lys Lys Tyr Asp Arg Phe Ala Asn His Phe Asp Pro Met Ser
        195                 200                 205

Pro Ile Phe Lys Glu Arg Glu Arg Phe Gln Val Leu Leu Ser Asp Leu
    210                 215                 220

Gly Leu Leu Ala Val Phe Tyr Gly Ile Lys Val Ala Val Ala Lys Lys
225                 230                 235                 240

Gly Ala Ala Trp Val Ala Cys Met Tyr Gly Val Pro Met Leu Gly Val
                245                 250                 255

Phe Thr Leu Phe Asp Ile Ile Thr Tyr Leu His His Thr His Gln Ser
            260                 265                 270

Ser Pro His Tyr Asp Ser Thr Glu Trp Asn Trp Ile Arg Gly Ala Leu
        275                 280                 285

Ser Ala Ile Asp Arg Asp Phe Gly Phe Met Asn Ser Val Phe His Asp
    290                 295                 300

Val Thr His Thr His Val Met His His Met Phe Ser Tyr Ile Pro His
305                 310                 315                 320

Tyr His Ala Lys Glu Ala Arg Asp Ala Ile Asn Thr Ile Gly Asp
                325                 330                 335

Tyr Tyr Met Ile Asp Arg Thr Pro Ile Leu Lys Ala Leu Trp Arg Glu
            340                 345                 350

Ala Lys Glu Cys Met Tyr Ile Glu Pro Asp Ser Lys Arg Lys Gly Val
        355                 360                 365

Tyr Trp Tyr His Lys Leu
    370
```

<210> SEQ ID NO 42
<211> LENGTH: 377

```
<212> TYPE: PRT
<213> ORGANISM: Stokesia laevis

<400> SEQUENCE: 42

Met Ala Ser Ser Gly Arg Met Ser Asp Leu Ser Asp Gly Lys Asn Leu
 1               5                  10                  15

Leu Lys Arg Val Pro Val Asp Pro Phe Thr Leu Ser Asp Ile Lys
             20                  25                  30

Lys Ala Ile Pro Pro His Cys Phe Lys Arg Ser Val Ile Arg Ser Ser
             35                  40                  45

Tyr Tyr Val Val His Asp Leu Ile Val Ser Tyr Phe Phe Phe Leu
 50                  55                  60

Ala Thr Thr Tyr Ile Thr Val Leu Pro Ala Pro Leu Ala Tyr Ile Ala
 65                  70                  75                  80

Trp Pro Val Tyr Trp Phe Cys Gln Ala Ser Ile Leu Thr Gly Leu Trp
             85                  90                  95

Val Ile Gly His Glu Cys Gly His His Ala Phe Ser Glu Tyr Gln Trp
             100                 105                 110

Ile Asp Asp Thr Val Gly Phe Ile Leu His Ser Ala Leu Leu Thr Pro
             115                 120                 125

Tyr Phe Ser Trp Lys Tyr Ser His Arg Asn His His Ala Asn Thr Asn
 130                 135                 140

Ser Leu Asp Asn Asp Glu Val Tyr Ile Pro Lys Arg Lys Ser Lys Val
145                 150                 155                 160

Lys Ile Tyr Ser Lys Ile Leu Asn Asn Pro Pro Gly Arg Val Phe Thr
             165                 170                 175

Leu Val Phe Arg Leu Thr Leu Gly Phe Pro Leu Tyr Leu Leu Thr Asn
             180                 185                 190

Ile Ser Gly Lys Lys Tyr Gln Arg Phe Ala Asn His Phe Asp Pro Leu
             195                 200                 205

Ser Pro Ile Phe Thr Glu Arg Glu Arg Ile Gln Val Leu Val Ser Asp
             210                 215                 220

Leu Gly Leu Leu Ala Val Ile Tyr Ala Ile Lys Leu Leu Val Ala Ala
225                 230                 235                 240

Lys Gly Ala Val Trp Val Thr Cys Ile Tyr Gly Val Pro Val Leu Gly
             245                 250                 255

Val Ser Val Phe Phe Val Leu Ile Thr Tyr Leu His His Thr His Leu
             260                 265                 270

Ser Leu Pro His Tyr Asp Ser Thr Glu Trp Asn Trp Ile Arg Gly Ala
             275                 280                 285

Leu Ser Thr Ile Asp Arg Asp Phe Gly Phe Leu Asn Arg Val Phe His
             290                 295                 300

Asp Val Thr His Thr His Val Leu His His Leu Ile Ser Tyr Ile Pro
305                 310                 315                 320

His Tyr His Ala Lys Glu Ala Arg Asp Ala Ile Lys Pro Val Leu Gly
             325                 330                 335

Asp Tyr Tyr Lys Ile Asp Arg Thr Pro Ile Phe Lys Ala Met Trp Arg
             340                 345                 350

Glu Ala Lys Glu Cys Ile Tyr Ile Glu Pro Asp Glu Asp Thr Glu His
             355                 360                 365

Lys Gly Val Tyr Trp Tyr His Lys Met
             370                 375

<210> SEQ ID NO 43
```

```
<211> LENGTH: 92
<212> TYPE: DNA
<213> ORGANISM: Arabidopsis thaliana

<400> SEQUENCE: 43
agagagagag attctgcgga ggagcttctt cttcgtaggg tgttcatcgt tattaacgtt     60
atcgccccta cgtcagctcc atctccagaa ac                                  92

<210> SEQ ID NO 44
<211> LENGTH: 1222
<212> TYPE: DNA
<213> ORGANISM: Arabidopsis thaliana

<400> SEQUENCE: 44
agagagagag attctgcgga ggagcttctt cttcgtaggg tgttcatcgt tattaacgtt     60
atcgccccta cgtcagctcc atctccaggt ccgtcgcttc tcttccattt cttctcattt    120
tcgattttga ttcttatttc tttccagtag ctcctgctct gtgaatttct ccgctcacga    180
tagatctgct tatactcctt acattcaacc ttagatctgg tctcgattct ctgtttctct    240
gtttttttct tttggtcgag aatctgatgt ttgtttatgt tctgtcacca ttaataataa    300
tgaactctct cattcataca atgattagtt tctctcgtct acaaaacgat atgttgcatt    360 ttcactttc ttctttttt ctaagatgat ttgctttgac caatttgttt agatctttat       420
tctattttat tttctggtgg gttggtggaa attgaaaaaa aaaaaacagc ataaattgtt    480
atttgttaat gtattcattt tttggctatt tgttctgggt aaaaatctgc ttctactatt    540
gaatctttcc tggatttttt actcctattg ggttttttata gtaaaaatac ataataaaag   600
gaaaacaaaa gttttataga ttctcttaaa ccccttacga taaagttgg aatcaaaata     660 attcaggatc agatgctctt tgattgattc agatgcgatt acagttgcat ggcaaatttt    720
ctagatccgt cgtcacattt tattttctgt ttaaatatct aaatctgata tatgatgtcg    780
acaaattctg gtggcttata catcacttca actgttttct tttggctttg tttgtcaact    840
tggttttcaa tacgatttgt gatttcgatc gctgaatttt taatacaagc aaactgatgt    900
taaccacaag caagagatgt gacctgcctt attaacatcg tattacttac tactagtcgt    960
attctcaacg caatcgtttt tgtatttctc acattatgcc gcttctctac tcttattcc    1020 ttttggtcca cgcatttcct atttgtggca atcccttcca caacctgatt tcccactttg   1080
gatcatttgt ctgaagactc tcttgaatcg ttaccacttg tttcttgtgc atgctctgtt   1140
ttttagaatt aatgataaaa ctattccata gtcttgagtt tcagcttgt tgattcttt     1200 gcttttggtt ttctgcagaa ac                                            1222

<210> SEQ ID NO 45
<211> LENGTH: 222
<212> TYPE: DNA
<213> ORGANISM: Arabidopsis thaliana

<400> SEQUENCE: 45
ggatgatggt gaagaaattg tcgacctttc tcttgtctgt ttgtcttttg ttaaagaagc     60
tatgcttcgt tttaataatc ttattgtcca ttttgttgtg ttatgacatt ttggctgctc    120
attatgttat gtgggaagtt agtgttcaaa tgttttgtgt cggtattgtt cttctcatcg    180
ctgttttgtt gggatcgtag aaatgtgacc ttcggacagt aa                      222

<210> SEQ ID NO 46
<211> LENGTH: 21
```

```
<212> TYPE: DNA
<213> ORGANISM: Artificial Sequence
<220> FEATURE:
<223> OTHER INFORMATION: primer

<400> SEQUENCE: 46
atgggaggtg gtggtcgcat g                                              21

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
ttaatacttg ttccggtacc a                                              21

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
atgggtgctg gtggaagaat aatg                                           24

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
tcataactta ttgaagtaat agtagacacc ttt                                 33

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
tcataactta ttgttgtaat a                                              21

<210> SEQ ID NO 51
<211> LENGTH: 17
<212> TYPE: DNA
<213> ORGANISM: Artificial Sequence
<220> FEATURE:
<223> OTHER INFORMATION: primer

<400> SEQUENCE: 51
gcaatccctc cccattg                                                   17

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
```

| | |
|---|---|
| tcacaattta tcataccaat aaacacc | 27 |

<210> SEQ ID NO 53
<211> LENGTH: 32
<212> TYPE: DNA
<213> ORGANISM: Artificial Sequence
<220> FEATURE:
<223> OTHER INFORMATION: primer

<400> SEQUENCE: 53

| | |
|---|---|
| atacaaaagc ttagagagag agattctgcg ga | 32 |

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54

| | |
|---|---|
| attcaatgca tgcaacataa tgagcagcca aaa | 33 |

<210> SEQ ID NO 55
<211> LENGTH: 33
<212> TYPE: DNA
<213> ORGANISM: Artificial Sequence
<220> FEATURE:
<223> OTHER INFORMATION: primer

<400> SEQUENCE: 55

| | |
|---|---|
| attcaataag cttatgggtg caggtggaag aat | 33 |

<210> SEQ ID NO 56
<211> LENGTH: 32
<212> TYPE: DNA
<213> ORGANISM: Artificial Sequence
<220> FEATURE:
<223> OTHER INFORMATION: primer

<400> SEQUENCE: 56

| | |
|---|---|
| atacaagcat gctcataact tattgttgta cc | 32 |

<210> SEQ ID NO 57
<211> LENGTH: 40
<212> TYPE: DNA
<213> ORGANISM: Artificial Sequence
<220> FEATURE:
<223> OTHER INFORMATION: primer

<400> SEQUENCE: 57

| | |
|---|---|
| aagcaatggg gtgggatggc tttcttcaga tctcccaccg | 40 |

<210> SEQ ID NO 58
<211> LENGTH: 40
<212> TYPE: DNA
<213> ORGANISM: Artificial Sequence
<220> FEATURE:
<223> OTHER INFORMATION: primer

<400> SEQUENCE: 58

| | |
|---|---|
| cggtgggaga tctgaagaaa gccatcccac cccattgctt | 40 |

<210> SEQ ID NO 59
<211> LENGTH: 26
<212> TYPE: DNA
<213> ORGANISM: Artificial Sequence

```
<220> FEATURE:
<223> OTHER INFORMATION: primer

<400> SEQUENCE: 59
gtcgacatac ttgttccggt accaga                                          26

<210> SEQ ID NO 60
<211> LENGTH: 39
<212> TYPE: DNA
<213> ORGANISM: Artificial Sequence
<220> FEATURE:
<223> OTHER INFORMATION: primer

<400> SEQUENCE: 60
cgattgcttt cttcagatct cccaccgaga aaggcggtt                            39

<210> SEQ ID NO 61
<211> LENGTH: 39
<212> TYPE: DNA
<213> ORGANISM: Artificial Sequence
<220> FEATURE:
<223> OTHER INFORMATION: primer

<400> SEQUENCE: 61
aaccgccttt ctcggtggga gatctgaaga aagcaatcc                            39

<210> SEQ ID NO 62
<211> LENGTH: 26
<212> TYPE: DNA
<213> ORGANISM: Artificial Sequence
<220> FEATURE:
<223> OTHER INFORMATION: primer

<400> SEQUENCE: 62
gtcgactaac ttattgttgt aatagt                                          26

<210> SEQ ID NO 63
<211> LENGTH: 40
<212> TYPE: DNA
<213> ORGANISM: Artificial Sequence
<220> FEATURE:
<223> OTHER INFORMATION: primer

<400> SEQUENCE: 63
gggattgctt tccttagatc tcccaccgag aaaggcggtt                           40

<210> SEQ ID NO 64
<211> LENGTH: 40
<212> TYPE: DNA
<213> ORGANISM: Artificial Sequence
<220> FEATURE:
<223> OTHER INFORMATION: primer

<400> SEQUENCE: 64
aaccgccttt ctcggtggga gatctaagga aagcaatccc                           40

<210> SEQ ID NO 65
<211> LENGTH: 26
<212> TYPE: DNA
<213> ORGANISM: Artificial Sequence
<220> FEATURE:
<223> OTHER INFORMATION: primer

<400> SEQUENCE: 65
gtcgactaac ttattgttgt aatagt                                          26
```

<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66
aaccgccttt ctcggtggga gatctgaaga aagcaatccc                     40

<210> SEQ ID NO 67
<211> LENGTH: 40
<212> TYPE: DNA
<213> ORGANISM: Artificial Sequence
<220> FEATURE:
<223> OTHER INFORMATION: primer

<400> SEQUENCE: 67
gggattgctt tcttcagatc tcccaccgag aaaggcggtt                     40

<210> SEQ ID NO 68
<211> LENGTH: 26
<212> TYPE: DNA
<213> ORGANISM: Artificial Sequence
<220> FEATURE:
<223> OTHER INFORMATION: primer

<400> SEQUENCE: 68
gtcgactcat aacttattgt tgtaat                                    26

<210> SEQ ID NO 69
<211> LENGTH: 40
<212> TYPE: DNA
<213> ORGANISM: Artificial Sequence
<220> FEATURE:
<223> OTHER INFORMATION: primer

<400> SEQUENCE: 69
cggtgggaga tctgaagaaa gcaatccctc cccattgctt                     40

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
aagcaatggg gagggattgc tttcttcaga tctcccaccg                     40

<210> SEQ ID NO 71
<211> LENGTH: 26
<212> TYPE: DNA
<213> ORGANISM: Artificial Sequence
<220> FEATURE:
<223> OTHER INFORMATION: primer

<400> SEQUENCE: 71
gtcgaccaat ttatgatacc aataaa                                    26

<210> SEQ ID NO 72
<211> LENGTH: 35
<212> TYPE: DNA
<213> ORGANISM: Artificial Sequence
<220> FEATURE:
<223> OTHER INFORMATION: primer

<400> SEQUENCE: 72
atacaaaagc ttataatggg aggtggtggt cgcat                     35

<210> SEQ ID NO 73
<211> LENGTH: 32
<212> TYPE: DNA
<213> ORGANISM: Artificial Sequence
<220> FEATURE:
<223> OTHER INFORMATION: primer

<400> SEQUENCE: 73
atacaaggat ccttaatact tgttccggta cc                        32

<210> SEQ ID NO 74
<211> LENGTH: 34
<212> TYPE: DNA
<213> ORGANISM: Artificial Sequence
<220> FEATURE:
<223> OTHER INFORMATION: primer

<400> SEQUENCE: 74
atacaagcgg ccgcagcgta atctggaaca tcgt                      34

<210> SEQ ID NO 75
<211> LENGTH: 35
<212> TYPE: DNA
<213> ORGANISM: Artificial Sequence
<220> FEATURE:
<223> OTHER INFORMATION: primer

<400> SEQUENCE: 75
atacaaaagc ttataatggg tgctggtgga agaat                     35

<210> SEQ ID NO 76
<211> LENGTH: 32
<212> TYPE: DNA
<213> ORGANISM: Artificial Sequence
<220> FEATURE:
<223> OTHER INFORMATION: primer

<400> SEQUENCE: 76
atacaaggat cctcataact tattgttgta at                        32

<210> SEQ ID NO 77
<211> LENGTH: 35
<212> TYPE: DNA
<213> ORGANISM: Artificial Sequence
<220> FEATURE:
<223> OTHER INFORMATION: primer

<400> SEQUENCE: 77
atacaaaagc ttataatgta cccatacgat gttcc                     35

<210> SEQ ID NO 78
<211> LENGTH: 34
<212> TYPE: DNA
<213> ORGANISM: Artificial Sequence
<220> FEATURE:
<223> OTHER INFORMATION: primer

<400> SEQUENCE: 78
atgagagctc gtttaaacga ttttaatgtt tagc                      34

<210> SEQ ID NO 79

```
<211> LENGTH: 30
<212> TYPE: DNA
<213> ORGANISM: Artificial Sequence
<220> FEATURE:
<223> OTHER INFORMATION: primer

<400> SEQUENCE: 79
atgagaattc ggccggccaa tagtctcgac                              30

<210> SEQ ID NO 80
<211> LENGTH: 31
<212> TYPE: DNA
<213> ORGANISM: Artificial Sequence
<220> FEATURE:
<223> OTHER INFORMATION: primer

<400> SEQUENCE: 80
tcatgaggcg cgccaaagca catacttatc g                            31

<210> SEQ ID NO 81
<211> LENGTH: 33
<212> TYPE: DNA
<213> ORGANISM: Artificial Sequence
<220> FEATURE:
<223> OTHER INFORMATION: primer

<400> SEQUENCE: 81
atgagcatgc aagcttcttc gcctggagga gag                          33

<210> SEQ ID NO 82
<211> LENGTH: 35
<212> TYPE: DNA
<213> ORGANISM: Artificial Sequence
<220> FEATURE:
<223> OTHER INFORMATION: primer

<400> SEQUENCE: 82
agctatgtac ccatacgatg ttccagatta cgctg                        35

<210> SEQ ID NO 83
<211> LENGTH: 35
<212> TYPE: DNA
<213> ORGANISM: Artificial Sequence
<220> FEATURE:
<223> OTHER INFORMATION: primer

<400> SEQUENCE: 83
tcgacagcgt aatctggaac atcgtatggg tacat                        35

<210> SEQ ID NO 84
<211> LENGTH: 47
<212> TYPE: DNA
<213> ORGANISM: Artificial Sequence
<220> FEATURE:
<223> OTHER INFORMATION: primer

<400> SEQUENCE: 84
gatccatgta cccaatacga tgttccagat tacgctctcg aggagct           47

<210> SEQ ID NO 85
<211> LENGTH: 37
<212> TYPE: DNA
<213> ORGANISM: Artificial Sequence
<220> FEATURE:
<223> OTHER INFORMATION: primer

<400> SEQUENCE: 85
```
ctcgagagcg taatctggaa catcgtatgg gtacatg    37

<210> SEQ ID NO 86
<211> LENGTH: 34
<212> TYPE: DNA
<213> ORGANISM: Artificial Sequence
<220> FEATURE:
<223> OTHER INFORMATION: primer

<400> SEQUENCE: 86
atgaggcgcg ccctttctct gacttttaac atcc    34

<210> SEQ ID NO 87
<211> LENGTH: 36
<212> TYPE: DNA
<213> ORGANISM: Artificial Sequence
<220> FEATURE:
<223> OTHER INFORMATION: primer

<400> SEQUENCE: 87
actggcatgc gtattgagat tgttttataa tatatg    36

<210> SEQ ID NO 88
<211> LENGTH: 32
<212> TYPE: DNA
<213> ORGANISM: Artificial Sequence
<220> FEATURE:
<223> OTHER INFORMATION: primer

<400> SEQUENCE: 88
atacaaaagc ttatgggagg tggtggtcgc at    32

<210> SEQ ID NO 89
<211> LENGTH: 32
<212> TYPE: DNA
<213> ORGANISM: Artificial Sequence
<220> FEATURE:
<223> OTHER INFORMATION: primer

<400> SEQUENCE: 89
atacaaggat ccatacttgt tccggtacca ga    32

<210> SEQ ID NO 90
<211> LENGTH: 32
<212> TYPE: DNA
<213> ORGANISM: Artificial Sequence
<220> FEATURE:
<223> OTHER INFORMATION: primer

<400> SEQUENCE: 90
atacaaaagc ttatgggtgc tggtggaaga at    32

<210> SEQ ID NO 91
<211> LENGTH: 32
<212> TYPE: DNA
<213> ORGANISM: Artificial Sequence
<220> FEATURE:
<223> OTHER INFORMATION: primer

<400> SEQUENCE: 91
atacaaggat cctaacttat tgttgtaata gt    32

<210> SEQ ID NO 92
<211> LENGTH: 32
<212> TYPE: DNA

```
<213> ORGANISM: Artificial Sequence
<220> FEATURE:
<223> OTHER INFORMATION: primer

<400> SEQUENCE: 92
atacaagtcg acatgggagg tggtggtcgc at                                32

<210> SEQ ID NO 93
<211> LENGTH: 32
<212> TYPE: DNA
<213> ORGANISM: Artificial Sequence
<220> FEATURE:
<223> OTHER INFORMATION: primer

<400> SEQUENCE: 93
atacaaggat ccatacttgt tccggtacca ga                                32

<210> SEQ ID NO 94
<211> LENGTH: 41
<212> TYPE: DNA
<213> ORGANISM: Artificial Sequence
<220> FEATURE:
<223> OTHER INFORMATION: primer

<400> SEQUENCE: 94
ataaccagca acaacagtga gagcagccac cttaagcgag c                      41

<210> SEQ ID NO 95
<211> LENGTH: 41
<212> TYPE: DNA
<213> ORGANISM: Artificial Sequence
<220> FEATURE:
<223> OTHER INFORMATION: primer

<400> SEQUENCE: 95
gctcgcttaa ggtggctgct ctcactgttg ttgctggtta t                      41

<210> SEQ ID NO 96
<211> LENGTH: 41
<212> TYPE: DNA
<213> ORGANISM: Artificial Sequence
<220> FEATURE:
<223> OTHER INFORMATION: primer

<400> SEQUENCE: 96
ttcttcctca gcctctctct tacctagctt ggcctctcta t                      41

<210> SEQ ID NO 97
<211> LENGTH: 41
<212> TYPE: DNA
<213> ORGANISM: Artificial Sequence
<220> FEATURE:
<223> OTHER INFORMATION: primer

<400> SEQUENCE: 97
atagagaggc caagctaggt aagagagagg ctgaggaaga a                      41

<210> SEQ ID NO 98
<211> LENGTH: 34
<212> TYPE: DNA
<213> ORGANISM: Artificial Sequence
<220> FEATURE:
<223> OTHER INFORMATION: primer

<400> SEQUENCE: 98
caattgtcta gattaatact tgttccggta ccag                              34
```

<210> SEQ ID NO 99
<211> LENGTH: 26
<212> TYPE: DNA
<213> ORGANISM: Artificial Sequence
<220> FEATURE:
<223> OTHER INFORMATION: primer

<400> SEQUENCE: 99
aagcttacca tgggaggtgg tggtcg                                    26

<210> SEQ ID NO 100
<211> LENGTH: 18
<212> TYPE: DNA
<213> ORGANISM: Artificial Sequence
<220> FEATURE:
<223> OTHER INFORMATION: primer

<400> SEQUENCE: 100
gaaacagcta tgaccatg                                             18

<210> SEQ ID NO 101
<211> LENGTH: 34
<212> TYPE: DNA
<213> ORGANISM: Artificial Sequence
<220> FEATURE:
<223> OTHER INFORMATION: primer

<400> SEQUENCE: 101
caattgtcta gatcataact tattgttgta atag                           34

<210> SEQ ID NO 102
<211> LENGTH: 29
<212> TYPE: DNA
<213> ORGANISM: Artificial Sequence
<220> FEATURE:
<223> OTHER INFORMATION: primer

<400> SEQUENCE: 102
aagcttacca tgggtgctgg tggaagaat                                 29

<210> SEQ ID NO 103
<211> LENGTH: 35
<212> TYPE: DNA
<213> ORGANISM: Artificial Sequence
<220> FEATURE:
<223> OTHER INFORMATION: primer

<400> SEQUENCE: 103
caattgtcta gatcacaatt tatgatacca ataaa                          35

<210> SEQ ID NO 104
<211> LENGTH: 34
<212> TYPE: DNA
<213> ORGANISM: Artificial Sequence
<220> FEATURE:
<223> OTHER INFORMATION: primer

<400> SEQUENCE: 104
atacaaggat ccaaatggga ggtggtggtc gcat                           34

<210> SEQ ID NO 105
<211> LENGTH: 34
<212> TYPE: DNA
<213> ORGANISM: Artificial Sequence
<220> FEATURE:

<223> OTHER INFORMATION: primer

<400> SEQUENCE: 105
atacaaggat ccaaatgggt gctggtggaa gaat            34

<210> SEQ ID NO 106
<211> LENGTH: 32
<212> TYPE: DNA
<213> ORGANISM: Artificial Sequence
<220> FEATURE:
<223> OTHER INFORMATION: primer

<400> SEQUENCE: 106
aggatcccta ccatgggtgc aggtggtcgg at            32

<210> SEQ ID NO 107
<211> LENGTH: 29
<212> TYPE: DNA
<213> ORGANISM: Artificial Sequence
<220> FEATURE:
<223> OTHER INFORMATION: primer

<400> SEQUENCE: 107
tctagattac attttatggt accagtaaa            29

<210> SEQ ID NO 108
<211> LENGTH: 31
<212> TYPE: DNA
<213> ORGANISM: Artificial Sequence
<220> FEATURE:
<223> OTHER INFORMATION: primer

<400> SEQUENCE: 108
agatctctac catgggtgcc cacggccatg g            31

<210> SEQ ID NO 109
<211> LENGTH: 49
<212> TYPE: DNA
<213> ORGANISM: Artificial Sequence
<220> FEATURE:
<223> OTHER INFORMATION: primer

<400> SEQUENCE: 109
agcttctcga gaccatggcg tacccgtacg acgtgcccga ctacgccag            49

<210> SEQ ID NO 110
<211> LENGTH: 49
<212> TYPE: DNA
<213> ORGANISM: Artificial Sequence
<220> FEATURE:
<223> OTHER INFORMATION: primer

<400> SEQUENCE: 110
gatcctggcg tagtcgggca cgtcgtacgg gtacgccatg gtctcgaga            49

<210> SEQ ID NO 111
<211> LENGTH: 31
<212> TYPE: DNA
<213> ORGANISM: Artificial Sequence
<220> FEATURE:
<223> OTHER INFORMATION: primer

<400> SEQUENCE: 111
atcctcgaga gagattctgc ggaggagctt c            31

```
<210> SEQ ID NO 112
<211> LENGTH: 34
<212> TYPE: DNA
<213> ORGANISM: Artificial Sequence
<220> FEATURE:
<223> OTHER INFORMATION: primer

<400> SEQUENCE: 112
atcggatcca tggttctgca gaaaaccaaa agca                                34

<210> SEQ ID NO 113
<211> LENGTH: 32
<212> TYPE: DNA
<213> ORGANISM: Artificial Sequence
<220> FEATURE:
<223> OTHER INFORMATION: primer

<400> SEQUENCE: 113
atctctagat gaggatgatg gtgaagaaat tg                                  32

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
atcaagctta ctgtccgaag gtcacatttc                                     30

<210> SEQ ID NO 115
<211> LENGTH: 21
<212> TYPE: DNA
<213> ORGANISM: Artificial Sequence
<220> FEATURE:
<223> OTHER INFORMATION: primer

<400> SEQUENCE: 115
ggaatgcatg tacatcgagc c                                              21

<210> SEQ ID NO 116
<211> LENGTH: 21
<212> TYPE: DNA
<213> ORGANISM: Artificial Sequence
<220> FEATURE:
<223> OTHER INFORMATION: primer

<400> SEQUENCE: 116
ggaacttgtg ttggcatggt g                                              21

<210> SEQ ID NO 117
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6, 9
<223> OTHER INFORMATION: n = A,T,C or G

<400> SEQUENCE: 117
tggccngtnt aytggttytg                                                20

<210> SEQ ID NO 118
<211> LENGTH: 20
<212> TYPE: DNA
```

```
<213> ORGANISM: Artificial Sequence
<220> FEATURE:
<223> OTHER INFORMATION: primer
<220> FEATURE:
<221> NAME/KEY: misc_feature
<222> LOCATION: 6
<223> OTHER INFORMATION: n = A,T,C or G

<400> SEQUENCE: 118
tcyttngcyt cyctccacat                                              20

<210> SEQ ID NO 119
<211> LENGTH: 21
<212> TYPE: DNA
<213> ORGANISM: Artificial Sequence
<220> FEATURE:
<223> OTHER INFORMATION: primer

<400> SEQUENCE: 119
atgggtgctg gtggtcggat g                                            21

<210> SEQ ID NO 120
<211> LENGTH: 21
<212> TYPE: DNA
<213> ORGANISM: Artificial Sequence
<220> FEATURE:
<223> OTHER INFORMATION: primer

<400> SEQUENCE: 120
gaacacgctt acacctagga c                                            21

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
atcaatccac tggtattcac                                              20

<210> SEQ ID NO 122
<211> LENGTH: 18
<212> TYPE: DNA
<213> ORGANISM: Artificial Sequence
<220> FEATURE:
<223> OTHER INFORMATION: primer

<400> SEQUENCE: 122
gtcctaggtg taagcgtg                                                18

<210> SEQ ID NO 123
<211> LENGTH: 29
<212> TYPE: DNA
<213> ORGANISM: Artificial Sequence
<220> FEATURE:
<223> OTHER INFORMATION: primer

<400> SEQUENCE: 123
aagcttacca tgggtgccca cggccatgg                                    29

<210> SEQ ID NO 124
<211> LENGTH: 31
<212> TYPE: DNA
<213> ORGANISM: Artificial Sequence
<220> FEATURE:
<223> OTHER INFORMATION: primer
```

<400> SEQUENCE: 124
ggcgcgccac catgggtgcc cacggccatg g                                       31

<210> SEQ ID NO 125
<211> LENGTH: 383
<212> TYPE: PRT
<213> ORGANISM: Arabidopsis thaliana

<400> SEQUENCE: 125

```
Met Gly Ala Gly Gly Arg Met Pro Val Pro Thr Ser Ser Lys Lys Ser
 1               5                  10                  15

Glu Thr Asp Thr Thr Lys Arg Val Pro Cys Glu Lys Pro Pro Phe Ser
             20                  25                  30

Val Gly Asp Leu Lys Lys Ala Ile Pro His Cys Phe Lys Arg Ser
         35                  40                  45

Ile Pro Arg Ser Phe Ser Tyr Leu Ile Ser Asp Ile Ile Ala Ser
 50                  55                  60

Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
            195                 200                 205

His Phe Phe Pro Asn Ala Pro Ile Tyr Asn Asp Arg Glu Arg Leu Gln
210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
            275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350
```

Val Ala Met Tyr Arg Glu Ala Lys Glu Cys Ile Tyr Val Glu Pro Asp
            355                 360                 365

Arg Glu Gly Asp Lys Lys Gly Val Tyr Trp Tyr Asn Asn Lys Leu
    370                 375                 380

<210> SEQ ID NO 126
<211> LENGTH: 384
<212> TYPE: PRT
<213> ORGANISM: Brassica napus

<400> SEQUENCE: 126

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Leu Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
        370                 375                 380

<210> SEQ ID NO 127
<211> LENGTH: 383
<212> TYPE: PRT
<213> ORGANISM: Glycine max

<400> SEQUENCE: 127

Met Gly Ala Gly Gly Arg Thr Asp Val Pro Ala Asn Arg Lys Ser
 1               5                  10                  15

Glu Val Asp Pro Leu Lys Arg Val Pro Phe Glu Lys Pro Gln Phe Ser
            20                  25                  30

Leu Ser Gln Ile Lys Lys Ala Ile Pro Pro His Cys Phe Gln Arg Ser
        35                  40                  45

Val Leu Arg Ser Phe Ser Tyr Val Val Tyr Asp Leu Thr Ile Ala Phe
    50                  55                  60

Cys Leu Tyr Tyr Val Ala Thr His Tyr Phe His Leu Leu Pro Gly Pro
65                  70                  75                  80

Leu Ser Phe Arg Gly Met Ala Ile Tyr Trp Ala Val Gln Gly Cys Ile
                85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Cys Ile Lys Trp Tyr Ser Lys Tyr Leu Asn Asn Pro Pro
                165                 170                 175

Gly Arg Val Leu Thr Leu Ala Val Thr Leu Thr Leu Gly Trp Pro Leu
            180                 185                 190

Tyr Leu Ala Leu Asn Val Ser Gly Arg Pro Tyr Asp Arg Phe Ala Cys
        195                 200                 205

His Tyr Asp Pro Tyr Gly Pro Ile Tyr Ser Asp Arg Glu Arg Leu Gln
    210                 215                 220

Ile Tyr Ile Ser Asp Ala Gly Val Leu Ala Val Val Tyr Gly Leu Phe
225                 230                 235                 240

Arg Leu Ala Met Ala Lys Gly Leu Ala Trp Val Val Cys Val Tyr Gly
                245                 250                 255

Val Pro Leu Leu Val Val Asn Gly Phe Leu Val Leu Ile Thr Phe Leu
            260                 265                 270

Gln His Thr His Pro Ala Leu Pro His Tyr Thr Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Glu Thr Pro Phe Val

```
            340                 345                 350
Lys Ala Met Trp Arg Glu Ala Arg Glu Cys Ile Tyr Val Glu Pro Asp
                355                 360                 365

Gln Ser Thr Glu Ser Lys Gly Val Phe Trp Tyr Asn Asn Lys Leu
    370                 375                 380

<210> SEQ ID NO 128
<211> LENGTH: 383
<212> TYPE: PRT
<213> ORGANISM: Sesamum indicum

<400> SEQUENCE: 128

Met Gly Ala Gly Gly Arg Met Ser Asp Pro Thr Thr Lys Asp Glu Gln
 1               5                  10                  15

Lys Lys Asn Pro Leu Gln Arg Val Pro Tyr Ala Lys Pro Pro Phe Thr
                20                  25                  30

Leu Gly Asp Ile Lys Lys Ala Ile Pro Pro His Cys Phe Glu Arg Ser
            35                  40                  45

Val Ser Arg Ser Phe Ser Tyr Val Val Tyr Asp Leu Val Ile Val Phe
    50                  55                  60

Leu Leu Tyr Tyr Ile Ala Thr Ser Tyr Phe His Leu Leu Pro Ser Pro
65                  70                  75                  80

Tyr Cys Tyr Leu Ala Trp Pro Ile Tyr Trp Ala Val Gln Gly Cys Val
                85                  90                  95

Cys Thr Gly Ile Trp Val Ile Ala His Glu Cys Gly His His Ala Phe
            100                 105                 110

Ser Asp Tyr Gln Trp Leu Asp Asp Thr Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Pro Lys Ser Arg Val Ser Trp Tyr Ser Lys Tyr Leu Asn Asn Pro Leu
                165                 170                 175

Gly Arg Val Ile Thr Leu Val Val Thr Leu Thr Leu Gly Trp Pro Leu
            180                 185                 190

Tyr Leu Leu Phe Asn Val Ser Gly Arg Pro Tyr Asn Arg Phe Ala Cys
        195                 200                 205

His Phe Asp Pro Tyr Gly Pro Ile Tyr Asn Asp Arg Glu Arg Leu Gln
    210                 215                 220

Ile Phe Ile Ser Asp Ala Gly Ile Ile Ala Ala Val Cys Val Leu Tyr
225                 230                 235                 240

Arg Val Ala Leu Val Lys Gly Leu Ala Trp Leu Val Cys Val Tyr Gly
                245                 250                 255

Val Pro Leu Leu Ile Val Asn Gly Phe Leu Val Leu Ile Thr Phe Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Val Leu
    290                 295                 300

Asn Lys Val Phe His Asn Ile Thr Asp Thr His Val Thr His His Leu
305                 310                 315                 320

Phe Ser Thr Met Pro His Tyr His Ala Met Glu Ala Thr Lys Ala Ile
                325                 330                 335
```

```
               Lys Pro Ile Leu Gly Gln Tyr Tyr Gln Phe Asp Gly Thr Pro Phe Tyr
                               340                 345                 350

Lys Ala Met Trp Arg Glu Ala Lys Glu Cys Leu Tyr Val Glu Pro Asp
                               355                 360                 365

Glu Ser Thr Pro Asp Lys Gly Val Phe Trp Tyr Lys Asn Lys Phe
                               370                 375                 380

<210> SEQ ID NO 129
<211> LENGTH: 1200
<212> TYPE: DNA
<213> ORGANISM: Ricinus communis
<220> FEATURE:
<221> NAME/KEY: CDS
<222> LOCATION: (1)...(1197)

<400> SEQUENCE: 129 atg gct tcc tcc tac cca tac gat gtt cca gat tac gct gga ggt ggt        48
Met Ala Ser Ser Tyr Pro Tyr Asp Val Pro Asp Tyr Ala Gly Gly Gly
  1               5                  10                  15 ggt agg atg tct act gtc ata acc agc aac aac agt gag aag aaa gga        96
Gly Arg Met Ser Thr Val Ile Thr Ser Asn Asn Ser Glu Lys Lys Gly
                 20                  25                  30 gga agc agt cac ctt aag agg gct cca cac act aag cct cct ttc aca       144
Gly Ser Ser His Leu Lys Arg Ala Pro His Thr Lys Pro Pro Phe Thr
             35                  40                  45 ctt ggt gac ctc aag aga gcc atc cca ccc cat tgc ttt gaa agg tct       192
Leu Gly Asp Leu Lys Arg Ala Ile Pro Pro His Cys Phe Glu Arg Ser
         50                  55                  60 ttt gtg aga tca ttc tcc tat gtt gcc tat gat gtc tgc tta agt ttt       240
Phe Val Arg Ser Phe Ser Tyr Val Ala Tyr Asp Val Cys Leu Ser Phe
 65                  70                  75                  80 ctt ttc tac tct atc gcc acc aac ttc ttc cct tac atc tct tct cca       288
Leu Phe Tyr Ser Ile Ala Thr Asn Phe Phe Pro Tyr Ile Ser Ser Pro
                 85                  90                  95 ctc tct tat gtc gct tgg ctg gtt tac tgg ctc ttc caa ggc tgc att       336
Leu Ser Tyr Val Ala Trp Leu Val Tyr Trp Leu Phe Gln Gly Cys Ile
            100                 105                 110 ctc act ggt ctt tgg gtc atc ggc cat gaa tgt ggc cat cat gct ttt       384
Leu Thr Gly Leu Trp Val Ile Gly His Glu Cys Gly His His Ala Phe
        115                 120                 125 agt gag tat cag ctg gct gat gac att gtt ggc cta att gtc cat tct       432
Ser Glu Tyr Gln Leu Ala Asp Asp Ile Val Gly Leu Ile Val His Ser
    130                 135                 140 gca ctt ctg gtt cca tac ttc tca tgg aaa tat agc cat aga agg cac       480
Ala Leu Leu Val Pro Tyr Phe Ser Trp Lys Tyr Ser His Arg Arg His
145                 150                 155                 160 cat tct aac ata gga tct ctc gag agg gac gaa gtg ttc gtc cca aaa       528
His Ser Asn Ile Gly Ser Leu Glu Arg Asp Glu Val Phe Val Pro Lys
                165                 170                 175 tca aag tct aaa att tca tgg tat tct aag tac tta aac aac cct cca       576
Ser Lys Ser Lys Ile Ser Trp Tyr Ser Lys Tyr Leu Asn Asn Pro Pro
            180                 185                 190 ggt agg gtt ttg aca ctt gct gcc act ctt ctc ctt ggc tgg cct tta       624
Gly Arg Val Leu Thr Leu Ala Ala Thr Leu Leu Leu Gly Trp Pro Leu
        195                 200                 205 tac tta gct ttc aat gtc tct ggt aga cct tac gat agg ttt gct tgc       672
Tyr Leu Ala Phe Asn Val Ser Gly Arg Pro Tyr Asp Arg Phe Ala Cys
    210                 215                 220 cat tat gat ccc tat ggc cca ata ttt tcc gaa aga gaa agg ctt cag       720
His Tyr Asp Pro Tyr Gly Pro Ile Phe Ser Glu Arg Glu Arg Leu Gln
225                 230                 235                 240
```

```
atc tac att gct gac ctc gga atc ttt gcc aca act ttt gtg ctt tat    768
Ile Tyr Ile Ala Asp Leu Gly Ile Phe Ala Thr Thr Phe Val Leu Tyr
            245                 250                 255 cag gct aca atg gca aaa ggg ttg gct tgg gta atg agg atc tat ggg    816
Gln Ala Thr Met Ala Lys Gly Leu Ala Trp Val Met Arg Ile Tyr Gly
            260                 265                 270 gtg cca ttg ctt att gtt aac tgt ttc ctt gtt atg atc aca tac ttg    864
Val Pro Leu Leu Ile Val Asn Cys Phe Leu Val Met Ile Thr Tyr Leu
            275                 280                 285 cag cac act cac cca gct att cca agg tat ggc tca tct gaa tgg gat    912
Gln His Thr His Pro Ala Ile Pro Arg Tyr Gly Ser Ser Glu Trp Asp
        290                 295                 300 tgg ctc agg gga gca atg gtg act gtc gat aga gat tat ggg gtg ttg    960
Trp Leu Arg Gly Ala Met Val Thr Val Asp Arg Asp Tyr Gly Val Leu
305                 310                 315                 320 aac aag gta ttc cat aac att gca gac act cat gta gct cat cat ctc    1008
Asn Lys Val Phe His Asn Ile Ala Asp Thr His Val Ala His His Leu
                325                 330                 335 ttt gct aca gtg cca cat tac cat gca atg gag gcc act aaa gca atc    1056
Phe Ala Thr Val Pro His Tyr His Ala Met Glu Ala Thr Lys Ala Ile
            340                 345                 350 aag cct ata atg gga gag tat tac agg tat gat ggt acc cca ttt tac    1104
Lys Pro Ile Met Gly Glu Tyr Tyr Arg Tyr Asp Gly Thr Pro Phe Tyr
            355                 360                 365 aag gca ttg tgg agg gag gca aag gag tgc ttg ttc gtc gag cca gat    1152
Lys Ala Leu Trp Arg Glu Ala Lys Glu Cys Leu Phe Val Glu Pro Asp
            370                 375                 380 gaa gga gct cct aca caa ggc gtt ttc tgg tac agg aac aag tat        1197
Glu Gly Ala Pro Thr Gln Gly Val Phe Trp Tyr Arg Asn Lys Tyr
385                 390                 395 taa                                                                 1200
```

```
<210> SEQ ID NO 130
<211> LENGTH: 1125
<212> TYPE: DNA
<213> ORGANISM: Crepis palaestina
<220> FEATURE:
<221> NAME/KEY: CDS
<222> LOCATION: (1)...(1122)

<400> SEQUENCE: 130
```

```
atg gct tcc tcc gga aga gga aga act tct gag aag tct gtt atg gag    48
Met Ala Ser Ser Gly Arg Gly Arg Thr Ser Glu Lys Ser Val Met Glu
1               5                   10                  15 aga gtg tct gtg gac cca gtg act ttc tct ctt tct gaa ctt aag caa    96
Arg Val Ser Val Asp Pro Val Thr Phe Ser Leu Ser Glu Leu Lys Gln
            20                  25                  30 gct att cca cct cat tgc ttc caa aga tct gtg att aga tct tct tat    144
Ala Ile Pro Pro His Cys Phe Gln Arg Ser Val Ile Arg Ser Ser Tyr
        35                  40                  45 tat gtg gtg caa gac ctt att att gct tat att ttc tat ttc ctt gct    192
Tyr Val Val Gln Asp Leu Ile Ile Ala Tyr Ile Phe Tyr Phe Leu Ala
    50                  55                  60 aac act tat att cca act ctt cca act tct ctt gct tat ctt gct tgg    240
Asn Thr Tyr Ile Pro Thr Leu Pro Thr Ser Leu Ala Tyr Leu Ala Trp
65                  70                  75                  80 cca gtg tat tgg ttt tgc caa gct tct gtt ctt act gga ctt tgg att    288
Pro Val Tyr Trp Phe Cys Gln Ala Ser Val Leu Thr Gly Leu Trp Ile
                85                  90                  95 ctt gga cat gaa tgc gga cat cat gct ttc tct aac tat act tgg ttc    336
```

```
Leu Gly His Glu Cys Gly His His Ala Phe Ser Asn Tyr Thr Trp Phe
        100                 105                 110 gat g

```
<400> SEQUENCE: 131 atg gct tcc tcc tat gac gac aga atg aag gac cat gat atg gat gaa      48
Met Ala Ser Ser Tyr Asp Asp Arg Met Lys Asp His Asp Met Asp Glu
1               5                   10                  15 aga gca cca att gac cct gct cct ttt tct ctt tct gat ctt aag aag      96
Arg Ala Pro Ile Asp Pro Ala Pro Phe Ser Leu Ser Asp Leu Lys Lys
            20                  25                  30 gct att cca gct cat tgc ttt aga aga tct gct gtt tgg tct tct tgc     144
Ala Ile Pro Ala His Cys Phe Arg Arg Ser Ala Val Trp Ser Ser Cys
        35                  40                  45 tat gtg gtg caa gac ctt att att act ttc ctt ttg tat act gtg gct     192
Tyr Val Val Gln Asp Leu Ile Ile Thr Phe Leu Leu Tyr Thr Val Ala
50                  55                  60 aac act tat att cca cat ctt cca cct cca ctt gtt tat ctt gct tgg     240
Asn Thr Tyr Ile Pro His Leu Pro Pro Pro Leu Val Tyr Leu Ala Trp
65                  70                  75                  80 cca gtg tat tgg ttc tgc caa tct tgc att ctt act gga ctt tgg gtt     288
Pro Val Tyr Trp Phe Cys Gln Ser Cys Ile Leu Thr Gly Leu Trp Val
                85                  90                  95 ctt gga cat gaa tgc gga cat cat gct ttc tct gag tat caa tgg att     336
Leu Gly His Glu Cys Gly His His Ala Phe Ser Glu Tyr Gln Trp Ile
            100                 105                 110 gac aac gct gtg gga ttc gtg ctt cat tct gct ctt ttg act cca tat     384
Asp Asn Ala Val Gly Phe Val Leu His Ser Ala Leu Leu Thr Pro Tyr
        115                 120                 125 ttc tct tgg aag tat tct cat aga aag cat cat gct aac act aac tct     432
Phe Ser Trp Lys Tyr Ser His Arg Lys His His Ala Asn Thr Asn Ser
130                 135                 140 ctt gag aac gag gag gtg tat att cca aga act caa tct caa ctt aga     480
Leu Glu Asn Glu Glu Val Tyr Ile Pro Arg Thr Gln Ser Gln Leu Arg
145                 150                 155                 160 act tat tct act tat gag ttc ctt gac aac act cca gga aga att ctt     528
Thr Tyr Ser Thr Tyr Glu Phe Leu Asp Asn Thr Pro Gly Arg Ile Leu
                165                 170                 175 att ctt gtg att atg ctt act ctt gga ttc cca ctt tat ctt ttg act     576
Ile Leu Val Ile Met Leu Thr Leu Gly Phe Pro Leu Tyr Leu Leu Thr
            180                 185                 190 aac gtg tct gga aag aag tat gac aga ttc act aac cat ttc gac cca     624
Asn Val Ser Gly Lys Lys Tyr Asp Arg Phe Thr Asn His Phe Asp Pro
        195                 200                 205 ctt tct cca att ttc act gag aga gag aga att caa gtt gct ctt tct     672
Leu Ser Pro Ile Phe Thr Glu Arg Glu Arg Ile Gln Val Ala Leu Ser
210                 215                 220 gat ctt gga att gtg gct gtg ttc tat gga ctt aag ttc ctt gtt caa     720
Asp Leu Gly Ile Val Ala Val Phe Tyr Gly Leu Lys Phe Leu Val Gln
225                 230                 235                 240 act aag gga ttt gga tgg gtt atg tgc atg tat gga gtg cca gtg att     768
Thr Lys Gly Phe Gly Trp Val Met Cys Met Tyr Gly Val Pro Val Ile
                245                 250                 255 gga ctt aac tct ttc att att gtg att act tat ctt cat cat act cat     816
Gly Leu Asn Ser Phe Ile Ile Val Ile Thr Tyr Leu His His Thr His
            260                 265                 270 ctt tct tct cca cat tat gat tct act gag tgg aac tgg att aag ggt     864
Leu Ser Ser Pro His Tyr Asp Ser Thr Glu Trp Asn Trp Ile Lys Gly
        275                 280                 285 gca ttg act act att gac aga gac ttc gga ctt ttg aac aga gtg ttc     912
Ala Leu Thr Thr Ile Asp Arg Asp Phe Gly Leu Leu Asn Arg Val Phe
290                 295                 300
```

-continued

| | | |
|---|---|---|
| cat gac gtg act cat act cat gtg ctt cat cat ctt ttc cca tat att<br>His Asp Val Thr His Thr His Val Leu His His Leu Phe Pro Tyr Ile<br>305                            310                      315                    320 | 960 |
| cca cat tat cat gct aag gag gct tct gag gct att aag cca att ctt<br>Pro His Tyr His Ala Lys Glu Ala Ser Glu Ala Ile Lys Pro Ile Leu<br>                      325                      330                    335 | 1008 |
| gga gac tat aga atg att gat aga act cca ttt ttc aag gct atg tgg<br>Gly Asp Tyr Arg Met Ile Asp Arg Thr Pro Phe Phe Lys Ala Met Trp<br>340                            345                      350 | 1056 |
| aga gag gct aag gag tgc atc tat att gaa caa gat gct gac tct aag<br>Arg Glu Ala Lys Glu Cys Ile Tyr Ile Glu Gln Asp Ala Asp Ser Lys<br>                      355                      360                    365 | 1104 |
| cat aag gga act tat tgg tat cat aag atg taa<br>His Lys Gly Thr Tyr Trp Tyr His Lys Met<br>370                            375 | 1137 |

<210> SEQ ID NO 132
<211> LENGTH: 1125
<212> TYPE: DNA
<213> ORGANISM: Crepis biennis
<220> FEATURE:
<221> NAME/KEY: CDS
<222> LOCATION: (1)...(1122)

<400> SEQUENCE: 132

| | |
|---|---|
| atg gct tcc tcc gga cat tca aga act tct aag aag tct gtt atg gag<br>Met Ala Ser Ser Gly His Ser Arg Thr Ser Lys Lys Ser Val Met Glu<br>1                    5                      10                    15 | 48 |
| aga gtg tct gtt gac cct gtg cct ttt tct ctt tct gat ctt aag caa<br>Arg Val Ser Val Asp Pro Val Pro Phe Ser Leu Ser Asp Leu Lys Gln<br>                  20                      25                    30 | 96 |
| gct att cca cct cat tgt ttc caa aga tct gtg att aga tct tct tat<br>Ala Ile Pro Pro His Cys Phe Gln Arg Ser Val Ile Arg Ser Ser Tyr<br>                  35                      40                    45 | 144 |
| tat gtg gtg cat gac ctt att att gct tat att ttc tat ttc ctt gct<br>Tyr Val Val His Asp Leu Ile Ile Ala Tyr Ile Phe Tyr Phe Leu Ala<br>50                            55                      60 | 192 |
| gac aag tat att cca att ctt cca gct cca ctt gct tat ctt gct tgg<br>Asp Lys Tyr Ile Pro Ile Leu Pro Ala Pro Leu Ala Tyr Leu Ala Trp<br>65                      70                      75                    80 | 240 |
| cca ctt tat tgg ttc tgt caa gct tct att ctt act gga ctt tgg att<br>Pro Leu Tyr Trp Phe Cys Gln Ala Ser Ile Leu Thr Gly Leu Trp Ile<br>                  85                      90                    95 | 288 |
| ctt gga cat gag tgt gga cat cat gct ttc tct gaa cat caa tgg gtt<br>Leu Gly His Glu Cys Gly His His Ala Phe Ser Glu His Gln Trp Val<br>                  100                    105                    110 | 336 |
| gat gac act gtg ggt ttc atg gtg cat tct ttc ctt ttg act cca tat<br>Asp Asp Thr Val Gly Phe Met Val His Ser Phe Leu Leu Thr Pro Tyr<br>115                          120                    125 | 384 |
| ttc tct tgg aag tat tct cat aga aac cat cat gct aac act tct tct<br>Phe Ser Trp Lys Tyr Ser His Arg Asn His His Ala Asn Thr Ser Ser<br>                  130                    135                    140 | 432 |
| att gac aac gac gag gtg tat att cca aag tct aag tct aag ctt gct<br>Ile Asp Asn Asp Glu Val Tyr Ile Pro Lys Ser Lys Ser Lys Leu Ala<br>145                          150                    155                    160 | 480 |
| ctt act tat aag ctt ttg aac aat cca cct gga aga ctt ttg gtt atg<br>Leu Thr Tyr Lys Leu Leu Asn Asn Pro Pro Gly Arg Leu Leu Val Met<br>                  165                    170                    175 | 528 |
| gtt att atg ttc act ctt gga ttc cca ctt tat ctt ttg act aac att<br>Val Ile Met Phe Thr Leu Gly Phe Pro Leu Tyr Leu Leu Thr Asn Ile<br>180                          185                    190 | 576 |

```
tct gga aag aag tat gac aga ttt gct aac cat ttc gat cca atg tct         624
Ser Gly Lys Lys Tyr Asp Arg Phe Ala Asn His Phe Asp Pro Met Ser
            195                 200                 205 cca att ttc aag gag aga gag aga ttc caa gtt ctt ttg tct gat ctt         672
Pro Ile Phe Lys Glu Arg Glu Arg Phe Gln Val Leu Leu Ser Asp Leu
    210                 215                 220 gga ctt ttg gct gtg ttc tat gga att aag gtt gct gtt gct aag aaa         720
Gly Leu Leu Ala Val Phe Tyr Gly Ile Lys Val Ala Val Ala Lys Lys
225                 230                 235                 240 gga gct gca tgg gtt gct tgt atg tat gga gtt cca atg ctt gga gtg         768
Gly Ala Ala Trp Val Ala Cys Met Tyr Gly Val Pro Met Leu Gly Val
                245                 250                 255 ttc act ctt ttc gac att att act tat ctt cat cat act cat caa tct         816
Phe Thr Leu Phe Asp Ile Ile Thr Tyr Leu His His Thr His Gln Ser
            260                 265                 270 tct cca cat tat gat tct act gag tgg aac tgg att aga ggt gca ttg         864
Ser Pro His Tyr Asp Ser Thr Glu Trp Asn Trp Ile Arg Gly Ala Leu
    275                 280                 285 tct gct att gat aga gac ttc ggt ttc atg aac tct gtg ttc cat gac         912
Ser Ala Ile Asp Arg Asp Phe Gly Phe Met Asn Ser Val Phe His Asp
290                 295                 300 gtg act cat act cat gtg atg cat cat atg ttc tct tat att cca cat         960
Val Thr His Thr His Val Met His His Met Phe Ser Tyr Ile Pro His
305                 310                 315                 320 tat cat gct aag gag gct aga gac gct att aac act att att gga gac        1008
Tyr His Ala Lys Glu Ala Arg Asp Ala Ile Asn Thr Ile Ile Gly Asp
                325                 330                 335 tat tat atg att gat aga act cca att ctt aag gct ctt tgg aga gag        1056
Tyr Tyr Met Ile Asp Arg Thr Pro Ile Leu Lys Ala Leu Trp Arg Glu
            340                 345                 350 gct aag gag tgt atg tat att gaa cca gac tct aag aga aag gga gtg        1104
Ala Lys Glu Cys Met Tyr Ile Glu Pro Asp Ser Lys Arg Lys Gly Val
    355                 360                 365 tat tgg tat cat aag ctt taa                                            1125
Tyr Trp Tyr His Lys Leu
370

<210> SEQ ID NO 133
<211> LENGTH: 1155
<212> TYPE: DNA
<213> ORGANISM: Lesquerella gracilis B
<220> FEATURE:
<221> NAME/KEY: CDS
<222> LOCATION: (1)...(1152)

<400> SEQUENCE: 133 atg gct tcc tcc gga aga att atg gtg act cca tct tct aag aag tct          48
Met Ala Ser Ser Gly Arg Ile Met Val Thr Pro Ser Ser Lys Lys Ser
1               5                   10                  15 gaa act gaa gct ctt aag aga gga cca tgt gaa aag cca cct ttc act          96
Glu Thr Glu Ala Leu Lys Arg Gly Pro Cys Glu Lys Pro Pro Phe Thr
            20                  25                  30 gtg aag gac ctt aag aag gct att cca caa cat tgt ttc caa aga tct         144
Val Lys Asp Leu Lys Lys Ala Ile Pro Gln His Cys Phe Gln Arg Ser
        35                  40                  45 att cca aga tct ttc tct tat ctt ttg act gac att act ctt gtg tct         192
Ile Pro Arg Ser Phe Ser Tyr Leu Leu Thr Asp Ile Thr Leu Val Ser
    50                  55                  60 tgt ttc tat tat gtg gct act aac tat ttc tct ctt ttg cca caa cca         240
Cys Phe Tyr Tyr Val Ala Thr Asn Tyr Phe Ser Leu Leu Pro Gln Pro
65                  70                  75                  80
```

| | | |
|---|---|---|
| ctt tct act tat ctt gct tgg cca ctt tat tgg gtg tgt caa gga tgt<br>Leu Ser Thr Tyr Leu Ala Trp Pro Leu Tyr Trp Val Cys Gln Gly Cys<br>                85                        90                        95 | 288 | |
| gtt ctt act gga att tgg gtt ctt gga cat gag tgt gga cat cat gct<br>Val Leu Thr Gly Ile Trp Val Leu Gly His Glu Cys Gly His His Ala<br>               100                      105                      110 | 336 | |
| ttc tct gat tat caa tgg ctt gat gac act gtg ggt ttc att ttc cat<br>Phe Ser Asp Tyr Gln Trp Leu Asp Asp Thr Val Gly Phe Ile Phe His<br>          115                      120                      125 | 384 | |
| tct ctt ttg ctt gtg cca tat ttc tct tgg aag tat tct cat aga aga<br>Ser Leu Leu Leu Val Pro Tyr Phe Ser Trp Lys Tyr Ser His Arg Arg<br>130                        135                      140 | 432 | |
| cat cat tct aac aac gga tct ctt gag aag gac gaa gtt ttt gtt cca<br>His His Ser Asn Asn Gly Ser Leu Glu Lys Asp Glu Val Phe Val Pro<br>145                        150                      155                      160 | 480 | |
| cct aag aaa gct gca gtg aag tgg tat gtg aag tat ctt aac aac cca<br>Pro Lys Lys Ala Ala Val Lys Trp Tyr Val Lys Tyr Leu Asn Asn Pro<br>                 165                      170                      175 | 528 | |
| ctt gga aga att ctt gtg ctt act gtg aga ttc att ctt gga tgg cca<br>Leu Gly Arg Ile Leu Val Leu Thr Val Arg Phe Ile Leu Gly Trp Pro<br>               180                      185                      190 | 576 | |
| ctt tat ctt gct ttc aac gtt tct gga aga cca tat gat gga ttt gct<br>Leu Tyr Leu Ala Phe Asn Val Ser Gly Arg Pro Tyr Asp Gly Phe Ala<br>             195                      200                      205 | 624 | |
| tct cat ttc ttc cca cat gct cca att ttc aag gac aga gag aga ctt<br>Ser His Phe Phe Pro His Ala Pro Ile Phe Lys Asp Arg Glu Arg Leu<br>      210                      215                      220 | 672 | |
| caa atc tat att tct gat gct gga att ctt gct gtg tgt tat gga ctt<br>Gln Ile Tyr Ile Ser Asp Ala Gly Ile Leu Ala Val Cys Tyr Gly Leu<br>225                        230                      235                      240 | 720 | |
| tat aga tat gct gca tct caa gga ctt act gct atg att tgt gtg tat<br>Tyr Arg Tyr Ala Ala Ser Gln Gly Leu Thr Ala Met Ile Cys Val Tyr<br>               245                      250                      255 | 768 | |
| gga gtg cca ctt ttg att gtg aac ttc ttc ctt gtg ctt gtg act ttc<br>Gly Val Pro Leu Leu Ile Val Asn Phe Phe Leu Val Leu Val Thr Phe<br>             260                      265                      270 | 816 | |
| ctt caa cat act cat cca tct ctt cca cat tat gat tct act gaa tgg<br>Leu Gln His Thr His Pro Ser Leu Pro His Tyr Asp Ser Thr Glu Trp<br>      275                      280                      285 | 864 | |
| gag tgg att aga gga gct ctt gtg act gtg gac aga gac tat gga att<br>Glu Trp Ile Arg Gly Ala Leu Val Thr Val Asp Arg Asp Tyr Gly Ile<br>      290                      295                      300 | 912 | |
| ctt aac aag gtg ttc cat aac att act gat act cat gtt gct cat cat<br>Leu Asn Lys Val Phe His Asn Ile Thr Asp Thr His Val Ala His His<br>305                        310                      315                      320 | 960 | |
| ctt ttc gct act att cca cat tat aac gct atg gaa gct act gag gct<br>Leu Phe Ala Thr Ile Pro His Tyr Asn Ala Met Glu Ala Thr Glu Ala<br>               325                      330                      335 | 1008 | |
| att aag cca att ctt gga gac tat tat cat ttt gat gga act cct tgg<br>Ile Lys Pro Ile Leu Gly Asp Tyr Tyr His Phe Asp Gly Thr Pro Trp<br>             340                      345                      350 | 1056 | |
| tat gtg gct atg tat aga gag gct aag gag tgt ctt tat gtt gaa cca<br>Tyr Val Ala Met Tyr Arg Glu Ala Lys Glu Cys Leu Tyr Val Glu Pro<br>             355                      360                      365 | 1104 | |
| gat act gag aga gga aag aag gga gtg tat tat tat aac aac aag ctt<br>Asp Thr Glu Arg Gly Lys Lys Gly Val Tyr Tyr Tyr Asn Asn Lys Leu<br>      370                      375                      380 | 1152 | |
| taa | 1155 | |

-continued

```
<210> SEQ ID NO 134
<211> LENGTH: 399
<212> TYPE: PRT
<213> ORGANISM: Ricinus communis

<400> SEQUENCE: 134

Met Ala Ser Ser Tyr Pro Tyr Asp Val Pro Asp Tyr Ala Gly Gly Gly
 1               5                  10                  15

Gly Arg Met Ser Thr Val Ile Thr Ser Asn Asn Ser Glu Lys Lys Gly
            20                  25                  30

Gly Ser Ser His Leu Lys Arg Ala Pro His Thr Lys Pro Pro Phe Thr
        35                  40                  45

Leu Gly Asp Leu Lys Arg Ala Ile Pro Pro His Cys Phe Glu Arg Ser
    50                  55                  60

Phe Val Arg Ser Phe Ser Tyr Val Ala Tyr Asp Val Cys Leu Ser Phe
65                  70                  75                  80

Leu Phe Tyr Ser Ile Ala Thr Asn Phe Phe Pro Tyr Ile Ser Ser Pro
                85                  90                  95

Leu Ser Tyr Val Ala Trp Leu Val Tyr Trp Leu Phe Gln Gly Cys Ile
            100                 105                 110

Leu Thr Gly Leu Trp Val Ile Gly His Glu Cys Gly His His Ala Phe
        115                 120                 125

Ser Glu Tyr Gln Leu Ala Asp Asp Ile Val Gly Leu Ile Val His Ser
    130                 135                 140

Ala Leu Leu Val Pro Tyr Phe Ser Trp Lys Tyr Ser His Arg Arg His
145                 150                 155                 160

His Ser Asn Ile Gly Ser Leu Glu Arg Asp Glu Val Phe Val Pro Lys
                165                 170                 175

Ser Lys Ser Lys Ile Ser Trp Tyr Ser Lys Tyr Leu Asn Asn Pro Pro
            180                 185                 190

Gly Arg Val Leu Thr Leu Ala Ala Thr Leu Leu Leu Gly Trp Pro Leu
        195                 200                 205

Tyr Leu Ala Phe Asn Val Ser Gly Arg Pro Tyr Asp Arg Phe Ala Cys
    210                 215                 220

His Tyr Asp Pro Tyr Gly Pro Ile Phe Ser Glu Arg Glu Arg Leu Gln
225                 230                 235                 240

Ile Tyr Ile Ala Asp Leu Gly Ile Phe Ala Thr Thr Phe Val Leu Tyr
                245                 250                 255

Gln Ala Thr Met Ala Lys Gly Leu Ala Trp Val Met Arg Ile Tyr Gly
            260                 265                 270

Val Pro Leu Leu Ile Val Asn Cys Phe Leu Val Met Ile Thr Tyr Leu
        275                 280                 285

Gln His Thr His Pro Ala Ile Pro Arg Tyr Gly Ser Ser Glu Trp Asp
    290                 295                 300

Trp Leu Arg Gly Ala Met Val Thr Val Asp Arg Asp Tyr Gly Val Leu
305                 310                 315                 320

Asn Lys Val Phe His Asn Ile Ala Asp Thr His Val Ala His His Leu
                325                 330                 335

Phe Ala Thr Val Pro His Tyr His Ala Met Glu Ala Thr Lys Ala Ile
            340                 345                 350

Lys Pro Ile Met Gly Glu Tyr Tyr Arg Tyr Asp Gly Thr Pro Phe Tyr
        355                 360                 365

Lys Ala Leu Trp Arg Glu Ala Lys Glu Cys Leu Phe Val Glu Pro Asp
    370                 375                 380
```

```
Glu Gly Ala Pro Thr Gln Gly Val Phe Trp Tyr Arg Asn Lys Tyr
385                 390                 395

<210> SEQ ID NO 135
<211> LENGTH: 374
<212> TYPE: PRT
<213> ORGANISM: Crepis palaestina

<400> SEQUENCE: 135

Met Ala Ser Ser Gly Arg Gly Arg Thr Ser Glu Lys Ser Val Met Glu
1               5                   10                  15

Arg Val Ser Val Asp Pro Val Thr Phe Ser Leu Ser Glu Leu Lys Gln
                20                  25                  30

Ala Ile Pro Pro His Cys Phe Gln Arg Ser Val Ile Arg Ser Ser Tyr
            35                  40                  45

Tyr Val Val Gln Asp Leu Ile Ile Ala Tyr Ile Phe Tyr Phe Leu Ala
    50                  55                  60

Asn Thr Tyr Ile Pro Thr Leu Pro Thr Ser Leu Ala Tyr Leu Ala Trp
65                  70                  75                  80

Pro Val Tyr Trp Phe Cys Gln Ala Ser Val Leu Thr Gly Leu Trp Ile
                85                  90                  95

Leu Gly His Glu Cys Gly His His Ala Phe Ser Asn Tyr Thr Trp Phe
            100                 105                 110

Asp Asp Thr Val Gly Phe Ile Leu His Ser Phe Leu Leu Thr Pro Tyr
            115                 120                 125

Phe Ser Trp Lys Phe Ser His Arg Asn His His Ser Asn Thr Ser Ser
130                 135                 140

Ile Asp Asn Asp Glu Val Tyr Ile Pro Lys Ser Lys Ser Lys Leu Ala
145                 150                 155                 160

Arg Ile Tyr Lys Leu Leu Asn Asn Pro Pro Gly Arg Leu Leu Val Leu
                165                 170                 175

Ile Ile Met Phe Thr Leu Gly Phe Pro Leu Tyr Leu Leu Thr Asn Ile
            180                 185                 190

Ser Gly Lys Lys Tyr Asp Arg Phe Ala Asn His Phe Asp Pro Met Ser
        195                 200                 205

Pro Ile Phe Lys Glu Arg Glu Arg Phe Gln Val Phe Leu Ser Asp Leu
210                 215                 220

Gly Leu Leu Ala Val Phe Tyr Gly Ile Lys Val Ala Val Ala Asn Lys
225                 230                 235                 240

Gly Ala Ala Trp Val Ala Cys Met Tyr Gly Val Pro Val Leu Gly Val
                245                 250                 255

Phe Thr Phe Phe Asp Val Ile Thr Phe Leu His His Thr His Gln Ser
            260                 265                 270

Ser Pro His Tyr Asp Ser Thr Glu Trp Asn Trp Ile Arg Gly Ala Leu
        275                 280                 285

Ser Ala Ile Asp Arg Asp Phe Gly Phe Leu Asn Ser Val Phe His Asp
    290                 295                 300

Val Thr His Thr His Val Met His His Leu Phe Ser Tyr Ile Pro His
305                 310                 315                 320

Tyr His Ala Lys Glu Ala Arg Asp Ala Ile Lys Pro Ile Leu Gly Asp
                325                 330                 335

Phe Tyr Met Ile Asp Arg Thr Pro Ile Leu Lys Ala Met Trp Arg Glu
            340                 345                 350

Gly Arg Glu Cys Met Tyr Ile Glu Pro Asp Ser Lys Leu Lys Gly Val
        355                 360                 365
```

Tyr Trp Tyr His Lys Leu
        370

<210> SEQ ID NO 136
<211> LENGTH: 378
<212> TYPE: PRT
<213> ORGANISM: Stokesia laevis B

<400> SEQUENCE: 136

Met Ala Ser Ser Tyr Asp Asp Arg Met Lys Asp His Asp Met Asp Glu
1               5                   10                  15

Arg Ala Pro Ile Asp Pro Ala Pro Phe Ser Leu Ser Asp Leu Lys Lys
            20                  25                  30

Ala Ile Pro Ala His Cys Phe Arg Arg Ser Ala Val Trp Ser Ser Cys
        35                  40                  45

Tyr Val Val Gln Asp Leu Ile Ile Thr Phe Leu Leu Tyr Thr Val Ala
    50                  55                  60

Asn Thr Tyr Ile Pro His Leu Pro Pro Pro Leu Val Tyr Leu Ala Trp
65                  70                  75                  80

Pro Val Tyr Trp Phe Cys Gln Ser Cys Ile Leu Thr Gly Leu Trp Val
                85                  90                  95

Leu Gly His Glu Cys Gly His His Ala Phe Ser Glu Tyr Gln Trp Ile
            100                 105                 110

Asp Asn Ala Val Gly Phe Val Leu His Ser Ala Leu Leu Thr Pro Tyr
        115                 120                 125

Phe Ser Trp Lys Tyr Ser His Arg Lys His His Ala Asn Thr Asn Ser
    130                 135                 140

Leu Glu Asn Glu Glu Val Tyr Ile Pro Arg Thr Gln Ser Gln Leu Arg
145                 150                 155                 160

Thr Tyr Ser Thr Tyr Glu Phe Leu Asp Asn Thr Pro Gly Arg Ile Leu
                165                 170                 175

Ile Leu Val Ile Met Leu Thr Leu Gly Phe Pro Leu Tyr Leu Leu Thr
            180                 185                 190

Asn Val Ser Gly Lys Lys Tyr Asp Arg Phe Thr Asn His Phe Asp Pro
        195                 200                 205

Leu Ser Pro Ile Phe Thr Glu Arg Glu Arg Ile Gln Val Ala Leu Ser
    210                 215                 220

Asp Leu Gly Ile Val Ala Val Phe Tyr Gly Leu Lys Phe Leu Val Gln
225                 230                 235                 240

Thr Lys Gly Phe Gly Trp Val Met Cys Met Tyr Gly Val Pro Val Ile
                245                 250                 255

Gly Leu Asn Ser Phe Ile Ile Val Ile Thr Tyr Leu His His Thr His
            260                 265                 270

Leu Ser Ser Pro His Tyr Asp Ser Thr Glu Trp Asn Trp Ile Lys Gly
        275                 280                 285

Ala Leu Thr Thr Ile Asp Arg Asp Phe Gly Leu Leu Asn Arg Val Phe
    290                 295                 300

His Asp Val Thr His Thr His Val Leu His His Leu Phe Pro Tyr Ile
305                 310                 315                 320

Pro His Tyr His Ala Lys Glu Ala Ser Glu Ala Ile Lys Pro Ile Leu
                325                 330                 335

Gly Asp Tyr Arg Met Ile Asp Arg Thr Pro Phe Phe Lys Ala Met Trp
            340                 345                 350

Arg Glu Ala Lys Glu Cys Ile Tyr Ile Glu Gln Asp Ala Asp Ser Lys

His Lys Gly Thr Tyr Trp Tyr His Lys Met
    370                 375

<210> SEQ ID NO 137
<211> LENGTH: 374
<212> TYPE: PRT
<213> ORGANISM: Crepis biennis

<400> SEQUENCE: 137

Met Ala Ser Ser Gly His Ser Arg Thr Ser Lys Lys Ser Val Met Glu
 1               5                  10                  15

Arg Val Ser Val Asp Pro Val Pro Phe Ser Leu Ser Asp Leu Lys Gln
            20                  25                  30

Ala Ile Pro Pro His Cys Phe Gln Arg Ser Val Ile Arg Ser Ser Tyr
        35                  40                  45

Tyr Val Val His Asp Leu Ile Ile Ala Tyr Ile Phe Tyr Phe Leu Ala
 50                  55                  60

Asp Lys Tyr Ile Pro Ile Leu Pro Ala Pro Leu Ala Tyr Leu Ala Trp
65                  70                  75                  80

Pro Leu Tyr Trp Phe Cys Gln Ala Ser Ile Leu Thr Gly Leu Trp Ile
            85                  90                  95

Leu Gly His Glu Cys Gly His His Ala Phe Ser Glu His Gln Trp Val
        100                 105                 110

Asp Asp Thr Val Gly Phe Met Val His Ser Phe Leu Leu Thr Pro Tyr
    115                 120                 125

Phe Ser Trp Lys Tyr Ser His Arg Asn His His Ala Asn Thr Ser Ser
130                 135                 140

Ile Asp Asn Asp Glu Val Tyr Ile Pro Lys Ser Lys Ser Lys Leu Ala
145                 150                 155                 160

Leu Thr Tyr Lys Leu Leu Asn Asn Pro Pro Gly Arg Leu Leu Val Met
                165                 170                 175

Val Ile Met Phe Thr Leu Gly Phe Pro Leu Tyr Leu Leu Thr Asn Ile
            180                 185                 190

Ser Gly Lys Lys Tyr Asp Arg Phe Ala Asn His Phe Asp Pro Met Ser
        195                 200                 205

Pro Ile Phe Lys Glu Arg Glu Arg Phe Gln Val Leu Leu Ser Asp Leu
    210                 215                 220

Gly Leu Leu Ala Val Phe Tyr Gly Ile Lys Val Ala Val Ala Lys Lys
225                 230                 235                 240

Gly Ala Ala Trp Val Ala Cys Met Tyr Gly Val Pro Met Leu Gly Val
                245                 250                 255

Phe Thr Leu Phe Asp Ile Ile Thr Tyr Leu His His Thr His Gln Ser
            260                 265                 270

Ser Pro His Tyr Asp Ser Thr Glu Trp Asn Trp Ile Arg Gly Ala Leu
        275                 280                 285

Ser Ala Ile Asp Arg Asp Phe Gly Phe Met Asn Ser Val Phe His Asp
    290                 295                 300

Val Thr His Thr His Val Met His His Met Phe Ser Tyr Ile Pro His
305                 310                 315                 320

Tyr His Ala Lys Glu Ala Arg Asp Ala Ile Asn Thr Ile Ile Gly Asp
                325                 330                 335

Tyr Tyr Met Ile Asp Arg Thr Pro Ile Leu Lys Ala Leu Trp Arg Glu
            340                 345                 350

```
Ala Lys Glu Cys Met Tyr Ile Glu Pro Asp Ser Lys Arg Lys Gly Val
        355                 360                 365

Tyr Trp Tyr His Lys Leu
    370

<210> SEQ ID NO 138
<211> LENGTH: 384
<212> TYPE: PRT
<213> ORGANISM: Lesquerella gracilis B

<400> SEQUENCE: 138

Met Ala Ser Ser Gly Arg Ile Met Val Thr Pro Ser Ser Lys Lys Ser
  1               5                  10                  15

Glu Thr Glu Ala Leu Lys Arg Gly Pro Cys Glu Lys Pro Pro Phe Thr
                 20                  25                  30

Val Lys Asp Leu Lys Lys Ala Ile Pro Gln His Cys Phe Gln Arg Ser
             35                  40                  45

Ile Pro Arg Ser Phe Ser Tyr Leu Leu Thr Asp Ile Thr Leu Val Ser
     50                  55                  60

Cys Phe Tyr Tyr Val Ala Thr Asn Tyr Phe Ser Leu Leu Pro Gln Pro
 65                  70                  75                  80

Leu Ser Thr Tyr Leu Ala Trp Pro Leu Tyr Trp Val Cys Gln Gly Cys
                 85                  90                  95

Val Leu Thr Gly Ile Trp Val Leu Gly His Glu Cys Gly His His Ala
                100                 105                 110

Phe Ser Asp Tyr Gln Trp Leu Asp Asp Thr Val Gly Phe Ile Phe His
            115                 120                 125

Ser Leu Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Arg Phe Ile Leu Gly Trp Pro
            180                 185                 190

Leu Tyr Leu Ala Phe Asn Val Ser Gly Arg Pro Tyr Asp Gly Phe Ala
    195                 200                 205

Ser His Phe Phe Pro His Ala Pro Ile Phe Lys Asp Arg Glu Arg Leu
210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
    275                 280                 285

Glu Trp Ile Arg Gly Ala Leu Val Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
            340                 345                 350
```

```
Tyr Val Ala Met Tyr Arg Glu Ala Lys Glu Cys Leu Tyr Val Glu Pro
        355                 360                 365

Asp Thr Glu Arg Gly Lys Lys Gly Val Tyr Tyr Asn Asn Lys Leu
    370                 375                 380

<210> SEQ ID NO 139
<211> LENGTH: 9
<212> TYPE: PRT
<213> ORGANISM: Human influenza virus

<400> SEQUENCE: 139

Tyr Pro Tyr Asp Val Pro Asp Tyr Ala
1               5

<210> SEQ ID NO 140
<211> LENGTH: 12
<212> TYPE: DNA
<213> ORGANISM: Ricinus communis

<400> SEQUENCE: 140
agaaaggagg aa                                                          12
```